US010836822B2

(12) United States Patent
Dobson et al.

(10) Patent No.: US 10,836,822 B2
(45) Date of Patent: Nov. 17, 2020

(54) ANTI-PAR2 ANTIBODIES AND USES THEREOF

(71) Applicant: MEDIMMUNE LIMITED, Cambridge (GB)

(72) Inventors: Claire Dobson, Cambridge (GB);
Richard Williams, Cambridge (GB);
Ian Gurrell, Cambridge (GB);
Sadhana Podichetty, Cambridge (GB);
David Fairman, Cambridge (GB);
Peter Thornton, Cambridge (GB);
Philip Newton, Cambridge (GB)

(73) Assignee: MedImmune Limited, Cambridge (GB)

( * ) Notice: Subject to any disclaimer, the term of this patent is extended or adjusted under 35 U.S.C. 154(b) by 31 days.

(21) Appl. No.: 15/923,374

(22) Filed: Mar. 16, 2018

(65) Prior Publication Data
US 2018/0305450 A1 Oct. 25, 2018

Related U.S. Application Data

(60) Provisional application No. 62/637,766, filed on Mar. 2, 2018, provisional application No. 62/472,462, filed on Mar. 16, 2017.

(51) Int. Cl.
A61K 39/395 (2006.01)
C07K 16/28 (2006.01)
A61K 39/00 (2006.01)
A61P 29/00 (2006.01)

(52) U.S. Cl.
CPC .............. C07K 16/28 (2013.01); A61P 29/00 (2018.01); A61K 2039/505 (2013.01); C07K 2317/33 (2013.01); C07K 2317/565 (2013.01); C07K 2317/622 (2013.01); C07K 2317/76 (2013.01); C07K 2317/92 (2013.01); C07K 2317/94 (2013.01)

(58) Field of Classification Search
None
See application file for complete search history.

(56) References Cited

U.S. PATENT DOCUMENTS

| | | | |
|---|---|---|---|
| 9,029,515 | B2 | 5/2015 | Pons et al. |
| 9,315,577 | B2 | 4/2016 | Foltz et al. |
| 2010/0119506 | A1 | 5/2010 | Litzenburger et al. |
| 2010/0216187 | A1 | 8/2010 | Lasters et al. |
| 2011/0311553 | A1 | 12/2011 | Litzenburger et al. |
| 2013/0011866 | A1 | 1/2013 | Igawa et al. |
| 2015/0266974 | A1 | 9/2015 | Pons et al. |

FOREIGN PATENT DOCUMENTS

| | | |
|---|---|---|
| WO | WO2011/031695 | 3/2011 |
| WO | WO2011/111007 | 9/2011 |
| WO | WO2014/028354 | 2/2014 |
| WO | WO2016/000813 | 1/2016 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Bonvin, et al., "Purpose-Oriented Antibody Libraries Incorporating Tailored CDR3 Sequences," Antibodies, Vo. 4, No. 2, May 20, 2015; 103-122.
Igawa, et al., "pH-dependent antigen-binding antibodies as a novel therapeutic modality," Biochimica Et Biophysica ACTA (BBA) Proteins & Protemoics, Elsevier, Netherlands, vol. 1844, No. 11, Aug. 12, 2014; 1943-19507.
Rudikoff, et al., "Single Amino Acid Substitution Altering Antigen-binding Specificity," Proceedings of the National Academy of Sciences, National Academy of Sciences, US., vol. 79, Mar. 1, 1982; 1979-1983.
Bove, et al., "Weight bearing as a measure of disease progression and efficacy of anti-inflammatory compounds in a model of monosodium iodoacetate-induced osteoarthritis," OsteoArthritis and Cartilage, vol. 11(11): 821-830 (2003).
Brekke, et al., "Therapeutic Antibodies for Human Diseases at the Dawn of the Twenty-First Century," Nature Reviews—Drug Discovery, vol. 2: 52-62 (2003).
Fernihough, et al., "Pain related behaviour in two models of osteoarthritis in the rat knee," Pain, vol. 112: 83-93 (2004).
Gieseler, et al., "Proteinase-activated receptors (PARs)—focus on receptor-receptor-interactions and their physiological and pathophysiological impact," Cell Communication and Signaling, vol. 11: 86 (2013).
Goodman, et al., "The Effects of Medications on Bone," Journal of the American Academy of Orthopaedic Surgeons, vol. 15: 450-460 (2007).
Granier, et al., "A new era of GPCR structural and chemical biology," Nature Chemical Biology, vol. 8(8): 670-673 (2014).
Igawa, et al., "Antibody recycling by engineered pH-dependent antigen binding improves the duration of antigen neutralization," Nature Biotechnology, vol. 28(11): 1203-1207 (2010).
Irving, et al., "Review article: appropriate use of corticosteroids in Crohn's disease," Alimentary Pharmacology & Therapeutics, vol. 26: 313-329 (2007).
Ito, et al., "The His-probe method: Effects of histidine residues introduced into the complementarity-determining regions of antibodies on antigen-antibody interactions at different pH values," FEBS, 309(1): 85-88 (1992).
Kalbhen, D.A., "Chemical Model of Osteoarthritis—a Pharmacological Evaluation," The Journal of Rheumatology, Special Issue vol. 14: 130-131 (1987).

(Continued)

Primary Examiner — Christine J Saoud
Assistant Examiner — Jon M Lockard

(57) ABSTRACT

The present disclosure provides antibodies and antigen-binding fragments capable of binding PAR2. In some embodiments, the anti-PAR2 antibodies or antigen-binding fragments thereof bind PAR2 in a pH-dependent manner. The disclosure further provides methods for making and using the antibodies and antigen-binding fragments.

13 Claims, 13 Drawing Sheets

Specification includes a Sequence Listing.

(56) References Cited

OTHER PUBLICATIONS

Kim, et al., "Kinetics of FcRn-mediated recycling of IgG and albumin in human: Pathophysiology and therapeutic implications using a simplified mechanism-based model," Clinical Immunology, vol. 122(2): 146-155 (2007).
Macfarlane, et al., "Proteinase-Activated Receptors," Pharmacological Reviews, vol. 53(2): 245-282 (2001).
Maggon, K., "Monoclonal Antibody "Gold Rush"," Current Medicinal Chemistry, vol. 14(18): 1978-1987 (2007).
Pyzik, et al., "FcRn: The architect behind the immune and nonimmune functions of IgG and albumin", The Journal of Immunology, vol. 194(10): 4595-4603 (2015).
Zhang, et al., "Structural Studies of G Protein-Coupled Receptors," Molecules and Cells, vol. 38(10): 836-842 (2015).
Zhang, et al., "High-resolution crystal structure of human Protease-Activated Receptor 1 bound to the antagonist vorapaxar," Nature, vol. 492(7429): 387-392 (2012).

\* cited by examiner

| Kabat Numbering | VH Sequences | | | | | | | | | | | | | | | | | | | | | | | | |
|---|---|---|---|---|---|---|---|---|---|---|---|---|---|---|---|---|---|---|---|---|---|---|---|---|---|
| | CDR 2 | | | | | | | | | | | | | | | | | CDR 3 | | | | | | | |
| | 50 | 51 | 52 | 52a | 53 | 54 | 55 | 56 | 57 | 58 | 59 | 60 | 61 | 62 | 63 | 64 | 65 | 95 | 96 | 97 | 98 | 99 | 100 | 101 | 102 |
| ParB0067 | T | I | S | Y | S | G | S | L | I | S | Y | A | D | S | V | K | G | I | N | N | D | P | M | D | V |
| PaB670129 | | | | H | | | H | | | H | | | | H | H | | | H | H | | | | | | |
| PaB670010 | | | | | | | | | H | | | | | | | | | | | | | | | | |
| PaB670020 | | | | | | | | | | | | | | | | | | | | H | | | | | |
| PaB670034 | | | | | | | | | | | | | | | | | | | | | | | | | |
| PaB670045 | | | | | | | | | | | | | | | | | | | H | H | | | | | |
| PaB670048 | | | | | | | | | | | | | | | | | | | H | H | | | | | H |
| PaB670064 | | | | | | | | | | | | | | | | | | | | | | | | | |
| PaB670066 | | | | | | | | | | | | | | | | | | | | | | | | | |
| PaB670067 | | | | | | | | | | | | | | | | | | | | | | | | | |
| PaB670068 | | | | | | | | | | | | | | | | | | | | | | | | | |
| PaB670070 | | | | | | | | | | | | | | | | | | | | | | | | | |
| PaB670071 | | | | | | | | | | | | | | | | | | | | | | | | | |
| PaB670073 | | | | | | | | | | | | | | | | | | | | | | | | | |
| PaB670075 | | | | | | | | | | | | | | | | | | | | | | | | | |
| PaB670076 | | | | | | | | | | | | | | | | | | | | | | | | | |
| PaB670077 | | | | | | | | | | | | | | | | | | | | | | | | | |
| PaB670078 | | | | | | | | | | | | | | | | | | | | | | | | | |
| PaB670079 | | | | | | | | | | | | | | | | | | | | | | | | | |
| PaB670080 | | | | | | | | | | | | | | | | | | | | | | | | | |
| PaB670081 | | | | H | | | H | H | | | H | H | | | H | H | | | | | | | | | |
| PaB670082 | | | | H | | H | | | | | | | H | | | H | | | | | | | | | |
| PaB670083 | | H | H | | | H | | H | | H | | | H | | | | | | | | | | | | |
| PaB670084 | | | | H | | | H | | | H | H | | | | H | | | | | | | | | | |
| PaB670085 | | | | | H | | H | | | | | H | H | | H | | | | | | | | | | |
| PaB670087 | | | | | H | | H | | | | | | H | H | | H | | | | | | | | | |
| PaB670088 | | | | | | H | | | H | | | | H | H | H | | | | | | | | | | |
| PaB670089 | | | | | H | | H | | | H | | | H | | H | | | | | | | | | | |
| PaB670090 | | | | | H | | H | H | | | H | | | H | | | H | | | | | | | | |
| PaB670091 | | | | H | | | H | | | H | H | H | H | | | | | | | | | | | | |
| PaB670092 | | | | | H | | H | | | | H | | | H | H | | | | | | | | | | |
| PaB670093 | | | | | H | H | H | | | H | | | | | | | | | | | | | | | |
| PaB670094 | | | | | H | | H | H | | H | | | | H | H | | | | | | | | | | |
| PaB670095 | | | | | H | | H | H | | | | | | H | H | H | | | | | | | | | |
| PaB670097 | | H | H | | | H | | H | | H | H | H | | | | | | | | | | | | | |
| PaB670098 | | | | H | | | H | | | H | H | | | | H | | H | | | | | | | | |
| PaB670099 | | | | | H | | H | | | | H | | | H | H | | | | | | | | | | |
| PaB670100 | | | | | H | | H | H | | | H | | H | H | | | | | | | | | | | |
| PaB670101 | | | | | | | | | | | | | | | | | | H | H | H | | H | | | H |
| PaB670102 | | | | | | | | | | | | | | | | | | | H | | | | | | H |
| PaB670103 | | | | | | | | | | | | | | | | | | | | | | | | | |

Figure 1A

| Kabat Numbering | VH Sequences | | | | | | | | | | | | | | | | | | | | | | | | |
|---|---|---|---|---|---|---|---|---|---|---|---|---|---|---|---|---|---|---|---|---|---|---|---|---|---|
| | CDR 2 | | | | | | | | | | | | | | | | | CDR 3 | | | | | | | |
| | 50 | 51 | 52 | 52a | 53 | 54 | 55 | 56 | 57 | 58 | 59 | 60 | 61 | 62 | 63 | 64 | 65 | 95 | 96 | 97 | 98 | 99 | 100 | 101 | 102 |
| ParB0067 | T | I | S | Y | S | G | S | L | I | S | Y | A | D | S | V | K | G | I | N | N | D | P | M | D | V |
| PaB670104 | | | | | | | | | | | | | | | | | | | | | | | | | |
| PaB670105 | | | | | | | | | | | | | | | | | | | | | | | | | |
| PaB670106 | | | | | | | | | | | | | | | | | | | | | | | | | |
| PaB670107 | | | | | | | | | | | | | | | | | | | | | | | | | |
| PaB670108 | | | | | | | | | | | | | | | | | | | | | | | | | |
| PaB670114 | | | | | | | | | | H | | | | | | | | | | H | | | | | |
| PaB670115 | | | H | | | | H | H | | H | H | | | H | H | | | | | H | | | | | |
| PaB670116 | | | H | | | | H | | | H | H | | | H | | | | | | H | | | | | |
| PaB670117 | | | | | | | H | | | H | | | H | H | H | | | | | H | | | | | |
| PaB670118 | | | | | H | | H | | | H | | | H | H | | | | | | H | | | | | |
| PaB670119 | | | | | H | | H | | | | H | | | H | H | | | | | H | | | | | |
| PaB670120 | | | | | H | | H | H | | | | | | H | H | H | | | | H | | | | | |
| PaB670121 | | | | | H | | H | | | | H | | | H | H | | | | | H | | | | | |
| PaB670122 | | | | | | | | | | H | | | | | | | | | H | H | | | | | |
| PaB670123 | | | H | | | | H | H | | H | H | | | H | H | | | | H | H | | | | | |
| PaB670125 | | | | | | | H | | | H | | | | H | H | H | | | H | H | | | | | |
| PaB670126 | | | | | | | H | | | H | | | H | | H | | | | H | H | | | | | |
| PaB670127 | | | | | | | H | | | H | | | | H | H | | | | H | H | | | | | |
| PaB670128 | | | | | | | H | | H | H | | | | H | H | H | | | H | H | | | | | |
| PaB670136 | | | | | | | H | H | H | | | | | H | H | H | | | H | H | | | | | H |
| PaB670137 | | | | | | | H | | | H | | | | H | H | | | | H | H | | | | | H |
| PaB670141 | | | | | | | | | | | | | | | | | | | | H | | | | | |
| PaB670142 | | | | | | | | | | | | | | | | | | | H | H | | | | | |
| PaB670143 | | | | | | | H | H | H | | | | | H | H | H | | | | | | | | | |
| PaB670144 | | | | | | | H | H | H | | | | | H | H | H | | | | H | | | | | |
| PaB670146 | | | | | | | | | | | | | | | | | | | | H | | | | | |
| PaB670148 | | | | | | | H | H | H | | | | | H | H | H | | | | | | | | | |
| PaB670149 | | | | | | | H | H | H | | | | | H | H | H | | | | H | | | | | |
| PaB670151 | | | | | | | | | | | | | | | | | | | | H | | | | | |
| PaB670152 | | | | | | | | | | | | | | | | | | | H | H | | | | | |
| PaB670153 | | | | | H | | H | H | | | | | | H | H | H | | | | | | | | | |
| PaB670156 | | | | | | | | | | | | | | | | | | | | H | | | | | |
| PaB670157 | | | | | | | | | | | | | | | | | | | H | H | | | | | |
| PaB670158 | | | | | | | H | H | H | | | | | H | H | H | | | | | | | | | |
| PaB670159 | | | | | | | H | H | H | | | | | H | H | H | | | | H | | | | | |
| PaB670160 | | | | | | | | | | | | | | | | | | | | H | | | | | |
| PaB670161 | | | | | | | | | | | | | | | | | | | H | H | | | | | |
| PaB670162 | | | | | | | H | H | H | | | | | H | H | H | | | | | | | | | |
| PaB670163 | | | | | | | H | H | H | | | | | H | H | H | | | | H | | | | | |

Figure 1B

| Kabat Numbering | VL Sequences ||||||||||||||
| | CDR 3 ||||||||||||||
| | 89 | 90 | 91 | 92 | 93 | 94 | 95 | 95a | 95b | 95c | 95d | 95e | 96 | 97 |
|---|---|---|---|---|---|---|---|---|---|---|---|---|---|---|
| ParB0067 | Q | T | W | D | G | N | P | T | T | G | E | T | N | V |
| PaB670129 | | | | | | | | | | | | | | |
| PaB670010 | | | | | | | | | | | | | | |
| PaB670020 | | | | | | | | | | | | | | |
| PaB670034 | | | | | | | | | H | | | | | |
| PaB670045 | | | | | | | | | | | | | | |
| PaB670048 | | | | | | | | | | | | | | |
| PaB670064 | H | | | H | H | | | H | | | | | | H |
| PaB670066 | H | H | | H | | | H | H | | | | | | H |
| PaB670067 | H | | | H | H | H | | H | | | | H | | |
| PaB670068 | | | | | H | H | | H | | | | H | H | |
| PaB670070 | | | | H | | H | H | | | H | | | | |
| PaB670071 | H | | | H | H | H | H | H | | | | H | | H |
| PaB670073 | | H | | H | | H | | H | H | | | H | | |
| PaB670075 | | H | | | | H | H | H | | | | | | H |
| PaB670076 | H | | | | H | H | H | | | | | H | | |
| PaB670077 | H | H | | H | | H | H | | | | | | | H |
| PaB670078 | H | H | | H | | H | | H | | | | H | | |
| PaB670079 | | H | | | | H | H | | | | | | | H |
| PaB670080 | | | | | | H | H | H | | | | | | H |
| PaB670081 | | | | | | | | | | | | | | |
| PaB670082 | | | | | | | | | | | | | | |
| PaB670083 | | | | | | | | | | | | | | |
| PaB670084 | | | | | | | | | | | | | | |
| PaB670085 | | | | | | | | | | | | | | |
| PaB670087 | | | | | | | | | | | | | | |
| PaB670088 | | | | | | | | | | | | | | |
| PaB670089 | | | | | | | | | | | | | | |
| PaB670090 | | | | | | | | | | | | | | |
| PaB670091 | | | | | | | | | | | | | | |
| PaB670092 | | | | | | | | | | | | | | |
| PaB670093 | | | | | | | | | | | | | | |
| PaB670094 | | | | | | | | | | | | | | |
| PaB670095 | | | | | | | | | | | | | | |
| PaB670097 | | | | | | | | | | | | | | |
| PaB670098 | | | | | | | | | | | | | | |
| PaB670099 | | | | | | | | | | | | | | |
| PaB670100 | | | | | | | | | | | | | | |
| PaB670101 | | | | | | | | | | | | | | |
| PaB670102 | | | | | | | | | | | | | | |
| PaB670103 | H | | | | | H | H | | | | | | | H |

Figure 2A

| Kabat Numbering | VL Sequences CDR 3 | | | | | | | | | | | | | |
|---|---|---|---|---|---|---|---|---|---|---|---|---|---|---|
| | 89 | 90 | 91 | 92 | 93 | 94 | 95 | 95a | 95b | 95c | 95d | 95e | 96 | 97 |
| ParB0067 | Q | T | W | D | G | N | P | T | T | G | E | T | N | V |
| PaB670104 |   | H |   |   |   | H | H | H |   |   |   |   |   |   |
| PaB670105 |   | H |   | H |   |   | H |   |   |   |   | H |   | H |
| PaB670106 | H |   |   |   | H |   | H | H | H | H |   |   |   | H |
| PaB670107 | H | H |   | H | H |   |   |   |   | H | H |   |   |   |
| PaB670108 |   | H |   | H |   | H | H | H |   |   |   |   |   |   |
| PaB670114 |   |   |   |   |   |   |   |   |   |   |   |   |   |   |
| PaB670115 |   |   |   |   |   |   |   |   |   |   |   |   |   |   |
| PaB670116 |   |   |   |   |   |   |   |   |   |   |   |   |   |   |
| PaB670117 |   |   |   |   |   |   |   |   |   |   |   |   |   |   |
| PaB670118 |   |   |   |   |   |   |   |   |   |   |   |   |   |   |
| PaB670119 |   |   |   |   |   |   |   |   |   |   |   |   |   |   |
| PaB670120 |   |   |   |   |   |   |   |   |   |   |   |   |   |   |
| PaB670121 |   |   |   |   |   |   |   |   |   |   |   |   |   |   |
| PaB670122 |   |   |   |   |   |   |   |   |   |   |   |   |   |   |
| PaB670123 |   |   |   |   |   |   |   |   |   |   |   |   |   |   |
| PaB670125 |   |   |   |   |   |   |   |   |   |   |   |   |   |   |
| PaB670126 |   |   |   |   |   |   |   |   |   |   |   |   |   |   |
| PaB670127 |   |   |   |   |   |   |   |   |   |   |   |   |   |   |
| PaB670128 |   |   |   |   |   |   |   |   |   |   |   |   |   |   |
| PaB670136 |   |   |   |   |   |   |   |   |   |   |   |   |   |   |
| PaB670137 |   |   |   |   |   |   |   |   |   |   |   |   |   |   |
| PaB670141 |   |   |   |   |   |   |   |   |   | H |   |   |   |   |
| PaB670142 |   |   |   |   |   |   |   |   |   | H |   |   |   |   |
| PaB670143 |   |   |   |   |   |   |   |   |   | H |   |   |   |   |
| PaB670144 |   |   |   |   |   |   |   |   |   | H |   |   |   |   |
| PaB670146 | H |   |   | H | H | H |   | H |   |   |   | H |   |   |
| PaB670148 | H |   |   | H | H | H |   | H |   |   |   | H |   |   |
| PaB670149 | H |   |   | H | H | H |   | H |   |   |   | H |   |   |
| PaB670151 | H |   |   |   | H | H | H |   |   |   |   | H |   |   |
| PaB670152 | H |   |   |   | H | H | H |   |   |   |   | H |   |   |
| PaB670153 | H |   |   |   | H | H | H |   |   |   |   | H |   |   |
| PaB670156 |   |   |   |   |   | H | H | H |   |   |   |   |   | H |
| PaB670157 |   |   |   |   |   | H | H | H |   |   |   |   |   | H |
| PaB670158 |   |   |   |   |   | H | H | H |   |   |   |   |   | H |
| PaB670159 |   |   |   |   |   | H | H | H |   |   |   |   |   | H |
| PaB670160 | H |   |   |   |   | H | H |   |   |   |   |   |   | H |
| PaB670161 | H |   |   |   |   | H | H |   |   |   |   |   |   | H |
| PaB670162 | H |   |   |   |   | H | H |   |   |   |   |   |   | H |
| PaB670163 | H |   |   |   |   | H | H |   |   |   |   |   |   | H |

Figure 2B

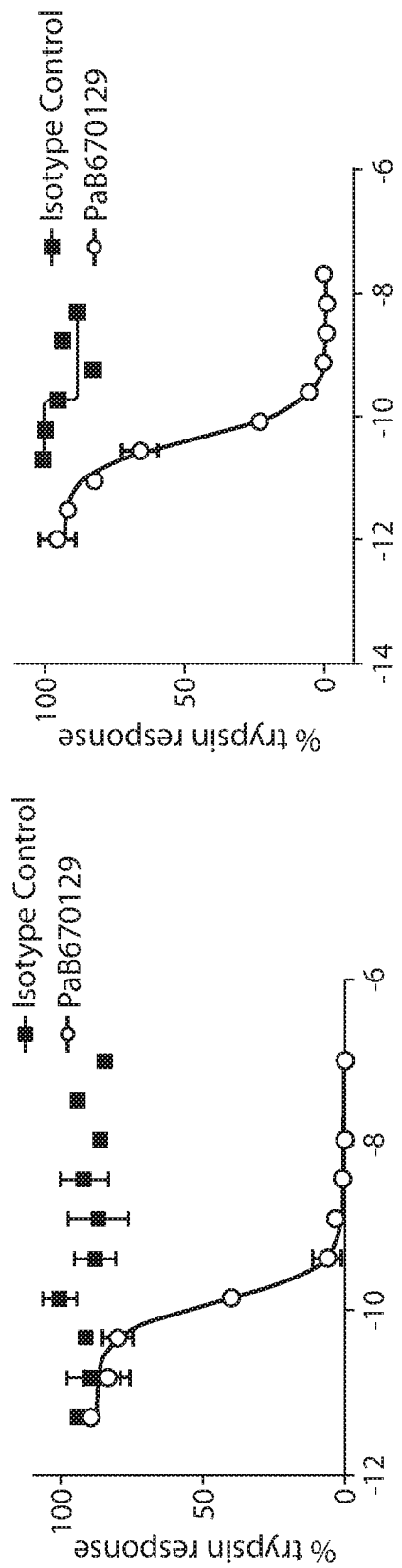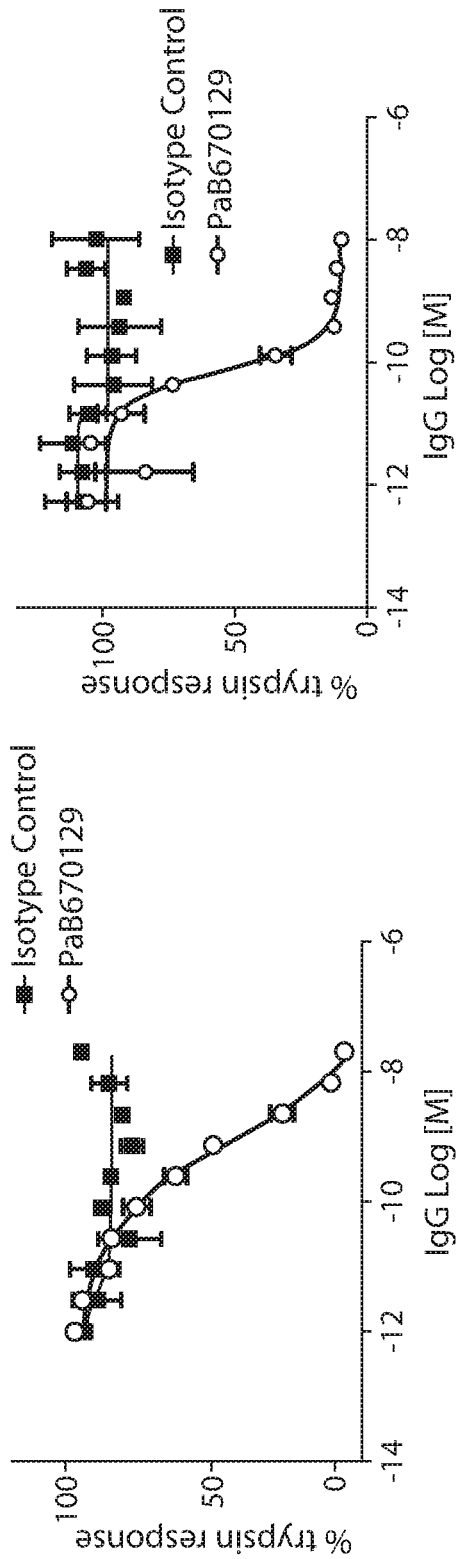
Figure 3A, Figure 3B, Figure 3C, Figure 3D

PAR2 FLIPR ASSAY POTENCY DATA IC$_{50}$

| | Human A549 FLIPR IC$_{50}$ (M) | SEM | n | Rat KNRK FLIPR IC$_{50}$ (M) | SEM | n | Cyno CYNOM-K1 FLIPR IC$_{50}$ (M) | SEM | n | Mouse LL/2 FLIPR IC$_{50}$ (M) | SEM | n |
|---|---|---|---|---|---|---|---|---|---|---|---|---|
| PaB0067 | 1.16E-10 | 1.47E-11 | 5 | 7.23E-12 | 1.48E-12 | 6 | 5.87E-11 | | | 2.58E-11 | 2.66E-12 | 2 |
| PaB670034 | 2.06E-10 | | 1 | 7.92E-12 | | 1 | | | | | | |
| PaB670045 | 1.42E-10 | | 1 | 1.02E-11 | | 1 | | | | | | |
| PaB670048 | 1.31E-10 | 6.15E-12 | 3 | 1.17E-11 | 2.41E-12 | 4 | | | | | | |
| PaB670061 | NI | | | NI | | 1 | | | | | | |
| PaB670062 | 2.34E-09 | | | 7.89E-10 | | 1 | | | | | | |
| PaB670066 | 7.22E-10 | | | 3.84E-09 | | 1 | | | | | | |
| PaB670075 | 8.04E-10 | | | NI | | | | | | | | |
| PaB670076 | 1.15E-10 | 5.10E-12 | 2 | 7.89E-11 | 3.82E-11 | 2 | | | | | | |
| PaB670077 | 9.28E-10 | | | 1.56E-09 | | 1 | | | | | | |
| PaB670078 | 5.88E-10 | | | 1.25E-09 | | 1 | | | | | | |
| PaB670079 | 7.01E-10 | | | 4.64E-10 | | 1 | | | | | | |
| PaB670080 | 2.61E-10 | 3.64E-11 | 2 | 1.44E-11 | | 1 | | | | | | |
| PaB670084 | 1.23E-10 | | | 2.27E-11 | 7.73E-12 | 2 | | | | | | |
| PaB670103 | 2.38E-10 | | | 1.46E-10 | | 1 | | | | | | |
| PaB670114 | 1.28E-10 | | | 1.35E-10 | | 1 | | | | | | |
| PaB670115 | 3.48E-10 | | | 2.97E-10 | | 1 | | | | | | |
| PaB670116 | 1.64E-10 | 8.95E-12 | 2 | 2.60E-08 | 2.02E-11 | 2 | | | | | | |
| PaB670117 | 1.41E-10 | | | 5.79E-10 | | 1 | | | | | | |
| PaB670118 | 1.08E-10 | | | 1.04E-10 | | 1 | | | | | | |
| PaB670119 | 1.50E-10 | | | 8.48E-11 | | 1 | | | | | | |
| PaB670120 | 1.13E-10 | | | 9.53E-10 | | 1 | | | | | | |
| PaB670121 | 2.18E-10 | | | 1.41E-10 | | 1 | | | | | | |
| PaB670122 | 2.55E-10 | | | NI | | | | | | | | |
| PaB670123 | NI | | | 2.54E-09 | | 1 | | | | | | |
| PaB670124 | 2.27E-10 | | | 1.34E-10 | | 1 | | | | | | |
| PaB670125 | 1.64E-10 | | | 3.95E-10 | | 1 | | | | | | |
| PaB670126 | 1.13E-10 | | | 2.12E-10 | | 1 | | | | | | |
| PaB670127 | 1.23E-10 | 4.05E-12 | 2 | 2.85E-10 | 8.33E-11 | 3 | 3.71E-11 | | | | | |
| PaB670128 | 1.09E-10 | 1.41E-11 | 4 | 5.21E-10 | 7.47E-11 | 6 | 4.64E-11 | 3.87E-12 | 3 | 5.09E-11 | 1.92E-11 | 2 |
| PaB670129 | NI | | | NI | | | | | | | | |
| PaB670130 | NI | | | NI | | | | | | | | |
| PaB670131 | NI | | | NI | | | | | | | | |
| PaB670132 | NI | | | NI | | | | | | | | |
| PaB670133 | NI | | | NI | | | | | | | | |
| PaB670134 | 1.37E-10 | 2.43E-11 | 2 | 7.04E-10 | | 1 | | | | | | |
| PaB670135 | 1.57E-10 | | | 4.32E-10 | 3.12E-11 | 2 | | | | | | |
| PaB670136 | 9.62E-11 | 7.73E-12 | 2 | 4.45E-10 | 7.38E-12 | 2 | | | | | | |
| PaB670139 | NI | | | 1.14E-09 | | 1 | | | | | | |
| PaB670140 | NI | | | 3.06E-11 | | 1 | | | | | | |
| PaB670129 Fab | 3.5E-09 | | | 3.44E-08 | | 1 | | | | | | |

Figure 3E

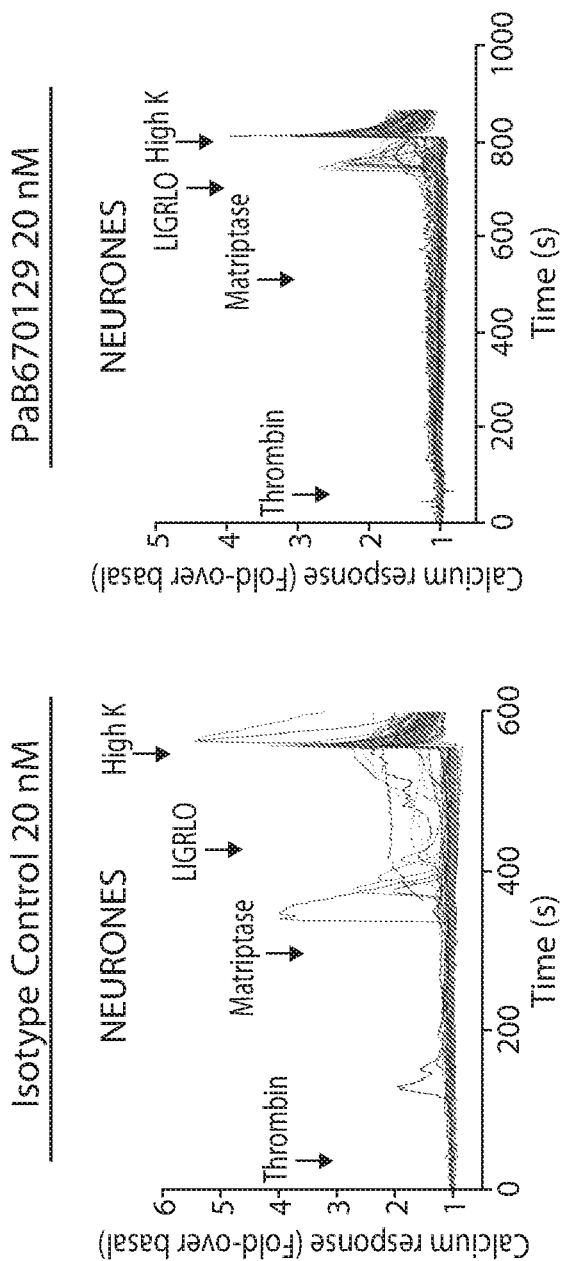
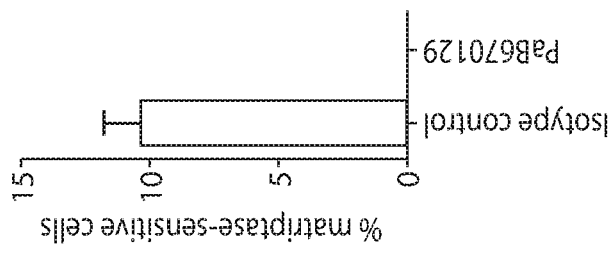
Figure 5A
Figure 5B
Figure 5C

ANTI-PAR2 ANTIBODIES AND USES THEREOF

CROSS-REFERENCE TO RELATED APPLICATION

This application claims the benefit of priority from U.S. Provisional Application No. 62/472,462, filed on Mar. 16, 2017 and from U.S. Provisional Application No. 62/637,766, filed on Mar. 2, 2018. The foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 16, 2018, is named 1848081-0002-093-101_SL.txt and is 351,646 bytes in size.

BACKGROUND OF THE DISCLOSURE

Chronic pain is a condition that can affect anyone and imposes a burden on patients, health care systems, and economies. Approximately 100 million people in the United States suffer from chronic pain and the total annual incremental cost of health care due to pain, including medical costs and the economic costs of lost time and wages, is estimated to be between $560 and $635 billion dollars (Institute of Medicine of The National Academies, 2011). Yet, in a survey of chronic pain sufferers, more than half felt they had little to no control over their pain (2006 Voices of Chronic Pain Survey, American Pain Foundation). Pain can be caused by a variety of conditions and diseases, from cancer, to diabetes, to arthritis, and can be classified into categories: nociceptive, neuropathic, and mixed type pain. Nociceptive pain is defined by stimulation of nerve fibers (e.g. by thermal, mechanical, or chemical stimuli) while neuropathic pain is pain caused by diverse causes such as nerve damage, diseases, and, importantly, inflammation. Inflammation, the process by which organisms recruit immune cells and release immune factors to the site of an injury or infection, can thus be both a helpful process of damage repair and a cause of pain.

Many treatments for pain inhibit inflammation. Two common classes of anti-inflammatory pain therapeutics are steroidal anti-inflammatory drugs and non-steroidal anti-inflammatory drugs (NSAIDs). Steroidal anti-inflammatory drugs typically suppress prostaglandins and leukotrienes, the products of inflammation. Such drugs are reliable and potent, but carry the risk of severe side effects, including, for example, reduced bone density, weight fluctuations, immune system suppression, and growth/puberty irregularities (Irving, P. M. et al. (2007) Aliment Pharmacol Ther. 26(3): 313-329; Goodman et al. J Am Acad Orthop Surg. 2007 August; 15(8):450-60). NSAIDs inhibit cyclooxygenase-1 and/or 2 (COX-1 and/or COX-2), which themselves catalyze the reaction of arachidonic acid into prostaglandins. Chronic pain and inflammation can require prolonged treatment, and prolonged inhibition of COX enzymes can lead to gastrointestinal tract problems, such as gastric bleeding and ulcers. Given the risks associated with such anti-inflammation pain treatments, there is a need for alternative approaches for treating pain.

G-Protein Coupled Receptors (GPCRs) are a family of membrane proteins that share a common structural motif of seven transmembrane domains connecting an N-terminal extracellular domain and a C-terminal intracellular domain (Granier et al, Nat Chem Biol. 2012 August; 8(8): 670-673). GPCRs sense extracellular signals such as photons, hormones, chemokines, etc. and activate intracellular G proteins. Many families of GPCRs exist, such as the Frizzled, Rhodopsin, Secretin, Adhesion, and protease activated receptor (PAR) families (Zhang et al. Nature. 2012 Dec. 20; 492(7429): 387-392; Zhang et al. Mol Cells. 2015 October; 38(10):836-42). While the various GPCR families share overall structural features, they exhibit different functions, bind to different ligands, and are activated by different mechanisms. Activation of the PAR family of GPCRs has been associated with inflammation and nociception (Gieseler et al Cell Commun Signal. 2013; 11: 86).

Four PAR receptors have been identified: PAR1, PAR2, PAR3, and PAR4 (Macfarlane et al. Pharmacol Rev. 2001 June; 53(2):245-82; Gieseler et al Cell Commun Signal. 2013; 11: 86). PAR2 activation has been shown to amplify inflammation and nociception, making its inhibition an attractive target for anti-inflammatory pain therapies. PARs, unlike other GPCRs, are activated by proteolytic cleavage of their extracellular domains, which reveals an N-terminal sequence that acts as a tethered-activating ligand. PAR2, in particular, is cleaved and activated by trypsin and tryptase.

PAR2 expression has been detected in vascularized tissues, airways, osteoblasts, cardiovascular tissue, keratinocytes, exocrine glands, leukocytes, mast cells, intestinal epithelium, kidney, neurons, pancreas, and a variety of smooth muscle types (Macfarlane supra). PAR2 has also been implicated in a variety of diseases or conditions associated with neurogenic inflammation, nociception and transmission of pain. PAR2 may be activated by several host and pathogen-derived serine proteases (e.g., trypsin, mast cell tryptase, tissue kallikreins, or members of the coagulation cascade TF-FVIIa and FVa-FXa).

Monoclonal antibodies have been shown to be useful in a variety of therapeutic applications and many antibody therapeutics are currently on the market (Maggon, Curr Med Chem. 2007; 14(18):1978-87; Brekke and Sandlie, Nat Rev Drug Discov 2: 52-62, 2003). The most common type of antibody in circulation in the blood stream is immunoglobulin G (IgG). The usefulness of an IgG antibody for therapeutic purposes depends on several factors, including the specificity of the antibody for its target, the strength of its binding to the target, as well as how efficiently the antibody can be produced and how quickly the antibody is cleared from the serum (the serum half-life of the antibody). The serum half-lives of antibodies are frequently regulated by FcRn (neonatal Fc receptor), which binds to the Fc domain of immunoglobulin G (IgG). In vivo, IgGs are thought to be taken up non-specifically by fluid-phase pinocytosis (Pyzik et al, J Immunol. 2015 May 15; 194(10):4595-603). Once in the endosome, IgG binds to FcRn, which sorts the IgG into recycling endosomes and back to the cell surface, away from lysosomes and away from degradation. While the recycling rate of IgG has been estimated to be 44% of the fractional catabolic rate, antibody therapeutics can still be depleted in a matter of days post-administration (Kim, Jonghan, et al. Clin. Immunol. 122.2 (2007): 146-155).

Pain associated with inflammation is often a chronic condition. Minimizing the dosage and the frequency of administration of a therapeutic molecule is desirable. Thus there is a need for new anti-inflammation pain therapeutics. Standard monoclonal antibodies are attractive candidates, but in some cases can be limited by their serum half-lives. As such, alternative treatments may be desired.

BRIEF SUMMARY OF THE DISCLOSURE

The present disclosure provides antibodies that bind PAR2. The antibodies of the disclosure are useful, inter alia, for inhibiting PAR2-mediated signaling and for treating diseases and disorders caused by or related to PAR2 activity and/or signaling.

In some embodiments, the disclosure provides for antibodies or antigen-binding fragments thereof that bind to PAR2 with a greater affinity at pH 7.4 than at pH 6.0. In some embodiments, the antibody or antigen-binding fragment binds to PAR2 with at least 5, 10, 20, 30, 40, 50, 60, 70, 80, 90 or 100 times greater affinity at pH 7.4 than at pH 6.0. In some embodiments, the disclosure provides for an antibody or antigen-binding fragment thereof comprising a heavy chain variable domain (VH) and a light chain variable domain (VL), wherein the VH comprises: i) a VH-CDR1 having the amino acid sequence of SEQ ID NO: 3, but wherein 1, 2, 3, 4, or 5 amino acid substitutions, deletions or insertions are optionally present in the sequence of SEQ ID NO: 3; ii) a VH-CDR2 having the amino acid sequence of SEQ ID NO: 4, but wherein 1, 2, 3, 4, or 5 amino acid substitutions, deletions or insertions are optionally present in the sequence of SEQ ID NO: 4; and iii) a VH-CDR3 having the amino acid sequence of SEQ ID NO: 5, but wherein 1, 2, 3, 4, or 5 amino acid substitutions, deletions or insertions are optionally present in the sequence of SEQ ID NO: 5; and wherein the VL comprises: i) a VL-CDR1 having the amino acid sequence of SEQ ID NO: 8; but wherein 1, 2, 3, 4, or 5 amino acid substitutions, deletions or insertions are optionally present in the sequence of SEQ ID NO: 8; ii) a VL-CDR2 having the amino acid sequence of SEQ ID NO: 9, but wherein 1, 2, 3, 4, or 5 amino acid substitutions, deletions or insertions are optionally present in the sequence of SEQ ID NO: 9; and iii) a VL-CDR3 having the amino acid sequence of SEQ ID NO: 10; but wherein 1, 2, 3, 4, or 5 amino acid substitutions, deletions or insertions are optionally present in the sequence of SEQ ID NO: 10; wherein the amino acid substitutions, deletions or insertions reduce the binding affinity of the antibody or antigen-binding fragment thereof for human PAR2 by no more than 1000, 800, 700, 500, 400, 300, 200, 100, 50 or 10-fold as compared to an antibody or antigen-binding fragment having a VH with an amino acid sequence of SEQ ID NO: 2 and VL with an amino acid sequence of SEQ ID NO: 7 when tested at a pH of 7.4 in a PAR2 binding assay. In some embodiments, the amino acid substitutions, deletions or insertions comprise a homologous substitution. In some embodiments, the antibody or antigen-binding fragment has no more than 1, 2, 3, 4, 5, 6, 7, 8, 9, or 10 amino acid substitutions, insertions or deletions in the VH CDRs as compared to the CDR amino acid sequences present in the sequence of SEQ ID NO: 2. In some embodiments, the antibody or antigen-binding fragment has no more than 1, 2, 3, 4, 5, 6, 7, 8, 9, or 10 amino acid substitutions, insertions or deletions in the VL CDRs as compared to the CDR amino acid sequences present in the sequence of SEQ ID NO: 7. In some embodiments, the 1, 2, 3, 4, 5, 6, 7, 8, 9, or 10 amino acid substitutions, insertions or deletions is 1, 2, 3, 4, 5, 6, 7, 8, 9, or 10 substitutions with a histidine.

In some embodiments, the disclosure provides for an antibody or antigen-binding fragment thereof comprising a heavy chain variable domain (VH) and a light chain variable domain (VL), wherein the VH comprises: i) a VH-CDR1 having the amino acid sequence of SEQ ID NO: 3; ii) a VH-CDR2 having the amino acid sequence of SEQ ID NO: 4, but wherein a histidine is optionally present at any one or more of the amino acid positions corresponding to positions 1-17 (e.g., positions 4, 5, and 7-17) of SEQ ID NO: 4; and iii) a VH-CDR3 having the amino acid sequence of SEQ ID NO: 5, but wherein a histidine is optionally present at any one or more of the amino acid positions corresponding to positions 1-8 of SEQ ID NO: 5; and wherein the VL comprises: i) a VL-CDR1 having the amino acid sequence of SEQ ID NO: 8; ii) a VL-CDR2 having the amino acid sequence of SEQ ID NO: 9; and iii) a VL-CDR3 having the amino acid sequence of SEQ ID NO: 10; but wherein a histidine is optionally present at any one or more of the amino acid positions corresponding to positions 1-14 of SEQ ID NO: 10. In some embodiments, the VH comprises: i) a VH-CDR1 having the amino acid sequence of SEQ ID NO: 3, ii) a VH-CDR2 having the amino acid sequence of SEQ ID NO: 4, iii) a VH-CDR3 having the amino acid sequence of SEQ ID NO: 5, and the VL comprises: i) a VL-CDR1 having the amino acid sequence of SEQ ID NO: 8, ii) a VL-CDR2 having the amino acid sequence of SEQ ID NO: 9, iii) a VL-CDR3 having the amino acid sequence of SEQ ID NO: 10. In some embodiments, the disclosure provides for an antibody or antigen-binding fragment thereof comprising a heavy chain variable domain (VH) and a light chain variable domain (VL), wherein the VH comprises: i) a VH-CDR1 having the amino acid sequence of SEQ ID NO: 13, ii) a VH-CDR2 having the amino acid sequence of SEQ ID NO: 14, iii) a VH-CDR3 having the amino acid sequence of SEQ ID NO: 15, and wherein the VL comprises: i) a VL-CDR1 having the amino acid sequence of SEQ ID NO: 18, ii) a VL-CDR2 having the amino acid sequence of SEQ ID NO: 19, iii) a VL-CDR3 having the amino acid sequence of SEQ ID NO: 20. In some embodiments, a histidine is present at the amino acid positions corresponding to positions 5, 8, 12, 16, and 17 of SEQ ID NO: 4; and wherein a histidine is present at the amino acid positions corresponding to positions 2 and 3 of SEQ ID NO: 5. In some embodiments, a histidine is present at the amino acid position corresponding to position 5 of SEQ ID NO: 4. In some embodiments, a histidine is present at the amino acid position corresponding to position 7 of SEQ ID NO: 4. In some embodiments, a histidine is present at the amino acid position corresponding to position 8 of SEQ ID NO: 4. In some embodiments, a histidine is present at the amino acid position corresponding to position 12 of SEQ ID NO: 4. In some embodiments, a histidine is present at the amino acid position corresponding to position 15 of SEQ ID NO: 4. In some embodiments, a histidine is present at the amino acid position corresponding to position 16 of SEQ ID NO: 4. In some embodiments, a histidine is present at the amino acid position corresponding to position 17 of SEQ ID NO: 4. In some embodiments, a histidine is present at the amino acid positions corresponding to positions 5 and 8 of SEQ ID NO: 4. In some embodiments, a histidine is present at the amino acid positions corresponding to positions 5, 8, 12, and 16 of SEQ ID NO: 4. In some embodiments, a histidine is present at the amino acid positions corresponding to positions 5, 8, 12, 16 and 17 of SEQ ID NO: 4. In some embodiments, a histidine is present at the amino acid position corresponding to position 2 of SEQ ID NO: 5. In some embodiments, a histidine is present at the amino acid position corresponding to position 3 of SEQ ID NO: 5. In some embodiments, a histidine is present at the amino acid positions corresponding to positions 2 and 3 of SEQ ID NO: 5. In some embodiments, a histidine is present at the amino acid position corresponding to position 1 of SEQ ID NO: 10. In some embodiments, a histidine is present at the amino acid position corresponding to position 5 of SEQ ID NO: 10. In some embodiments, a histidine is present at the amino acid position corresponding to position 6 of SEQ ID NO: 10. In some embodiments, a histidine is present at the amino acid position corresponding to position 14 of SEQ ID NO: 10. In some embodiments, the VH-CDR2 comprises an amino acid sequence selected from the group consisting of: SEQ ID NOs: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 384, 394, 404, 414, 424, 434, 444, 454, 464, 474, 484, 494, 504, 514, 524, 534, 544, 554, 564, 574, 584, 594, 604, 614, 624, 634, 644, 654, 664, 674, 684, 694, 704, 714, 724, 734, 744, 754, 764, 774, 784, 794, and 811-818. In some embodiments, the VH-CDR3 comprises an amino acid sequence selected from the group consisting of: SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, and 819-820. In some embodiments, the VL-CDR3 comprises an amino acid sequence selected from the group consisting of: SEQ ID NOs: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790 and 800. In some embodiments, the VH-CDR2 comprises an amino acid sequence corresponding to SEQ ID NO: 14; wherein the VH-CDR3 comprises an amino acid sequence corresponding to SEQ ID NO: 15, and wherein the VL-CDR3 comprises an amino acid sequence corresponding to SEQ ID NO: 20. In some embodiments, the VH-CDR2 comprises an amino acid sequence corresponding to SEQ ID NO: 811; the VH-CDR3 comprises an amino acid sequence corresponding to SEQ ID NO: 819, and the VL-CDR3 comprises an amino acid sequence corresponding to SEQ ID NO: 10 or 20. In some embodiments, the VH-CDR2 comprises an amino acid sequence corresponding to SEQ ID NO: 814; the VH-CDR3 comprises an amino acid sequence corresponding to SEQ ID NO: 820, and the VL-CDR3 comprises an amino acid sequence corresponding to SEQ ID NO: 10 or 20. In some embodiments, the VH-CDR2 comprises an amino acid sequence corresponding to SEQ ID NO: 816; the VH-CDR3 comprises an amino acid sequence corresponding to SEQ ID NO: 15, and the VL-CDR3 comprises an amino acid sequence corresponding to SEQ ID NO: 10 or 20. In some embodiments, the VH-CDR2 comprises an amino acid sequence corresponding to SEQ ID NO: 818; the VH-CDR3 comprises an amino acid sequence corresponding to SEQ ID NO: 15, and the VL-CDR3 comprises an amino acid sequence corresponding to SEQ ID NO: 10 or 20. In some embodiments, the VH comprises framework regions that are at least 90% identical to each of SEQ ID NOs: 803-806. In some embodiments, the VH comprises framework regions that are at least 95% identical to each of SEQ ID NOs: 803-806. In some embodiments, the VH comprises framework regions corresponding to SEQ ID NOs: 803-806. In some embodiments, the VL comprises framework regions that are at least 90% identical to each of SEQ ID NOs: 807-810. In some embodiments, the VL comprises framework regions that are at least 95% identical to each of SEQ ID NOs: 807-810. In some embodiments, the VL comprises framework regions corresponding to SEQ ID NOs: 807-810. In some embodiments, the VH comprises an amino acid sequence that is at least 80%, 85%, 90%, 92%, 93%, 95%, 97%, 98%, 99% or 100% identical to a sequence selected from the group consisting of: SEQ ID NOs: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 382, 392, 402, 412, 422, 432, 442, 452, 462, 472, 482, 492, 502, 512, 522, 532, 542, 552, 562, 572, 582, 592, 602, 612, 622, 632, 642, 652, 662, 672, 682, 692, 702, 712, 722, 732, 742, 752, 762, 772, 782, and 792. In some embodiments, the VL comprises an amino acid sequence that is at least 80%, 85%, 90%, 92%, 93%, 95%, 97%, 98%, 99% or 100% identical to a sequence selected from the group consisting of: SEQ ID NOs: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 387, 397, 407, 417, 427, 437, 447, 457, 467, 477, 487, 497, 507, 517, 527, 537, 547, 557, 567, 577, 587, 597, 607, 617, 627, 637, 647, 657, 667, 677, 687, 697, 707, 717, 727, 737, 747, 757, 767, 777, 787, and 797. In some embodiments, the VH comprises an amino acid sequence that is at least 80%, 85%, 90%, 92%, 93%, 95%, 97%, 99% or 100% identical to SEQ ID NO: 12 and wherein the VL comprises an amino acid sequence that is at least 80%, 85%, 90%, 92%, 93%, 95%, 97%, 99% or 100% identical to SEQ ID NO: 17. In some embodiments, the VH comprises the amino acid sequence of SEQ ID NO: 12, and wherein the VL comprises the amino acid sequence of SEQ ID NO: 17. In some embodiments, the VH comprises an amino acid sequence corresponding to SEQ ID NO: 821 and the VL comprises an amino acid sequence corresponding to SEQ ID NO: 7 or 17. In some embodiments, the VH comprises an amino acid sequence corresponding to SEQ ID NO: 824 and the VL comprises an amino acid sequence corresponding to SEQ ID NO: 7 or 17. In some embodiments, the VH comprises an amino acid sequence corresponding to SEQ ID NO: 827 and the VL comprises an amino acid sequence corresponding to SEQ ID NO: 7 or 17. In some embodiments, the VH comprises an amino acid sequence corresponding to SEQ ID NO: 831 and the VL comprises an amino acid sequence corresponding to SEQ ID NO: 7 or 17. In some embodiments, the antibody or antigen-binding fragment is an antigen-binding fragment. In some embodiments, the antigen-binding fragment is an scFv. In some embodiments, the antigen-binding fragment is a Fab'. In some embodiments, the antibody or antigen-binding fragment is an antibody. In some embodiments, the antibody is a monoclonal antibody. In some embodiments, the antibody is an IgG antibody. In some embodiments, the antibody or antigen-binding fragment is humanized. In some embodiments, the antibody or antigen-binding fragment is human. In some embodiments, the VH is encoded by a nucleic acid comprising a nucleotide sequence that is at least 90% identity to any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, 791, and 833-841. In some embodiments, the VH is encoded by a nucleic acid comprising a nucleotide sequence that is at least 95% identity to any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, 791, and 833-841. In some embodiments, the VH is encoded by a nucleic acid comprising the nucleotide sequence of any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, 791, and 833-841. In some embodiments, the VL is encoded by a nucleic acid comprising a nucleotide sequence that is at least 90% identity to any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and 796. In some embodiments, the VL is encoded by a nucleic acid comprising a nucleotide sequence that is at least 95% identity to any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and 796. In some embodiments, the VL is encoded by a nucleic acid comprising the nucleotide sequence of any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and 796. In some embodiments, the VH is encoded by a nucleic acid comprising a nucleotide sequence that is at least 90% identity to SEQ ID NO: 11. In some embodiments, the VH is encoded by a nucleic acid comprising a nucleotide sequence that is at least 95% identity to SEQ ID NO: 11. In some embodiments, the VH is encoded by a nucleic acid comprising the nucleotide sequence of SEQ ID NO: 11. In some embodiments, the VL is encoded by a nucleic acid comprising a nucleotide sequence that is at least 90% identity to SEQ ID NO: 16. In some embodiments, the VL is encoded by a nucleic acid comprising a nucleotide sequence that is at least 95% identity to SEQ ID NO: 16. In some embodiments, the VL is encoded by a nucleic acid comprising the nucleotide sequence of SEQ ID NO: 16. In some embodiments, the antibody or antigen-binding fragment binds to PAR2. In some embodiments, the antibody or antigen-binding fragment prevents trypsin, tryptase and/or matriptase from interacting with PAR2. In some embodiments, the antibody or antigen-binding fragment prevents trypsin, tryptase and/or matriptase from cleaving PAR2. In some embodiments, the antibody or antigen-binding fragment prevents cleavage of the PAR2 extracellular domain. In some embodiments, the antibody or antigen-binding fragment inhibits exposure of the tethered ligand. In some embodiments, the antibody or antigen-binding fragment prevents the tethered ligand from interacting with the second transmembrane loop of PAR2. In some embodiments, the antibody or antigen-binding fragment binds to PAR2 with greater affinity at a pH of 7.4 than at a pH of 6.0. In some embodiments, the antibody or antigen-binding fragment has an IC50 of less than 100 nM when competing with an antibody or antigen-binding fragment having the CDRs of SEQ ID NOs: 3-5 and 8-10 at a pH of 7.4 in a PAR2 binding assay. In some embodiments, the antibody or antigen-binding fragment has an IC50 of less than 50 nM when competing with an antibody or antigen-binding fragment having the CDRs of SEQ ID NOs: 3-5 and 8-10 at a pH of 7.4 in a PAR2 binding assay. In some embodiments, the antibody or antigen-binding fragment has an IC50 of less than 40 nM when competing with an antibody or antigen-binding fragment having the CDRs of SEQ ID NOs: 3-5 and 8-10 at a pH of 7.4 in a PAR2 binding assay. In some embodiments, the antibody or antigen-binding fragment has an IC50 of greater than 500 nM when competing with an antibody or antigen-binding fragment having the CDRs of SEQ ID NOs: 3-5 and 8-10 at a pH of 6.0 in a PAR2 binding assay. In some embodiments, the antibody or antigen-binding fragment has an IC50 of greater than 1000 nM when competing with an antibody or antigen-binding fragment having the CDRs of SEQ ID NOs: 3-5 and 8-10 at a pH of 6.0 in a PAR2 binding assay. In some embodiments, the antibody or antigen-binding fragment has an IC50 of greater than 1100 nM when competing with an antibody or antigen-binding fragment having the CDRs of SEQ ID NOs: 3-5 and 8-10 at a pH of 6.0 in a PAR2 binding assay. In some embodiments, the antibody or antigen-binding fragment has an IC50 more than 20 times lower at a pH of 7.4 than at a pH of 6.0 when competing with an antibody or antigen-binding fragment having the CDRs of SEQ ID NOs: 3-5 and 8-10 in a PAR2 binding assay. In some embodiments, the antibody or antigen-binding fragment has an IC50 more than 25 times lower at a pH of 7.4 than at a pH of 6.0 when competing with an antibody or antigen-binding fragment having the CDRs of SEQ ID NOs: 3-5 and 8-10 in a PAR2 binding assay. In some embodiments, the antibody or antigen-binding fragment has an IC50 more than 30 times lower at a pH of 7.4 than at a pH of 6.0 when competing with an antibody or antigen-binding fragment having the CDRs of SEQ ID NOs: 3-5 and 8-10 in a PAR2 binding assay. In some embodiments, the antibody or antigen-binding fragment has an IC50 of less than $3.0 \times 10^{-10}$ M in a calcium influx assay in human A549 cells. In some embodiments, the antibody or antigen-binding fragment has an IC50 of less than $1.5 \times 10^{-10}$ M in a calcium influx assay in human A549 cells. In some embodiments, the antibody or antigen-binding fragment has an IC50 of less than $7.0 \times 10^{-10}$ M in a calcium influx assay in rat KNRK cells. In some embodiments, the antibody or antigen-binding fragment has an IC50 of less than $5.5 \times 10^{-10}$ M in a calcium influx assay in rat KNRK cells. In some embodiments, the antibody or antigen-binding fragment has an IC50 of less than $7.0 \times 10^{-11}$ M in a calcium influx assay in cynomolgus monkey CYNOM-K1 cells. In some embodiments, the antibody or antigen-binding fragment has an IC50 of less than $5.0 \times 10^{-11}$ M in a calcium influx assay in cynomolgus monkey CYNOM-K1 cells. In some embodiments, the antibody or antigen-binding fragment has an IC50 of less than $6.0 \times 10^{-11}$ M in a calcium influx assay in murine LL/2 cells. In some embodiments, the antibody or antigen-binding fragment has an IC50 of less than $4.0 \times 10^{-11}$ M in a calcium influx assay in murine LL/2 cells. In some embodiments, the antibody or antigen-binding fragment is cleared more slowly from serum of a treated patient than an antibody or antigen-binding fragment lacking histidine modifications. In some embodiments, the optionally present histidine or histidines reduce the binding affinity of the antibody or antigen-binding fragment thereof for human PAR2 by no more than 1000, 800, 700, 500, 400, 300, 200, 100, 50 or 10-fold as compared to an antibody or antigen-binding fragment having a VH with an amino acid sequence of SEQ ID NO: 2 and VL with an amino acid sequence of SEQ ID NO: 7 when tested at a pH of 7.4 in a PAR2 binding assay.

In some embodiments, the disclosure provides for a nucleic acid capable of expressing any of the antibodies or antigen-binding fragments disclosed herein. In some embodiments, the nucleic acid comprises a nucleotide sequence that is at least 90% identical to any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, 791, and 833-841. In some embodiments, the nucleic acid comprises a nucleotide sequence that is at least 95% identical to any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, 791, and 833-841. In some embodiments, the nucleic acid comprises the nucleotide sequence of any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, 791, and 833-841. In some embodiments, the disclosure provides for a nucleic acid comprising a nucleotide sequence that is at least 90% identical to any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and 796. In some embodiments, the nucleic acid comprises a nucleotide sequence that is at least 95% identical to any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and 796. In some embodiments, the nucleic acid comprises the nucleotide sequence of any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and 796. In some embodiments, the disclosure provides for a nucleic acid comprising a nucleotide sequence that is at least 90% identical to SEQ ID NO: 11. In some embodiments, the nucleic acid comprises a nucleotide sequence that is at least 95% identical to SEQ ID NO: 11. In some embodiments, the nucleic acid comprises the nucleotide sequence of SEQ ID NO: 11. In some embodiments, the disclosure provides for a nucleic acid comprising a nucleotide sequence that is at least 90% identical to SEQ ID NO: 16. In some embodiments, the nucleic acid comprises a nucleotide sequence that is at least 95% identical to SEQ ID NO: 16. In some embodiments, the nucleic acid comprises the nucleotide sequence of SEQ ID NO: 16.

In some embodiments, the disclosure provides for a vector comprising any of the nucleic acids disclosed herein. In some embodiments, the disclosure provides for a set of vectors comprising any one or more of the nucleic acids disclosed herein.

In some embodiments, the disclosure provides for a host cell comprising any one or more of the vectors disclosed herein.

In some embodiments, the disclosure provides for a composition comprising a pharmaceutically acceptable carrier and any of the antibodies or antigen-binding fragments disclosed herein.

In some embodiments, the disclosure provides for a lyophilized composition comprising any of the antibody or antigen-binding fragment thereof disclosed herein.

In some embodiments, the disclosure provides for a reconstituted lyophilized composition comprising any of the antibodies or antigen-binding fragments thereof disclosed herein. In some embodiments, the composition is formulated for administration by lozenge, spray, oral administration, delayed release or sustained release, transmucosal administration, syrup, mucoadhesive, buccal formulation, mucoadhesive tablet, topical administration, parenteral administration, injection, subdermal administration, oral solution, rectal administration, buccal administration or transdermal administration.

In some embodiments, the disclosure provides for a kit comprising any of the antibodies or antigen-binding fragments disclosed herein or any of the compositions disclosed herein.

In some embodiments, the disclosure provides for a method for treating pain in a subject in need thereof, comprising administering to the subject a pharmaceutically effective amount of any of the antibodies or antigen-binding fragments disclosed herein. In some embodiments, the disclosure provides for a method for treating pain in a subject in need thereof, comprising administering to the subject a pharmaceutically effective amount of any of the compositions disclosed herein. In some embodiments, the pain is selected from the group consisting of: nociceptive, neuropathic, and mix-type pain. In some embodiments, the pain is associated with a headache, chronic headache, a migraine headache, a cancer, a viral infection, rheumatoid arthritis, osteoarthritis, Crohn's disease, liver disease, multiple sclerosis, spinal cord injury, post herpetic neuralgia, diabetic neuropathy, lower back pain, inflammatory heart disease, kidney disease, gastritis, gingivitis, periodontal disease, asthma, chronic obstructive pulmonary disease, autoimmune disease, irritable bowel syndrome, fibromyalgia, leg pains, restless leg syndrome, diabetic neuropathy, an allergic condition, a surgical procedure, acute or chronic physical injury, bone fracture or a crush injury, spinal cord injury, an inflammatory disease, a non-inflammatory neuropathic or dysfunctional pain condition, or a combination thereof. In some embodiments, the pain is osteoarthritis pain. In some embodiments, the subject is a human.

In some embodiments, the disclosure provides for a method of producing any of the antibodies or antigen-binding fragments disclosed herein, comprising the steps of: expressing any of the nucleic acids disclosed herein in a cultured cell, purifying the antibody or antigen-binding fragment.

BRIEF DESCRIPTION OF THE DRAWINGS

FIGS. 1A and 1B are tables illustrating the sequence differences in VH VH CDR2 (SEQ ID NOS 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 384, 394, 404, 414, 424, 434, 444, 454, 464, 474, 484, 494, 504, 514, 524, 534, 544, 554, 564, 574, 584, 594, 604, 614, 624, 634, 644, 654, 664, 674, 684, 694, 704, 714, 724, 734, 744, 754, 764, 774, 784, and 794, respectively, in order of appearance) and CDR3 (SEQ ID NOS 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, and 795, respectively, in order of appearance) of various clones as compared to the same CDRs of Par0067. CDR1 and the framework regions are the same for Par0067 and for all of the clones indicated (i.e., Par0067 and each of the clones comprised the sequences of SEQ ID NOs: 3 and 803-806).

FIGS. 2A and 2B are tables illustrating the sequence differences in VL CDR3 (SEQ ID NOS 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, and 800, respectively, in order of appearance) of various clones as compared to the same CDR of Par0067. CDR1, CDR2 and the framework regions are the same for Par0067 and for all of the clones indicated (i.e., the clones comprised the sequences of SEQ ID NOs: 8, 9, and 807-810).

FIGS. 3A-3E provide IC50 data from a cell potency assay using various IgG-based antibodies. The types of cells used in each of the cell assays are indicated. NI=non-inhibitory.

FIGS. 5A-5F illustrate the results from experiments in which rat dorsal root ganglia (DRG) sensory neurons or non-neuronal cells were treated with matriptase in the presence or absence of PaB670129 (also referred to herein as PaB670129). Rat DRG sensory neurones pre-treated with isotype control (20 nM) display matriptase-induced calcium transients (5A). Sensory neurons pre-treated with PaB670129 IgG1TM (20 nM) do not respond to matriptase (5B); % of neurones responding to matriptase quantified in (5C). Non-neuronal cells of the DRG pre-treated with isotype control (20 nM) also display matriptase-induced calcium transients (8D), but non-neuronal cells pre-treated with PaB670129 IgG1TM (20 nM) do not (5E); % of non-neuronal cell responding to matriptase quantified in (5F). FIGS. 5A-5E disclose "LIGRLO" as SEQ ID NO: 832

DETAILED DESCRIPTION

Figure 4A:
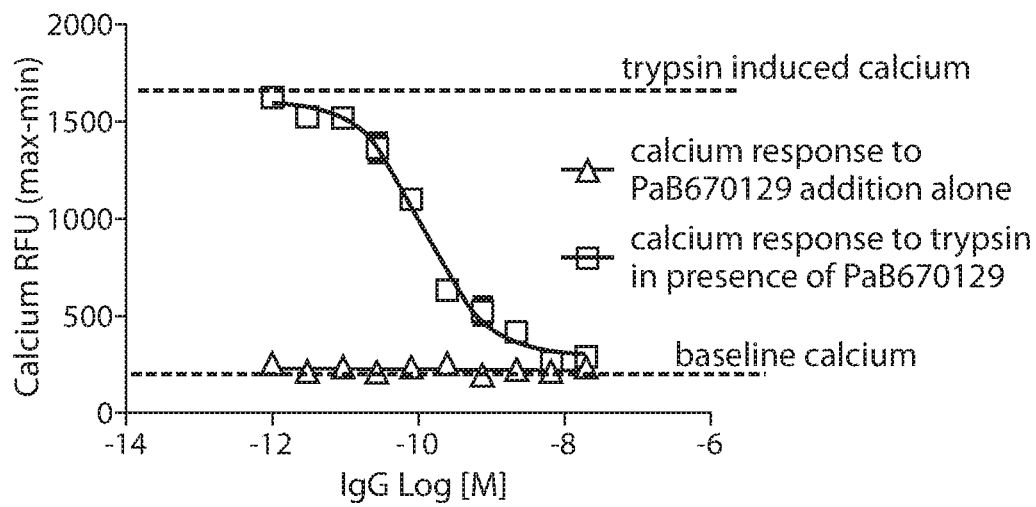
FIG. 4A provides IC50 curves for PaB670129 against trypsin in A549 cells, relative to agonistic responses to the antibody at the equivalent concentrations.

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs.

Although any methods and materials similar or equivalent to those described herein can be used in the practice or testing of the present disclosure, the preferred methods and materials are now described.

A. Definitions

As used in this specification and the appended claims, the singular form "a", "an" and "the" include plural referents unless the context clearly dictates otherwise.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The expressions "protease activated receptor 2," "PAR2," and the like, as used herein, refer to a human PAR2 protein having an amino acid sequence that is at least 90%, 91%, 92%, 93%, 94%, 95%, 96%, 97%, 98%, 99%, or 100% identical to the amino acid sequence of any of SEQ ID NO: 801, or biologically active fragments thereof.

The term "tethered ligand" refers to a region of the N-terminal portion of PAR2 that binds to and activates the PAR2 receptor itself. In some embodiments, the tethered ligand portion of PAR2 is not exposed until a protease (e.g., thrombin or trypsin) proteolytically cleaves a portion of the PAR2 enzyme. In some embodiments, the tethered ligand corresponds to a polypeptide that is at least 90%, 91%, 92%, 93%, 94%, 95%, 96%, 97%, 98%, 99%, or 100% identical to the amino acid sequence of any of SEQ ID NO: 802

As used herein, "an antibody that binds PAR2", "anti-PAR2 antibody," and the like includes antibodies, and antigen-binding fragments thereof, that bind membrane-bound PAR2 or fragments thereof. In some embodiments, an anti-PAR2 antibody or antigen binding fragment thereof binds to the tethered ligand portion of PAR2.

B. Antibodies and Antigen-Binding Fragments Thereof

As used herein, "antibodies or antigen binding fragments of the disclosure" refer to any one or more of the antibodies and antigen binding fragments provided herein. Antibodies and antigen binding fragments of the disclosure comprise a heavy chain (VH) comprising a heavy chain variable domain and a light chain (VL) comprising a light chain variable domain. A VH domain comprises three CDRs, such as any of the CDRs provided herein and as defined or identified by the Chothia, Kabat or IMGT systems. These CDRs are typically interspersed with framework regions (FR), and together comprise the VH domain. Similarly, a VL comprises three CDRs, such as any of the CDRs provided herein and as defined by the Chothia, Kabat or IMGT systems. These CDRs are typically interspersed with framework regions (FR), and together comprise the VL domain. The FR regions, such as FR1, FR2, FR3, and/or FR4 can similarly be defined or identified by the Chothia, Kabat or IMGT systems. Throughout the application, when CDRs are indicated as being, as identified or as defined by the Chothia, Kabat or IMGT systems, what is meant is that the CDRs are in accordance with that system (e.g., the Chothia CDRs, Kabat CDRs or the IMGT CDRs). Any of these terms can be used to indicate whether the Chothia, Kabat or IMGT CDRs are being referred to.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

In some embodiments, the disclosure provides for antibodies or antigen-binding fragments thereof that bind to PAR2 with a greater affinity at pH 7.4 than at pH 6.0. In some embodiments, the antibody or antigen-binding fragment binds to PAR2 with at least 5, 10, 20, 30, 40, 50, 60, 70, 80, 90 or 100 times greater affinity at pH 7.4 than at pH 6.0. In some embodiments, the disclosure provides for an antibody or antigen-binding fragment thereof comprising a heavy chain variable domain (VH) and a light chain variable domain (VL), wherein the VH comprises: i) a VH-CDR1 having the amino acid sequence of SEQ ID NO: 3, but wherein 1, 2, 3, 4, or 5 amino acid substitutions, deletions or insertions are optionally present in the sequence of SEQ ID NO: 3; ii) a VH-CDR2 having the amino acid sequence of SEQ ID NO: 4, but wherein 1, 2, 3, 4, or 5 amino acid substitutions, deletions or insertions are optionally present in the sequence of SEQ ID NO: 4; and iii) a VH-CDR3 having the amino acid sequence of SEQ ID NO: 5, but wherein 1, 2, 3, 4, or 5 amino acid substitutions, deletions or insertions are optionally present in the sequence of SEQ ID NO: 5; and wherein the VL comprises: i) a VL-CDR1 having the amino acid sequence of SEQ ID NO: 8; but wherein 1, 2, 3, 4, or 5 amino acid substitutions, deletions or insertions are optionally present in the sequence of SEQ ID NO: 8; ii) a VL-CDR2 having the amino acid sequence of SEQ ID NO: 9, but wherein 1, 2, 3, 4, or 5 amino acid substitutions, deletions or insertions are optionally present in the sequence of SEQ ID NO: 9; and iii) a VL-CDR3 having the amino acid sequence of SEQ ID NO: 10; but wherein 1, 2, 3, 4, or 5 amino acid substitutions, deletions or insertions are optionally present in the sequence of SEQ ID NO: 10; wherein the amino acid substitutions, deletions or insertions reduce the binding affinity of the antibody or antigen-binding fragment thereof for human PAR2 by no more than 1000, 800, 700, 500, 400, 300, 200, 100, 50, 10 or 5-fold as compared to an antibody or antigen-binding fragment having a VH with an amino acid sequence of SEQ ID NO: 2 and VL with an amino acid sequence of SEQ ID NO: 7 when tested at a pH of 7.4 in a PAR2 binding assay. In some embodiments, the amino acid substitutions, deletions or insertions comprise a homologous substitution. In some embodiments, the antibody or antigen-binding fragment has no more than 1, 2, 3, 4, 5, 6, 7, 8, 9, or 10 amino acid substitutions, insertions or deletions in the VH CDRs as compared to the CDR amino acid sequences present in the sequence of SEQ ID NO: 2. In some embodiments, the antibody or antigen-binding fragment has no more than 1, 2, 3, 4, 5, 6, 7, 8, 9, or 10 amino acid substitutions, insertions or deletions in the VL CDRs as compared to the CDR amino acid sequences present in the sequence of SEQ ID NO: 7. In some embodiments, the 1, 2, 3, 4, 5, 6, 7, 8, 9, or 10 amino acid substitutions, insertions or deletions is 1, 2, 3, 4, 5, 6, 7, 8, 9, or 10 substitutions with a histidine.

In some embodiments, the disclosure provides for an antibody or antigen-binding fragment thereof comprising a heavy chain variable domain (VH) and a light chain variable domain (VL), wherein the VH comprises: i) a VH-CDR1 having the amino acid sequence of SEQ ID NO: 13, but wherein 1, 2, 3, 4, or 5 amino acid substitutions, deletions or insertions are optionally present in the sequence of SEQ ID NO: 13; ii) a VH-CDR2 having the amino acid sequence of SEQ ID NO: 14, but wherein 1, 2, 3, 4, or 5 amino acid substitutions, deletions or insertions are optionally present in the sequence of SEQ ID NO: 14; and iii) a VH-CDR3 having the amino acid sequence of SEQ ID NO: 15, but wherein 1, 2, 3, 4, or 15 amino acid substitutions, deletions or insertions are optionally present in the sequence of SEQ ID NO: 15; and wherein the VL comprises: i) a VL-CDR1 having the amino acid sequence of SEQ ID NO: 18; but wherein 1, 2, 3, 4, or 5 amino acid substitutions, deletions or insertions are optionally present in the sequence of SEQ ID NO: 18; ii) a VL-CDR2 having the amino acid sequence of SEQ ID NO: 19, but wherein 1, 2, 3, 4, or 5 amino acid substitutions, deletions or insertions are optionally present in the sequence of SEQ ID NO: 19; and iii) a VL-CDR3 having the amino acid sequence of SEQ ID NO: 20; but wherein 1, 2, 3, 4, or 5 amino acid substitutions, deletions or insertions are optionally present in the sequence of SEQ ID NO: 20; wherein the amino acid substitutions, deletions or insertions reduce the binding affinity of the antibody or antigen-binding fragment thereof for human PAR2 by no more than 1000, 800, 700, 500, 400, 300, 200, 100, 50, 10 or 5-fold as compared to an antibody or antigen-binding fragment having a VH with an amino acid sequence of SEQ ID NO: 12 and VL with an amino acid sequence of SEQ ID NO: 17 when tested at a pH of 7.4 in a PAR2 binding assay. In some embodiments, the amino acid substitutions, deletions or insertions comprise a homologous substitution. In some embodiments, the antibody or antigen-binding fragment has no more than 1, 2, 3, 4, 5, 6, 7, 8, 9, or 10 amino acid substitutions, insertions or deletions in the VH CDRs as compared to the CDR amino acid sequences present in the sequence of SEQ ID NO: 12. In some embodiments, the antibody or antigen-binding fragment has no more than 1, 2, 3, 4, 5, 6, 7, 8, 9, or 10 amino acid substitutions, insertions or deletions in the VL CDRs as compared to the CDR amino acid sequences present in the sequence of SEQ ID NO: 17. In some embodiments, the disclosure provides for an antibody or antigen-binding fragment thereof comprising a heavy chain variable domain (VH) and a light chain variable domain (VL), wherein the VH comprises: i) a VH-CDR1 having the amino acid sequence of SEQ ID NO: 13, ii) a VH-CDR2 having the amino acid sequence of SEQ ID NO: 14, iii) a VH-CDR3 having the amino acid sequence of SEQ ID NO: 15, and wherein the VL comprises: i) a VL-CDR1 having the amino acid sequence of SEQ ID NO: 18, ii) a VL-CDR2 having the amino acid sequence of SEQ ID NO: 19, iii) a VL-CDR3 having the amino acid sequence of SEQ ID NO: 20. In some embodiments, the 1, 2, 3, 4, 5, 6, 7, 8, 9, or 10 amino acid substitutions, insertions or deletions is 1, 2, 3, 4, 5, 6, 7, 8, 9, or 10 substitutions with a histidine.

In some embodiments, the disclosure provides for an antibody or antigen-binding fragment, wherein the antibody or antigen-binding fragment comprises a light chain variable (VL) domain and a heavy chain variable (VH) domain; wherein the VH domain comprises at least one, two or all three of the CDRs (e.g., as measured using any of the Chothia, IMGT or Kabat systems) of the amino acid sequence set forth in any one of SEQ ID NOs: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 382, 392, 402, 412, 422, 432, 442, 452, 462, 472, 482, 492, 502, 512, 522, 532, 542, 552, 562, 572, 582, 592, 602, 612, 622, 632, 642, 652, 662, 672, 682, 692, 702, 712, 722, 732, 742, 752, 762, 772, 782, and 792. In some embodiments, the disclosure provides for an antibody or antigen-binding fragment, wherein the antibody or antigen-binding fragment comprises a light chain variable (VL) domain and a heavy chain variable (VH) domain; wherein the VH domain comprises CDR1, CDR2 and CDR3 (e.g., as measured using any of the Chothia, IMGT or Kabat systems) of the amino acid sequence set forth in any one of SEQ ID NOs: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 382, 392, 402, 412, 422, 432, 442, 452, 462, 472, 482, 492, 502, 512, 522, 532, 542, 552, 562, 572, 582, 592, 602, 612, 622, 632, 642, 652, 662, 672, 682, 692, 702, 712, 722, 732, 742, 752, 762, 772, 782, and 792. In some embodiments, the disclosure provides for an antibody or antigen-binding fragment, wherein the antibody or antigen-binding fragment comprises a light chain variable (VL) domain and a heavy chain variable (VH) domain; wherein the VH domain comprises at least one, two or all three of the CDRs (e.g., as measured using any of the Chothia, IMGT or Kabat systems) of the amino acid sequence set forth in SEQ ID NO: 2 or 12. In some embodiments, the disclosure provides for an antibody or antigen-binding fragment, wherein the antibody or antigen-binding fragment comprises a light chain variable (VL) domain and a heavy chain variable (VH) domain; wherein the VL domain comprises at least one, two or all three of the CDRs (e.g., as measured using any of the Chothia, IMGT or Kabat systems) of the amino acid sequence set forth in any one of SEQ ID NOs: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 387, 397, 407, 417, 427, 437, 447, 457, 467, 477, 487, 497, 507, 517, 527, 537, 547, 557, 567, 577, 587, 597, 607, 617, 627, 637, 647, 657, 667, 677, 687, 697, 707, 717, 727, 737, 747, 757, 767, 777, 787, and 797. In some embodiments, the disclosure provides for an antibody or antigen-binding fragment, wherein the antibody or antigen-binding fragment comprises a light chain variable (VL) domain and a heavy chain variable (VH) domain; wherein the VL domain comprises CDR1, CDR2 and CDR3 (e.g., as measured using any of the Chothia, IMGT or Kabat systems) of the amino acid sequence set forth in any one of SEQ ID NOs: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 387, 397, 407, 417, 427, 437, 447, 457, 467, 477, 487, 497, 507, 517, 527, 537, 547, 557, 567, 577, 587, 597, 607, 617, 627, 637, 647, 657, 667, 677, 687, 697, 707, 717, 727, 737, 747, 757, 767, 777, 787, and 797. In some embodiments, the disclosure provides for an antibody or antigen-binding fragment, wherein the antibody or antigen-binding fragment comprises a light chain variable (VL) domain and a heavy chain variable (VH) domain; wherein the VL domain comprises at least one, two or all three of the CDRs (e.g., as measured using any of the Chothia, IMGT or Kabat systems) of the amino acid sequence set forth in SEQ ID NO: 7 or 17. In some embodiments, the disclosure provides for an antibody or antigen-binding fragment, wherein the antibody or antigen-binding fragment comprises a light chain variable (VL) domain and a heavy chain variable (VH) domain; wherein the VH domain comprises CDR1, CDR2 and CDR3 (e.g., as measured using any of the Chothia, IMGT or Kabat systems) of the amino acid sequence set forth in any one of SEQ ID NOs: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 382, 392, 402, 412, 422, 432, 442, 452, 462, 472, 482, 492, 502, 512, 522, 532, 542, 552, 562, 572, 582, 592, 602, 612, 622, 632, 642, 652, 662, 672, 682, 692, 702, 712, 722, 732, 742, 752, 762, 772, 782, and 792, and wherein the VL domain comprises CDR1, CDR2 and CDR3 (e.g., as measured using any of the Chothia, IMGT or Kabat systems) of the amino acid sequence set forth in any one of SEQ ID NOs: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 387, 397, 407, 417, 427, 437, 447, 457, 467, 477, 487, 497, 507, 517, 527, 537, 547, 557, 567, 577, 587, 597, 607, 617, 627, 637, 647, 657, 667, 677, 687, 697, 707, 717, 727, 737, 747, 757, 767, 777, 787, and 797. In some embodiments, the disclosure provides for an antibody or antigen-binding fragment, wherein the antibody or antigen-binding fragment comprises a light chain variable (VL) domain and a heavy chain variable (VH) domain; wherein the VH domain comprises CDR1, CDR2 and CDR3 (e.g., as measured using any of the Chothia, IMGT or Kabat systems) of the amino acid sequence set forth in SEQ ID NO: 2 or 12, and wherein the VL domain comprises CDR1, CDR2 and CDR3 (e.g., as measured using any of the Chothia, IMGT or Kabat systems) of the amino acid sequence set forth in SEQ ID NO: 7 or 17.

Once the nucleotide sequences encoding such antibodies have been determined, chimeric or humanized antibodies may be produced by recombinant methods. Nucleic acids encoding the antibodies are introduced into host cells and expressed using materials and procedures generally known in the art, and as disclosed herein. In some embodiments, the VH is encoded by a nucleic acid comprising a nucleotide sequence that is at least 80%, 85%, 90%, 91%, 92%, 93%, 94%, 95%, 96%, 97%, 98%, 99% or 100% identity to any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, 791, and 833-841. In some embodiments, the VH is encoded by a nucleic acid comprising a nucleotide sequence that is at least 80%, 85%, 90%, 91%, 92%, 93%, 94%, 95%, 96%, 97%, 98%, 99% or 100% identity to SEQ ID NO: 1 or 11. In some embodiments, the VL is encoded by a nucleic acid comprising a nucleotide sequence that is at least 80%, 85%, 90%, 91%, 92%, 93%, 94%, 95%, 96%, 97%, 98%, 99% or 100% identity to any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and 796. In some embodiments, the VL is encoded by a nucleic acid comprising a nucleotide sequence that is at least 80%, 85%, 90%, 91%, 92%, 93%, 94%, 95%, 96%, 97%, 98%, 99% or 100% identity to SEQ ID NO: 6 or 16.

The present disclosure includes anti-PAR2 antibodies and antigen-binding fragments thereof that bind PAR2. In some embodiments, the antibody is a neutralizing and/or blocking anti-PAR2 antibody or antigen-binding fragment. A "neutralizing" or "blocking" antibody or antigen-binding fragment, as used herein, is intended to refer to an antibody or antigen-binding fragment whose binding to PAR2: (i) interferes with the interaction between PAR2 and a protease (e.g., trypsin, tryptase and/or matriptase); (ii) inhibits the cleavage of PAR2 by a protease; (iii) inhibits PAR2 signalling or PAR2 activation; and/or (iv) results in inhibition of at least one biological function of PAR2. In some embodiments, the antibodies or antigen-binding fragments of the disclosure inhibit activation of PAR2. In some embodiments, the antibodies or antigen-binding fragments inhibit conversion of inactive, uncleaved PAR2 into active, cleaved PAR2. In some embodiments, the antibodies or antigen-binding fragments inhibit exposure of the tethered ligand. In some embodiments, the antibodies or antigen-binding fragments inhibit activation of a PAR2 receptor by its tethered ligand. In some embodiments, the antibodies or antigen-binding fragments inhibit binding of the tethered ligand to the second transmembrane domain of PAR2. The inhibition caused by an anti-PAR2 neutralizing or blocking antibody need not be complete so long as it is detectable using an appropriate assay. In some embodiments, the antibody or antigen-binding fragment thereof inhibits PAR2 activity at least 10%, 20%, 30%, 40%, 50%, 60%, 70%, 80%, 90% or 100% as compared to uninhibited active PAR2. Some examples of assays for detecting activity of a representative anti-PAR2 antibody or antigen-binding fragment are described in the Exemplification section. The skilled worker is aware of additional anti-PAR2 antibody activity assays.

In particular embodiments, any of the antibodies or antigen-binding fragments disclosed herein interferes with the interaction between PAR2 and a protease. In some embodiments, the protease is trypsin. In some embodiments, the protease is neutrophil elastase. In some embodiments, the protease is neutrophil proteinase 3. In some embodiments, the protease is mast cell tryptase. In some embodiments, the protease is tissue factor/factor VIIa/factor Xa. In some embodiments, the protease is a kallikrein-related peptidase. In some embodiments, the protease is membrane-tethered serine proteinase-1/matriptase 1. In some embodiments, the protease is parasite cysteine proteinase. In some embodiments, the anti-PAR2 antibodies or antigen-binding fragments block the interaction between PAR2 and a protease (e.g., trypsin) in vitro, with an $IC_{50}$ value of less than about 15 nM, as measured by a binding assay such as that described in the Exemplification section. In certain embodiments, the antibodies or antigen-binding fragments of the present disclosure block the interaction between PAR2 and a protease (e.g., trypsin) in vitro at a pH of 7.4 with an $IC_{50}$ value of less than about 200 nM, 150 nM, 100 nM, 50 nM, 40 nM, 30 nM, 20 nM, 10 nM, 1 nM, 500 pM, 400 pM, 200 pM, 100 pM, 50 pM, 5 pM, 1 pM or 0.1 pM. In certain embodiments, the antibodies or antigen-binding fragments of the present disclosure block the interaction between PAR2 and a protease (e.g., trypsin) in vitro at a pH of 6.0 with an $IC_{50}$ value of greater than about 300 nM, 500 nM, 750 nM, 1000 nM, 1100 nM, or 1200 nM. In certain embodiments, the $IC_{50}$ of the anti-PAR2 antibody or fragment thereof is measured in an epitope competition assay, such as the epitope competition assay described in the Exemplification section provided herein. In some embodiments, the $IC_{50}$ of the anti-PAR2 antibody or fragment thereof is measured in a cell potency assay. In some embodiments, the cell potency assay utilizes a human cell (e.g., A549 cell), a rat cell (e.g., KNRK cell), a cynomolgus monkey cell (e.g., CYNOM-K1 cell), or a murine cell (e.g., an LL/2 cell). In some embodiments, the cell potency assay utilizes a calcium influx assay (e.g., the calcium influx assay described in the Exemplification section provided herein). In some embodiments, the antibody or antigen-binding fragment inhibits calcium influx in the calcium influx assay with an $IC_{50}$ of less than 1 nM, 500 pM, 400 pM, 200 pM, 100 pM, 50 pM, 10 pM, 5 pM, 1 pM or 0.1 pM. In some embodiments, the antibodies or antigen-binding fragments prevent abnormal activation of PAR2 by trypsin. In some embodiments, the antibodies or antigen-binding fragments inhibit/reduce inflammation-induced pain.

In particular embodiments, any of the antibodies or antigen-binding fragments disclosed herein interfere with the interaction between PAR2 and a protease (e.g., trypsin). In some embodiments, the antibodies prevent a protease (e.g., trypsin) from binding, cleaving, and/or activating PAR2. The present disclosure provides for anti-PAR2 antibodies and antigen-binding fragments thereof that bind PAR2 molecules with high affinity at physiological, extracellular pH (i.e. pH 7.4). In some embodiments, antibodies and antigen-binding fragments of antibodies bind PAR2 at pH 7.4 (e.g., at 25° C. or 37° C.) with a $K_D$ of less than about 5 nM, 1 nM, 900 pM, 800 pM, 700 pM, 650 pM, 600 pM, 500 pM, 200 pM, 100 pM or 50 pM. In some embodiments, antibodies and antigen-binding fragments of antibodies bind PAR2 at a slightly acidic pH (such as pH 6.0) (e.g., at 25° C. or 37° C.) with a $K_D$ of greater than about 1 nM, 5 nM, 10 nM, 15 nM, 20 nM, 25 nM, 30 nM, 40 nM, 50 nM, 60 nM, 80 nM, or 100 nM. In some embodiments, the slightly acidic pH is the pH of an endosomal compartment. In some embodiments, $K_D$ can be measured in accordance with currently standard methods, such as using Surface Plasmon Resonance (SPR) or Quartz Crystal Microbalance (QCM).

The present disclosure also includes anti-PAR2 antibodies and antigen-binding fragments thereof that specifically bind to PAR2 with a dissociative half-life (t½) of greater than about 1.5 minutes, 1.75 minutes, 2 minutes, 2.5 minutes, 3 minutes, 5 minutes, 10 minutes, 20 minutes, or 30 minutes as measured using an assay such as surface plasmon resonance at 25° C. or 37° C. at pH 7.4. In some embodiments, anti-PAR2 antibodies and antigen-binding fragments thereof bind to PAR2 with a dissociative half-life (t½) of less than about 1 minute, 45 seconds, 30 seconds, 20 seconds, 15 seconds, 13 seconds, 7 seconds, 5 seconds, or 3 seconds as measured using an assay such as surface plasmon resonance at 25° C. or 37° C. at a slightly acidic pH (e.g., pH 6). In some embodiments, the slightly acidic pH is the pH of an endosomal compartment. In some embodiments, $K_D$ can be measured in accordance with currently standard methods, such as using Surface Plasmon Resonance (SPR) or Quartz Crystal Microbalance (QCM).

The antibodies or antigen-binding fragments of the present disclosure may possess one or more of the aforementioned biological characteristics, or any combinations thereof. Other biological characteristics of the antibodies of the present disclosure will be evident to a person of ordinary skill in the art from a review of the present disclosure including the Exemplification section provided herein.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In some embodiments, any of the antibodies or antigen-binding fragments disclosed herein comprise 1, 2, 3, 4, 5, 6, 7, 8, 9, 10, 11, 12, 13, 14, 15, 16, 17, 18, 19, or 20 conservative amino acid substitutions as compared to a reference sequence (e.g., any of the amino acid sequences of SEQ ID NOs: 2, 7, 12 or 17). A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (W.B. Saunders, Co., 2000). An antibody may be part of a larger fusion molecule, formed by covalent or non-covalent association of the antibody with one or more other proteins or peptides.

Non-limiting examples of antigen-binding fragments include: (i) Fab fragments; (ii) Fab' fragments; (iii) F(ab')2 fragments; (iv) Fd fragments; (v) Fv fragments; (vi) single-chain Fv (scFv) molecules; (vii) dAb fragments; and (viii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, cameliid antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), adnectins, small modular immunopharmaceuticals (SMIPs), and shark variable IgNAR domains, are also encompassed within the expression "antigen-binding fragment," as used herein.

An antigen-binding fragment of an antibody will typically comprise at least one variable domain (e.g., at least one of a VH or VL). The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) VH-CH1; (ii) VH-CH2; (iii) VH-CH3; (iv) VH-CH1-CH2; (V) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. In some embodiments, the hinge region comprises a glycine-serine linker.

Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

In certain embodiments of the disclosure, the anti-PAR2 antibodies of the disclosure are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs, and in some embodiments, CDR3. However, the term "human antibody", as used herein, is not intended to include antibodies in which CDR sequences derived from the germline of another mammalian species, such as a mouse, have been grafted onto human framework sequences.

The antibodies of the disclosure may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human $IgG_4$ hinge can significantly reduce the appearance of the second form (Angal et al. (1993) Molecular Immunology 30:105) to levels typically observed using a human $IgG_1$ hinge. The current disclosure contemplates antibodies having one or more mutations in the hinge, CH2 or CH3 region which may be desirable, for example, in production, to improve the yield of the desired antibody form.

The antibodies of the disclosure may be isolated antibodies or isolated antigen-binding fragments. An "isolated antibody" or "isolated antigen-binding fragment," as used herein, means an antibody or antigen-binding fragment that has been identified and separated and/or recovered from at least one component of its natural environment. For example, an antibody or antigen-binding fragment that has been separated or removed from at least one component of an organism, or from a tissue or cell in which the antibody naturally exists or is naturally produced, is an "isolated antibody" or an "isolated antigen-binding fragment" for purposes of the present disclosure. An isolated antibody also includes an antibody in situ within a recombinant cell. Isolated antibodies or antigen-binding fragments are antibodies or antigen-binding fragments that have been subjected to at least one purification or isolation step. According to certain embodiments, an isolated antibody or antigen-binding fragment may be substantially free of other cellular material and/or chemicals.

The anti-PAR2 antibodies or antigen-binding fragments disclosed herein may comprise one or more amino acid substitutions, insertions and/or deletions in the framework and/or CDR regions of the heavy and light chain variable domains as compared to the corresponding germline sequences from which the antibodies were derived. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody or antigen-binding fragment was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). In some embodiments, the VH framework region 1 comprises an amino acid sequence that is at least 80%, 85%, 90%, 91%, 92%, 93%, 94%, 95%, 96%, 97%, 98%, 99% or 100% identical to the sequence of SEQ ID NO: 803. In some embodiments, the VH framework region 2 comprises an amino acid sequence that is at least 80%, 85%, 90%, 91%, 92%, 93%, 94%, 95%, 96%, 97%, 98%, 99% or 100% identical to the sequence of SEQ ID NO: 804. In some embodiments, the VH framework region 3 comprises an amino acid sequence that is at least 80%, 85%, 90%, 91%, 92%, 93%, 94%, 95%, 96%, 97%, 98%, 99% or 100% identical to the sequence of SEQ ID NO: 805. In some embodiments, the VH framework region 4 comprises an amino acid sequence that is at least 80%, 85%, 90%, 91%, 92%, 93%, 94%, 95%, 96%, 97%, 98%, 99% or 100% identical to the sequence of SEQ ID NO: 806. In some embodiments, the VL framework region 1 comprises an amino acid sequence that is at least 80%, 85%, 90%, 91%, 92%, 93%, 94%, 95%, 96%, 97%, 98%, 99% or 100% identical to the sequence of SEQ ID NO: 807. In some embodiments, the VL framework region 2 comprises an amino acid sequence that is at least 80%, 85%, 90%, 91%, 92%, 93%, 94%, 95%, 96%, 97%, 98%, 99% or 100% identical to the sequence of SEQ ID NO: 808. In some embodiments, the VL framework region 3 comprises an amino acid sequence that is at least 80%, 85%, 90%, 91%, 92%, 93%, 94%, 95%, 96%, 97%, 98%, 99% or 100% identical to the sequence of SEQ ID NO: 809. In some embodiments, the VL framework region 4 comprises an amino acid sequence that is at least 80%, 85%, 90%, 91%, 92%, 93%, 94%, 95%, 96%, 97%, 98%, 99% or 100% identical to the sequence of SEQ ID NO: 810. In some embodiments, the VH framework comprises 1, 2, 3, 4, 5, 6, 7, 8, 9 or 10 conservative substitutions as compared to a reference sequence of any one of SEQ ID NOs: 803-806. In some embodiments, the VL framework comprises 1, 2, 3, 4, 5, 6, 7, 8, 9 or 10 conservative substitutions as compared to a reference sequence of any one of SEQ ID NOs: 807-810.

Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes anti-PAR2 antibodies comprising variants of any of the VH, VL, and/or CDR amino acid sequences disclosed herein having one or more conservative substitutions. For example, the present disclosure includes anti-PAR2 antibodies having VH, VL, and/or CDR amino acid sequences with, e.g., 10, 9, 8, 7, 6, 5, 4, 3, 2, or 1 conservative amino acid substitutions relative to any of the VH, VL, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

It should be noted that any portion of any of the antibodies or antigen-binding fragments of the disclosure may be similarly modified, such as with an epitope tag, a PEG moiety or moieties, and the like. Moreover, the antibodies or antigen-binding fragments may comprise more than one epitope tags, such as 2 epitope tags, or may include 0 epitope tags.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402. In some embodiments, the sequences are compared using EMBOSS Needle pairwise sequence alignment.

In some embodiments, the antibody or antigen-binding fragment is an antigen-binding fragment. In some embodiments, the antigen-binding fragment is an scFv. In some embodiments, the antigen-binding fragment is a Fab'. In some embodiments, the antibody or antigen-binding fragment is an antibody. In some embodiments, the antibody is a monoclonal antibody.

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63). In many cases, hybridomas are used to generate an initial antibody of murine or rodent origin. That initial antibody may then be modified, such as using recombinant techniques to produce rodent variants, chimeric antibodies, humanized antibodies and the like. Other methods exist to produce an initial antibody, and such methods are known in the art. However, regardless of the method used to generate an initial antibody or even a variant of that initial antibody, any given antibody of non-human origin can then be modified to increase its humanness.

Antibodies or antigen-binding fragments of the disclosure can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in Methods in Molecular Biology 178:1-37 (O'Brien et al., ed., Human Press, Totowa, N.J., 2001). For example, one method of generating antibodies of interest is through the use of a phage antibody library as described in Lee et al., J. Mol. Biol. (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies of the disclosure can be obtained by designing a suitable antigen screening procedure to select for the phage clone of interest followed by construction of a full length antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3. It can be advantageous to increase the humanness of a non-human antibody to make it more suitable for use in human subject and cells, whether for diagnostic, therapeutic, or research purposes. Antibodies may be modified for use as therapeutics. Examples of such antibodies (including antibody fragments) include chimeric, humanized, and fully human antibodies. Numerous methods exist in the art for the generation of chimeric, humanized and human antibodies. In the context of the present disclosure, an antibody is considered humanized if at least one of the VH domain or VL domain is humanized. Moreover, a VH or VL domain is humanized if the amino acid sequence of at least a portion of at least one of the FR regions has been modified, relative to a parent non-human (e.g., murine) antibody, such that the amino acid sequence of that portion corresponds to that of a human antibody or a human consensus sequence. In certain embodiments, at least one, two, three, or four FR regions of the VH domain and/or at least one, two, three, or four FR regions of the VL domain have been modified (in whole or in part) so that their sequence is more closely related to a human sequence. For any of the foregoing in certain embodiments, a humanized antibody fragment may be provided in the context of a human or non-human light chain and/or heavy chain constant region (e.g., comprising a CL and one or more of a CH1, hinge, CH2, and/or CH3 domains). In certain embodiments, a humanized antibody or antigen binding fragment of the disclosure is provided in the context of human light and/or heavy chain constant domains, when present. Antibodies and antibody binding fragments combining any of the humanized light chain variable domains and/or heavy chain variable domains described herein are exemplary of antibodies and antigen binding fragments of the disclosure. In some embodiments, the antibody or antigen-binding fragment is humanized. In some embodiments, the antibody or antigen-binding fragment is chimeric. In some embodiments, the antibody or antigen-binding fragment is human.

According to certain embodiments of the present disclosure, anti-PAR2 antibodies are provided comprising an Fc domain comprising one or more mutations which enhance or diminish antibody binding to the FcRn receptor, e.g., at acidic pH as compared to neutral pH. For example, the present disclosure includes anti-PAR2 antibodies comprising a mutation in the CH2 or a CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., D297A) modification. All possible combinations of the foregoing Fc domain mutations, and other mutations within the antibody variable domains disclosed herein, are contemplated within the scope of the present disclosure. In some embodiments, antibodies comprise the triple mutation L234F/L235E/P331S ("TM"). TM causes a profound decrease in the binding activity of human IgG1 molecules to human C1q, CD64, CD32A and CD16. See, e.g., Oganesyan et al., Acta Crystallogr D Biol Crystallogr. 64:700-704 (2008). Antibodies with increased half-lives may also be generated by modifying amino acid residues identified as involved in the interaction between the Fc and the FcRn receptor. For example, the introduction of the triple mutation M252Y/S254T/T256E ('YTE') into the CH2 domain of human immunoglobulin G (IgG) molecules causes an increase in their binding to the human neonatal Fc receptor (FcRn). See U.S. Pat. No. 7,083,784, the contents of which are herein incorporated by reference in its entirety. In some embodiments, the antibodies comprise the YTE modifications.

According to certain embodiments of the present disclosure, anti-PAR2 antibodies are provided comprising one or more mutations in the VH and/or VL domains which enhance or diminish antibody binding to PAR2, e.g., at acidic pH as compared to neutral pH. For example, the present disclosure includes anti-PAR2 antibodies comprising a mutation in the CDR2 (SEQ ID NO: 4) or a CDR3 (SEQ ID NO: 5) region of the VH domain and/or the CDR3 (SEQ ID NO: 10) of the VL domain, wherein the mutation(s) replace one or more amino acids with histidine and decreases the affinity of the VH and/or VL domain to PAR2 in an acidic environment (e.g., in an endosome where pH ranges from about 5.5 to about 6.0). Such mutations may result in an increase in serum half-life of the antibody when administered to an animal. Non-limiting examples of such VH modifications include, e.g., a modification at amino acid positions 4, 5, 7, 8, 10, 11, 12, 14, 15, 16, and 17 of CDR2 (SEQ ID NO: 4) and 1, 2, 4, 5, and 7 of CDR3 (SEQ ID NO: 5). Non-limiting examples of such VL modifications include, e.g., a modification at positions 1, 2, 4, 5, 6, 7, 8, 9, 12, and 14 of CDR3 (SEQ ID NO: 10). In yet another embodiment, the VH comprises modifications at positions 5, 8, 12, 16, and 17 of CDR2 (SEQ ID NO: 4) and positions 2 and 3 of CDR3 (SEQ ID NO: 5). All possible combinations of the foregoing VH and VL domain mutations, and other mutations within the Fc domain disclosed herein, are contemplated within the scope of the present disclosure.

In some embodiments, the disclosure provides for an antibody or antigen-binding fragment thereof comprising a heavy chain variable domain (VH) and a light chain variable domain (VL), wherein the VH comprises: i) a VH-CDR1 having the amino acid sequence of SEQ ID NO: 3; ii) a VH-CDR2 having the amino acid sequence of SEQ ID NO: 4, but wherein a histidine is optionally present at any one or more of the amino acid positions corresponding to positions 1-17 (e.g., 4, 5, and 7-17) of SEQ ID NO: 4; and iii) a VH-CDR3 having the amino acid sequence of SEQ ID NO: 5, but wherein a histidine is optionally present at any one or more of the amino acid positions corresponding to positions 1-8 of SEQ ID NO: 5; and wherein the VL comprises: i) a VL-CDR1 having the amino acid sequence of SEQ ID NO: 8; ii) a VL-CDR2 having the amino acid sequence of SEQ ID NO: 9; and iii) a VL-CDR3 having the amino acid sequence of SEQ ID NO: 10; but wherein a histidine is optionally present at any one or more of the amino acid positions corresponding to positions 1-14 of SEQ ID NO: 10. In some embodiments, the VH comprises: i) a VH-CDR1 having the amino acid sequence of SEQ ID NO: 3, ii) a VH-CDR2 having the amino acid sequence of SEQ ID NO: 4, iii) a VH-CDR3 having the amino acid sequence of SEQ ID NO: 5, and wherein the VL comprises: i) a VL-CDR1 having the amino acid sequence of SEQ ID NO: 8, ii) a VL-CDR2 having the amino acid sequence of SEQ ID NO: 9, iii) a VL-CDR3 having the amino acid sequence of SEQ ID NO: 10. In some embodiments, the antibody or antigen fragment thereof has a histidine at the amino acid position corresponding to any one or more of positions 7, 8, 12, 15, 16, or 17 of SEQ ID NO: 4. In some embodiments, the antibody or antigen fragment thereof has a histidine at the amino acid position corresponding to any one or more of positions 2 or 3 of SEQ ID NO: 5. In some embodiments, the antibody or antigen fragment thereof has a histidine at the amino acid position corresponding to any one or more of positions 1, 5, 6, or 14 of SEQ ID NO: 10. In some embodiments, a histidine is present at the amino acid positions corresponding to positions 5, 8, 12, 16, and 17 of SEQ ID NO: 4; and wherein a histidine is present at the amino acid positions corresponding to positions 2 and 3 of SEQ ID NO: 5. In some embodiments, the VH-CDR2 comprises an amino acid sequence selected from the group consisting of: SEQ ID NOs: 4, 14, 24, 34, 44, 54, 64, 74, 84, 94, 104, 114, 124, 134, 144, 154, 164, 174, 184, 194, 204, 214, 224, 234, 244, 254, 264, 274, 284, 294, 304, 314, 324, 334, 344, 354, 364, 374, 384, 394, 404, 414, 424, 434, 444, 454, 464, 474, 484, 494, 504, 514, 524, 534, 544, 554, 564, 574, 584, 594, 604, 614, 624, 634, 644, 654, 664, 674, 684, 694, 704, 714, 724, 734, 744, 754, 764, 774, 784, 794, and 811-818. In some embodiments, the VH-CDR3 comprises an amino acid sequence selected from the group consisting of: SEQ ID NOs: 5, 15, 25, 35, 45, 55, 65, 75, 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, and 819-820. In some embodiments, the VL-CDR3 comprises an amino acid sequence selected from the group consisting of: SEQ ID NOs: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790 and 800. In some embodiments, the VH-CDR2 comprises an amino acid sequence corresponding to SEQ ID NO: 14; wherein the VH-CDR3 comprises an amino acid sequence corresponding to SEQ ID NO: 15, and wherein the VL-CDR3 comprises an amino acid sequence corresponding to SEQ ID NO: 20. In some embodiments, the VH-CDR2 comprises an amino acid sequence corresponding to SEQ ID NO: 811; the VH-CDR3 comprises an amino acid sequence corresponding to SEQ ID NO: 819, and the VL-CDR3 comprises an amino acid sequence corresponding to SEQ ID NO: 10 or 20. In some embodiments, the VH-CDR2 comprises an amino acid sequence corresponding to SEQ ID NO: 814; the VH-CDR3 comprises an amino acid sequence corresponding to SEQ ID NO: 820, and the VL-CDR3 comprises an amino acid sequence corresponding to SEQ ID NO: 10 or 20. In some embodiments, the VH-CDR2 comprises an amino acid sequence corresponding to SEQ ID NO: 816; the VH-CDR3 comprises an amino acid sequence corresponding to SEQ ID NO: 15, and the VL-CDR3 comprises an amino acid sequence corresponding to SEQ ID NO: 10 or 20. In some embodiments, the VH-CDR2 comprises an amino acid sequence corresponding to SEQ ID NO: 818; the VH-CDR3 comprises an amino acid sequence corresponding to SEQ ID NO: 15, and the VL-CDR3 comprises an amino acid sequence corresponding to SEQ ID NO: 10 or 20. In some embodiments, the VH comprises framework regions that are each at least 80%, 85%, 90%, 91%, 92%, 93%, 94%, 95%, 96%, 97%, 98%, 99% or 100% identical to SEQ ID NOs: 803-806. In some embodiments, the VL comprises framework regions that are each at least 80%, 85%, 90%, 91%, 92%, 93%, 94%, 95%, 96%, 97%, 98%, 99% or 100% identical to SEQ ID NOs: 807-810. In some embodiments, the VH comprises an amino acid sequence that is at least 80%, 85%, 90%, 91%, 92%, 93%, 94%, 95%, 96%, 97%, 98%, 99% or 100% identical to any of the sequences selected from the group consisting of: SEQ ID NOs: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 382, 392, 402, 412, 422, 432, 442, 452, 462, 472, 482, 492, 502, 512, 522, 532, 542, 552, 562, 572, 582, 592, 602, 612, 622, 632, 642, 652, 662, 672, 682, 692, 702, 712, 722, 732, 742, 752, 762, 772, 782, and 792. In some embodiments, the VL comprises an amino acid sequence that is at least 80%, 85%, 90%, 91%, 92%, 93%, 94%, 95%, 96%, 97%, 98%, 99% or 100% identical to any of the sequences selected from the group consisting of: SEQ ID NOs: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 387, 397, 407, 417, 427, 437, 447, 457, 467, 477, 487, 497, 507, 517, 527, 537, 547, 557, 567, 577, 587, 597, 607, 617, 627, 637, 647, 657, 667, 677, 687, 697, 707, 717, 727, 737, 747, 757, 767, 777, 787, and 797. In some embodiments, the VH comprises an amino acid sequence corresponding to SEQ ID NO: 12 and the VL comprises an amino acid sequence corresponding to SEQ ID NO: 17. In some embodiments, the VH comprises an amino acid sequence corresponding to SEQ ID NO: 821 and the VL comprises an amino acid sequence corresponding to SEQ ID NO: 7 or 17. In some embodiments, the VH comprises an amino acid sequence corresponding to SEQ ID NO: 824 and the VL comprises an amino acid sequence corresponding to SEQ ID NO: 7 or 17. In some embodiments, the VH comprises an amino acid sequence corresponding to SEQ ID NO: 827 and the VL comprises an amino acid sequence corresponding to SEQ ID NO: 7 or 17. In some embodiments, the VH comprises an amino acid sequence corresponding to SEQ ID NO: 831 and the VL comprises an amino acid sequence corresponding to SEQ ID NO: 7 or 17.

The present disclosure also includes anti-PAR2 antibodies comprising a chimeric heavy chain constant (CH) region, wherein the chimeric CH region comprises segments derived from the CH regions of more than one immunoglobulin isotype. For example, the antibodies of the disclosure may comprise a chimeric CH region comprising part or all of a CH2 domain derived from a human $IgG_1$, human $IgG_2$ or human $IgG_4$ molecule, combined with part or all of a CH3 domain derived from a human $IgG_1$, human $IgG_2$ or human $IgG_4$ molecule. According to certain embodiments, the antibodies of the disclosure comprise a chimeric CH region having a chimeric hinge region. For example, a chimeric hinge may comprise an "upper hinge" amino acid sequence (amino acid residues from positions 216 to 227 according to EU numbering) derived from a human $IgG_1$, a human $IgG_2$ or a human $IgG_4$ hinge region, combined with a "lower hinge" sequence (amino acid residues from positions 228 to 236 according to EU numbering) derived from a human $IgG_1$, a human $IgG_2$ or a human $IgG_4$ hinge region.

According to certain embodiments, the chimeric hinge region comprises amino acid residues derived from a human $IgG_1$ or a human $IgG_4$ upper hinge and amino acid residues derived from a human $IgG_2$ lower hinge. An antibody comprising a chimeric CH region as described herein may, in certain embodiments, exhibit modified Fc effector functions without adversely affecting the therapeutic or pharmacokinetic properties of the antibody. (See, e.g., US 2015-0203591 A1).

The present disclosure includes anti-PAR2 antibodies or antigen-binding fragments which interact with one or more amino acids of PAR2. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids of PAR2. Alternatively, the epitope may consist of a plurality of non-contiguous amino acids (or amino acid sequences) of PAR2.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267 (2):252-259; Engen and Smith (2001) Anal. Chem. 73:256A-265A.

The present disclosure further includes anti-PAR2 antibodies or antigen-binding fragments thereof that bind to the same epitope as any of the antibodies or antigen-binding fragments described herein (e.g., an antibody or antigen-binding fragment comprising the amino acid sequences of SEQ ID NOs: 12 and 17). Likewise, the present disclosure also includes anti-PAR2 antibodies and antigen-binding fragments that compete for binding to PAR2 with any of the antibodies or antigen-binding fragments described herein (e.g., an antibody or antigen-binding fragment comprising the amino acid sequences of SEQ ID NOs: 12 and 17). The skilled worker can easily determine whether an antibody binds to the same epitope as, or competes for binding with, a reference anti-PAR2 antibody by using routine methods known in the art and exemplified herein. For example, to determine if a test antibody binds to the same epitope as a reference anti-PAR2 antibody of the disclosure, the reference antibody is allowed to bind to a PAR2 protein. Next, the ability of a test antibody to bind to the PAR2 molecule is assessed. If the test antibody is able to bind to PAR2 following saturation binding with the reference anti-PAR2 antibody, it can be concluded that the test antibody binds to a different epitope than the reference anti-PAR2 antibody. On the other hand, if the test antibody is not able to bind to the PAR2 molecule following saturation binding with the reference anti-PAR2 antibody, then the test antibody may bind to the same epitope as the epitope bound by the reference anti-PAR2 antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502).

Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-PAR2 antibody, the above-described binding methodology is performed in two orientations: In a first orientation, the reference antibody is allowed to bind to a PAR2 protein under saturating conditions followed by assessment of binding of the test antibody to the PAR2 molecule. In a second orientation, the test antibody is allowed to bind to a PAR2 molecule under saturating conditions followed by assessment of binding of the reference antibody to the PAR2 molecule. If, in both orientations, only the first (saturating) antibody is capable of binding to the PAR2 molecule, then it is concluded that the test antibody and the reference antibody compete for binding to PAR2. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Methods for generating monoclonal antibodies, including fully human monoclonal antibodies are known in the art. Any such known methods can be used in the context of the present disclosure to make human antibodies that specifically bind to human PAR2.

Using VELOCIMMUNE™ technology, for example, or any other known method for generating fully human monoclonal antibodies, high affinity chimeric antibodies to PAR2 are initially isolated having a human variable region and a mouse constant region. As in the experimental section below, the antibodies are characterized and selected for desirable characteristics, including affinity, selectivity, epitope, etc. If necessary, mouse constant regions are replaced with a desired human constant region, for example wild-type or modified $IgG_1$ or $IgG_4$, to generate a fully human anti-PAR2 antibody. While the constant region selected may vary according to specific use, high affinity antigen-binding and target specificity characteristics reside in the variable region. In certain instances, fully human anti-PAR2 antibodies are isolated directly from antigen-positive B cells.

The anti-PAR2 antibodies and antibody fragments of the present disclosure encompass proteins having amino acid sequences that may vary from those of the described antibodies but that retain the ability to bind PAR2 (e.g., SEQ ID NO: 801), or more specifically in some embodiments, a PAR2 tethered ligand (e.g., SEQ ID NO: 802). Such variant antibodies and antibody fragments comprise one or more additions, deletions, or substitutions of amino acids when compared to a parent sequence, but exhibit biological activity that is essentially equivalent to that of the described antibodies. Likewise, the anti-PAR2 antibody-encoding DNA sequences of the present disclosure encompass sequences that comprise one or more additions, deletions, or substitutions of nucleotides when compared to the disclosed sequences, but that encode an anti-PAR2 antibody or antibody fragment that is essentially bioequivalent to an anti-PAR2 antibody or antibody fragment of the disclosure. Examples of such variant amino acid and DNA sequences are discussed above.

Two antibodies or antigen-binding fragments are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies or antigen-binding fragments will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In some embodiments, two antibodies or antigen-binding fragments are bioequivalent if there are no clinically meaningful differences in their safety, purity, and potency.

In some embodiments, two antibodies or antigen-binding fragments are bioequivalent if a patient can be switched one or more times between the reference product and the biological product without an expected increase in the risk of adverse effects, including a clinically significant change in immunogenicity, or diminished effectiveness, as compared to continued therapy without such switching.

In some embodiments, two antibodies or antigen-binding fragments are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-PAR2 antibodies of the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies or antigen-binding fragments may include anti-PAR2 antibody variants comprising amino acid changes which modify the glycosylation characteristics of the antibodies or antigen-binding fragments, e.g., mutations which eliminate or remove glycosylation.

The present disclosure, according to certain embodiments, provides anti-PAR2 antibodies or antigen-binding fragments that bind to human PAR2 but not to PAR2 from other species. The present disclosure also includes anti-PAR2 antibodies that bind to human PAR2 and to PAR2 from one or more non-human species. For example, the anti-PAR2 antibodies of the disclosure may bind to human PAR2 and may bind or not bind, as the case may be, to one or more of mouse, rat, guinea pig, hamster, gerbil, pig, cat, dog, rabbit, goat, sheep, cow, horse, camel, cynomolgus monkey, marmoset, rhesus or chimpanzee PAR2. According to certain embodiments, the antibodies or antigen-binding fragments bind to PAR2 in human A549 cells, rat KNRK cells, cynomolgus monkey CYNOM-K1 cells or mouse LL/2 cells.

The disclosure encompasses anti-PAR2 monoclonal antibodies conjugated to a therapeutic moiety ("immunoconjugate"), such as a cytotoxin, a chemotherapeutic, an immunosuppressant or a radioisotope. Examples of suitable cytotoxic agents and chemotherapeutic agents for forming immunoconjugates are known in the art (see for example, WO 05/103081).

In some embodiments, the antibodies of the present disclosure may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer ei a/., 2004, Trends Biotechnol. 22:238-244. The anti-PAR2 antibodies or antigen-binding fragments of the present disclosure can be linked to or co-expressed with another functional molecule, e.g., another peptide or protein. For example, an antibody or antigen-binding fragment thereof can be functionally linked (e.g., by chemical coupling, genetic fusion, noncovalent association or otherwise) to one or more other molecular entities, such as another antibody or antigen-binding fragment to produce a bi-specific or a multispecific antibody with a second binding specificity. For example, the present disclosure includes bi-specific antibodies wherein one arm of an immunoglobulin is specific for human PAR2 or a fragment thereof, and the other arm of the immunoglobulin is specific for a second therapeutic target or is conjugated to a therapeutic moiety.

An exemplary bi-specific antibody or antigen-binding fragment format that can be used in the context of the present disclosure involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-lg, Quadroma, knobs-into-holes, common light chain (e.g., common light chain with knobs-into-holes, etc.), CrossMab, CrossFab, (SEED) body, leucine zipper, Duobody, lgG1/lgG2, dual acting Fab (DAF)-lgG, and Mab<2> bispecific formats (see, e.g., Klein et al. 2012, mAbs 4:6, 1 –1 1, and references cited therein, for a review of the foregoing formats). Bispecific antibodies or antigen-binding fragments can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. C em. Soc. [Epub: Dec. 4, 2012]).

C. Nucleic Acids and Expression Systems

In some embodiments, the disclosure provides for a nucleic acid capable of expressing any of the antibodies of antigen-binding fragments disclosed herein. The nucleic acids may be single-stranded or double-stranded, DNA or RNA molecules. In further embodiments, the antibody or antigen-binding fragment nucleic acid sequences can be isolated, recombinant, and/or fused with a heterologous nucleotide sequence, or in a DNA library. In some embodiments, the nucleic acid comprises a nucleotide sequence that is at least 80%, 85%, 90%, 91%, 92%, 93%, 94%, 95%, 96%, 97%, 98%, 99% or 100% identical to any one of SEQ ID NOs: 1, 11, 21, 31, 41, 51, 61, 71, 81, 91, 101, 111, 121, 131, 141, 151, 161, 171, 181, 191, 201, 211, 221, 231, 241, 251, 261, 271, 281, 291, 301, 311, 321, 331, 341, 351, 361, 371, 381, 391, 401, 411, 421, 431, 441, 451, 461, 471, 481, 491, 501, 511, 521, 531, 541, 551, 561, 571, 581, 591, 601, 611, 621, 631, 641, 651, 661, 671, 681, 691, 701, 711, 721, 731, 741, 751, 761, 771, 781, and/or 791. In some embodiments, the nucleic acid comprises a nucleotide sequence that is at least 80%, 85%, 90%, 91%, 92%, 93%, 94%, 95%, 96%, 97%, 98%, 99% or 100% identical to any one of SEQ ID NOs: 6, 16, 26, 36, 46, 56, 66, 76, 86, 96, 106, 116, 126, 136, 146, 156, 166, 176, 186, 196, 206, 216, 226, 236, 246, 256, 266, 276, 286, 296, 306, 316, 326, 336, 346, 356, 366, 376, 386, 396, 406, 416, 426, 436, 446, 456, 466, 476, 486, 496, 506, 516, 526, 536, 546, 556, 566, 576, 586, 596, 606, 616, 626, 636, 646, 656, 666, 676, 686, 696, 706, 716, 726, 736, 746, 756, 766, 776, 786, and/or 796. In particular embodiments, the nucleic acid comprises a nucleotide sequence that is at least 80%, 85%, 90%, 91%, 92%, 93%, 94%, 95%, 96%, 97%, 98%, 99% or 100% identical to SEQ ID NO: 1, 6, 11 and/or 16

In certain embodiments, nucleic acids encoding antibodies or antigen-binding fragments also include nucleotide sequences that hybridize under highly stringent conditions to a polynucleotide encoding any of the above-mentioned antibodies or antigen-binding fragments nucleotide sequence, or complement sequences thereof. In some embodiments, the nucleic acids hybridize under highly stringent conditions to a polynucleotide encoding an amino acid sequence that is at least 80%, 85%, 90%, 91%, 92%, 93%, 94%, 95%, 96%, 97%, 98%, 99% or 100% identical to any one of SEQ ID NOs: 2, 12, 22, 32, 42, 52, 62, 72, 82, 92, 102, 112, 122, 132, 142, 152, 162, 172, 182, 192, 202, 212, 222, 232, 242, 252, 262, 272, 282, 292, 302, 312, 322, 332, 342, 352, 362, 372, 382, 392, 402, 412, 422, 432, 442, 452, 462, 472, 482, 492, 502, 512, 522, 532, 542, 552, 562, 572, 582, 592, 602, 612, 622, 632, 642, 652, 662, 672, 682, 692, 702, 712, 722, 732, 742, 752, 762, 772, 782, and 792. In some embodiments, the nucleic acids hybridize under highly stringent conditions to a polynucleotide encoding an amino acid sequence that is at least 80%, 85%, 90%, 91%, 92%, 93%, 94%, 95%, 96%, 97%, 98%, 99% or 100% identical to any one of SEQ ID NOs: 7, 17, 27, 37, 47, 57, 67, 77, 87, 97, 107, 117, 127, 137, 147, 157, 167, 177, 187, 197, 207, 217, 227, 237, 247, 257, 267, 277, 287, 297, 307, 317, 327, 337, 347, 357, 367, 377, 387, 397, 407, 417, 427, 437, 447, 457, 467, 477, 487, 497, 507, 517, 527, 537, 547, 557, 567, 577, 587, 597, 607, 617, 627, 637, 647, 657, 667, 677, 687, 697, 707, 717, 727, 737, 747, 757, 767, 777, 787, and 797. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids encoding the antibody or antigen-binding fragment thereof due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In some embodiments, the disclosure provides for a vector comprising any of the nucleic acids disclosed herein. In some embodiments, the disclosure provides for a host cell comprising any of the vectors disclosed herein.

Regardless of when an antibody of the disclosure is a full length antibody or an antigen binding fragment, antibodies and antigen binding fragments of the disclosure can be recombinantly expressed in cell lines. In these embodiments, sequences encoding particular antibodies or antigen binding fragments can be used for transformation of a suitable host cell, such as a mammalian host cell or yeast host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

According to certain embodiments of the disclosure, a nucleic acid molecule encoding the amino acid sequence of a heavy chain constant region (all or a portion), a heavy chain variable region of the disclosure, a light chain constant region, or a light chain variable region of the disclosure is inserted into an appropriate expression vector using standard ligation techniques. In a preferred embodiment, the heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, Meth. Enzymol. Vol. 185, Academic Press. N.Y. In the context of antibody expression, both the heavy and light chain may be expressed from the same vector (e.g., from the same or different promoters present on the same vector) or the heavy and light chains may be expressed from different vectors. In certain embodiments, the heavy and light chains are expressed from different vectors which are transfected into the same host cell and co-expressed. Regardless of when the heavy and light chains are expressed in the same host cell from the same or a different vector, the chains can then associate to form an antibody (or antibody fragment, depending on the portions of the heavy and light chain being expressed).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. These portions of vectors are well known, and there are numerous generally available vectors that can be selected and used for the expression of proteins. One can readily select vectors based on the desired host cell and application.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

The expression and cloning vectors of the disclosure will typically contain a promoter that is recognized by the host organism and operably linked to the molecule encoding heavy and/or light chain. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding the heavy chain or light chain comprising an antibody or antigen binding fragment of the disclosure. In certain embodiments, the same promoter is used for both the heavy and light chain. In other embodiments, different promoters (present on the same or different vectors) are used for each.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bernoist and Chambon, 1981, Nature 290:304-10); the CMV promoter; the promoter contained in the 3' long terminal repeat of Rous sarcoma virus (Yamamoto et al., 1980, Cell 22:787-97); the herpes thymidine kinase promoter (Wagner et al., 1981, Proc. Natl. Acad. Sci. USA 78:1444-45); the regulatory sequences of the metallothionine gene (Brinster et al., 1982, Nature 296:39-42); prokaryotic expression vectors such as the beta-lactamase promoter (Villa-Kamaroff et al., 1978, Proc. Natl. Acad. Sci. USA 75:3727-31); or the tac promoter (DeBoer et al., 1983, Proc. Natl. Acad. Sci. USA 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-46; Ornitz et al., 1986, Cold Spring Harbor Symp. Quant. Biol. 50:399-409 (1986); MacDonald, 1987, Hepatology 7:425-515); the insulin gene control region that is active in pancreatic beta cells (Hanahan, 1985, Nature 315:115-22); the immunoglobulin gene control region that is active in lymphoid cells (Grosschedl et al., 1984, Cell 38:647-58; Adames et al., 1985, Nature 318:533-38; Alexander et al., 1987, Mol. Cell. Biol. 7:1436-44); the mouse mammary tumor virus control region that is active in testicular, breast, lymphoid and mast cells (Leder et al., 1986, Cell 45:485-95); the albumin gene control region that is active in liver (Pinkert et al., 1987, Genes and Devel. 1:268-76); the alpha-feto-protein gene control region that is active in liver (Krumlauf et al., 1985, Mol. Cell. Biol. 5:1639-48; Hammer et al., 1987, Science 235:53-58); the alpha 1-antitrypsin gene control region that is active in liver (Kelsey et al., 1987, Genes and Devel. 1:161-71); the beta-globin gene control region that is active in myeloid cells (Mogram et al., 1985, Nature 315:338-40; Kollias et al., 1986, Cell 46:89-94); the myelin basic protein gene control region that is active in oligodendrocyte cells in the brain (Readhead et al., 1987, Cell 48:703-12); the myosin light chain-2 gene control region that is active in skeletal muscle (Sani, 1985, Nature 314:283-86); and the gonadotropic releasing hormone gene control region that is active in the hypothalamus (Mason et al., 1986, Science 234:1372-78).

The vector may also include an enhancer sequence to increase transcription of DNA encoding light chain or heavy chain.

Expression vectors of the disclosure may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain comprising an antibody or antigen binding fragment of the disclosure has been inserted into the proper site of the vector, the completed vector may be inserted into a suitable host cell for amplification and/or polypeptide expression. The transformation of an expression vector into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled worker.

The host cell, when cultured under appropriate conditions, synthesizes the antibody or antigen binding fragment of the disclosure that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as host cells for expression are well known in the art and include, but are not limited to, many immortalized cell lines available from the American Type Culture Collection (A.T.C.C.), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In another embodiment, one may select a cell line from the B cell lineage that does not make its own antibody but has a capacity to make and secrete a heterologous antibody (e.g., mouse myeloma cell lines NS0 and SP2/0). In other embodiments, a cell other than a mammalian cell is used, such as a yeast cell line (e.g., Pichia).

In certain embodiments, the cell line stably expresses an antibody or antigen binding fragment of the disclosure. In other embodiments, the cells transiently express an antibody or antigen binding fragment of the disclosure.

D. Therapeutic Formulation and Administration

The disclosure provides pharmaceutical compositions comprising the anti-PAR2 antibodies or antigen-binding fragments thereof of the present disclosure. The pharmaceutical compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-31 1.

The dose of antibody administered to a patient may vary depending upon the age and the size of the patient, target disease, conditions, route of administration, and the like. The preferred dose is typically calculated according to body weight or body surface area. Depending on the severity of the condition, the frequency and the duration of the treatment can be adjusted. Effective dosages and schedules for administering anti-PAR2 antibodies or antigen-binding fragments may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intrathecal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In some embodiments, the antibodies and antigen-binding fragments thereof have utility in treating conditions and disorders associated with the central nervous system, and, particularly associated with the brain. While various factors must be considered when administering a macromolecule such as an antibody or antigen-binding fragment to a subject's brain, i.e., ability of the antibody or antigen-binding fragment to cross the blood-brain-barrier (BBB), the skilled worker is aware of methods of administering such macromolecules to the brain. For example, in some embodiments, the antibody or antigen-binding fragment is covalently modified with one or more cationic polyamines, such as hexamethylenediamine or tetramethylenediamine in order to increase the likelihood that the antibody or antigen-binding fragment is internalized across the BBB. In some embodiments, the antibody or antigen-binding fragment is a bispecific antibody or antigen-binding fragment, wherein the antibody or fragment targets PAR2 and also targets a receptor that facilitates transport across the BBB (e.g., transferrin receptor, insulin receptor and TMEM30A). In some embodiments, the antibody or antigen-binding fragment is conjugated to an agent that targets a receptor that facilitates transport across the BBB (e.g., transferrin receptor, insulin receptor and TMEM30A). In some embodiments, the BBB is temporarily disrupted prior to or during administration of the antibody or fragment. In some embodiments the BBB is temporarily disrupted by means of ultrasound, radiation, biochemical treatment (e.g., with a $K_{Ca}$ receptor agonist such as NS-1619), or intra-arterial infusion of concentrated hyperosmotic solutions.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUIIVIALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intrathecal, intracutaneous and intramuscular injections, drip infusions, etc. These injectable preparations may be prepared by methods publicly known. For example, the injectable preparations may be prepared, e.g., by dissolving, suspending or emulsifying any of the antibodies or antigen-binding fragments disclosed herein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody or antigen-binding fragment is contained in about 5 to about 100 mg and in about 10 to about 250 mg for the other dosage forms.

E. Therapeutic Uses of the Antibodies

For any of the methods described herein, the disclosure contemplates the use of any of the antibodies or antigen-binding fragments of the disclosure.

In some embodiments, the disclosure provides for a method of treating a disorder in a subject in which undesired and/or aberrant PAR2 activity is involved, comprising administering any of the antibodies or antigen-binding fragments described herein. As used herein, "disorder", "condition" and "disease" are used interchangeably to refer to any of the disorders, conditions or diseases disclosed herein. In some embodiments, the disease/disorder/condition in which undesired and/or aberrant PAR2 activity is involved is a disease/disorder/condition associated with aberrant or undesired inflammation. Examples of diseases/disorders/conditions in which aberrant or undesired PAR2 activity is involved include acute or chronic pain, acute or chronic itch, acute or chronic inflammation (e.g., acute or chronic inflammation of the joints, lungs, brain, gastrointestinal tract, periodontium, skin, and vascular systems), autoimmune disorders, periodontitis, osteoarthritis, rheumatoid arthritis, inflammatory bowel disease, arthritis, psoriasis, obesity, diabetes, cardiovascular disease, pancreatitis, cancer (e.g., breast, lung, colon, stomach or prostate cancer), asthma, fibrosis, gastric ulcers, fibrosis or fibrotic disorders, Alzheimer's Disease, Parkinson's Disease, contract dermatitis, Crohn's Disease, ulcerative colitis, adult respiratory distress syndrome (ARDS), glomerulonephritis, and meningitis. In some embodiments, the disclosure provides for methods of treating a subject with metabolic syndrome, or one or more conditions associated with metabolic syndrome, such as visceral fat deposition, hypertension, impaired glucose and insulin homeostasis, insulin resistance, endothelial damage, cardiovascular hypertrophy, inflammation, vascular inflammation, atherosclerosis, ventricular contractile dysfunction, fibrosis and fatty liver disease. In particular embodiments, the disclosure provides for methods of treating pain, e.g., pain associated with any of the diseases/disorders/conditions disclosed herein (e.g., osteoarthritic pain). In some embodiments, the subject is a mammal. In some embodiments, the subject is a human.

In some embodiments, the disclosure provides for a method of interfering with the interaction between a protease (e.g., trypsin) and PAR2, comprising the step of administering any of the antibodies or antigen-binding fragments described herein to a cell. In some embodiments, the disclosure provides for a method of inhibiting exposure of the tethered ligand of PAR2 on a cell, comprising the step of administering any of the antibodies or antigen-binding fragments described herein to a cell. In some embodiments, the disclosure provides for a method of inhibiting the interaction between the tethered ligand of PAR2 and the second transmembrane loop of the PAR2 protein, comprising the step of administering any of the antibodies or antigen-binding fragments described herein to a cell. In some embodiments, the disclosure provides for a method of inhibiting activation of a PAR2 receptor on a cell, comprising the step of administering any of the antibodies or antigen-binding fragments described herein to a cell. In some embodiments, the cell is a neuron (e.g., a sensory neuron). In some embodiments, the cell is in vitro. In other embodiments, the cell is in a subject. In some embodiments, the subject is a mammal. In some embodiments, the subject is a human. In some embodiments, the subject suffers from any of disorders disclosed herein.

For any of the methods described herein, the disclosure contemplates the combination of any step or steps of one method with any step or steps from another method. These methods involve administering to an individual in need thereof an effective amount of a compound of the disclosure appropriate for the particular disease or condition. In specific embodiments, these methods involve delivering any of the antibodies or antigen-binding fragments disclosed herein to the cells of a subject in need thereof.

The terms "treatment", "treating", "alleviation" and the like are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes any one or more of: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). For example, "treatment" of pain (e.g., osteoarthritic pain) involves a reduction, arrest, alleviation, or elimination of pain symptoms in the treated subject. The population of subjects treated by the method of the disease includes subjects suffering from the undesirable condition or disease, as well as subjects at risk for development of the condition or disease.

For any of the methods described herein, the disclosure contemplates the use of any of the antibodies or antigen-binding fragments described throughout the application. In addition, for any of the methods described herein, the disclosure contemplates the combination of any step or steps of one method with any step or steps from another method.

In certain embodiments, the present invention provides methods of treating conditions associated with any of the diseases/conditions/disorders disclosed herein, e.g., acute or chronic pain (e.g., osteoarthritic pain). These methods involve administering to the individual a therapeutically effective amount of any of the antibodies or antigen-binding fragments as described above. These methods are particularly aimed at therapeutic and prophylactic treatments of animals, and more particularly, humans. The disclosure contemplates all combinations of any of the foregoing aspects and embodiments, as well as combinations with any of the embodiments set forth in the detailed description and examples.

By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, any of the antibodies or antigen-binding fragments of the present invention can be administered alone or in combination with one or more additional compounds or therapies for treating any of the diseases/conditions/disorders disclosed herein, e.g., acute or chronic pain (e.g., osteoarthritic pain). For example, any of the antibodies or antigen-binding fragments disclosed herein can be co-administered in conjunction with one or more therapeutic compounds. When co-administration is indicated, the combination therapy may encompass simultaneous or alternating administration. In addition, the combination may encompass acute or chronic administration. Optionally, the antibody/antigen-binding fragment and additional compounds act in an additive or synergistic manner for treating any of the diseases/conditions/disorders disclosed herein, e.g., acute or chronic pain (e.g., osteoarthritic pain). Additional compounds to be used in combination therapies include, but are not limited to, small molecules, polypeptides, antibodies, antisense oligonucleotides, and siRNA molecules. In some embodiments, the additional compound is any one or more of: an anti-inflammatory drug, analgesic, a nonsteroidal anti-inflammatory drug (NSAID), corticosteroid, hyaluronic acid, acetaminophen, codeine, lorcet, lortab, vicodin, hydrocodone, morphine, oxycontin, Roxicodone, Percocet, aspirin, celecoxib, pregabalin, joint fusion, joint replacement, abatacept, adalimumab, anakinra, certolizumab, etanercept, golimumab, infliximab, rituximab, tocilizumab and tofacitinib. Depending on the nature of the combinatory therapy, administration of the antibodies or antigen binding disclosures of the disclosure may be continued while the other therapy is being administered and/or thereafter. Administration of the antibodies or antigen-binding fragments may be made in a single dose, or in multiple doses. In some instances, administration of the antibodies or antigen binding fragments is commenced at least several days prior to the other therapy, while in other instances, administration is begun either immediately before or at the time of the administration of the other therapy. In some embodiments, any of the additional compounds disclosed herein is conjugated to any of the antibodies or antigen-binding fragments disclosed herein.

In another example of combination therapy, any of the antibodies or antigen-binding fragments of the disclosure can be used as part of a therapeutic regimen combined with one or more additional treatment modalities. By way of example, such other treatment modalities include, but are not limited to, dietary therapy, occupational therapy, physical therapy, psychiatric therapy, massage, acupuncture, acupressure, mobility aids, assistance animals, and the like.

Note that although the antibodies or antigen-binding fragments described herein can be used in combination with other therapies, in certain embodiments, an antibody or antigen-binding fragment is provided as the sole form of therapy. Regardless of whether administrated alone or in combination with other medications or therapeutic regiments, the dosage, frequency, route of administration, and timing of administration of the antibodies or antigen-binding fragments is determined by a physician based on the condition and needs of the patient.

According to certain embodiments of the present disclosure, multiple doses of an anti-PAR2 antibody or antigen-binding fragment thereof (or a pharmaceutical composition comprising a combination of an anti-PAR2 antibody and any of the additional therapies mentioned herein) may be administered to a subject over a defined time course. The methods according to this aspect of the disclosure comprise sequentially administering to a subject multiple doses of an anti-PAR2 antibody or antigen-binding fragment of the disclosure. As used herein, "sequentially administering" means that each dose of anti-PAR2 antibody or antigen-binding fragment is administered to the subject at a different point in time, e.g., on different days separated by a predetermined interval (e.g., hours, days, weeks or months). The present disclosure includes methods which comprise sequentially administering to the patient a single initial dose of an anti-PAR2 antibody or antigen-binding fragment, followed by one or more secondary doses of the anti-PAR2 antibody or antigen-binding fragment, and optionally followed by one or more tertiary doses of the anti-PAR2 antibody or antigen-binding fragment.

The terms "initial dose," "secondary doses," and "tertiary doses," refer to the temporal sequence of administration of the anti-PAR2 antibody or antigen-binding fragment of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-PAR2 antibody or antigen-binding fragment, but generally may differ from one another in terms of frequency of administration. In certain embodiments, however, the amount of anti-PAR2 antibody or antigen-binding fragment contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

F. Diagnostic/Other Uses of the Antibodies or Antigen Binding Fragments

The anti-PAR2 antibodies of the present disclosure may also be used to detect and/or measure PAR2, or PAR2-expressing cells in a sample, e.g., for diagnostic purposes. For example, an anti-PAR2 antibody, or antigen-binding fragment thereof, may be used to diagnose a condition or disease characterized by aberrant expression (e.g., over-expression, under-expression, lack of expression, etc.) of PAR2. Exemplary diagnostic assays for PAR2 may comprise, e.g., contacting a sample obtained from a patient, with an anti-PAR2 antibody of the disclosure, wherein the anti-PAR2 antibody is labeled with a detectable label or reporter molecule.

Alternatively, an unlabeled anti-PAR2 antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure PAR2 in a sample include enzyme-linked immunosorbent assay (ELISA), radioimmunoassay (MA), and fluorescence-activated cell sorting (FACS).

The compositions of the disclosure have numerous uses. For example, the antibodies and antigen binding fragments of the disclosure are useful for studying preferential cell and tissue distribution in cells and in tissues in vitro and/or in vivo. Similarly, the antibodies and antigen binding fragments, either alone or conjugated to a heterologous agent are useful as imaging agents, such as for ex vivo or in vivo diagnostic applications. For example, the antibodies or antigen binding fragments conjugated to a radioactive moiety are useful for ex vivo or in vivo imaging studies. Similarly, any of the antibodies or antigen binding fragments of the disclosure are similarly useful.

When used in vitro, the antibodies and antigen binding fragments of the disclosure are suitable for identifying binding partners for the antibody or antigen binding fragment being delivered (e.g., identifying proteins or peptides that bind the antibody or antigen binding fragment), and for evaluating localization and trafficking. Similarly, when used in vivo, the antibodies or antigen-binding fragments are useful for identifying binding partners for the antibody or antigen-binding fragment being delivered (e.g., identifying proteins or peptides that bind the antibody or antigen-binding fragment), for evaluating localization and trafficking, for evaluating biodistribution and half-life, and for evaluating immunogenicity.

G. Animal/Cell Models

Numerous animal models are known to the skilled worker that would be useful for examining any of the antibodies or fragments thereof. See, e.g., Kuyinu et al., 2016, J Orthop Surg Res, 11(19): 10.1186/s13018-016-0346-5. In some embodiments, the animal model is a pain-based model generated by treatment of the animal with a chemical, such as sodium monoiodoacetate (MIA) or carrageenan. In some embodiments, the chemical is injected at the site of where the pain is to be induced in the animal. In some embodiments, the animal model is an animal in which an injury is introduced postoperatively (e.g., incisional), such as anterior cruciate ligament transection, meniscectomy, or medial meniscal transection. In some embodiments, the animal model is one associated with an inflammatory condition, such as lower esophageal irritation, colon inflammation, stomach ulceration, urinary bladder inflammation, pancreatic inflammation and uterine inflammation. See, e.g., the animal models referred to in National Research Council Committee on Recognition and Alleviation of Pain in Laboratory Animals, "Models of Pain," 2009.

H. Kits

In certain embodiments, the invention also provides a pharmaceutical package or kit comprising one or more containers filled with at least one antibody or antigen-binding fragment of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

EXAMPLES

The following examples are put forth so as to provide those of ordinary skill in the art with a complete disclosure and description of how to make and use the methods and compositions of the disclosure, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Antibodies with pH Sensitive Binding for PAR2

Generation of Recombinant Human, Rat and Cynomolgus PAR2 and PAR1 Proteins.

The human, rat and cynomolgus (*Macaca fascicularis*) PAR2 (Proteinase-Activated Receptor 2) constructs comprising extracellular residues 1-75 were designed with N-terminal AviTag™ (Avidity LLC) and C-terminal Flag and poly Histidine tags and cloned into the vector pDEST12.2 OriP FH (Life Technologies). The human PAR1 (Proteinase-Activated Receptor 1) construct comprising extracellular residues 1-102 was designed with C-terminal Flag and poly Histidine tags and cloned into the vector pDEST12.2 OriP FH (Life Technologies). The constructs were expressed in HEK293 cells and purified from the media using standard affinity and size exclusion chromatography purification. To generate biotinylated proteins the AviTag™ was biotinylated enzymatically according to the manufacturer's instructions.

Construction of Combinatorial Histidine Scanning Libraries

Split pool oligonucleotides were designed to introduce histidine or the wild type amino acid at each position of either the VHCDR2, VHCDR3 or VLCDR3 of Par0067. Three Par0067 scFv phage display libraries were subsequently constructed in which there were between 0% and 100% histidine residues in either the VHCDR2, VHCDR3 or VLCDR3.

Selection of pH Sensitive Par0067 Variant scFv's

The combinatorial histidine scanning libraries were subjected to affinity based phage display selections with the aim of isolating Par0067 variants which bind to PAR2 at pH 7.4 but with reduced binding at pH 6.0. To achieve this, four rounds of selection were performed with each library using decreasing concentrations of biotinylated recombinant human PAR2 (Hawkins, R E et al., 1992 Aug. 5; 226(3): 889-96). At each round, phage were pre-incubated for 1 hour with streptavidin coated paramagnetic beads (Dynabeads®) to remove any streptavidin binders. The streptavidin beads were subsequently removed with a DYNAL® magnet and discarded and the remaining phage added to biotinylated recombinant human PAR2 at pH 7.4. The selection proceeded for 2 hours before adding streptavidin coated paramagnetic beads to capture the biotinylated recombinant human PAR2 bound phage. The beads were washed 5-times with PBS Tween (PBST) prior to elution of specific scFv in low pH buffer (pH 5.5-pH 6.0). The selected scFv-phage particles were then rescued as described previously (Osbourn J K. et al. Immunotechnology, 2(3):181-96, 1996), and the selection process was repeated in the presence of decreasing concentrations of biotinylated PAR2 (1 nM-0.05 nM over 4 rounds).

Reformatting of scFv to IgG1-TM

Antibodies were converted from scFv to whole immunoglobulin G1 triple mutant (IgG1-TM, IgG1 Fc sequence incorporating mutations L234F, L235E and P331S) antibody format essentially as described by Persic et al. (1997, Gene, 187, 9-18) with the following modifications. An OriP fragment was included in the expression vectors to facilitate use with CHO-transient cells and to allow episomal replication. The variable heavy (VH) domain was cloned into a vector containing the human heavy chain constant domains and regulatory elements to express whole IgG1-TM heavy chain in mammalian cells. Similarly, the variable light (VL) domain was cloned into a vector for the expression of the human light chain (lambda) constant domains and regulatory elements to express whole IgG light chain in mammalian cells. To obtain IgGs, the heavy and light chain IgG expressing vectors were transfected into CHO-transient mammalian cells (Daramola et al. Biotechnol Prog 30(1):132-41 (2014)). IgGs were expressed and secreted into the medium. Harvests were filtered prior to purification, then IgG was purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralized by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG (Mach et al., Anal. Biochem. 200(1):74-80 (1992)). The purified IgG were analyzed for aggregation and degradation purity using SEC-HPLC and by SDS-PAGE.

Screening for pH Sensitive Par0067 Variant scFv's and IgG's

In order to screen for and profile antibodies with potential pH dependent binding a biochemical epitope competition assay format was used. The assay, which used Homogeneous Time Resolved Fluorescence (HTRF™) technology, was designed to evaluate the ability of test antibodies (scFv or IgG) to inhibit the interaction of the parent Par0067 IgG antibody binding to the human PAR2 extracellular domain (ECD). Importantly the assay was implemented at two different pH values (pH 7.4 and pH 6.0).

Parallel assays at pH 7.4 and pH 6.0 (as described above) were first used to screen crude un-purified scFv (bacterial extracts) in a single point 384 well high throughput screen (HTS). This single point parallel HTS format enabled the screening of many 1000's of test scFv and those antibodies which resulted in reduced inhibition of the interaction of parent Par0067 IgG binding to human PAR2 at pH 6.0 versus pH 7.4 were taken forward for further characterisation. Subsequently the same epitope competition assay approach was then implemented in a multipoint dose response $IC_{50}$ format to test both purified scFv and purified IgG (in the latter case a minor modification of the assay design was required as set out in Section C). Again assays were implemented at pH 7.4 and pH 6.0 however in these experiments we were most interested in test antibodies where dose response inhibition curves showed a large rightward shift (i.e. significantly increased $IC_{50}$ value) at pH 6.0 relative to corresponding dose response inhibition curves observed at pH 7.4.

The following protocol includes methods for both single point testing of crude un-purified scFv and subsequent testing of purified scFv and IgG.

Section A: Generic Assay Conditions:

Assay Buffers:

Assay buffers were made fresh on the day of use. For experiments at pH 7.4 DPBS (Gibco 14190-086) was supplemented with KF (0.4M) (VWR, 103444T) and BSA (0.1% w/v) (PAA, K05-013) followed by rechecking the pH and fine adjusting to pH 7.4 as required. For experiments at pH 6.0, while keeping all other buffer components identical with the pH 7.4 assay buffer outlined above, the pH 6.0 assay buffer was formulated using a base buffer of 200 mM MES (Sigma, M-5287) (as opposed to DPBS). After addition of KF (0.4 M) and BSA (0.1% w/v) the 200 mM MES based buffer was then adjusted to pH 6.0 with HCL.

Assay Plates:

Assays were performed using black shallow well 384 plates (Round bottom, non-binding) (Corning, 4514)

Assay Volume:

20 µl

Incubation and Plate Reading:

Assay plates were incubated for 2 hrs at RT before reading using a standard HTRF™ read protocol on an Envision plate reader.

Section B: Testing of scFv: (Un Purified Bacterial Lysates and Purified scFv)

Addition Order and Assay Components:

| | Total | nsb | Test |
|---|---|---|---|
| Par0067 IgG (x4 [final]) | 5 µl | 5 µl | 5 µl |
| Test scFv (x4 [final]) | — | — | 5 µl |
| Assay Buffer | 5 µl | 5 µl | — |
| Bio-human-PAR2 ECD (x4 [final]) | 5 µl | — | 5 µl |
| Assay Buffer | — | 5 µl | — |
| Europium Cryptate Labelled Streptavidin plus $XL^{665}$ labelled anti-human-Fc (both x4 [final]) | 5 µl | 5 µl | 5 µl |

Par0067 IgG Preparation/Addition:

Unlabelled purified Par0067 IgG (generated in house) was made up to a concentration of 4.44 nM (1.11 nM final [assay]) in each of the two assay buffers previously described in Section A (pH 7.4 & pH 6.0). 5 µl/well of the appropriate pH 4.44 nM Par0067 IgG solution was added to all wells of the relevant assay plate (pH 7.4 and pH 6.0).

Test scFv Preparation/Addition:

a) For parallel single point HTS of crude un-purified bacterial lysate scFv samples at both pH 7.4 and pH 6.0 samples were first pre-diluted to 40% of their neat concentration using either pH 7.4 or pH 6.0 assay buffer as appropriate. Subsequently 5 µl of 40% pre-diluted sample was then transferred into the appropriate assay (pH 7.4 or pH 6.0) in order to give a final assay sample concentration of 10.0% (in the 20 µl final assay volume). The parent Par0067 scFv was included in all HTS experiments as a control as were specific pH dependent antibodies as those became available (for benchmarking).

b) For multipoint dose response $IC_{50}$ testing of purified scFv antibody, samples were tested from a top final assay of ¼ of the neat undiluted sample (i.e. no pre-dilution step was performed). Duplicate 11 point 1:3 serial dilutions then were prepared on 384 well polypropylene Greiner plates in each of the two assay buffers (pH 7.4 & 6.0). 5 µl per well of each serial dilution was transferred from the relevant pH scFv dilution plate to the corresponding assay plate (pH 7.4 and pH 6.0). 5 µl of the appropriate pH assay buffer was added to the total and non-specific wells. The parent Par0067 purified scFv was included in all multipoint dose response $IC_{50}$ experiments as a control as were specific pH dependent purified scFv as those became available (for benchmarking). Data are presented in Table 1.

Biotinylated Human PAR2 ECD Preparation/Addition:

In house generated biotinylated human PAR2 ECD was diluted into each of the two assay buffers (pH 7.4 & pH 6.0) to give working solutions at 4.0 nM (1 nM final assay concentration). 5 µl/well of the appropriate 4.0 nM biotinylated human PAR2 ECD working solution was then added to all wells of the corresponding assay plate (pH 7.4 and pH 6.0) with the exception of the negative binding control wells. 5 µl/well of the appropriate pH assay buffer was added to the negative binding wells.

HTRF Detection Reagent Preparation/Addition:

Europium Cryptate Labelled Streptavidin (CisBio, 610SAKLB) and XL$^{665}$ Labelled Anti-Human-Fc (CisBio, 61HFCXLB) were each diluted into each pH assay buffer (pH 7.4, & pH 6.0) to give combined working solutions at concentrations of 6.0 nM (Europium Cryptate Labelled Streptavidin) and 40 nM (XL$^{665}$ Labelled Anti-Human-Fc). Allowing for the ×4 fold dilution into the assay this resulted in final assay concentrations of 1.5 nM (Europium Cryptate Labelled Streptavidin) and 10 nM (XL$^{665}$ Labelled Anti-Human-Fc). 5 µl/well of the relevant pH combined HTRF™ detection reagent working solution was then added to all wells of the corresponding assay plate (pH 7.4 and pH 6.0).

Section C: Testing of Purified IgG:

Addition Order and Assay Components:

|  | Total | nsb | Test |
|---|---|---|---|
| Dylight$^{650}$ labelled Par0067 IgG (x4 [final]) | 5 µl | 5 µl | 5 µl |
| Test IgG (x4 [final]) | — | — | 5 µl |
| Assay Buffer | 5 µl | 5 µl | — |
| Bio-human-PAR2 ECD (x4 [final]) | 5 µl | — | 5 µl |
| Assay Buffer | — | 5 µl | — |
| Europium Cryptate Labelled Streptavidin (x4 [final]) | 5 µl | 5 µl | 5 µl |

Par0067 IgG Dylight650 Labelling:

Dylight$^{650}$ labelling of Par0067 IgG was performed using a Dylight$^{650}$ labelling kit (Thermo Scientific Cat. No. 84536). Labelling of in-house generated purified Par0067 IgG was performed according to the manufacturer's recommended labelling procedure. The final Dylight$^{650}$ labelled Par0067 IgG concentration was determined as 0.56 mg/ml with a mean Dylight$^{650}$ to IgG dye incorporation ratio of 2.7 moles dye/mole IgG.

Dylight$^{650}$ Labelled Par0067 IgG Preparation/Addition:

Dylight$^{650}$ labelled Par0067 IgG (0.56 mg/ml, 3,733 nM) was made up to a concentration of 4.44 nM (to give 1.11 nM final [assay]) in each of the two assay buffers previously described in the materials section (pH 7.4 & pH 6.0). 5 µl/well of the appropriate pH 4.44 nM Dylight$^{650}$ Par0067 IgG solution was added to all wells of the relevant assay plate (pH 7.4 and pH 6.0).

Test IgG Serial Dilution/Addition:

Parent Par0067 IgG (used as a reference/control in all assays) was pre-diluted to give a 2000 nM stock in each of the two different pH assay buffers (in order to give a top final assay IgG concentration of 500 nM). All test, or other reference/control IgG were tested from a top final assay concentration of ¼ of the neat undiluted sample (i.e. no pre-dilution step was performed). Duplicate 11 point 1:3 serial dilutions then were prepared on 384 well polypropylene Greiner plates in each of the two assay buffers (pH 7.4 & 6.0). 5 µl per well was transferred from the relevant pH IgG dilution plate to the corresponding assay plate (pH 7.4 and pH 6.0). 5 ul of the appropriate pH assay buffer was added to the total and non-specific wells.

Biotinylated Human PAR2 ECD Preparation/Addition:

In house generated biotinylated human PAR2 ECD was diluted into each of the two assay buffers (pH 7.4 & pH 6.0) to give working solutions at 4.0 nM (1 nM final assay concentration). 5 µl/well of the appropriate 4.0 nM biotinylated human PAR2 ECD working solution was then added to all wells of the corresponding assay plate (pH 7.4 and pH 6.0) with the exception of the negative binding control wells. 5 µl/well of the appropriate pH assay buffer was added to the negative binding wells.

HTRF Detection Reagent Preparation/Addition:

Europium Cryptate Labelled Streptavidin (CisBio, 610SAKLB) was diluted into each pH assay buffer (pH 7.4, & pH 6.0) to give work solutions at a concentration of 6.0 nM. Allowing for the ×4 fold dilution into the assay this resulted in a final assay Europium Cryptate Labelled Streptavidin concentration of 1.5 nM. 5 µl/well of the relevant pH Europium Cryptate Labelled Streptavidin working solution was then added to all wells of the corresponding assay plate (pH 7.4 and pH 6.0).

Section D: Data Analysis:

665 nm and 620 nm counts were first converted to 665/620 ratio values. Delta F (%) was then calculated according to the following equation:

Delta $F(\%)$=((sample ratio−negative ratio)/negative ratio)*100

Negative ratio values were calculated in the absence of Par0067 IgG from the relevant negative binding control wells.

% Specific Binding was then calculated according to the following equation:

% Specific Binding={(Sample % Delta $F$−Negative Binding % Delta $F$)/(Total Binding % Delta $F$−Negative Binding % Delta $F$)}*100

For single point HTS % Specific Binding at pH 6.0 versus pH 7.4 was plotted on x and y axes, respectively, in order to visualise the distribution of scFv with reduced inhibition (higher % Specific Binding) at pH 6.0 relative to pH 7.4.

For multipoint dose response curves % Specific Binding values were plotted versus test purified antibody concentration (scFv or IgG). $IC_{50}$ values were determined via a sigmoidal dose response inhibition variable slope curve fit (4 parameter logistic equation) using Graphpad Prism Software.

TABLE 1

Par0067 Epitope Competition Assay

| Clone (scFv) | pH 7.4 $IC_{50}$ (nM) | pH 6.0 $IC_{50}$ (nM) | Variant: Fold $IC_{50}$ (pH 6.0 v pH 7.4) | Fold $IC_{50}$ pH 7.4 (Variant v Par0067) |
|---|---|---|---|---|
| Par0067 | 3.3 | 3.6 | 1.1 | 1.0 |
| PaB670010 | 15.4 | 41.8 | 2.7 | 4.7 |
| PaB670020 | 5.6 | 18.5 | 3.3 | 1.7 |
| PaB670034 | 5.6 | 14.2 | 2.5 | 1.7 |
| PaB670045 | 9.8 | 72.5 | 7.4 | 3.0 |
| PaB670048 | 14.5 | 139.4 | 9.6 | 4.4 |
| PaB670064 | 67.1 | 289.9 | 4.3 | 20.3 |
| PaB670066 | 52.2 | 486.9 | 9.3 | 15.8 |
| PaB670067 | 14.4 | 113.2 | 7.9 | 4.4 |
| PaB670068 | 77.8 | 447.6 | 5.8 | 23.6 |
| PaB670070 | 60.4 | 270.0 | 4.5 | 18.3 |
| PaB670071 | 101.2 | 424.8 | 4.2 | 30.7 |
| PaB670073 | 72.1 | 428.3 | 5.9 | 21.8 |
| PaB670075 | 101.8 | 603.0 | 5.9 | 30.8 |
| PaB670076 | 46.2 | 291.8 | 6.3 | 14.0 |
| PaB670077 | 55.4 | 619.9 | 11.2 | 16.8 |
| PaB670078 | 33.3 | 319.2 | 9.6 | 10.1 |
| PaB670079 | 44.2 | 489.8 | 11.1 | 13.4 |
| PaB670080 | 16.6 | 158.1 | 9.5 | 5.0 |
| PaB670081 | 51.4 | 260.0 | 5.1 | 15.6 |
| PaB670082 | 25.4 | 77.9 | 3.1 | 7.7 |
| PaB670083 | 45.2 | 151.8 | 3.4 | 13.7 |
| PaB670084 | 54.5 | 282.7 | 5.2 | 16.5 |
| PaB670085 | 48.1 | 154.7 | 3.2 | 14.6 |
| PaB670087 | 40.9 | 130.7 | 3.2 | 12.4 |
| PaB670088 | 29.8 | 114.7 | 3.8 | 9.0 |
| PaB670089 | 29.9 | 134.0 | 4.5 | 9.1 |
| PaB670090 | 22.6 | 85.5 | 3.8 | 6.8 |
| PaB670091 | 25.2 | 98.9 | 3.9 | 7.6 |
| PaB670092 | 41.1 | 193.5 | 4.7 | 12.5 |
| PaB670093 | 18.6 | 58.7 | 3.2 | 5.6 |
| PaB670094 | 72.5 | 236.8 | 3.3 | 22.0 |
| PaB670095 | 20.0 | 113.2 | 5.7 | 6.1 |
| PaB670097 | 21.8 | 77.9 | 3.6 | 6.6 |
| PaB670098 | 65.9 | 210.3 | 3.2 | 20.0 |
| PaB670099 | 12.9 | 62.4 | 4.8 | 3.9 |
| PaB670100 | 20.3 | 69.0 | 3.4 | 6.2 |
| PaB670101 | 146.9 | 496.5 | 3.4 | 44.5 |
| PaB670102 | 5.3 | 13.7 | 2.6 | 1.6 |
| PaB670103 | 27.9 | 203.5 | 7.3 | 8.5 |
| PaB670104 | 21.7 | 202.2 | 9.3 | 6.6 |
| PaB670105 | 74.4 | 495.5 | 6.7 | 22.5 |
| PaB670106 | 312.8 | 1188.0 | 3.8 | 94.8 |
| PaB670107 | 42.7 | 463.9 | 10.9 | 12.9 |
| PaB670108 | 29.1 | 148.6 | 5.1 | 8.8 |

Recombination of Multiple Histidines into a Single scFv

Histidine residues from scFv which demonstrated pH dependent binding in the Par0067 epitope competition binding assay were recombined using site directed mutagenesis (Reikofski J and Tao B Y, 1992, Biotechnol Adv, 10(4): 535-547). Resulting scFv which contained histidines in two different CDRs were retested in the competition binding assay as whole immunoglobulin G1 triple mutant (IgG1-TM) (Table 2) to identify variants with further improvements in pH dependent binding compared to the parent antibody, Par0067.

Sequence alignments for each of the histidine modified clones as compared to the reference Par0067 antibody CDR sequences are provided in FIGS. 1A-1B and 2A-2B.

TABLE 2

Par0067 Epitope Competition Assay

| Clone (IgG) | pH 7.4 $IC_{50}$ (nM) | pH 6.0 $IC_{50}$ (nM) | Variant: Fold $IC_{50}$ (pH 6.0 v pH 7.4) | Fold $IC_{50}$ pH 7.4 (Variant v Par0067) |
|---|---|---|---|---|
| Par0067 | 0.835 | 0.790 | 0.95 | 1.00 |
| PaB670045 | 2.9 | 25.8 | 8.9 | 3.5 |
| PaB670048 | 5.7 | 48.2 | 8.5 | 6.8 |
| PaB670128 | 32.8 | IC | ND | 39.3 |
| PaB670129 | 56.1 | IC | ND | 67.2 |
| PaB670084 | 10.3 | 64.6 | 6.3 | 12.3 |
| PaB670141 | 2.4 | 13.9 | 5.9 | 2.8 |
| PaB670142 | 4.8 | 67.1 | 14.0 | 5.7 |
| PaB670143 | 3.4 | 40.0 | 11.8 | 4.0 |
| PaB670144 | 29.0 | 564.8 | 19.5 | 34.7 |
| PaB670146 | 91.9 | 784.3 | 8.5 | 110.1 |
| PaB670148 | 48.5 | 844.6 | 17.4 | 58.1 |
| PaB670149 | 504.9 | IC | ND | 604.7 |
| PaB670151 | 69.5 | 796.0 | 11.5 | 83.2 |
| PaB670152 | 438.8 | 6604.0 | 15.1 | 525.5 |
| PaB670153 | 93.0 | 1639.0 | 17.6 | 111.4 |
| PaB670156 | 7.0 | 190.0 | 27.2 | 8.4 |
| PaB670157 | 15.8 | 932.4 | 59.0 | 18.9 |
| PaB670158 | 6.8 | 477.0 | 69.8 | 8.2 |
| PaB670159 | 161.0 | IC | ND | 192.8 |
| PaB670160 | 16.9 | 634.3 | 37.5 | 20.2 |
| PaB670161 | 47.9 | 1899.0 | 39.6 | 57.4 |
| PaB670162 | 11.4 | 906.2 | 79.5 | 13.7 |
| PaB670163 | 145.1 | IC | ND | 173.8 |

IC = Incomplete Curve;
ND = Not Demonstrated

Affinity of Anti-PAR2 Fabs for Human, Rat and Cynomolgus PAR2 as Determined by BIACORE™

Antigen binding fragments (Fabs) of the anti-PAR2 antibodies were expressed (Spooner J. et al. (2015) Biotechnol Bioeng. 112:1472-7) and the affinity for recombinant PAR2 of various species (human, rat and cynomolgus) determined by Biacore.

Biacore Affinity Analysis

The affinity of the anti-PAR2 Fabs was measured using the Biacore T100 at 25° C. at various pH's (pH 7.4, pH 6.0 and pH 5.6). The experiments were carried out using recombinant human, rat and cynomolgus PAR2 with an N-terminal Avi tag and C-terminal Flag-His tags.

Streptavidin was covalently immobilised to a C1 chip surface using standard amine coupling techniques at a concentration of 4 µg/ml in 10 mM Sodium acetate pH 4.5. A final streptavidin surface of approximately 30-100 RUs was achieved. Recombinant biotinylated PAR2 species (produced in-house) were titrated onto the streptavidin chip surface at 4 µg/ml in HBS-EP+ buffer to enable Fab binding at saturation ($R_{max}$). This low level of analyte binding ensured minimal mass transport effects.

The anti-PAR2 Fabs were serially diluted (0.39 nM-25 nM) in HBS-EP+ buffer pH 7.4 or MES-BS-EP+ pH 6.0 buffer or in MES-BS-EP+ pH 5.6 buffer and flowed over the chip at 50 µl/min, with 3 minutes association and up to 30 minutes dissociation. Multiple buffer-only injections were made under the same conditions to allow for double reference subtraction of the final sensorgram sets, which were analysed using the BiaEval software (version 2.0.1). The chip surface was fully regenerated with pulses of 4 M $MgCl_2$.

BiaCore affinity results for select clones are provided below in Tables 3-13.

TABLE 3

Par0067 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 6.66E+6 | 4.96E-5 | 7.5 | 50.1 |
| 6.0 | Human | 3.12E+6 | 9.72E-5 | 31.2 | 39.3 |
| 7.4 | Rat | 5.16E+6 | 1.94E-4 | 37.6 | 111 |
| 6.0 | Rat | 3.21E+6 | 5.44E-4 | 170 | 100 |

TABLE 4

PaB670048 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 4.20E+6 | 5.19E-4 | 124 | 69.0 |
| 6.0 | Human | 1.94E+6 | 4.97E-3 | 2569 | 58.3 |
| 7.4 | Rat | 5.24E+6 | 3.07E-3 | 586 | 124.7 |
| 6.0 | Rat | 4.00E+6 | 2.05E-2 | 5120 | 105.2 |

TABLE 5

PaB670084 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 6.49E+6 | 1.62E-3 | 250 | 68.4 |
| 6.0 | Human | 1.73E+6 | 7.63E-3 | 4,410 | 104.6 |
| 7.4 | Rat | 6.83E+6 | 8.37E-3 | 1226 | 97.6 |
| 6.0 | Rat | 2.57E+6 | 2.77E-2 | 10,800 | 91.97 |

TABLE 6

PaB670076 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 5.84E+6 | 1.21E-3 | 207 | 63.5 |
| 6.0 | Human | 1.11E+6 | 5.14E-3 | 4,611 | 99.51 |
| 7.4 | Rat | 6.34E+6 | 1.07E-2 | 1,689 | 87.9 |
| 6.0 | Rat | 1.66E+6 | 5.10E-2 | 30,730 | 82.61 |

TABLE 7

PaB670120 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 5.54E+6 | 1.37E-3 | 247 | 61.62 |
| 6.0 | Human | 3.48E+6 | 2.10E-2 | 6,047 | 94.67 |
| 7.4 | Rat | 5.62E+6 | 1.46E-2 | 2,606 | 84.23 |
| 6.0 | Rat | 8.26E+6 | 0.281 | 34,040 | 73.35 |

TABLE 8

PaB670128 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 5.95E+6 | 3.65E-3 | 613 | 59.57 |
| 6.0 | Human | 2.22E+6 | 4.57E-2 | 20,062 | 79.4 |
| 7.4 | Rat | 6.49E+6 | 1.96E-2 | 3,023 | 80.86 |
| 6.0 | Rat | 1.79E+6 | 6.89E-2 | 38,520 | 63.26 |

TABLE 9

PaB670048 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 5.59E+6 | 5.80E-4 | 104 | 58.53 |
| 6.0 | Human | 1.84E+6 | 4.58E-3 | 2,488 | 93.02 |
| 7.4 | Rat | 7.46E+6 | 3.25E-3 | 435 | 81.2 |
| 6.0 | Rat | 4.84E+6 | 2.17E-2 | 4,483 | 80.14 |

TABLE 10

PaB670129 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 8.20E+6 | 5.04E-3 | 614 | 54.98 |
| 6.0 | Human | 1.59E+6 | 5.54E-2 | 34,840 | 76.02 |
| 7.4 | Rat | 8.82E+6 | 2.63E-2 | 2,979 | 73.16 |
| 6.0 | Rat | 1.45E+6 | 8.41E-2 | 57,910 | 67.27 |

TABLE 11

PaB670136 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 5.17E+6 | 4.95E-3 | 957 | 50.27 |
| 6.0 | Human | 7.92E+8 | 14.9 | 18,840 | 67.97 |
| 7.4 | Rat | 7.57E+6 | 3.14E-2 | 4,149 | 73.24 |
| 6.0 | Rat | 1.57E+6 | 5.89E-2 | 37,550 | 47.7 |

TABLE 12

PaB670103 Fab.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 3.52E+6 | 1.11E-4 | 32.5 | 46.3 |
| 6.0 | Human | 3.36E+5 | 6.07E-4 | 1,805 | 70.66 |
| 7.4 | Rat | 3.04E+6 | 5.58E-4 | 184 | 74.2 |
| 6.0 | Rat | 5.31E+5 | 5.42E-3 | 10,200 | 69.58 |

TABLE 13

PaB670129 Fab at 3 different pH's.

| pH | Species | $k_a$ (M$^{-1}$ s$^{-1}$) | $k_d$ (s$^{-1}$) | $K_D$ (pM) | Rmax |
|---|---|---|---|---|---|
| 7.4 | Human | 7.14E+6 | 5.34E-3 | 747.8 | 75.9 |
|  |  | 6.81E+6 | 5.30E-3 | 778.0 | 66.5 |
| 6.0 | Human | 1.56E+6 | 5.76E-2 | 36,910 | 58.1 |
|  |  | 3.26E+6 | 0.109 | 33,500 | 48.4 |
| 5.6 | Human | 1.33E+6 | 0.112 | 84,550 | 42.5 |
| 7.4 | Cynomolgus | 6.67E+6 | 2.23E-3 | 333.3 | 59.7 |
|  |  | 6.59E+6 | 2.21E-3 | 335.0 | 51.9 |
| 6.0 | Cynomolgus | 2.14E+6 | 2.75E-2 | 12,840 | 49.6 |
|  |  | 1.74E+6 | 2.36E-2 | 13,560 | 44.2 |
| 5.6 | Cynomolgus | 3.66E+6 | 0.139 | 37,840 | 41.3 |

Example 2: Cell-Based PAR2 and PAR1 Activity Assay

Human A549 cells, rat KNRK, mouse LL/2 or cynomolgus CYNOM-K1 cells expressing endogenous PAR2, or human 1321N1-hPAR2-cl8 cells overexpressing human PAR2 were seeded at 5,000 (human, cyno) or 7,000 (mouse, rat) cells per well on PDL-coated Tissue Culture Plates, (Greiner Bio-One). Cells were loaded with Fluo-Screen Quest™ Fluo-8 No Wash Calcium dye (AAT Bioquest, Inc). Cells were pre-treated with IgGs or Fabs diluted in assay buffer (HBSS, 0.1% BSA, 20 mM HEPES) for 1 h at room temperature. For mouse and cyno assays, cells were pre-treated with 0.5 nM or 10 nM thrombin, respectively, to desensitize PAR1 activity. PAR2 calcium responses to 11 nM (human), 400 nM (mouse) or 80 nM (rat, cyno) trypsin (Polymun) were measured on a Fluorescent Imaging Plate Reader (FLIPR) Tetra (Molecular Devices). To determine functional activity against human PAR1, thrombin driven calcium responses in the A549 human cell line were determined also on the FLIPR tetra and in these assays neutralising anti-PAR1 IgGs WEDE15 (Beckman Coulter) and ATAP2 (Life Technologies) were used as positive controls. To determine functional activity against diverse proteases, 1321N1-hPAR2-cl8 cells overexpressing human PAR2 were pre-treated with PaB670129, prior to stimulating calcium release with 0.5 nM trypsin, 500 nM tryptase or 1 nM matriptase. Fluorescence measurements were measured before, during, and after protease addition and peak RFU calculated per well. % responses (relative to protease alone) were calculated against antibody concentration and IC50s determined using GraphPad Prism software.

Figure 4B:
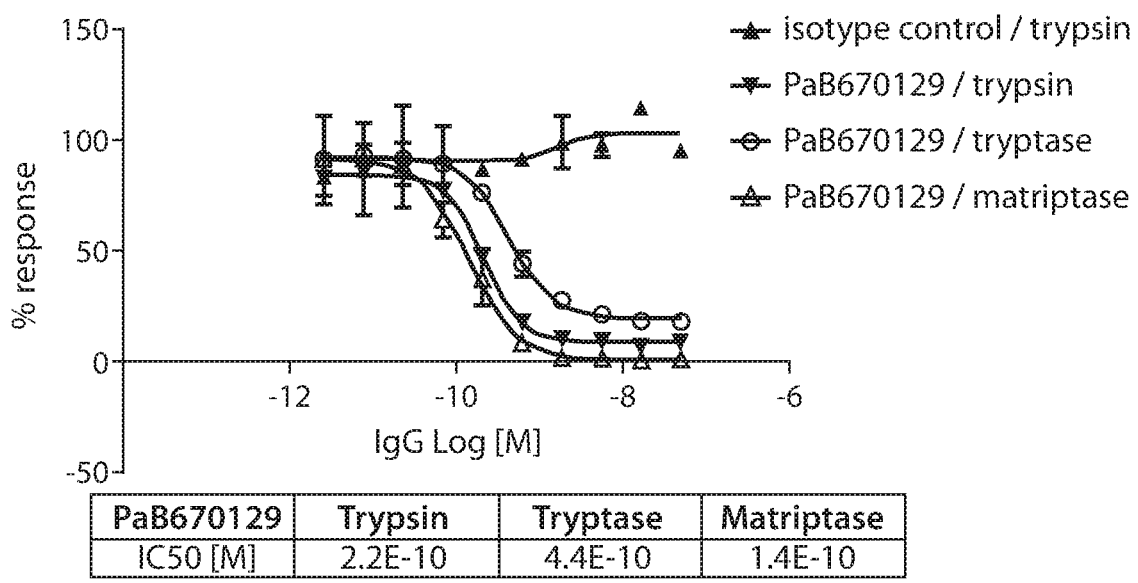
FIG. 4B provides IC50 curves for PaB670129 against different PAR2 protease activators.
Figure 6:
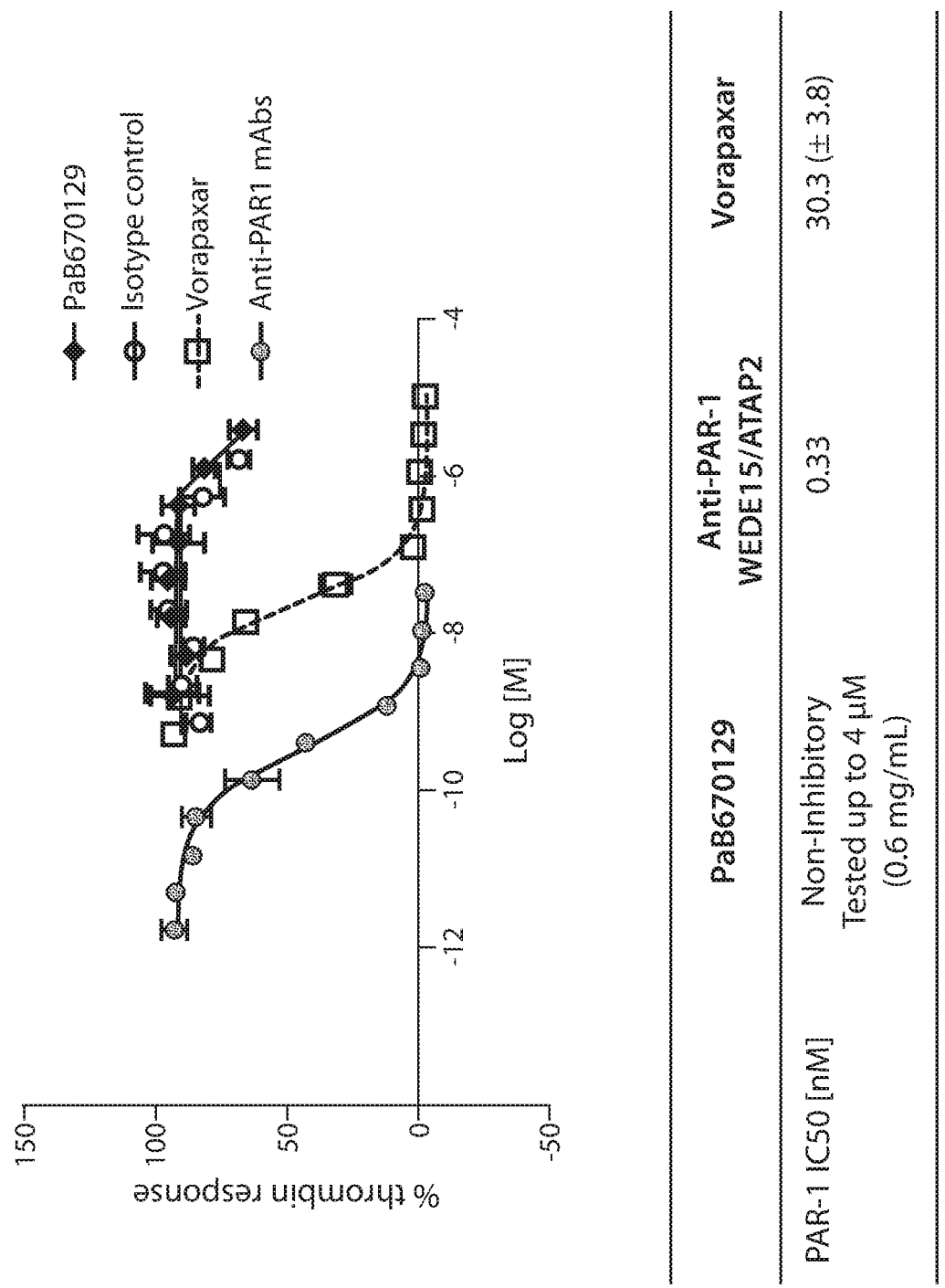
FIG. 6 illustrates the effects of PaB670129 (versus anti-PAR1 antibodies or Vorapaxar) on thrombin-induced PAR1 activation in human A549 cells.

Results from human, cynomologus-monkey, rat, and mouse cells in these assays are provided in FIGS. 3A-3D, respectively, calculated PAR2 IC50s in FIG. 3E and FIG. 6 (PAR1 specificity data). IC50 calculations demonstrate that PaB670129 potently inhibits trypsin-induced PAR2 calcium responses in human, mouse, rat and cyno cells expressing endogenous PAR2 (FIG. 3E). Furthermore in human A549 cells, thrombin-induced PAR1 activation is not inhibited by PaB670129 but can be effectively blocked by the Vorapaxar and anti-PAR1 monoclonal antibodies (FIG. 6). These data demonstrate that PaB670129 is a potent and specific antagonist of PAR2. Application of PaB670129 alone to PAR2-expressing cells has no effect on basal cellular calcium levels, demonstrating that PaB670129 lacks any agonistic activity at PAR2 (FIG. 4A). Furthermore, PaB670129 potently antagonizes PAR2-evoked responses to diverse proteases including trypsin, tryptase and matriptase (FIG. 4B).

Primary DRG Glial-Neuronal PAR2 Calcium Assay

Figure 5F:
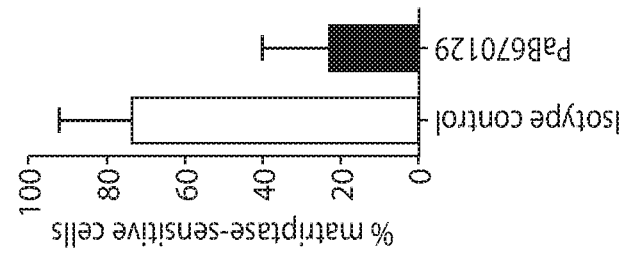
Figure 5E:
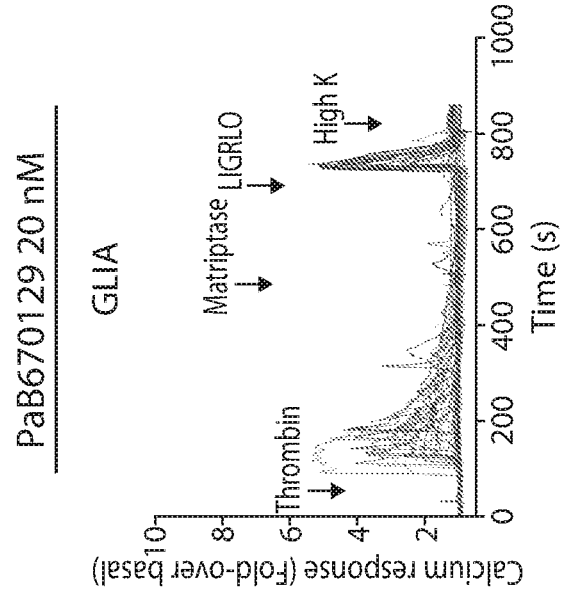
Figure 5D:
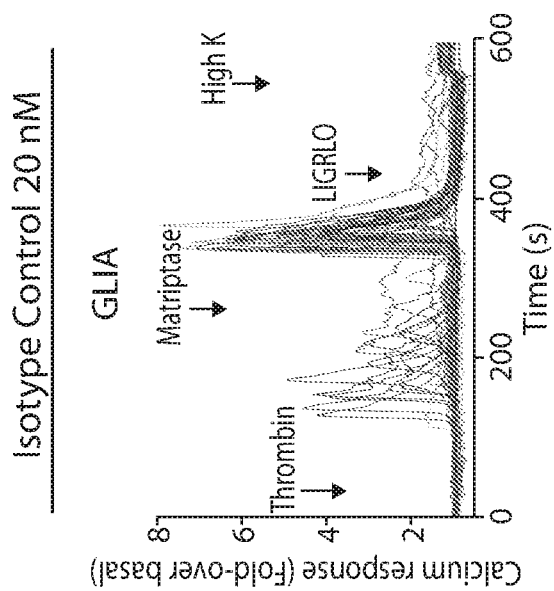

Dissociated cultures of Sprague dawley rat pup dorsal root ganglia (DRG) were prepared and grown on laminin and PDL-coated Tissue Culture Plates (Greiner Bio-One). Plates were incubated at 37 degrees for 24-72 hours before use in the assay. Cells were loaded with 2 Fura-2 calcium dye (Life Technologies). Cells were incubated in imaging buffer (HBSS, 20 mM HEPES, 0.1 mM Sulfinpyrazone, 10 µM PAR1 antagonist Vorapaxar) containing PAR2 antibodies at 20 nM. Intracellular calcium was then quantified by Fura-2 ratiometric imaging on an Olympus IX81 microscope equipped with a Xenon arc lamp exciting at 340 and 380 nm in response to application of the agonists thrombin (Sigma) and matriptase (R&D Systems) PAR2 activating peptide LIGRLO (SEQ ID NO: 832), (Peptides International) and high extracellular potassium (50 mM). Number of neurones versus glia was calculated per field of view (neurones defined as showing response to high potassium). Total matriptase-sensitive neurones and glia were then calculated per field of view. Results from the calcium assay are provided in FIGS. 5A-F and illustrate that the PaB670129 antibody effectively reduced sensitivity to matriptase in DRG neuronal (FIG. 5A-C) and non-neuronal cells (FIG. 5D-F).

Example 3: Effects of an Anti-PAR2 Antibody in a Rat Model of Inflammatory Joint Pain Intra-articular administration of Monosodium Iodoacetate (MIA) in the ipsilateral knee of Sprague Dawley rats leads to development of a robust and long-lasting hyperalgesia and allodynia associated initially with an inflammatory response. The development of these signs in this animal model are believed to be clinically relevant; reflecting the symptoms displayed by patients presenting with chronic inflammatory pain associated with underlying conditions such as osteoarthritis (OA) or rheumatoid arthritis (Bove et al., 2003; Fernihough et al., 2004; Kalbhen 1987). It has previously been demonstrated that (using weight-bearing as an end-point) the time course of MIA induced hyperalgesia follows a bi-phasic pattern with an early, predominantly inflammatory, component which is Cox-2 sensitive; and markedly reduced by the gold standard Celecoxib. This early inflammatory phase gives way to a more chronic pain phenotype which is Pregabalin (PGB) sensitive and Celecoxib insensitive suggesting an underlying more neuropathic-type component.

Weight Bearing:

Naive rats distribute their body weight equally between the two hind paws. However, when the injected (left) hind knee is inflamed and/or painful, the weight is re-distributed so that less weight is put on the affected limb (decrease in weight bearing on injured limb). Weight bearing through each hind limb is measured using a rat incapacitance tester (Linton Instruments, UK).

Sprague Dawley rats were placed in the incapacitance tester with the hind paws on separate sensors and the average force exerted by both hind limbs was recorded over 4 seconds.

Procedure:

After delivery, rats underwent a minimum habituation period of 7 days prior to study commencement. Naïve rats were acclimatised to the procedure room in their home cages, with food and water available ad libitum. Habituations to the weight bearing chamber were performed over several days. Base line weight bearing readings were taken on the final day.

On Day 0, following the final baseline reading, animals were anaesthetised using isoflurane and oxygen mixed 3:1 in sterile conditions. The left knee area was shaved and cleaned with a dilute hibiscrub solution.

Osteoarthritis (OA) was induced via injection of MIA (Sigma, 12512) solution, 25 µl of 80 mg/ml, (2 mg) into the knee joint of the left hind leg. Sham animals were injected with saline. Animals were allowed to recover in a warmed environment, before being returned to their home cage.

Animals develop an inflammatory response post MIA and may guard and lick the affected area. Rats were therefore carefully monitored for unexpected signs of distress or severe pain, so that any animal displaying such signs could be culled immediately.

Animals were weighed daily for the first week and then every few days after. Weight bearing was assessed on Days 3, 7, 10 & 14, following injection of MIA, for development of chronic pain. On day 18, weight bearing measurements were taken and animals were ranked and randomised to treatment groups according to their MIA window in a Latin square design.

Antibody Dosing Regimen:

Animals were treated with Par0067 (PAR2+ve) 10 mg/kg or isotype control (PAR2-ve) 10 mg/kg i.v. on day 18 and further weight bearing measurements were taken 4 hours and 1, 2, 6, 8, 10 & 14 days post antibody dosing.

Pregabalin & Celecoxib Dosing Regimen:

Animals were dosed with PGB (30 mg/kg p.o; 2 ml/kg) or Celecoxib (50 mg/kg p.o; 2 ml/kg) daily on days 24, 25, 26, 27 and 28 post MIA injection. Weight bearing assessments were taken 1 hr post dosing on days 24, 26 and 28 and a further reading was taken post cessation of drug treatment on day 32.

On day 1, 2, 6, 10 and 14 post dosing, after weight bearing assessment, 400 µl of blood was taken via the tail vein for pk analysis from Antibody and Isotype control treated groups (n=5/group).

Evaluation of Study:

Weight bearing (g) readings were taken for both right and left hind paws and the difference calculated. Data are expressed as % ratio ipsilateral/contralateral ((WB left/WB right)*100) (mean±s.e.m.).

Calculation:

Ipsilateral reading/contralateral reading×100. Naïve WB difference−pre dose WB difference was defined as the MIA window.

Statistical Analysis:

Repeated measures ANOVA followed by Planned comparison test using InVivoStat (invivostat.co.uk), (p<0.05 considered significant). Data were analysed by comparing treatment groups to vehicle control group at each time point.

Injection of 2 mg MIA into the knee joint caused a marked inflammation and hypersensitivity response apparent from day 3 as detected by a shift in weight bearing between injured and non-injured hind paws. This MIA-induced hyperactivity response was still evident in all groups up until day 18 (and beyond for vehicle-treated control animals) at which point the first test agents were administered. Injection of saline had no effect on weight bearing.

Figure 7A:
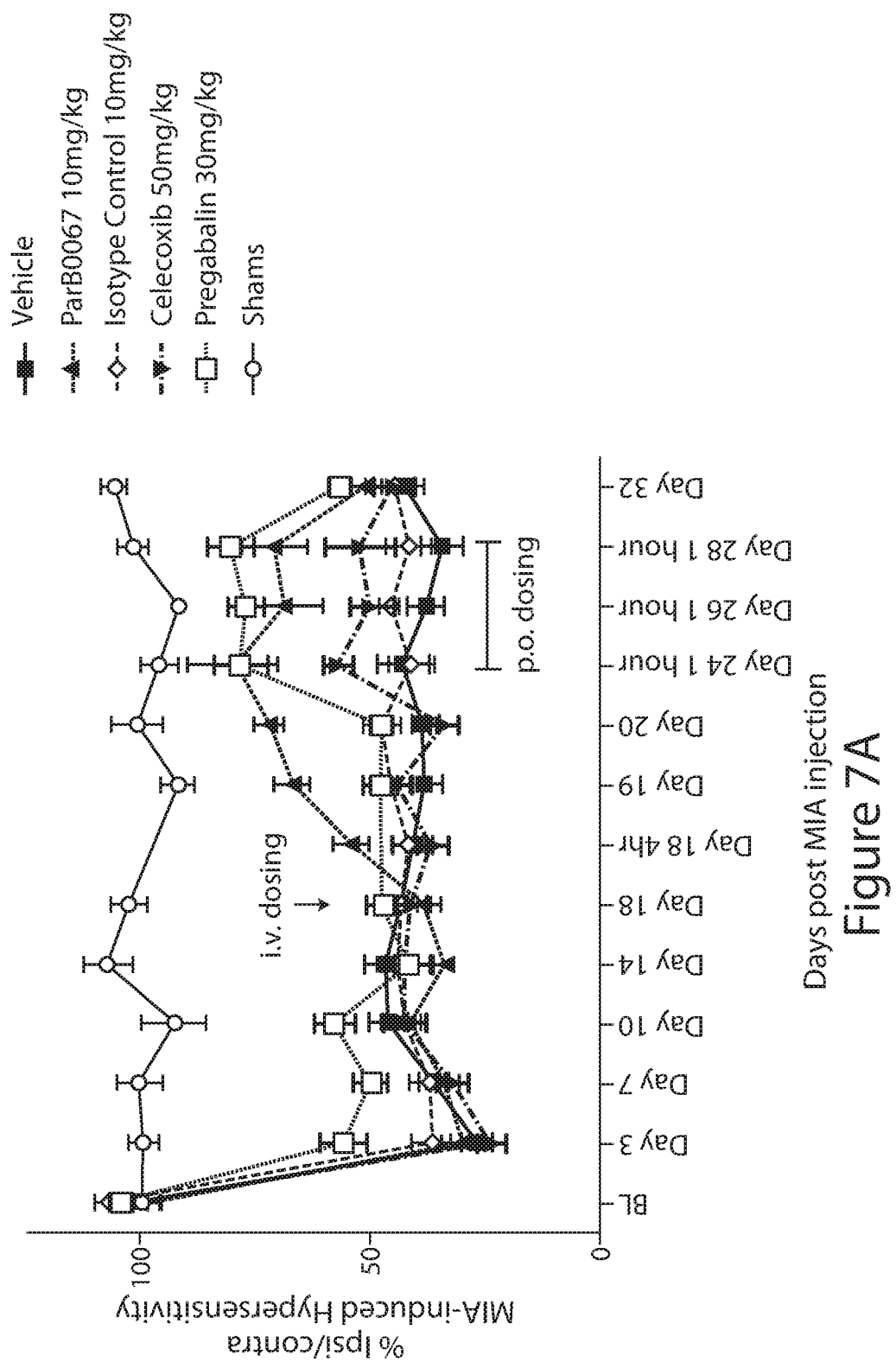
FIG. 7A depicts a graph illustrating the effect of different treatments (including a PAR2 antibody, Par0067) on the percent ipsilateral/contralateral hypersensitivity induced by monoiodoacetate (MIA) in rat.

As demonstrated in FIG. 7A, a significant and marked reversal of hypersensitivity was seen after daily administration of Pregabalin (30 mg/kg) from day 24-28 with a weak residual effect still apparent after prior cessation of treatment on day 32. In contrast, daily administration of Celecoxib (50 mg/kg) from day 24-28 showed only a weak reversal of hypersensitivity at best. This pharmacological profile suggests that the hyperactivity observed during this phase of the MIA response is predominantly neuropathic, rather than inflammatory, in nature.

Figure 7B:
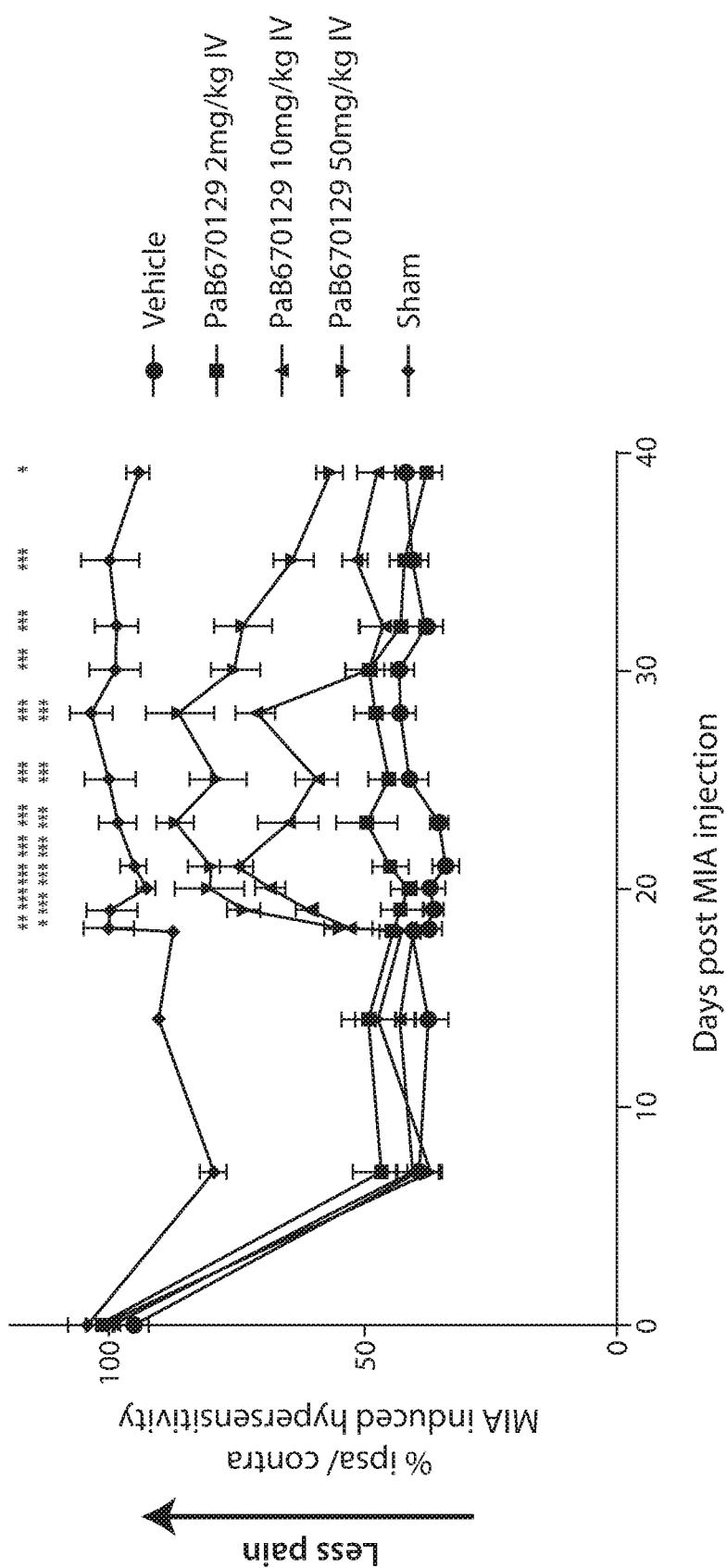
FIG. 7B depicts a graph illustrating the effect of different doses of PaB670129 or an isotype control antibody on the percent ipsilateral/contralateral hypersensitivity induced by MIA in rat. "i.v." means intravenous, and "p.o." means per os (oral). Statistical analysis—Repeated measures ANOVA, followed by a planned comparison test, using invivostat. Significant hyperalgesia (*** $P<0.001$) post injection of MIA with vehicle from day 7 to day when compared to baseline and sham. * $P<0.05$,  $P<0.01$, * $P<0.001$ Significant reversal of hyperalgesia when compared to vehicle at each time point.

As also demonstrated in FIG. 7A, a significant reversal of hypersensitivity was seen with Par0067 from 4 hours post dose, through until day 28 (10 days post dose). No effect was seen with Isotype Control during the same time period. FIG. 7B illustrates the effect of treatment with different concentrations of Par0067.

Example 4: The Effect of the PAR2 Antibody, PaB670129 on Reversal of Partial Nerve Ligation—Induced Mechanical Hyperalgesia in Female C57BL/6 Mice Introduction Partial ligation of the sciatic nerve (PNL) as described by Seltzer (1990) is one of a number of nerve ligation models which are reported to serve as pre-clinical models of neuropathic pain. It produces a profound mechanical hyperalgesia which can be measured using an analgysemeter as described by Randall and Selitto (1957). This example describes the effects of the administration of the anti PAR2 antibody PaB670129, on hyperalgesia in this nerve injury/neuropathic pain model.

Procedure

Sixty female C57BL/6 mice underwent insertion of transponders for identification purposes at least 5 days before the start of the study. Mechanical hyperalgesia was determined using an analgysemeter (Randall & Selitto 1957) (Ugo Basile). An increasing force was applied to the dorsal surface of each hind paw in turn until a withdrawal response was observed. The application of force was halted at this point and the weight in grams recorded. Data was expressed as withdrawal threshold in grams for ipsilateral and contralateral paws. Following the establishment of baseline readings, mice were divided into 2 groups with approximately equal ipsilateral/contralateral ratios which underwent surgery to partially ligate the sciatic nerve or served as sham operated controls. Operated mice were anaesthetised with isoflurane. Following this, approximately 1 cm of the left sciatic nerve was exposed by blunt dissection through an incision at the level of the mid thigh. A suture (8/0 Virgin Silk: Ethicon) was then passed through the dorsal third of the nerve and tied tightly. The incision was then closed using glue and the mice were allowed to recover for at least six days prior to commencement of testing. Sham operated mice underwent the same protocol, but following exposure of the nerve, the mice were sutured and allowed to recover.

Mice were tested for onset of hyperalgesia on days 7 and 10 post surgery. Any mice showing an ipsilateral/contralateral ratio of greater than 80% were classed as non-responders and removed from the study. Following testing on day 10, mice were further sub-divided into groups giving the final treatment groups;

A. Group 1: Sham operated+Isotype control 10 mg/kgs.c (N=10)

B. Group 2: Nerve Ligated+Isotype control 10 mg/kgs.c (N=9)

C. Group 3: Nerve ligated+Etanercept 0.3 mg/kg s.c. (N=9)

D. Group 4: Nerve ligated+PaB670129 3 mg/kg s.c. (N=9)

E. Group 5: Nerve ligated+PaB670129 10 mg/kg s.c. (N=9)

F. Group 6: Nerve ligated+PaB670129 50 mg/kg s.c. (N=9)

Mice were administered control or test molecules diluted in Phosphate Buffered Saline, (PBS) on day 13 and were re-tested for changes in mechanical hyperalgesia at 4 hours post dose and also on 1, 2, 4 and 7 days post dose.

Data Analysis

Ipsilateral and contralateral readings were taken for each animal at each test time. Weight bearing through ipsilateral and contralateral hind limbs was expressed as a ratio and the group data were analysed (PRISM) using 2-way ANOVA and pairwise comparisons where appropriate were made using Tukey's test.

Results

Figure 8:
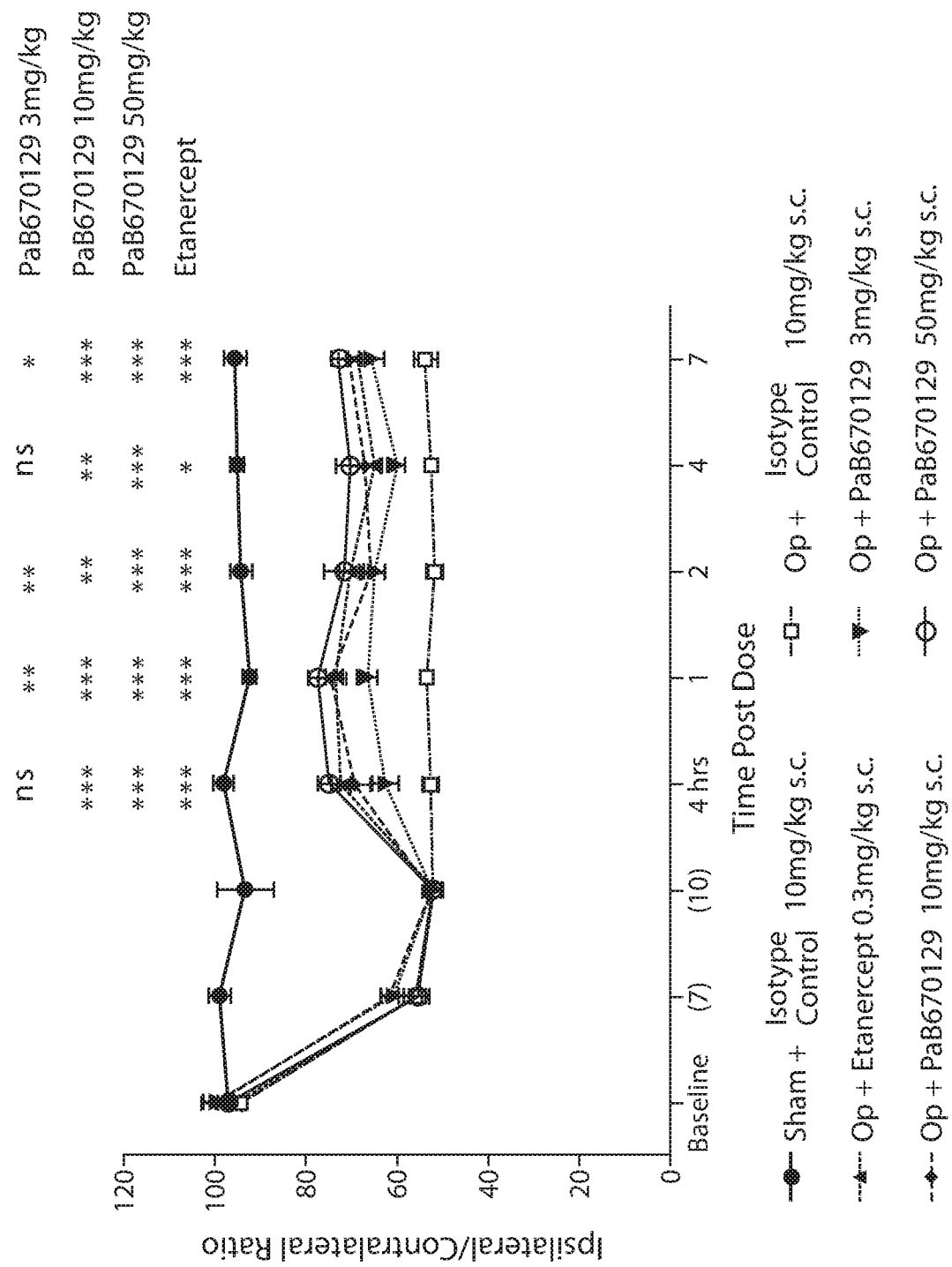
FIG. 8 depicts a graph illustrating the effect of different doses of PaB670129 or an isotype control antibody on the percent ipsilateral/contralateral hypersensitivity induced by peripheral nerve partial ligation in mouse. "s.c." means sub-cutaneous. N=9-10 per group. Data were analyzed using 2-way ANOVA with time and treatment as dependent factors. Subsequent statistical significance was obtained using Tukey's Post Hoc test. Individual comparisons shown * $P<0.05$;  $P<0.01$; * $P<0.001$ vs. Op+isotype control 10 mg/kg.

Partial ligation of the sciatic nerve caused a mechanical hyperalgesia which manifested as a significant reduction in the ipsilateral/contralateral ratio on day 7 and 10 when compared to sham operated controls. Following treatment with isotype control, operated mice did not show any change in the level of mechanical hyperalgesia from pre-dose levels indicating a lack of effect. The administration of the internal gold standard, etanercept (0.3 mg/kg s.c.) caused a significant reversal of the hyperalgesia from 4 hours through to 7 days post dose in agreement with the results seen in previous studies. PaB670129, caused a reversal of the ipsilateral/contralateral ratio in a dose related fashion with peak effects being seen at both 10 mg/kg and 50 mg/kg. The lowest dose of 3 mg/kg whilst significant at 1, 2 and 7 days post dose showed a smaller effect (see FIG. 8).

Partial ligation of the sciatic nerve induced a long lasting mechanical hyperalgesia consistent with previously reported results. Without wishing to be bound by theory, this is believed to serve as a pre-clinical correlate of the pain observed in neuropathic pain. The administration of PaB670129, showed a significant and dose related reversal of this hyperalgesia indicating a potential use of PAR2 antibodies in the treatment of neuropathic pain.

BIBLIOGRAPHY

Persic, L. et al. An integrated vector system for the eukaryotic expression of antibodies or their fragments after selection from phage display libraries. Gene 187, 9-18 (1997).

Reikofski J and Tao B Y (1992) Polymerase chain reaction (PCR) techniques for site-directed mutagenesis. Biotechnol Adv, 10(4): 535-547.

Bove S E, Calcaterra S L, Brooker R M, Huber C M, Guzman R E, Juneau P L, et al. Weight bearing as a measure of disease progression and efficacy of anti-inflammatory compounds in a model of monosodium iodoacetate-induced osteoarthritis. Osteoarthritis Cartilage 2003; 11 (11): 821-30. eng.

Fernihough J, Gentry C, Malcangio M, Fox A, Rediske J, Pellas T, et al. Pain related behaviour in two models of osteoarthritis in the rat knee. Pain 2004; 112 (1-2): 83-93. eng.

Kalbhen D A. Chemical model of osteoarthritis—a pharmacological evaluation. J Rheumatol 1987; 14 Spec No: 130-1. eng.

Clark R A, Shoaib M, Hewitt K N, Stanford S C, Bate S T (2012), A comparison of InVivoStat with other statistical software packages for analysis of data generated from animal experiments, J Psychopharmacology, 26(8), 1136-1142.

Myska Improving Biosensor Analysis. Journal of Molecular Recognition. 1999

D. G. Myska Improving Biosensor Analysis. Journal of Molecular Recognition. 1999; 12: 279-284.

Myska D G, Improving Biosensor Analysis. Journal of Molecular Recognition. 1999; 12: 279-284.

A. W. Drake, M. L. Tang, G. A. Papalia, G. Landes, M. Haak-Frendscho, S. L. Klakamp, Biacore surface matrix effects on the binding kinetics and affinity of an antigen/antibody complex, Anal. Biochem. 429 (2012) 58-69

Pace C N, Vajdos F, Fee L, Grisley G and Grey T, How to measure and predict the molar absorption coefficient of a protein, Protein Sci. 1995; 4: 2411-2423.

Spooner J, Keen J, Nayyar K, Birkett N, Bond N, Bannister D, Tigue N, Higazi D, Kemp B, Vaughan T, Kippen A, Buchanan A. (2015) Evaluation of strategies to control Fab light chain dimer during mammalian expression and purification: A universal one-step process for purification of correctly assembled Fab. Biotechnol Bioeng. 112: 1472-7.

Daramola O, Stevenson J, Dean G, Hatton D, Pettman G, Holmes W, Field R (2014) A high yielding CHO transient system: co-expression of genes encoding EBNA-1 and GS enhances transient protein expression. Biotechnol Prog. 30(1):132-41.

Mach H, Middaugh C R, Lewis R V (1992) Statistical determination of the average values of the extinction coefficients of tryptophan and tyrosine in native proteins. Anal. Biochem. 200(1):74-80.

Seltzer Z, Dubner R, Shir Y (1990). A novel behavioural model of neuropathic pain disorders produced in rats by partial sciatic nerve injury. Pain 43: 205-218

Randall L O, Selitto J J (1957). A method for measurement of analgesic activity on inflamed tissue. Arch Int Pharmacodyn Ther. 111(4): 409-419

SEQUENCE LISTING:
PRT = amino acid sequence

| SEQ ID NO: | clone name | Type |
| --- | --- | --- |
| 1 | ZZ15D2-D02 (Par0067) | VH DNA |
| 2 | ZZ15D2-D02 (Par0067) | VH PRT |
| 3 | ZZ15D2-D02 (Par0067) | CDR1 PRT |
| 4 | ZZ15D2-D02 (Par0067) | CDR2 PRT |
| 5 | ZZ15D2-D02 (Par0067) | CDR3 PRT |
| 6 | ZZ15D2-D02 (Par0067) | VL DNA |
| 7 | ZZ15D2-D02 (Par0067) | VL PRT |
| 8 | ZZ15D2-D02 (Par0067) | CDR1 PRT |
| 9 | ZZ15D2-D02 (Par0067) | CDR2 PRT |
| 10 | ZZ15D2-D02 (Par0067) | CDR3 PRT |
| 11 | ZZ1RUE-F02 (PaB670129) | VH DNA |
| 12 | ZZ1RUE-F02 (PaB670129) | VH PRT |
| 13 | ZZ1RUE-F02 (PaB670129) | CDR1 PRT |
| 14 | ZZ1RUE-F02 (PaB670129) | CDR2 PRT |
| 15 | ZZ1RUE-F02 (PaB670129) | CDR3 PRT |
| 16 | ZZ1RUE-F02 (PaB670129) | VL DNA |
| 17 | ZZ1RUE-F02 (PaB670129) | VL PRT |
| 18 | ZZ1RUE-F02 (PaB670129) | CDR1 PRT |
| 19 | ZZ1RUE-F02 (PaB670129) | CDR2 PRT |
| 20 | ZZ1RUE-F02 (PaB670129) | CDR3 PRT |
| 21 | ZZ1DRB-B08 (PaB670010) | VH DNA |
| 22 | ZZ1DRB-B08 (PaB670010) | VH PRT |
| 23 | ZZ1DRB-B08 (PaB670010) | CDR1 PRT |
| 24 | ZZ1DRB-B08 (PaB670010) | CDR2 PRT |
| 25 | ZZ1DRB-B08 (PaB670010) | CDR3 PRT |
| 26 | ZZ1DRB-B08 (PaB670010) | VL DNA |
| 27 | ZZ1DRB-B08 (PaB670010) | VL PRT |
| 28 | ZZ1DRB-B08 (PaB670010) | CDR1 PRT |
| 29 | ZZ1DRB-B08 (PaB670010) | CDR2 PRT |
| 30 | ZZ1DRB-B08 (PaB670010) | CDR3 PRT |
| 31 | ZZ1IGD-D05 (PaB670020) | VH DNA |
| 32 | ZZ1IGD-D05 (PaB670020) | VH PRT |
| 33 | ZZ1IGD-D05 (PaB670020) | CDR1 PRT |
| 34 | ZZ1IGD-D05 (PaB670020) | CDR2 PRT |
| 35 | ZZ1IGD-D05 (PaB670020) | CDR3 PRT |
| 36 | ZZ1IGD-D05 (PaB670020) | VL DNA |
| 37 | ZZ1IGD-D05 (PaB670020) | VL PRT |
| 38 | ZZ1IGD-D05 (PaB670020) | CDR1 PRT |
| 39 | ZZ1IGD-D05 (PaB670020) | CDR2 PRT |
| 40 | ZZ1IGD-D05 (PaB670020) | CDR3 PRT |
| 41 | ZZ1IGF-B11 (PaB670034) | VH DNA |
| 42 | ZZ1IGF-B11 (PaB670034) | VH PRT |
| 43 | ZZ1IGF-B11 (PaB670034) | CDR1 PRT |
| 44 | ZZ1IGF-B11 (PaB670034) | CDR2 PRT |
| 45 | ZZ1IGF-B11 (PaB670034) | CDR3 PRT |
| 46 | ZZ1IGF-B11 (PaB670034) | VL DNA |
| 47 | ZZ1IGF-B11 (PaB670034) | VL PRT |
| 48 | ZZ1IGF-B11 (PaB670034) | CDR1 PRT |
| 49 | ZZ1IGF-B11 (PaB670034) | CDR2 PRT |
| 50 | ZZ1IGF-B11 (PaB670034) | CDR3 PRT |
| 51 | ZZ1KX3-F01 (PaB670045) | VH DNA |
| 52 | ZZ1KX3-F01 (PaB670045) | VH PRT |
| 53 | ZZ1KX3-F01 (PaB670045) | CDR1 PRT |
| 54 | ZZ1KX3-F01 (PaB670045) | CDR2 PRT |
| 55 | ZZ1KX3-F01 (PaB670045) | CDR3 PRT |
| 56 | ZZ1KX3-F01 (PaB670045) | VL DNA |
| 57 | ZZ1KX3-F01 (PaB670045) | VL PRT |
| 58 | ZZ1KX3-F01 (PaB670045) | CDR1 PRT |
| 59 | ZZ1KX3-F01 (PaB670045) | CDR2 PRT |
| 60 | ZZ1KX3-F01 (PaB670045) | CDR3 PRT |
| 61 | ZZ1KX4-E11 (PaB670048) | VH DNA |
| 62 | ZZ1KX4-E11 (PaB670048) | VH PRT |
| 63 | ZZ1KX4-E11 (PaB670048) | CDR1 PRT |
| 64 | ZZ1KX4-E11 (PaB670048) | CDR2 PRT |
| 65 | ZZ1KX4-E11 (PaB670048) | CDR3 PRT |
| 66 | ZZ1KX4-E11 (PaB670048) | VL DNA |
| 67 | ZZ1KX4-E11 (PaB670048) | VL PRT |

SEQUENCE LISTING: PRT = amino acid sequence

| SEQ ID NO: | clone name | Type |
|---|---|---|
| 68 | ZZ1KX4-E11 (PaB670048) | CDR1 PRT |
| 69 | ZZ1KX4-E11 (PaB670048) | CDR2 PRT |
| 70 | ZZ1KX4-E11 (PaB670048) | CDR3 PRT |
| 71 | ZZ1KX6-B09 (PaB670064) | VH DNA |
| 72 | ZZ1KX6-B09 (PaB670064) | VH PRT |
| 73 | ZZ1KX6-B09 (PaB670064) | CDR1 PRT |
| 74 | ZZ1KX6-B09 (PaB670064) | CDR2 PRT |
| 75 | ZZ1KX6-B09 (PaB670064) | CDR3 PRT |
| 76 | ZZ1KX6-B09 (PaB670064) | VL DNA |
| 77 | ZZ1KX6-B09 (PaB670064) | VL PRT |
| 78 | ZZ1KX6-B09 (PaB670064) | CDR1 PRT |
| 79 | ZZ1KX6-B09 (PaB670064) | CDR2 PRT |
| 80 | ZZ1KX6-B09 (PaB670064) | CDR3 PRT |
| 81 | ZZ1KX6-D05 (PaB670066) | VH DNA |
| 82 | ZZ1KX6-D05 (PaB670066) | VH PRT |
| 83 | ZZ1KX6-D05 (PaB670066) | CDR1 PRT |
| 84 | ZZ1KX6-D05 (PaB670066) | CDR2 PRT |
| 85 | ZZ1KX6-D05 (PaB670066) | CDR3 PRT |
| 86 | ZZ1KX6-D05 (PaB670066) | VL DNA |
| 87 | ZZ1KX6-D05 (PaB670066) | VL PRT |
| 88 | ZZ1KX6-D05 (PaB670066) | CDR1 PRT |
| 89 | ZZ1KX6-D05 (PaB670066) | CDR2 PRT |
| 90 | ZZ1KX6-D05 (PaB670066) | CDR3 PRT |
| 91 | ZZ1KXE-A05 (PaB670067) | VH DNA |
| 92 | ZZ1KXE-A05 (PaB670067) | VH PRT |
| 93 | ZZ1KXE-A05 (PaB670067) | CDR1 PRT |
| 94 | ZZ1KXE-A05 (PaB670067) | CDR2 PRT |
| 95 | ZZ1KXE-A05 (PaB670067) | CDR3 PRT |
| 96 | ZZ1KXE-A05 (PaB670067) | VL DNA |
| 97 | ZZ1KXE-A05 (PaB670067) | VL PRT |
| 98 | ZZ1KXE-A05 (PaB670067) | CDR1 PRT |
| 99 | ZZ1KXE-A05 (PaB670067) | CDR2 PRT |
| 100 | ZZ1KXE-A05 (PaB670067) | CDR3 PRT |
| 101 | ZZ1KXE-B01 (PaB670068) | VH DNA |
| 102 | ZZ1KXE-B01 (PaB670068) | VH PRT |
| 103 | ZZ1KXE-B01 (PaB670068) | CDR1 PRT |
| 104 | ZZ1KXE-B01 (PaB670068) | CDR2 PRT |
| 105 | ZZ1KXE-B01 (PaB670068) | CDR3 PRT |
| 106 | ZZ1KXE-B01 (PaB670068) | VL DNA |
| 107 | ZZ1KXE-B01 (PaB670068) | VL PRT |
| 108 | ZZ1KXE-B01 (PaB670068) | CDR1 PRT |
| 109 | ZZ1KXE-B01 (PaB670068) | CDR2 PRT |
| 110 | ZZ1KXE-B01 (PaB670068) | CDR3 PRT |
| 111 | ZZ1KXE-D06 (PaB670070) | VH DNA |
| 112 | ZZ1KXE-D06 (PaB670070) | VH PRT |
| 113 | ZZ1KXE-D06 (PaB670070) | CDR1 PRT |
| 114 | ZZ1KXE-D06 (PaB670070) | CDR2 PRT |
| 115 | ZZ1KXE-D06 (PaB670070) | CDR3 PRT |
| 116 | ZZ1KXE-D06 (PaB670070) | VL DNA |
| 117 | ZZ1KXE-D06 (PaB670070) | VL PRT |
| 118 | ZZ1KXE-D06 (PaB670070) | CDR1 PRT |
| 119 | ZZ1KXE-D06 (PaB670070) | CDR2 PRT |
| 120 | ZZ1KXE-D06 (PaB670070) | CDR3 PRT |
| 121 | ZZ1L3F-A02 (PaB670071) | VH DNA |
| 122 | ZZ1L3F-A02 (PaB670071) | VH PRT |
| 123 | ZZ1L3F-A02 (PaB670071) | CDR1 PRT |
| 124 | ZZ1L3F-A02 (PaB670071) | CDR2 PRT |
| 125 | ZZ1L3F-A02 (PaB670071) | CDR3 PRT |
| 126 | ZZ1L3F-A02 (PaB670071) | VL DNA |
| 127 | ZZ1L3F-A02 (PaB670071) | VL PRT |
| 128 | ZZ1L3F-A02 (PaB670071) | CDR1 PRT |
| 129 | ZZ1L3F-A02 (PaB670071) | CDR2 PRT |
| 130 | ZZ1L3F-A02 (PaB670071) | CDR3 PRT |
| 131 | ZZ1L3F-H03 (PaB670073) | VH DNA |
| 132 | ZZ1L3F-H03 (PaB670073) | VH PRT |
| 133 | ZZ1L3F-H03 (PaB670073) | CDR1 PRT |
| 134 | ZZ1L3F-H03 (PaB670073) | CDR2 PRT |
| 135 | ZZ1L3F-H03 (PaB670073) | CDR3 PRT |
| 136 | ZZ1L3F-H03 (PaB670073) | VL DNA |
| 137 | ZZ1L3F-H03 (PaB670073) | VL PRT |
| 138 | ZZ1L3F-H03 (PaB670073) | CDR1 PRT |
| 139 | ZZ1L3F-H03 (PaB670073) | CDR2 PRT |
| 140 | ZZ1L3F-H03 (PaB670073) | CDR3 PRT |
| 141 | ZZ1NHH-A05 (PaB670075) | VH DNA |
| 142 | ZZ1NHH-A05 (PaB670075) | VH PRT |
| 143 | ZZ1NHH-A05 (PaB670075) | CDR1 PRT |
| 144 | ZZ1NHH-A05 (PaB670075) | CDR2 PRT |
| 145 | ZZ1NHH-A05 (PaB670075) | CDR3 PRT |
| 146 | ZZ1NHH-A05 (PaB670075) | VL DNA |
| 147 | ZZ1NHH-A05 (PaB670075) | VL PRT |
| 148 | ZZ1NHH-A05 (PaB670075) | CDR1 PRT |
| 149 | ZZ1NHH-A05 (PaB670075) | CDR2 PRT |
| 150 | ZZ1NHH-A05 (PaB670075) | CDR3 PRT |
| 151 | ZZ1NHH-F09 (PaB670076) | VH DNA |
| 152 | ZZ1NHH-F09 (PaB670076) | VH PRT |
| 153 | ZZ1NHH-F09 (PaB670076) | CDR1 PRT |
| 154 | ZZ1NHH-F09 (PaB670076) | CDR2 PRT |
| 155 | ZZ1NHH-F09 (PaB670076) | CDR3 PRT |
| 156 | ZZ1NHH-F09 (PaB670076) | VL DNA |
| 157 | ZZ1NHH-F09 (PaB670076) | VL PRT |
| 158 | ZZ1NHH-F09 (PaB670076) | CDR1 PRT |
| 159 | ZZ1NHH-F09 (PaB670076) | CDR2 PRT |
| 160 | ZZ1NHH-F09 (PaB670076) | CDR3 PRT |
| 161 | ZZ1OZJ-C11 (PaB670077) | VH DNA |
| 162 | ZZ1OZJ-C11 (PaB670077) | VH PRT |
| 163 | ZZ1OZJ-C11 (PaB670077) | CDR1 PRT |
| 164 | ZZ1OZJ-C11 (PaB670077) | CDR2 PRT |
| 165 | ZZ1OZJ-C11 (PaB670077) | CDR3 PRT |
| 166 | ZZ1OZJ-C11 (PaB670077) | VL DNA |
| 167 | ZZ1OZJ-C11 (PaB670077) | VL PRT |
| 168 | ZZ1OZJ-C11 (PaB670077) | CDR1 PRT |
| 169 | ZZ1OZJ-C11 (PaB670077) | CDR2 PRT |
| 170 | ZZ1OZJ-C11 (PaB670077) | CDR3 PRT |
| 171 | ZZ1OZJ-G03 (PaB670078) | VH DNA |
| 172 | ZZ1OZJ-G03 (PaB670078) | VH PRT |
| 173 | ZZ1OZJ-G03 (PaB670078) | CDR1 PRT |
| 174 | ZZ1OZJ-G03 (PaB670078) | CDR2 PRT |
| 175 | ZZ1OZJ-G03 (PaB670078) | CDR3 PRT |
| 176 | ZZ1OZJ-G03 (PaB670078) | VL DNA |
| 177 | ZZ1OZJ-G03 (PaB670078) | VL PRT |
| 178 | ZZ1OZJ-G03 (PaB670078) | CDR1 PRT |
| 179 | ZZ1OZJ-G03 (PaB670078) | CDR2 PRT |
| 180 | ZZ1OZJ-G03 (PaB670078) | CDR3 PRT |
| 181 | ZZ1OZJ-G05 (PaB670079) | VH DNA |
| 182 | ZZ1OZJ-G05 (PaB670079) | VH PRT |
| 183 | ZZ1OZJ-G05 (PaB670079) | CDR1 PRT |
| 184 | ZZ1OZJ-G05 (PaB670079) | CDR2 PRT |
| 185 | ZZ1OZJ-G05 (PaB670079) | CDR3 PRT |
| 186 | ZZ1OZJ-G05 (PaB670079) | VL DNA |
| 187 | ZZ1OZJ-G05 (PaB670079) | VL PRT |
| 188 | ZZ1OZJ-G05 (PaB670079) | CDR1 PRT |
| 189 | ZZ1OZJ-G05 (PaB670079) | CDR2 PRT |
| 190 | ZZ1OZJ-G05 (PaB670079) | CDR3 PRT |
| 191 | PaB670080 | VH DNA |
| 192 | PaB670080 | VH PRT |
| 193 | PaB670080 | CDR1 PRT |
| 194 | PaB670080 | CDR2 PRT |
| 195 | PaB670080 | CDR3 PRT |
| 196 | PaB670080 | VL DNA |
| 197 | PaB670080 | VL PRT |
| 198 | PaB670080 | CDR1 PRT |
| 199 | PaB670080 | CDR2 PRT |
| 200 | PaB670080 | CDR3 PRT |
| 201 | ZZ1OZA-C01 (PaB670081) | VH DNA |
| 202 | ZZ1OZA-C01 (PaB670081) | VH PRT |
| 203 | ZZ1OZA-C01 (PaB670081) | CDR1 PRT |
| 204 | ZZ1OZA-C01 (PaB670081) | CDR2 PRT |
| 205 | ZZ1OZA-C01 (PaB670081) | CDR3 PRT |
| 206 | ZZ1OZA-C01 (PaB670081) | VL DNA |
| 207 | ZZ1OZA-C01 (PaB670081) | VL PRT |
| 208 | ZZ1OZA-C01 (PaB670081) | CDR1 PRT |
| 209 | ZZ1OZA-C01 (PaB670081) | CDR2 PRT |
| 210 | ZZ1OZA-C01 (PaB670081) | CDR3 PRT |
| 211 | ZZ1OZA-D02 (PaB670082) | VH DNA |
| 212 | ZZ1OZA-D02 (PaB670082) | VH PRT |
| 213 | ZZ1OZA-D02 (PaB670082) | CDR1 PRT |
| 214 | ZZ1OZA-D02 (PaB670082) | CDR2 PRT |
| 215 | ZZ1OZA-D02 (PaB670082) | CDR3 PRT |

SEQUENCE LISTING:
PRT = amino acid sequence

| SEQ ID NO: | clone name | Type |
|---|---|---|
| 216 | ZZ1OZA-D02 (PaB670082) | VL DNA |
| 217 | ZZ1OZA-D02 (PaB670082) | VL PRT |
| 218 | ZZ1OZA-D02 (PaB670082) | CDR1 PRT |
| 219 | ZZ1OZA-D02 (PaB670082) | CDR2 PRT |
| 220 | ZZ1OZA-D02 (PaB670082) | CDR3 PRT |
| 221 | ZZ1OZB-H05 (PaB670083) | VH DNA |
| 222 | ZZ1OZB-H05 (PaB670083) | VH PRT |
| 223 | ZZ1OZB-H05 (PaB670083) | CDR1 PRT |
| 224 | ZZ1OZB-H05 (PaB670083) | CDR2 PRT |
| 225 | ZZ1OZB-H05 (PaB670083) | CDR3 PRT |
| 226 | ZZ1OZB-H05 (PaB670083) | VL DNA |
| 227 | ZZ1OZB-H05 (PaB670083) | VL PRT |
| 228 | ZZ1OZB-H05 (PaB670083) | CDR1 PRT |
| 229 | ZZ1OZB-H05 (PaB670083) | CDR2 PRT |
| 230 | ZZ1OZB-H05 (PaB670083) | CDR3 PRT |
| 231 | ZZ1PXA-A05 (PaB670084) | VH DNA |
| 232 | ZZ1PXA-A05 (PaB670084) | VH PRT |
| 233 | ZZ1PXA-A05 (PaB670084) | CDR1 PRT |
| 234 | ZZ1PXA-A05 (PaB670084) | CDR2 PRT |
| 235 | ZZ1PXA-A05 (PaB670084) | CDR3 PRT |
| 236 | ZZ1PXA-A05 (PaB670084) | VL DNA |
| 237 | ZZ1PXA-A05 (PaB670084) | VL PRT |
| 238 | ZZ1PXA-A05 (PaB670084) | CDR1 PRT |
| 239 | ZZ1PXA-A05 (PaB670084) | CDR2 PRT |
| 240 | ZZ1PXA-A05 (PaB670084) | CDR3 PRT |
| 241 | ZZ1ODR-A02 (PaB670085) | VH DNA |
| 242 | ZZ1ODR-A02 (PaB670085) | VH PRT |
| 243 | ZZ1ODR-A02 (PaB670085) | CDR1 PRT |
| 244 | ZZ1ODR-A02 (PaB670085) | CDR2 PRT |
| 245 | ZZ1ODR-A02 (PaB670085) | CDR3 PRT |
| 246 | ZZ1ODR-A02 (PaB670085) | VL DNA |
| 247 | ZZ1ODR-A02 (PaB670085) | VL PRT |
| 248 | ZZ1ODR-A02 (PaB670085) | CDR1 PRT |
| 249 | ZZ1ODR-A02 (PaB670085) | CDR2 PRT |
| 250 | ZZ1ODR-A02 (PaB670085) | CDR3 PRT |
| 251 | ZZ1ODR-B05 (PaB670087) | VH DNA |
| 252 | ZZ1ODR-B05 (PaB670087) | VH PRT |
| 253 | ZZ1ODR-B05 (PaB670087) | CDR1 PRT |
| 254 | ZZ1ODR-B05 (PaB670087) | CDR2 PRT |
| 255 | ZZ1ODR-B05 (PaB670087) | CDR3 PRT |
| 256 | ZZ1ODR-B05 (PaB670087) | VL DNA |
| 257 | ZZ1ODR-B05 (PaB670087) | VL PRT |
| 258 | ZZ1ODR-B05 (PaB670087) | CDR1 PRT |
| 259 | ZZ1ODR-B05 (PaB670087) | CDR2 PRT |
| 260 | ZZ1ODR-B05 (PaB670087) | CDR3 PRT |
| 261 | ZZ1ODR-B11 (PaB670088) | VH DNA |
| 262 | ZZ1ODR-B11 (PaB670088) | VH PRT |
| 263 | ZZ1ODR-B11 (PaB670088) | CDR1 PRT |
| 264 | ZZ1ODR-B11 (PaB670088) | CDR2 PRT |
| 265 | ZZ1ODR-B11 (PaB670088) | CDR3 PRT |
| 266 | ZZ1ODR-B11 (PaB670088) | VL DNA |
| 267 | ZZ1ODR-B11 (PaB670088) | VL PRT |
| 268 | ZZ1ODR-B11 (PaB670088) | CDR1 PRT |
| 269 | ZZ1ODR-B11 (PaB670088) | CDR2 PRT |
| 270 | ZZ1ODR-B11 (PaB670088) | CDR3 PRT |
| 271 | ZZ1ODR-C05 (PaB670089) | VH DNA |
| 272 | ZZ1ODR-C05 (PaB670089) | VH PRT |
| 273 | ZZ1ODR-C05 (PaB670089) | CDR1 PRT |
| 274 | ZZ1ODR-C05 (PaB670089) | CDR2 PRT |
| 275 | ZZ1ODR-C05 (PaB670089) | CDR3 PRT |
| 276 | ZZ1ODR-C05 (PaB670089) | VL DNA |
| 277 | ZZ1ODR-C05 (PaB670089) | VL PRT |
| 278 | ZZ1ODR-C05 (PaB670089) | CDR1 PRT |
| 279 | ZZ1ODR-C05 (PaB670089) | CDR2 PRT |
| 280 | ZZ1ODR-C05 (PaB670089) | CDR3 PRT |
| 281 | ZZ1ODR-F02 (PaB670090) | VH DNA |
| 282 | ZZ1ODR-F02 (PaB670090) | VH PRT |
| 283 | ZZ1ODR-F02 (PaB670090) | CDR1 PRT |
| 284 | ZZ1ODR-F02 (PaB670090) | CDR2 PRT |
| 285 | ZZ1ODR-F02 (PaB670090) | CDR3 PRT |
| 286 | ZZ1ODR-F02 (PaB670090) | VL DNA |
| 287 | ZZ1ODR-F02 (PaB670090) | VL PRT |
| 288 | ZZ1ODR-F02 (PaB670090) | CDR1 PRT |
| 289 | ZZ1ODR-F02 (PaB670090) | CDR2 PRT |
| 290 | ZZ1ODR-F02 (PaB670090) | CDR3 PRT |
| 291 | ZZ1ODR-G02 (PaB670091) | VH DNA |
| 292 | ZZ1ODR-G02 (PaB670091) | VH PRT |
| 293 | ZZ1ODR-G02 (PaB670091) | CDR1 PRT |
| 294 | ZZ1ODR-G02 (PaB670091) | CDR2 PRT |
| 295 | ZZ1ODR-G02 (PaB670091) | CDR3 PRT |
| 296 | ZZ1ODR-G02 (PaB670091) | VL DNA |
| 297 | ZZ1ODR-G02 (PaB670091) | VL PRT |
| 298 | ZZ1ODR-G02 (PaB670091) | CDR1 PRT |
| 299 | ZZ1ODR-G02 (PaB670091) | CDR2 PRT |
| 300 | ZZ1ODR-G02 (PaB670091) | CDR3 PRT |
| 301 | ZZ1ODR-G11 (PaB670092) | VH DNA |
| 302 | ZZ1ODR-G11 (PaB670092) | VH PRT |
| 303 | ZZ1ODR-G11 (PaB670092) | CDR1 PRT |
| 304 | ZZ1ODR-G11 (PaB670092) | CDR2 PRT |
| 305 | ZZ1ODR-G11 (PaB670092) | CDR3 PRT |
| 306 | ZZ1ODR-G11 (PaB670092) | VL DNA |
| 307 | ZZ1ODR-G11 (PaB670092) | VL PRT |
| 308 | ZZ1ODR-G11 (PaB670092) | CDR1 PRT |
| 309 | ZZ1ODR-G11 (PaB670092) | CDR2 PRT |
| 310 | ZZ1ODR-G11 (PaB670092) | CDR3 PRT |
| 311 | ZZ1ODR-H04 (PaB670093) | VH DNA |
| 312 | ZZ1ODR-H04 (PaB670093) | VH PRT |
| 313 | ZZ1ODR-H04 (PaB670093) | CDR1 PRT |
| 314 | ZZ1ODR-H04 (PaB670093) | CDR2 PRT |
| 315 | ZZ1ODR-H04 (PaB670093) | CDR3 PRT |
| 316 | ZZ1ODR-H04 (PaB670093) | VL DNA |
| 317 | ZZ1ODR-H04 (PaB670093) | VL PRT |
| 318 | ZZ1ODR-H04 (PaB670093) | CDR1 PRT |
| 319 | ZZ1ODR-H04 (PaB670093) | CDR2 PRT |
| 320 | ZZ1ODR-H04 (PaB670093) | CDR3 PRT |
| 321 | ZZ1ODS-B08 (PaB670094) | VH DNA |
| 322 | ZZ1ODS-B08 (PaB670094) | VH PRT |
| 323 | ZZ1ODS-B08 (PaB670094) | CDR1 PRT |
| 324 | ZZ1ODS-B08 (PaB670094) | CDR2 PRT |
| 325 | ZZ1ODS-B08 (PaB670094) | CDR3 PRT |
| 326 | ZZ1ODS-B08 (PaB670094) | VL DNA |
| 327 | ZZ1ODS-B08 (PaB670094) | VL PRT |
| 328 | ZZ1ODS-B08 (PaB670094) | CDR1 PRT |
| 329 | ZZ1ODS-B08 (PaB670094) | CDR2 PRT |
| 330 | ZZ1ODS-B08 (PaB670094) | CDR3 PRT |
| 331 | ZZ1ODS-H05 (PaB670095) | VH DNA |
| 332 | ZZ1ODS-H05 (PaB670095) | VH PRT |
| 333 | ZZ1ODS-H05 (PaB670095) | CDR1 PRT |
| 334 | ZZ1ODS-H05 (PaB670095) | CDR2 PRT |
| 335 | ZZ1ODS-H05 (PaB670095) | CDR3 PRT |
| 336 | ZZ1ODS-H05 (PaB670095) | VL DNA |
| 337 | ZZ1ODS-H05 (PaB670095) | VL PRT |
| 338 | ZZ1ODS-H05 (PaB670095) | CDR1 PRT |
| 339 | ZZ1ODS-H05 (PaB670095) | CDR2 PRT |
| 340 | ZZ1ODS-H05 (PaB670095) | CDR3 PRT |
| 341 | ZZ1ODT-E11 (PaB670097) | VH DNA |
| 342 | ZZ1ODT-E11 (PaB670097) | VH PRT |
| 343 | ZZ1ODT-E11 (PaB670097) | CDR1 PRT |
| 344 | ZZ1ODT-E11 (PaB670097) | CDR2 PRT |
| 345 | ZZ1ODT-E11 (PaB670097) | CDR3 PRT |
| 346 | ZZ1ODT-E11 (PaB670097) | VL DNA |
| 347 | ZZ1ODT-E11 (PaB670097) | VL PRT |
| 348 | ZZ1ODT-E11 (PaB670097) | CDR1 PRT |
| 349 | ZZ1ODT-E11 (PaB670097) | CDR2 PRT |
| 350 | ZZ1ODT-E11 (PaB670097) | CDR3 PRT |
| 351 | ZZ1ODT-G01 (PaB670098) | VH DNA |
| 352 | ZZ1ODT-G01 (PaB670098) | VH PRT |
| 353 | ZZ1ODT-G01 (PaB670098) | CDR1 PRT |
| 354 | ZZ1ODT-G01 (PaB670098) | CDR2 PRT |
| 355 | ZZ1ODT-G01 (PaB670098) | CDR3 PRT |
| 356 | ZZ1ODT-G01 (PaB670098) | VL DNA |
| 357 | ZZ1ODT-G01 (PaB670098) | VL PRT |
| 358 | ZZ1ODT-G01 (PaB670098) | CDR1 PRT |
| 359 | ZZ1ODT-G01 (PaB670098) | CDR2 PRT |
| 360 | ZZ1ODT-G01 (PaB670098) | CDR3 PRT |
| 361 | PaB670099 | VH DNA |
| 362 | PaB670099 | VH PRT |
| 363 | PaB670099 | CDR1 PRT |

SEQUENCE LISTING: PRT = amino acid sequence

| SEQ ID NO: | clone name | Type |
|---|---|---|
| 364 | PaB670099 | CDR2 PRT |
| 365 | PaB670099 | CDR3 PRT |
| 366 | PaB670099 | VL DNA |
| 367 | PaB670099 | VL PRT |
| 368 | PaB670099 | CDR1 PRT |
| 369 | PaB670099 | CDR2 PRT |
| 370 | PaB670099 | CDR3 PRT |
| 371 | PaB670100 | VH DNA |
| 372 | PaB670100 | VH PRT |
| 373 | PaB670100 | CDR1 PRT |
| 374 | PaB670100 | CDR2 PRT |
| 375 | PaB670100 | CDR3 PRT |
| 376 | PaB670100 | VL DNA |
| 377 | PaB670100 | VL PRT |
| 378 | PaB670100 | CDR1 PRT |
| 379 | PaB670100 | CDR2 PRT |
| 380 | PaB670100 | CDR3 PRT |
| 381 | ZZ1ODO-H01 (PaB670101) | VH DNA |
| 382 | ZZ1ODO-H01 (PaB670101) | VH PRT |
| 383 | ZZ1ODO-H01 (PaB670101) | CDR1 PRT |
| 384 | ZZ1ODO-H01 (PaB670101) | CDR2 PRT |
| 385 | ZZ1ODO-H01 (PaB670101) | CDR3 PRT |
| 386 | ZZ1ODO-H01 (PaB670101) | VL DNA |
| 387 | ZZ1ODO-H01 (PaB670101) | VL PRT |
| 388 | ZZ1ODO-H01 (PaB670101) | CDR1 PRT |
| 389 | ZZ1ODO-H01 (PaB670101) | CDR2 PRT |
| 390 | ZZ1ODO-H01 (PaB670101) | CDR3 PRT |
| 391 | ZZ1PXS-F08 (PaB670102) | VH DNA |
| 392 | ZZ1PXS-F08 (PaB670102) | VH PRT |
| 393 | ZZ1PXS-F08 (PaB670102) | CDR1 PRT |
| 394 | ZZ1PXS-F08 (PaB670102) | CDR2 PRT |
| 395 | ZZ1PXS-F08 (PaB670102) | CDR3 PRT |
| 396 | ZZ1PXS-F08 (PaB670102) | VL DNA |
| 397 | ZZ1PXS-F08 (PaB670102) | VL PRT |
| 398 | ZZ1PXS-F08 (PaB670102) | CDR1 PRT |
| 399 | ZZ1PXS-F08 (PaB670102) | CDR2 PRT |
| 400 | ZZ1PXS-F08 (PaB670102) | CDR3 PRT |
| 401 | ZZ1RCX-C09 (PaB670103) | VH DNA |
| 402 | ZZ1RCX-C09 (PaB670103) | VH PRT |
| 403 | ZZ1RCX-C09 (PaB670103) | CDR1 PRT |
| 404 | ZZ1RCX-C09 (PaB670103) | CDR2 PRT |
| 405 | ZZ1RCX-C09 (PaB670103) | CDR3 PRT |
| 406 | ZZ1RCX-C09 (PaB670103) | VL DNA |
| 407 | ZZ1RCX-C09 (PaB670103) | VL PRT |
| 408 | ZZ1RCX-C09 (PaB670103) | CDR1 PRT |
| 409 | ZZ1RCX-C09 (PaB670103) | CDR2 PRT |
| 410 | ZZ1RCX-C09 (PaB670103) | CDR3 PRT |
| 411 | PaB670104 | VH DNA |
| 412 | PaB670104 | VH PRT |
| 413 | PaB670104 | CDR1 PRT |
| 414 | PaB670104 | CDR2 PRT |
| 415 | PaB670104 | CDR3 PRT |
| 416 | PaB670104 | VL DNA |
| 417 | PaB670104 | VL PRT |
| 418 | PaB670104 | CDR1 PRT |
| 419 | PaB670104 | CDR2 PRT |
| 420 | PaB670104 | CDR3 PRT |
| 421 | ZZ1RD0-D01 (PaB670105) | VH DNA |
| 422 | ZZ1RD0-D01 (PaB670105) | VH PRT |
| 423 | ZZ1RD0-D01 (PaB670105) | CDR1 PRT |
| 424 | ZZ1RD0-D01 (PaB670105) | CDR2 PRT |
| 425 | ZZ1RD0-D01 (PaB670105) | CDR3 PRT |
| 426 | ZZ1RD0-D01 (PaB670105) | VL DNA |
| 427 | ZZ1RD0-D01 (PaB670105) | VL PRT |
| 428 | ZZ1RD0-D01 (PaB670105) | CDR1 PRT |
| 429 | ZZ1RD0-D01 (PaB670105) | CDR2 PRT |
| 430 | ZZ1RD0-D01 (PaB670105) | CDR3 PRT |
| 431 | ZZ1RD0-G02 (PaB670106) | VH DNA |
| 432 | ZZ1RD0-G02 (PaB670106) | VH PRT |
| 433 | ZZ1RD0-G02 (PaB670106) | CDR1 PRT |
| 434 | ZZ1RD0-G02 (PaB670106) | CDR2 PRT |
| 435 | ZZ1RD0-G02 (PaB670106) | CDR3 PRT |
| 436 | ZZ1RD0-G02 (PaB670106) | VL DNA |
| 437 | ZZ1RD0-G02 (PaB670106) | VL PRT |
| 438 | ZZ1RD0-G02 (PaB670106) | CDR1 PRT |
| 439 | ZZ1RD0-G02 (PaB670106) | CDR2 PRT |
| 440 | ZZ1RD0-G02 (PaB670106) | CDR3 PRT |
| 441 | ZZ1RD3-D09 (PaB670107) | VH DNA |
| 442 | ZZ1RD3-D09 (PaB670107) | VH PRT |
| 443 | ZZ1RD3-D09 (PaB670107) | CDR1 PRT |
| 444 | ZZ1RD3-D09 (PaB670107) | CDR2 PRT |
| 445 | ZZ1RD3-D09 (PaB670107) | CDR3 PRT |
| 446 | ZZ1RD3-D09 (PaB670107) | VL DNA |
| 447 | ZZ1RD3-D09 (PaB670107) | VL PRT |
| 448 | ZZ1RD3-D09 (PaB670107) | CDR1 PRT |
| 449 | ZZ1RD3-D09 (PaB670107) | CDR2 PRT |
| 450 | ZZ1RD3-D09 (PaB670107) | CDR3 PRT |
| 451 | ZZ1RD3-H03 (PaB670108) | VH DNA |
| 452 | ZZ1RD3-H03 (PaB670108) | VH PRT |
| 453 | ZZ1RD3-H03 (PaB670108) | CDR1 PRT |
| 454 | ZZ1RD3-H03 (PaB670108) | CDR2 PRT |
| 455 | ZZ1RD3-H03 (PaB670108) | CDR3 PRT |
| 456 | ZZ1RD3-H03 (PaB670108) | VL DNA |
| 457 | ZZ1RD3-H03 (PaB670108) | VL PRT |
| 458 | ZZ1RD3-H03 (PaB670108) | CDR1 PRT |
| 459 | ZZ1RD3-H03 (PaB670108) | CDR2 PRT |
| 460 | ZZ1RD3-H03 (PaB670108) | CDR3 PRT |
| 461 | ZZ1RUC-C01 (PaB670114) | VH DNA |
| 462 | ZZ1RUC-C01 (PaB670114) | VH PRT |
| 463 | ZZ1RUC-C01 (PaB670114) | CDR1 PRT |
| 464 | ZZ1RUC-C01 (PaB670114) | CDR2 PRT |
| 465 | ZZ1RUC-C01 (PaB670114) | CDR3 PRT |
| 466 | ZZ1RUC-C01 (PaB670114) | VL DNA |
| 467 | ZZ1RUC-C01 (PaB670114) | VL PRT |
| 468 | ZZ1RUC-C01 (PaB670114) | CDR1 PRT |
| 469 | ZZ1RUC-C01 (PaB670114) | CDR2 PRT |
| 470 | ZZ1RUC-C01 (PaB670114) | CDR3 PRT |
| 471 | ZZ1RUC-G02 (PaB670115) | VH DNA |
| 472 | ZZ1RUC-G02 (PaB670115) | VH PRT |
| 473 | ZZ1RUC-G02 (PaB670115) | CDR1 PRT |
| 474 | ZZ1RUC-G02 (PaB670115) | CDR2 PRT |
| 475 | ZZ1RUC-G02 (PaB670115) | CDR3 PRT |
| 476 | ZZ1RUC-G02 (PaB670115) | VL DNA |
| 477 | ZZ1RUC-G02 (PaB670115) | VL PRT |
| 478 | ZZ1RUC-G02 (PaB670115) | CDR1 PRT |
| 479 | ZZ1RUC-G02 (PaB670115) | CDR2 PRT |
| 480 | ZZ1RUC-G02 (PaB670115) | CDR3 PRT |
| 481 | ZZ1RUC-B04 (PaB670116) | VH DNA |
| 482 | ZZ1RUC-B04 (PaB670116) | VH PRT |
| 483 | ZZ1RUC-B04 (PaB670116) | CDR1 PRT |
| 484 | ZZ1RUC-B04 (PaB670116) | CDR2 PRT |
| 485 | ZZ1RUC-B04 (PaB670116) | CDR3 PRT |
| 486 | ZZ1RUC-B04 (PaB670116) | VL DNA |
| 487 | ZZ1RUC-B04 (PaB670116) | VL PRT |
| 488 | ZZ1RUC-B04 (PaB670116) | CDR1 PRT |
| 489 | ZZ1RUC-B04 (PaB670116) | CDR2 PRT |
| 490 | ZZ1RUC-B04 (PaB670116) | CDR3 PRT |
| 491 | ZZ1RUC-A06 (PaB670117) | VH DNA |
| 492 | ZZ1RUC-A06 (PaB670117) | VH PRT |
| 493 | ZZ1RUC-A06 (PaB670117) | CDR1 PRT |
| 494 | ZZ1RUC-A06 (PaB670117) | CDR2 PRT |
| 495 | ZZ1RUC-A06 (PaB670117) | CDR3 PRT |
| 496 | ZZ1RUC-A06 (PaB670117) | VL DNA |
| 497 | ZZ1RUC-A06 (PaB670117) | VL PRT |
| 498 | ZZ1RUC-A06 (PaB670117) | CDR1 PRT |
| 499 | ZZ1RUC-A06 (PaB670117) | CDR2 PRT |
| 500 | ZZ1RUC-A06 (PaB670117) | CDR3 PRT |
| 501 | ZZ1RUC-A07 (PaB670118) | VH DNA |
| 502 | ZZ1RUC-A07 (PaB670118) | VH PRT |
| 503 | ZZ1RUC-A07 (PaB670118) | CDR1 PRT |
| 504 | ZZ1RUC-A07 (PaB670118) | CDR2 PRT |
| 505 | ZZ1RUC-A07 (PaB670118) | CDR3 PRT |
| 506 | ZZ1RUC-A07 (PaB670118) | VL DNA |
| 507 | ZZ1RUC-A07 (PaB670118) | VL PRT |
| 508 | ZZ1RUC-A07 (PaB670118) | CDR1 PRT |
| 509 | ZZ1RUC-A07 (PaB670118) | CDR2 PRT |
| 510 | ZZ1RUC-A07 (PaB670118) | CDR3 PRT |
| 511 | ZZ1RUC-G08 (PaB670119) | VH DNA |

SEQUENCE LISTING:
PRT = amino acid sequence

| SEQ ID NO: | clone name | Type |
|---|---|---|
| 512 | ZZ1RUC-G08 (PaB670119) | VH PRT |
| 513 | ZZ1RUC-G08 (PaB670119) | CDR1 PRT |
| 514 | ZZ1RUC-G08 (PaB670119) | CDR2 PRT |
| 515 | ZZ1RUC-G08 (PaB670119) | CDR3 PRT |
| 516 | ZZ1RUC-G08 (PaB670119) | VL DNA |
| 517 | ZZ1RUC-G08 (PaB670119) | VL PRT |
| 518 | ZZ1RUC-G08 (PaB670119) | CDR1 PRT |
| 519 | ZZ1RUC-G08 (PaB670119) | CDR2 PRT |
| 520 | ZZ1RUC-G08 (PaB670119) | CDR3 PRT |
| 521 | ZZ1RUC-C11 (PaB670120) | VH DNA |
| 522 | ZZ1RUC-C11 (PaB670120) | VH PRT |
| 523 | ZZ1RUC-C11 (PaB670120) | CDR1 PRT |
| 524 | ZZ1RUC-C11 (PaB670120) | CDR2 PRT |
| 525 | ZZ1RUC-C11 (PaB670120) | CDR3 PRT |
| 526 | ZZ1RUC-C11 (PaB670120) | VL DNA |
| 527 | ZZ1RUC-C11 (PaB670120) | VL PRT |
| 528 | ZZ1RUC-C11 (PaB670120) | CDR1 PRT |
| 529 | ZZ1RUC-C11 (PaB670120) | CDR2 PRT |
| 530 | ZZ1RUC-C11 (PaB670120) | CDR3 PRT |
| 531 | ZZ1RUC-H11 (PaB670121) | VH DNA |
| 532 | ZZ1RUC-H11 (PaB670121) | VH PRT |
| 533 | ZZ1RUC-H11 (PaB670121) | CDR1 PRT |
| 534 | ZZ1RUC-H11 (PaB670121) | CDR2 PRT |
| 535 | ZZ1RUC-H11 (PaB670121) | CDR3 PRT |
| 536 | ZZ1RUC-H11 (PaB670121) | VL DNA |
| 537 | ZZ1RUC-H11 (PaB670121) | VL PRT |
| 538 | ZZ1RUC-H11 (PaB670121) | CDR1 PRT |
| 539 | ZZ1RUC-H11 (PaB670121) | CDR2 PRT |
| 540 | ZZ1RUC-H11 (PaB670121) | CDR3 PRT |
| 541 | ZZ1RUD-A02 (PaB670122) | VH DNA |
| 542 | ZZ1RUD-A02 (PaB670122) | VH PRT |
| 543 | ZZ1RUD-A02 (PaB670122) | CDR1 PRT |
| 544 | ZZ1RUD-A02 (PaB670122) | CDR2 PRT |
| 545 | ZZ1RUD-A02 (PaB670122) | CDR3 PRT |
| 546 | ZZ1RUD-A02 (PaB670122) | VL DNA |
| 547 | ZZ1RUD-A02 (PaB670122) | VL PRT |
| 548 | ZZ1RUD-A02 (PaB670122) | CDR1 PRT |
| 549 | ZZ1RUD-A02 (PaB670122) | CDR2 PRT |
| 550 | ZZ1RUD-A02 (PaB670122) | CDR3 PRT |
| 551 | ZZ1RUD-H03 (PaB670123) | VH DNA |
| 552 | ZZ1RUD-H03 (PaB670123) | VH PRT |
| 553 | ZZ1RUD-H03 (PaB670123) | CDR1 PRT |
| 554 | ZZ1RUD-H03 (PaB670123) | CDR2 PRT |
| 555 | ZZ1RUD-H03 (PaB670123) | CDR3 PRT |
| 556 | ZZ1RUD-H03 (PaB670123) | VL DNA |
| 557 | ZZ1RUD-H03 (PaB670123) | VL PRT |
| 558 | ZZ1RUD-H03 (PaB670123) | CDR1 PRT |
| 559 | ZZ1RUD-H03 (PaB670123) | CDR2 PRT |
| 560 | ZZ1RUD-H03 (PaB670123) | CDR3 PRT |
| 561 | ZZ1RUD-H06 (PaB670125) | VH DNA |
| 562 | ZZ1RUD-H06 (PaB670125) | VH PRT |
| 563 | ZZ1RUD-H06 (PaB670125) | CDR1 PRT |
| 564 | ZZ1RUD-H06 (PaB670125) | CDR2 PRT |
| 565 | ZZ1RUD-H06 (PaB670125) | CDR3 PRT |
| 566 | ZZ1RUD-H06 (PaB670125) | VL DNA |
| 567 | ZZ1RUD-H06 (PaB670125) | VL PRT |
| 568 | ZZ1RUD-H06 (PaB670125) | CDR1 PRT |
| 569 | ZZ1RUD-H06 (PaB670125) | CDR2 PRT |
| 570 | ZZ1RUD-H06 (PaB670125) | CDR3 PRT |
| 571 | ZZ1RUD-B08 (PaB670126) | VH DNA |
| 572 | ZZ1RUD-B08 (PaB670126) | VH PRT |
| 573 | ZZ1RUD-B08 (PaB670126) | CDR1 PRT |
| 574 | ZZ1RUD-B08 (PaB670126) | CDR2 PRT |
| 575 | ZZ1RUD-B08 (PaB670126) | CDR3 PRT |
| 576 | ZZ1RUD-B08 (PaB670126) | VL DNA |
| 577 | ZZ1RUD-B08 (PaB670126) | VL PRT |
| 578 | ZZ1RUD-B08 (PaB670126) | CDR1 PRT |
| 579 | ZZ1RUD-B08 (PaB670126) | CDR2 PRT |
| 580 | ZZ1RUD-B08 (PaB670126) | CDR3 PRT |
| 581 | ZZ1RUD-H10 (PaB670127) | VH DNA |
| 582 | ZZ1RUD-H10 (PaB670127) | VH PRT |
| 583 | ZZ1RUD-H10 (PaB670127) | CDR1 PRT |
| 584 | ZZ1RUD-H10 (PaB670127) | CDR2 PRT |
| 585 | ZZ1RUD-H10 (PaB670127) | CDR3 PRT |
| 586 | ZZ1RUD-H10 (PaB670127) | VL DNA |
| 587 | ZZ1RUD-H10 (PaB670127) | VL PRT |
| 588 | ZZ1RUD-H10 (PaB670127) | CDR1 PRT |
| 589 | ZZ1RUD-H10 (PaB670127) | CDR2 PRT |
| 590 | ZZ1RUD-H10 (PaB670127) | CDR3 PRT |
| 591 | ZZ1RUE-A01 (PaB670128) | VH DNA |
| 592 | ZZ1RUE-A01 (PaB670128) | VH PRT |
| 593 | ZZ1RUE-A01 (PaB670128) | CDR1 PRT |
| 594 | ZZ1RUE-A01 (PaB670128) | CDR2 PRT |
| 595 | ZZ1RUE-A01 (PaB670128) | CDR3 PRT |
| 596 | ZZ1RUE-A01 (PaB670128) | VL DNA |
| 597 | ZZ1RUE-A01 (PaB670128) | VL PRT |
| 598 | ZZ1RUE-A01 (PaB670128) | CDR1 PRT |
| 599 | ZZ1RUE-A01 (PaB670128) | CDR2 PRT |
| 600 | ZZ1RUE-A01 (PaB670128) | CDR3 PRT |
| 601 | ZZ1RUF-A01 (PaB670136) | VH DNA |
| 602 | ZZ1RUF-A01 (PaB670136) | VH PRT |
| 603 | ZZ1RUF-A01 (PaB670136) | CDR1 PRT |
| 604 | ZZ1RUF-A01 (PaB670136) | CDR2 PRT |
| 605 | ZZ1RUF-A01 (PaB670136) | CDR3 PRT |
| 606 | ZZ1RUF-A01 (PaB670136) | VL DNA |
| 607 | ZZ1RUF-A01 (PaB670136) | VL PRT |
| 608 | ZZ1RUF-A01 (PaB670136) | CDR1 PRT |
| 609 | ZZ1RUF-A01 (PaB670136) | CDR2 PRT |
| 610 | ZZ1RUF-A01 (PaB670136) | CDR3 PRT |
| 611 | ZZ1RUF-B06 (PaB670137) | VH DNA |
| 612 | ZZ1RUF-B06 (PaB670137) | VH PRT |
| 613 | ZZ1RUF-B06 (PaB670137) | CDR1 PRT |
| 614 | ZZ1RUF-B06 (PaB670137) | CDR2 PRT |
| 615 | ZZ1RUF-B06 (PaB670137) | CDR3 PRT |
| 616 | ZZ1RUF-B06 (PaB670137) | VL DNA |
| 617 | ZZ1RUF-B06 (PaB670137) | VL PRT |
| 618 | ZZ1RUF-B06 (PaB670137) | CDR1 PRT |
| 619 | ZZ1RUF-B06 (PaB670137) | CDR2 PRT |
| 620 | ZZ1RUF-B06 (PaB670137) | CDR3 PRT |
| 621 | PaB670141 | VH DNA |
| 622 | PaB670141 | VH PRT |
| 623 | PaB670141 | CDR1 PRT |
| 624 | PaB670141 | CDR2 PRT |
| 625 | PaB670141 | CDR3 PRT |
| 626 | PaB670141 | VL DNA |
| 627 | PaB670141 | VL PRT |
| 628 | PaB670141 | CDR1 PRT |
| 629 | PaB670141 | CDR2 PRT |
| 630 | PaB670141 | CDR3 PRT |
| 631 | PaB670142 | VH DNA |
| 632 | PaB670142 | VH PRT |
| 633 | PaB670142 | CDR1 PRT |
| 634 | PaB670142 | CDR2 PRT |
| 635 | PaB670142 | CDR3 PRT |
| 636 | PaB670142 | VL DNA |
| 637 | PaB670142 | VL PRT |
| 638 | PaB670142 | CDR1 PRT |
| 639 | PaB670142 | CDR2 PRT |
| 640 | PaB670142 | CDR3 PRT |
| 641 | PaB670143 | VH DNA |
| 642 | PaB670143 | VH PRT |
| 643 | PaB670143 | CDR1 PRT |
| 644 | PaB670143 | CDR2 PRT |
| 645 | PaB670143 | CDR3 PRT |
| 646 | PaB670143 | VL DNA |
| 647 | PaB670143 | VL PRT |
| 648 | PaB670143 | CDR1 PRT |
| 649 | PaB670143 | CDR2 PRT |
| 650 | PaB670143 | CDR3 PRT |
| 651 | PaB670144 | VH DNA |
| 652 | PaB670144 | VH PRT |
| 653 | PaB670144 | CDR1 PRT |
| 654 | PaB670144 | CDR2 PRT |
| 655 | PaB670144 | CDR3 PRT |
| 656 | PaB670144 | VL DNA |
| 657 | PaB670144 | VL PRT |
| 658 | PaB670144 | CDR1 PRT |
| 659 | PaB670144 | CDR2 PRT |

SEQUENCE LISTING: PRT = amino acid sequence

| SEQ ID NO: | clone name | Type |
|---|---|---|
| 660 | PaB670144 | CDR3 PRT |
| 661 | PaB670146 | VH DNA |
| 662 | PaB670146 | VH PRT |
| 663 | PaB670146 | CDR1 PRT |
| 664 | PaB670146 | CDR2 PRT |
| 665 | PaB670146 | CDR3 PRT |
| 666 | PaB670146 | VL DNA |
| 667 | PaB670146 | VL PRT |
| 668 | PaB670146 | CDR1 PRT |
| 669 | PaB670146 | CDR2 PRT |
| 670 | PaB670146 | CDR3 PRT |
| 671 | PaB670148 | VH DNA |
| 672 | PaB670148 | VH PRT |
| 673 | PaB670148 | CDR1 PRT |
| 674 | PaB670148 | CDR2 PRT |
| 675 | PaB670148 | CDR3 PRT |
| 676 | PaB670148 | VL DNA |
| 677 | PaB670148 | VL PRT |
| 678 | PaB670148 | CDR1 PRT |
| 679 | PaB670148 | CDR2 PRT |
| 680 | PaB670148 | CDR3 PRT |
| 681 | PaB670149 | VH DNA |
| 682 | PaB670149 | VH PRT |
| 683 | PaB670149 | CDR1 PRT |
| 684 | PaB670149 | CDR2 PRT |
| 685 | PaB670149 | CDR3 PRT |
| 686 | PaB670149 | VL DNA |
| 687 | PaB670149 | VL PRT |
| 688 | PaB670149 | CDR1 PRT |
| 689 | PaB670149 | CDR2 PRT |
| 690 | PaB670149 | CDR3 PRT |
| 691 | PaB670151 | VH DNA |
| 692 | PaB670151 | VH PRT |
| 693 | PaB670151 | CDR1 PRT |
| 694 | PaB670151 | CDR2 PRT |
| 695 | PaB670151 | CDR3 PRT |
| 696 | PaB670151 | VL DNA |
| 697 | PaB670151 | VL PRT |
| 698 | PaB670151 | CDR1 PRT |
| 699 | PaB670151 | CDR2 PRT |
| 700 | PaB670151 | CDR3 PRT |
| 701 | PaB670152 | VH DNA |
| 702 | PaB670152 | VH PRT |
| 703 | PaB670152 | CDR1 PRT |
| 704 | PaB670152 | CDR2 PRT |
| 705 | PaB670152 | CDR3 PRT |
| 706 | PaB670152 | VL DNA |
| 707 | PaB670152 | VL PRT |
| 708 | PaB670152 | CDR1 PRT |
| 709 | PaB670152 | CDR2 PRT |
| 710 | PaB670152 | CDR3 PRT |
| 711 | PaB670153 | VH DNA |
| 712 | PaB670153 | VH PRT |
| 713 | PaB670153 | CDR1 PRT |
| 714 | PaB670153 | CDR2 PRT |
| 715 | PaB670153 | CDR3 PRT |
| 716 | PaB670153 | VL DNA |
| 717 | PaB670153 | VL PRT |
| 718 | PaB670153 | CDR1 PRT |
| 719 | PaB670153 | CDR2 PRT |
| 720 | PaB670153 | CDR3 PRT |
| 721 | PaB670156 | VH DNA |
| 722 | PaB670156 | VH PRT |
| 723 | PaB670156 | CDR1 PRT |
| 724 | PaB670156 | CDR2 PRT |
| 725 | PaB670156 | CDR3 PRT |
| 726 | PaB670156 | VL DNA |
| 727 | PaB670156 | VL PRT |
| 728 | PaB670156 | CDR1 PRT |
| 729 | PaB670156 | CDR2 PRT |
| 730 | PaB670156 | CDR3 PRT |
| 731 | PaB670157 | VH DNA |
| 732 | PaB670157 | VH PRT |
| 733 | PaB670157 | CDR1 PRT |
| 734 | PaB670157 | CDR2 PRT |
| 735 | PaB670157 | CDR3 PRT |
| 736 | PaB670157 | VL DNA |
| 737 | PaB670157 | VL PRT |
| 738 | PaB670157 | CDR1 PRT |
| 739 | PaB670157 | CDR2 PRT |
| 740 | PaB670157 | CDR3 PRT |
| 741 | PaB670158 | VH DNA |
| 742 | PaB670158 | VH PRT |
| 743 | PaB670158 | CDR1 PRT |
| 744 | PaB670158 | CDR2 PRT |
| 745 | PaB670158 | CDR3 PRT |
| 746 | PaB670158 | VL DNA |
| 747 | PaB670158 | VL PRT |
| 748 | PaB670158 | CDR1 PRT |
| 749 | PaB670158 | CDR2 PRT |
| 750 | PaB670158 | CDR3 PRT |
| 751 | PaB670159 | VH DNA |
| 752 | PaB670159 | VH PRT |
| 753 | PaB670159 | CDR1 PRT |
| 754 | PaB670159 | CDR2 PRT |
| 755 | PaB670159 | CDR3 PRT |
| 756 | PaB670159 | VL DNA |
| 757 | PaB670159 | VL PRT |
| 758 | PaB670159 | CDR1 PRT |
| 759 | PaB670159 | CDR2 PRT |
| 760 | PaB670159 | CDR3 PRT |
| 761 | PaB670160 | VH DNA |
| 762 | PaB670160 | VH PRT |
| 763 | PaB670160 | CDR1 PRT |
| 764 | PaB670160 | CDR2 PRT |
| 765 | PaB670160 | CDR3 PRT |
| 766 | PaB670160 | VL DNA |
| 767 | PaB670160 | VL PRT |
| 768 | PaB670160 | CDR1 PRT |
| 769 | PaB670160 | CDR2 PRT |
| 770 | PaB670160 | CDR3 PRT |
| 771 | PaB670161 | VH DNA |
| 772 | PaB670161 | VH PRT |
| 773 | PaB670161 | CDR1 PRT |
| 774 | PaB670161 | CDR2 PRT |
| 775 | PaB670161 | CDR3 PRT |
| 776 | PaB670161 | VL DNA |
| 777 | PaB670161 | VL PRT |
| 778 | PaB670161 | CDR1 PRT |
| 779 | PaB670161 | CDR2 PRT |
| 780 | PaB670161 | CDR3 PRT |
| 781 | PaB670162 | VH DNA |
| 782 | PaB670162 | VH PRT |
| 783 | PaB670162 | CDR1 PRT |
| 784 | PaB670162 | CDR2 PRT |
| 785 | PaB670162 | CDR3 PRT |
| 786 | PaB670162 | VL DNA |
| 787 | PaB670162 | VL PRT |
| 788 | PaB670162 | CDR1 PRT |
| 789 | PaB670162 | CDR2 PRT |
| 790 | PaB670162 | CDR3 PRT |
| 791 | PaB670163 | VH DNA |
| 792 | PaB670163 | VH PRT |
| 793 | PaB670163 | CDR1 PRT |
| 794 | PaB670163 | CDR2 PRT |
| 795 | PaB670163 | CDR3 PRT |
| 796 | PaB670163 | VL DNA |
| 797 | PaB670163 | VL PRT |
| 798 | PaB670163 | CDR1 PRT |
| 799 | PaB670163 | CDR2 PRT |
| 800 | PaB670163 | CDR3 PRT |

SEQ ID NO: 801- Human PAR2 Preproprotein
(GenBank Accession No. NP_005233.3)
MRSPSAAWLLGAAILLAASLSCSGTIQGTNRSSKGRSLIGKVDGTSHV

TGKGVTVETVFSVDEFSASVLTGKLTTVFLPIVYTIVFVVGLPSNGMA

LWVFLFRTKKKHPAVIYMANLALADLLSVIWFPLKIAYHIHGNNWIYG

EALCNVLIGFFYGNMYCSILFMTCLSVQRYWVIVNPMGHSRKKANIAI

GISLAIWLLILLVTIPLYVVKQTIFIPALNITTCHDVLPEQLLVGDMF

NYFLSLAIGVFLFPAFLTASAYVLMIRMLRSSAMDENSEKKRKRAIKL

IVTVLAMYLICFTPSNLLLVVHYFLIKSQGQSHVYALYIVALCLSTLN

SCIDPFVYYFVSHDFRDHAKNALLCRSVRTVKQMQVSLTSKKHSRKSS

SYSSSSTTVKTSY

SEQ ID NO: 802- Human PAR2 Tethered Ligand
SLIGKVDGTSHVTGKGVTVETVFSVDEFSASVLTGKLTT SEQ ID NO: 803- Exemplary VH Framework Region 1
EVQLLESGGGLVQPGGSLRLSCAASGFTFS SEQ ID NO: 804- Exemplary VH Framework Region 2
WVRQAPGKGLEWVS SEQ ID NO: 805- Exemplary VH Framework Region 3
RFTISRDNSKNTLYLQMNSLRAEDTAVYYCAR SEQ ID NO: 806- Exemplary VH Framework Region 4
WGQGTLVTVSS SEQ ID NO: 807- Exemplary VL Framework Region 1
SIELTQPPSVSVSPGQTASITC SEQ ID NO: 808- Exemplary VL Framework Region 2
WYQQKPGQSPVLVIY SEQ ID NO: 809- Exemplary VL Framework Region 3
GIPERFSGSNSGNTATLTISGTQAMDEADYYC SEQ ID NO: 810- Exemplary VL Framework Region 4
FGGGTKLTVL SEQ ID NO: 811- Exemplary VH CDR2
TISYSGSHISYHDSVHH SEQ ID NO: 812- Exemplary VH CDR2
TISYHGSLISYHDSVHH SEQ ID NO: 813- Exemplary VH CDR2
TISYHGSHISYADSVHH SEQ ID NO: 814- Exemplary VH CDR2
TISYHGSHISYHDSVKH SEQ ID NO: 815- Exemplary VH CDR2
TISYHGSHISYHDSVHG SEQ ID NO: 816- Exemplary VH CDR2
TISYHGSLISYADSVKG SEQ ID NO: 817- Exemplary VH CDR2
TISYSGSHISYADSVKG SEQ ID NO: 818- Exemplary VH CDR2
TISYHGSHISYADSVKG SEQ ID NO: 819- Exemplary VH CDR3
IHNDPMDV SEQ ID NO: 820- Exemplary VH CDR3
INHDPMDV -continued SEQ ID NO: 821-- Exemplary VH
EVQLLESGGGLVQPGGSLRLSCAASGFTFSSYAMNWVRQAPGKGLEWV

STISYHGSHISYHDSVHHRFTISRDNSKNTLYLQMNSLRAEDTAVYYC

ARIHHDPMDVWGQGTLVTVSS

SEQ ID NO: 822-- Exemplary VH
EVQLLESGGGLVQPGGSLRLSCAASGFTFSSYAMNWVRQAPGKGLEWV

STISYSGSHISYHDSVHHRFTISRDNSKNTLYLQMNSLRAEDTAVYYC

ARIHHDPMDVWGQGTLVTVSS

SEQ ID NO: 823-- Exemplary VH
EVQLLESGGGLVQPGGSLRLSCAASGFTFSSYAMNWVRQAPGKGLEWV

STISYHGSLISYHDSVHHRFTISRDNSKNTLYLQMNSLRAEDTAVYYC

ARIHHDPMDVWGQGTLVTVSS

SEQ ID NO: 824-- Exemplary VH
EVQLLESGGGLVQPGGSLRLSCAASGFTFSSYAMNWVRQAPGKGLEWV

STISYHGSHISYADSVHHRFTISRDNSKNTLYLQMNSLRAEDTAVYYC

ARIHHDPMDVWGQGTLVTVSS

SEQ ID NO: 825-- Exemplary VH
EVQLLESGGGLVQPGGSLRLSCAASGFTFSSYAMNWVRQAPGKGLEWV

STISYHGSHISYHDSVKHRFTISRDNSKNTLYLQMNSLRAEDTAVYYC

ARIHHDPMDVWGQGTLVTVSS

SEQ ID NO: 826-- Exemplary VH
EVQLLESGGGLVQPGGSLRLSCAASGFTFSSYAMNWVRQAPGKGLEWV

STISYHGSHISYHDSVHGRFTISRDNSKNTLYLQMNSLRAEDTAVYYC

ARIHHDPMDVWGQGTLVTVSS

SEQ ID NO: 827-- Exemplary VH
EVQLLESGGGLVQPGGSLRLSCAASGFTFSSYAMNWVRQAPGKGLEWV

STISYHGSHISYHDSVHHRFTISRDNSKNTLYLQMNSLRAEDTAVYYC

ARINHDPMDVWGQGTLVTVSS

SEQ ID NO: 828-- Exemplary VH
EVQLLESGGGLVQPGGSLRLSCAASGFTFSSYAMNWVRQAPGKGLEWV

STISYHGSHISYHDSVHHRFTISRDNSKNTLYLQMNSLRAEDTAVYYC

ARIHNDPMDVWGQGTLVTVSS

SEQ ID NO: 829-- Exemplary VH
EVQLLESGGGLVQPGGSLRLSCAASGFTFSSYAMNWVRQAPGKGLEWV

STISYHGSLISYADSVKGRFTISRDNSKNTLYLQMNSLRAEDTAVYYC

ARIHHDPMDVWGQGTLVTVSS

SEQ ID NO: 830-- Exemplary VH
EVQLLESGGGLVQPGGSLRLSCAASGFTFSSYAMNWVRQAPGKGLEWV

STISYSGSHISYADSVKGRFTISRDNSKNTLYLQMNSLRAEDTAVYYC

ARIHHDPMDVWGQGTLVTVSS

SEQ ID NO: 831-- Exemplary VH
EVQLLESGGGLVQPGGSLRLSCAASGFTFSSYAMNWVRQAPGKGLEWV

STISYHGSHISYADSVKGRFTISRDNSKNTLYLQMNSLRAEDTAVYYC

ARIHHDPMDVWGQGTLVTVSS

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An antibody or antigen-binding fragment thereof that binds to PAR2 comprising a heavy chain variable domain (VH) and a light chain variable domain (VL), wherein the VH comprises:
    i) a VH-CDR1 having the amino acid sequence of SEQ ID NO: 13,
    ii) a VH-CDR2 having the amino acid sequence of SEQ ID NO: 14,
    iii) a VH-CDR3 having the amino acid sequence of SEQ ID NO: 15,
    and wherein the VL comprises:
    i) a VL-CDR1 having the amino acid sequence of SEQ ID NO: 18,
    ii) a VL-CDR2 having the amino acid sequence of SEQ ID NO: 19,
    iii) a VL-CDR3 having the amino acid sequence of SEQ ID NO: 20.
2. The antibody or antigen-binding fragment thereof of claim 1, wherein the VH comprises an amino acid sequence that is at least 80%, 85%, 90%, 92%, 93%, 95%, 97%, 99% or 100% identical to SEQ ID NO: 12 and wherein the VL comprises an amino acid sequence that is at least 80%, 85%, 90%, 92%, 93%, 95%, 97%, 99% or 100% identical to SEQ ID NO: 17.
3. The antibody or antigen-binding fragment of claim 1, wherein the antigen-binding fragment is an scFv or a Fab'.
4. The antibody or antigen-binding fragment of claim 1, wherein the antibody is a monoclonal antibody.
5. The antibody or antigen-binding fragment of claim 1, wherein the antibody or antigen-binding fragment prevents trypsin, tryptase and/or matriptase from interacting with PAR2.
6. The antibody or antigen-binding fragment of claim 1, wherein the antibody or antigen-binding fragment binds to PAR2 with greater affinity at a pH of 7.4 than at a pH of 6.0.
7. A composition comprising a pharmaceutically acceptable carrier and the antibody or antigen-binding fragment of claim 1.
8. A kit comprising the composition of claim 7.
9. A kit comprising the antibody or antigen-binding fragment of claim 1.
10. The antibody or antigen-binding fragment of claim 1, wherein the VH comprises an amino acid sequence corresponding to SEQ ID NO: 12 and wherein the VL comprises an amino acid sequence corresponding to SEQ ID NO: 17.
11. A composition comprising a pharmaceutically acceptable carrier and the antibody or antigen-binding fragment of claim 10.
12. A method for treating pain in a subject in need thereof, comprising administering to the subject a pharmaceutically effective amount of the antibody or antigen-binding fragment of claim 10.
13. A method for treating pain in a subject in need thereof, comprising administering to the subject a pharmaceutically effective amount of the antibody or antigen-binding fragment of claim 1.

* * * * *

SEQUENCE LISTING

```
<160> NUMBER OF SEQ ID NOS: 841

<210> SEQ ID NO 1
<211> LENGTH: 351
<212> TYPE: DNA
<213> ORGANISM: Homo sapiens

<400> SEQUENCE: 1
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca acagcaagaa caccctgtac     240
ctgcagatga acagcctgag ggccgaggac accgccgtgt actactgcgc ccgcatcaac     300 aacgaccta tggatgtgtg gggccagggc accctggtga cagtgagctc a               351

<210> SEQ ID NO 2
<211> LENGTH: 117
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 3
<211> LENGTH: 5
<212> TYPE: PRT
<213> ORGANISM: Homo sapiens

<400> SEQUENCE: 3

Ser Tyr Ala Met Asn
1               5

<210> SEQ ID NO 4
<211> LENGTH: 17
```

```
<212> TYPE: PRT
<213> ORGANISM: Homo sapiens

<400> SEQUENCE: 4

Thr Ile Ser Tyr Ser Gly Ser Leu Ile Ser Tyr Ala Asp Ser Val Lys
1               5                   10                  15

Gly

<210> SEQ ID NO 5
<211> LENGTH: 8
<212> TYPE: PRT
<213> ORGANISM: Homo sapiens

<400> SEQUENCE: 5

Ile Asn Asn Asp Pro Met Asp Val
1               5

<210> SEQ ID NO 6
<211> LENGTH: 333
<212> TYPE: DNA
<213> ORGANISM: Homo sapiens

<400> SEQUENCE: 6
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggccatg     240
gacgaggccg actactactg ccagacctgg gacgggaacc cgacgacggg cgagaccaac     300
gtgttcggcg gagggaccaa gttaaccgtc cta                                  333

<210> SEQ ID NO 7
<211> LENGTH: 111
<212> TYPE: PRT
<213> ORGANISM: Homo sapiens

<400> SEQUENCE: 7

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 8
<211> LENGTH: 11
<212> TYPE: PRT
<213> ORGANISM: Homo sapiens

<400> SEQUENCE: 8

Ser Gly Asp Asn Leu Gly Lys Lys Tyr Val Gln
```

<210> SEQ ID NO 9
<211> LENGTH: 7
<212> TYPE: PRT
<213> ORGANISM: Homo sapiens

<400> SEQUENCE: 9

Asp Asp Ser Asn Arg Pro Ser
1               5

<210> SEQ ID NO 10
<211> LENGTH: 14
<212> TYPE: PRT
<213> ORGANISM: Homo sapiens

<400> SEQUENCE: 10

Gln Thr Trp Asp Gly Asn Pro Thr Thr Gly Glu Thr Asn Val
1               5                   10

<210> SEQ ID NO 11
<211> LENGTH: 351
<212> TYPE: DNA
<213> ORGANISM: Homo sapiens

<400> SEQUENCE: 11
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggtcgca catcagctac     180
cacgacagcg tgcatcacag gttcaccatc agcagggaca acagcaagaa caccctgtac     240
ctgcagatga acagcctgag ggccgaggac accgccgtgt actactgcgc ccgcatccac     300
cacgacccta tggatgtgtg gggccagggc accctggtga cagtgagctc a              351

<210> SEQ ID NO 12
<211> LENGTH: 117
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser Val
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
            115

<210> SEQ ID NO 13
<211> LENGTH: 5

<210> SEQ ID NO 13
<211> LENGTH: 5 (implied)
<212> TYPE: PRT
<213> ORGANISM: Homo sapiens

<400> SEQUENCE: 13

Ser Tyr Ala Met Asn
1               5

<210> SEQ ID NO 14
<211> LENGTH: 17
<212> TYPE: PRT
<213> ORGANISM: Homo sapiens

<400> SEQUENCE: 14

Thr Ile Ser Tyr His Gly Ser His Ile Ser Tyr His Asp Ser Val His
1               5                   10                  15

His

<210> SEQ ID NO 15
<211> LENGTH: 8
<212> TYPE: PRT
<213> ORGANISM: Homo sapiens

<400> SEQUENCE: 15

Ile His His Asp Pro Met Asp Val
1               5

<210> SEQ ID NO 16
<211> LENGTH: 333
<212> TYPE: DNA
<213> ORGANISM: Homo sapiens

<400> SEQUENCE: 16
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg agggaccaa gttaaccgtc cta                                   333

<210> SEQ ID NO 17
<211> LENGTH: 111
<212> TYPE: PRT
<213> ORGANISM: Homo sapiens

<400> SEQUENCE: 17

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu

<210> SEQ ID NO 18
<211> LENGTH: 11
<212> TYPE: PRT
<213> ORGANISM: Homo sapiens

<400> SEQUENCE: 18

Ser Gly Asp Asn Leu Gly Lys Lys Tyr Val Gln
1               5                   10

<210> SEQ ID NO 19
<211> LENGTH: 7
<212> TYPE: PRT
<213> ORGANISM: Homo sapiens

<400> SEQUENCE: 19

Asp Asp Ser Asn Arg Pro Ser
1               5

<210> SEQ ID NO 20
<211> LENGTH: 14
<212> TYPE: PRT
<213> ORGANISM: Homo sapiens

<400> SEQUENCE: 20

Gln Thr Trp Asp Gly Asn Pro Thr Thr Gly Glu Thr Asn Val
1               5                   10

<210> SEQ ID NO 21
<211> LENGTH: 351
<212> TYPE: DNA
<213> ORGANISM: Homo sapiens

<400> SEQUENCE: 21
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg gtgtccacc atcagctaca gcgggtcgct gatccactac     180
gccgacagcg tgaagggcag gttcaccatc agcaggaca acagcaagaa caccctgtac     240
ctgcagatga acagcctgag ggccgaggac accgccgtgt actactgcgc ccgcatcaac     300 aacgaccta tggatgtgtg gggccagggc accctggtga cagtgagctc a              351

<210> SEQ ID NO 22
<211> LENGTH: 117
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Arg Ile Asn Asn Asp Pro Met Asp Val Trp Gly Gln Gly Thr Leu
            100                 105                 110

Val Thr Val Ser Ser
            115

<210> SEQ ID NO 23
<211> LENGTH: 5
<212> TYPE: PRT
<213> ORGANISM: Homo sapiens

<400> SEQUENCE: 23

Ser Tyr Ala Met Asn
1               5

<210> SEQ ID NO 24
<211> LENGTH: 17
<212> TYPE: PRT
<213> ORGANISM: Homo sapiens

<400> SEQUENCE: 24

Thr Ile Ser Tyr Ser Gly Ser Leu Ile His Tyr Ala Asp Ser Val Lys
1               5                   10                  15

Gly

<210> SEQ ID NO 25
<211> LENGTH: 8
<212> TYPE: PRT
<213> ORGANISM: Homo sapiens

<400> SEQUENCE: 25

Ile Asn Asn Asp Pro Met Asp Val
1               5

<210> SEQ ID NO 26
<211> LENGTH: 333
<212> TYPE: DNA
<213> ORGANISM: Homo sapiens

<400> SEQUENCE: 26
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggccatg     240
gacgaggccg actactactg ccagacctgg gacgggaacc cgacgacggg cgagaccaac     300
gtgttcggcg agggaccaa gttaaccgtc cta                                   333

<210> SEQ ID NO 27
<211> LENGTH: 111
<212> TYPE: PRT
<213> ORGANISM: Homo sapiens

<400> SEQUENCE: 27

Ser Ile Glu Leu Thr Gln Pro Pro Ser Val Ser Val Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
            35                  40                  45
```

Asp Asp Ser Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 28
<211> LENGTH: 11
<212> TYPE: PRT
<213> ORGANISM: Homo sapiens

<400> SEQUENCE: 28

Ser Gly Asp Asn Leu Gly Lys Lys Tyr Val Gln
1               5                   10

<210> SEQ ID NO 29
<211> LENGTH: 7
<212> TYPE: PRT
<213> ORGANISM: Homo sapiens

<400> SEQUENCE: 29

Asp Asp Ser Asn Arg Pro Ser
1               5

<210> SEQ ID NO 30
<211> LENGTH: 14
<212> TYPE: PRT
<213> ORGANISM: Homo sapiens

<400> SEQUENCE: 30

Gln Thr Trp Asp Gly Asn Pro Thr Thr Gly Glu Thr Asn Val
1               5                   10

<210> SEQ ID NO 31
<211> LENGTH: 351
<212> TYPE: DNA
<213> ORGANISM: Homo sapiens

<400> SEQUENCE: 31
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa cacccctgtac     240 ctgcagatga acagcctgag gccgaggac accgccgtgt actactgcgc ccgcatcaac      300
cacgacccta tggatgtgtg gggccagggc accctggtga cagtgagctc a              351

<210> SEQ ID NO 32
<211> LENGTH: 117
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
            115

<210> SEQ ID NO 33
<211> LENGTH: 5
<212> TYPE: PRT
<213> ORGANISM: Homo sapiens

<400> SEQUENCE: 33

Ser Tyr Ala Met Asn
1               5

<210> SEQ ID NO 34
<211> LENGTH: 17
<212> TYPE: PRT
<213> ORGANISM: Homo sapiens

<400> SEQUENCE: 34

Thr Ile Ser Tyr Ser Gly Ser Leu Ile Ser Tyr Ala Asp Ser Val Lys
1               5                   10                  15

Gly

<210> SEQ ID NO 35
<211> LENGTH: 8
<212> TYPE: PRT
<213> ORGANISM: Homo sapiens

<400> SEQUENCE: 35

Ile Asn His Asp Pro Met Asp Val
1               5

<210> SEQ ID NO 36
<211> LENGTH: 333
<212> TYPE: DNA
<213> ORGANISM: Homo sapiens

<400> SEQUENCE: 36
agtatcgagc tgacccagcc ccccagcgtg agcgtgtccc caggccagac cgccagcatc        60
acctgcagcg gcgacaacct gggcaagaaa tacgtgcagt ggtatcagca gaagcccggc       120
cagtcccccg tgctggtgat ctacgacgac agcaacaggc ccagcggcat ccccgagagg       180
ttcagcggca gcaacagcgg caacaccgcc accctgacca tcagcggcac ccaggccatg       240
gacgaggccg actactactg ccagacctgg gacgggaacc cgacgacggg cgagaccaac       300
gtgttcggcg agggaccaa gttaaccgtc cta                                     333

<210> SEQ ID NO 37
<211> LENGTH: 111
<212> TYPE: PRT
<213> ORGANISM: Homo sapiens

<400> SEQUENCE: 37

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 38
<211> LENGTH: 11
<212> TYPE: PRT
<213> ORGANISM: Homo sapiens

<400> SEQUENCE: 38

Ser Gly Asp Asn Leu Gly Lys Lys Tyr Val Gln
1               5                   10

<210> SEQ ID NO 39
<211> LENGTH: 7
<212> TYPE: PRT
<213> ORGANISM: Homo sapiens

<400> SEQUENCE: 39

Asp Asp Ser Asn Arg Pro Ser
1               5

<210> SEQ ID NO 40
<211> LENGTH: 14
<212> TYPE: PRT
<213> ORGANISM: Homo sapiens

<400> SEQUENCE: 40

Gln Thr Trp Asp Gly Asn Pro Thr Thr Gly Glu Thr Asn Val
1               5                   10

<210> SEQ ID NO 41
<211> LENGTH: 351
<212> TYPE: DNA
<213> ORGANISM: Homo sapiens

<400> SEQUENCE: 41
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa cacccctgtac     240 ctgcagatga acagcctgag ggccgaggac accgccgtgt actactgcgc ccgcatcaac     300
aacgacccta tggatgtgtg gggccagggc accctggtga cagtgagctc a              351

<210> SEQ ID NO 42

<211> LENGTH: 117
<212> TYPE: PRT
<213> ORGANISM: Homo sapiens

<400> SEQUENCE: 42

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115
```

<210> SEQ ID NO 43
<211> LENGTH: 5
<212> TYPE: PRT
<213> ORGANISM: Homo sapiens

<400> SEQUENCE: 43

```
Ser Tyr Ala Met Asn
1               5
```

<210> SEQ ID NO 44
<211> LENGTH: 17
<212> TYPE: PRT
<213> ORGANISM: Homo sapiens

<400> SEQUENCE: 44

```
Thr Ile Ser Tyr Ser Gly Ser Leu Ile Ser Tyr Ala Asp Ser Val Lys
1               5                   10                  15

Gly
```

<210> SEQ ID NO 45
<211> LENGTH: 8
<212> TYPE: PRT
<213> ORGANISM: Homo sapiens

<400> SEQUENCE: 45

```
Ile Asn Asn Asp Pro Met Asp Val
1               5
```

<210> SEQ ID NO 46
<211> LENGTH: 333
<212> TYPE: DNA
<213> ORGANISM: Homo sapiens

<400> SEQUENCE: 46

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
```

```
ttcagcggca gcaacagcgg caacaccgcc accctgacca tcagcggcac ccaggccatg    240
gacgaggccg actactactg ccagacctgg gacgggaacc cgacgcacgg cgagaccaac    300
gtgttcggcg agggaccaa gttaaccgtc cta                                  333
```

<210> SEQ ID NO 47
<211> LENGTH: 111
<212> TYPE: PRT
<213> ORGANISM: Homo sapiens

<400> SEQUENCE: 47

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr His
                85                  90                  95

Gly Glu Thr Asn Val Phe Gly Gly Thr Lys Leu Thr Val Leu
            100                 105                 110

<210> SEQ ID NO 48
<211> LENGTH: 11
<212> TYPE: PRT
<213> ORGANISM: Homo sapiens

<400> SEQUENCE: 48

Ser Gly Asp Asn Leu Gly Lys Lys Tyr Val Gln
1               5                   10

<210> SEQ ID NO 49
<211> LENGTH: 7
<212> TYPE: PRT
<213> ORGANISM: Homo sapiens

<400> SEQUENCE: 49

Asp Asp Ser Asn Arg Pro Ser
1               5

<210> SEQ ID NO 50
<211> LENGTH: 14
<212> TYPE: PRT
<213> ORGANISM: Homo sapiens

<400> SEQUENCE: 50

Gln Thr Trp Asp Gly Asn Pro Thr His Gly Glu Thr Asn Val
1               5                   10

<210> SEQ ID NO 51
<211> LENGTH: 351
<212> TYPE: DNA
<213> ORGANISM: Homo sapiens

<400> SEQUENCE: 51

```
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
```

```
ccaggcaagg gcctggagtg ggtgtccacc atcagctaca gcgggtcgct gatcagctac    180
gccgacagcg tgaagggcag gttcaccatc agcagggaca cagcaagaa  cacctgta     240 ctgcagatga acagcctgag ggccgaggac accgccgtgt actactgcgc ccgcatccac    300
cacgacccta tggatgtgtg gggccagggc accctggtga cagtgagctc a             351
```

<210> SEQ ID NO 52
<211> LENGTH: 117
<212> TYPE: PRT
<213> ORGANISM: Homo sapiens

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115
```

<210> SEQ ID NO 53
<211> LENGTH: 5
<212> TYPE: PRT
<213> ORGANISM: Homo sapiens

<400> SEQUENCE: 53

```
Ser Tyr Ala Met Asn
1               5
```

<210> SEQ ID NO 54
<211> LENGTH: 17
<212> TYPE: PRT
<213> ORGANISM: Homo sapiens

<400> SEQUENCE: 54

```
Thr Ile Ser Tyr Ser Gly Ser Leu Ile Ser Tyr Ala Asp Ser Val Lys
1               5                   10                  15

Gly
```

<210> SEQ ID NO 55
<211> LENGTH: 8
<212> TYPE: PRT
<213> ORGANISM: Homo sapiens

<400> SEQUENCE: 55

```
Ile His His Asp Pro Met Asp Val
1               5
```

<210> SEQ ID NO 56
<211> LENGTH: 333

<212> TYPE: DNA
<213> ORGANISM: Homo sapiens

<400> SEQUENCE: 56

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg agggaccaa gttaaccgtc cta                                 333
```

<210> SEQ ID NO 57
<211> LENGTH: 111
<212> TYPE: PRT
<213> ORGANISM: Homo sapiens

<400> SEQUENCE: 57

```
Ser Ile Glu Leu Thr Gln Pro Pro Ser Val Ser Val Ser Pro Gly Gln
1               5                   10                  15
Thr Ala Ser Ile Thr Cys Ser Gly Asp Asn Leu Gly Lys Lys Tyr Val
            20                  25                  30
Gln Trp Tyr Gln Gln Lys Pro Gly Gln Ser Pro Val Leu Val Ile Tyr
        35                  40                  45
Asp Asp Ser Asn Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln Thr Trp Asp Gly Asn Pro Thr Thr
                85                  90                  95
Gly Glu Thr Asn Val Phe Gly Gly Gly Thr Lys Leu Thr Val Leu
            100                 105                 110
```

<210> SEQ ID NO 58
<211> LENGTH: 11
<212> TYPE: PRT
<213> ORGANISM: Homo sapiens

<400> SEQUENCE: 58

```
Ser Gly Asp Asn Leu Gly Lys Lys Tyr Val Gln
1               5                   10
```

<210> SEQ ID NO 59
<211> LENGTH: 7
<212> TYPE: PRT
<213> ORGANISM: Homo sapiens

<400> SEQUENCE: 59

```
Asp Asp Ser Asn Arg Pro Ser
1               5
```

<210> SEQ ID NO 60
<211> LENGTH: 14
<212> TYPE: PRT
<213> ORGANISM: Homo sapiens

<400> SEQUENCE: 60

```
Gln Thr Trp Asp Gly Asn Pro Thr Thr Gly Glu Thr Asn Val
1               5                   10
```

<210> SEQ ID NO 61
<211> LENGTH: 351
<212> TYPE: DNA
<213> ORGANISM: Homo sapiens

<400> SEQUENCE: 61
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctaca gcgggtcgct gatcagctac   180
gccgacagcg tgaagggcag gttcaccatc agcagggaca caagcaagaa caccctgtac   240
ctgcagatga acagcctgag ggccgaggac accgccgtgt actactgcgc ccgcatccac   300
cacgacccta tggatcactg gggccagggc accctggtga cagtgagctc a            351

<210> SEQ ID NO 62
<211> LENGTH: 117
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp His Trp Gly Gln Gly Thr Leu
            100                 105                 110

Val Thr Val Ser Ser
        115

<210> SEQ ID NO 63
<211> LENGTH: 5
<212> TYPE: PRT
<213> ORGANISM: Homo sapiens

<400> SEQUENCE: 63

Ser Tyr Ala Met Asn
1               5

<210> SEQ ID NO 64
<211> LENGTH: 17
<212> TYPE: PRT
<213> ORGANISM: Homo sapiens

<400> SEQUENCE: 64

Thr Ile Ser Tyr Ser Gly Ser Leu Ile Ser Tyr Ala Asp Ser Val Lys
1               5                   10                  15

Gly

<210> SEQ ID NO 65
<211> LENGTH: 8

```
<212> TYPE: PRT
<213> ORGANISM: Homo sapiens

<400> SEQUENCE: 65

Ile His His Asp Pro Met Asp His
1               5

<210> SEQ ID NO 66
<211> LENGTH: 333
<212> TYPE: DNA
<213> ORGANISM: Homo sapiens

<400> SEQUENCE: 66
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120 cagtccccccg tgctggtgat ctacgacgac agcaacaggc ccagcggcat ccccgagagg    180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                  333

<210> SEQ ID NO 67
<211> LENGTH: 111
<212> TYPE: PRT
<213> ORGANISM: Homo sapiens

<400> SEQUENCE: 67

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 68
<211> LENGTH: 11
<212> TYPE: PRT
<213> ORGANISM: Homo sapiens

<400> SEQUENCE: 68

Ser Gly Asp Asn Leu Gly Lys Lys Tyr Val Gln
1               5                   10

<210> SEQ ID NO 69
<211> LENGTH: 7
<212> TYPE: PRT
<213> ORGANISM: Homo sapiens

<400> SEQUENCE: 69

Asp Asp Ser Asn Arg Pro Ser
1               5
```

<210> SEQ ID NO 70
<211> LENGTH: 14
<212> TYPE: PRT
<213> ORGANISM: Homo sapiens

<400> SEQUENCE: 70

Gln Thr Trp Asp Gly Asn Pro Thr Thr Gly Glu Thr Asn Val
1               5                   10

<210> SEQ ID NO 71
<211> LENGTH: 351
<212> TYPE: DNA
<213> ORGANISM: Homo sapiens

<400> SEQUENCE: 71
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg gtgtccacc atcagctaca gcgggtcgct gatcagctac      180
gccgacagcg tgaagggcag gttcaccatc agcagggaca acagcaagaa caccctgtac     240
ctgcagatga acagcctgag ggccgaggac accgccgtgt actactgcgc ccgcatcaac     300
aacgacccta tggatgtgtg gggccagggc accctggtga cagtgagctc a              351

<210> SEQ ID NO 72
<211> LENGTH: 117
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 73
<211> LENGTH: 5
<212> TYPE: PRT
<213> ORGANISM: Homo sapiens

<400> SEQUENCE: 73

Ser Tyr Ala Met Asn
1               5

<210> SEQ ID NO 74
<211> LENGTH: 17
<212> TYPE: PRT
<213> ORGANISM: Homo sapiens

<400> SEQUENCE: 74

Thr Ile Ser Tyr Ser Gly Ser Leu Ile Ser Tyr Ala Asp Ser Val Lys
1               5                   10                  15
Gly

<210> SEQ ID NO 75
<211> LENGTH: 8
<212> TYPE: PRT
<213> ORGANISM: Homo sapiens

<400> SEQUENCE: 75

Ile Asn Asn Asp Pro Met Asp Val
1               5

<210> SEQ ID NO 76
<211> LENGTH: 333
<212> TYPE: DNA
<213> ORGANISM: Homo sapiens

<400> SEQUENCE: 76
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg caccacaacc cgcacacggg ggagaccaac     300
cacttcggcg gagggaccaa gttaaccgtc cta                                  333

<210> SEQ ID NO 77
<211> LENGTH: 111
<212> TYPE: PRT
<213> ORGANISM: Homo sapiens

<400> SEQUENCE: 77

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp His His Asn Pro His Thr
                85                  90                  95

Gly Glu Thr Asn His Phe Gly Gly Gly Thr Lys Leu Thr Val Leu
            100                 105                 110

<210> SEQ ID NO 78
<211> LENGTH: 11
<212> TYPE: PRT
<213> ORGANISM: Homo sapiens

<400> SEQUENCE: 78

Ser Gly Asp Asn Leu Gly Lys Lys Tyr Val Gln
1               5                   10

<210> SEQ ID NO 79
<211> LENGTH: 7
<212> TYPE: PRT
<213> ORGANISM: Homo sapiens

<400> SEQUENCE: 79

Asp Asp Ser Asn Arg Pro Ser
1               5

<210> SEQ ID NO 80
<211> LENGTH: 14
<212> TYPE: PRT
<213> ORGANISM: Homo sapiens

<400> SEQUENCE: 80

His Thr Trp His His Asn Pro His Thr Gly Glu Thr Asn His
1               5                   10

<210> SEQ ID NO 81
<211> LENGTH: 351
<212> TYPE: DNA
<213> ORGANISM: Homo sapiens

<400> SEQUENCE: 81
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac      240 ctgcagatga acagcctgag ggccgaggac accgccgtgt actactgcgc cgcatcaac      300 aacgacccta tggatgtgtg gggccagggc accctggtga cagtgagctc a              351

<210> SEQ ID NO 82
<211> LENGTH: 117
<212> TYPE: PRT
<213> ORGANISM: Homo sapiens

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 83
<211> LENGTH: 5
<212> TYPE: PRT
<213> ORGANISM: Homo sapiens

<400> SEQUENCE: 83

Ser Tyr Ala Met Asn
1               5

<210> SEQ ID NO 84
<211> LENGTH: 17
<212> TYPE: PRT
<213> ORGANISM: Homo sapiens

<400> SEQUENCE: 84

Thr Ile Ser Tyr Ser Gly Ser Leu Ile Ser Tyr Ala Asp Ser Val Lys
1               5                   10                  15

Gly

<210> SEQ ID NO 85
<211> LENGTH: 8
<212> TYPE: PRT
<213> ORGANISM: Homo sapiens

<400> SEQUENCE: 85

Ile Asn Asn Asp Pro Met Asp Val
1               5

<210> SEQ ID NO 86
<211> LENGTH: 333
<212> TYPE: DNA
<213> ORGANISM: Homo sapiens

<400> SEQUENCE: 86

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtccccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccaccactgg cacgggaacc accacgggg ggagaccaac   300
cacttcggcg agggaccaa gttaaccgtc cta                                 333
```

<210> SEQ ID NO 87
<211> LENGTH: 111
<212> TYPE: PRT
<213> ORGANISM: Homo sapiens

<400> SEQUENCE: 87

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His His Trp His Gly Asn His His Thr
                85                  90                  95

Gly Glu Thr Asn His Phe Gly Gly Gly Thr Lys Leu Thr Val Leu
            100                 105                 110

<210> SEQ ID NO 88
<211> LENGTH: 11
<212> TYPE: PRT
<213> ORGANISM: Homo sapiens

<400> SEQUENCE: 88

Ser Gly Asp Asn Leu Gly Lys Lys Tyr Val Gln
1               5                   10

<210> SEQ ID NO 89
<211> LENGTH: 7
<212> TYPE: PRT
<213> ORGANISM: Homo sapiens

<400> SEQUENCE: 89

Asp Asp Ser Asn Arg Pro Ser
1               5

<210> SEQ ID NO 90
<211> LENGTH: 14
<212> TYPE: PRT
<213> ORGANISM: Homo sapiens

<400> SEQUENCE: 90

His His Trp His Gly Asn His His Thr Gly Glu Thr Asn His
1               5                   10

<210> SEQ ID NO 91
<211> LENGTH: 351
<212> TYPE: DNA
<213> ORGANISM: Homo sapiens

<400> SEQUENCE: 91
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac      240
ctgcagatga acagcctgag ggccgaggac accgccgtgt actactgcgc cgcatcaac      300
aacgacccta tggatgtgtg gggccagggc accctggtga cagtgagctc a              351

<210> SEQ ID NO 92
<211> LENGTH: 117
<212> TYPE: PRT
<213> ORGANISM: Homo sapiens

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 93
<211> LENGTH: 5
<212> TYPE: PRT
<213> ORGANISM: Homo sapiens

<400> SEQUENCE: 93

Ser Tyr Ala Met Asn
1               5

<210> SEQ ID NO 94
<211> LENGTH: 17
<212> TYPE: PRT
<213> ORGANISM: Homo sapiens

<400> SEQUENCE: 94

Thr Ile Ser Tyr Ser Gly Ser Leu Ile Ser Tyr Ala Asp Ser Val Lys
1               5                   10                  15

Gly

<210> SEQ ID NO 95
<211> LENGTH: 8
<212> TYPE: PRT
<213> ORGANISM: Homo sapiens

<400> SEQUENCE: 95

Ile Asn Asn Asp Pro Met Asp Val
1               5

<210> SEQ ID NO 96
<211> LENGTH: 333
<212> TYPE: DNA
<213> ORGANISM: Homo sapiens

<400> SEQUENCE: 96
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg caccaccacc gacgcatggg ggagcacaac     300
gtgttcggcg agggaccaa gttaaccgtc cta                                   333

<210> SEQ ID NO 97
<211> LENGTH: 111
<212> TYPE: PRT
<213> ORGANISM: Homo sapiens

<400> SEQUENCE: 97

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser

```
                    50                  55                  60
Asn Ser Gly Asn Thr Ala Thr Leu Thr Ile Ser Gly Thr Gln Ala Met
 65                  70                  75                  80

Asp Glu Ala Asp Tyr Tyr Cys His Thr Trp His His Pro Thr His
                 85                  90                  95

Gly Glu His Asn Val Phe Gly Gly Gly Thr Lys Leu Thr Val Leu
            100                 105                 110

<210> SEQ ID NO 98
<211> LENGTH: 11
<212> TYPE: PRT
<213> ORGANISM: Homo sapiens

<400> SEQUENCE: 98

Ser Gly Asp Asn Leu Gly Lys Lys Tyr Val Gln
 1               5                  10

<210> SEQ ID NO 99
<211> LENGTH: 7
<212> TYPE: PRT
<213> ORGANISM: Homo sapiens

<400> SEQUENCE: 99

Asp Asp Ser Asn Arg Pro Ser
 1               5

<210> SEQ ID NO 100
<211> LENGTH: 14
<212> TYPE: PRT
<213> ORGANISM: Homo sapiens

<400> SEQUENCE: 100

His Thr Trp His His Pro Thr His Gly Glu His Asn Val
 1               5                  10

<210> SEQ ID NO 101
<211> LENGTH: 351
<212> TYPE: DNA
<213> ORGANISM: Homo sapiens

<400> SEQUENCE: 101
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa cacccctgtac    240 ctgcagatga acagcctgag ggccgaggac accgccgtgt actactgcgc ccgcatcaac     300
aacgaccctc tggatgtgtg gggccagggc accctggtga cagtgagctc a              351

<210> SEQ ID NO 102
<211> LENGTH: 117
<212> TYPE: PRT
<213> ORGANISM: Homo sapiens

<400> SEQUENCE: 102

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
```

```
                    35                  40                  45
Ser Thr Ile Ser Tyr Ser Gly Ser Leu Ile Ser Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Asn Asn Asp Pro Met Asp Val Trp Gly Gln Gly Thr Leu
             100                 105                 110

Val Thr Val Ser Ser
        115

<210> SEQ ID NO 103
<211> LENGTH: 5
<212> TYPE: PRT
<213> ORGANISM: Homo sapiens

<400> SEQUENCE: 103

Ser Tyr Ala Met Asn
1               5

<210> SEQ ID NO 104
<211> LENGTH: 17
<212> TYPE: PRT
<213> ORGANISM: Homo sapiens

<400> SEQUENCE: 104

Thr Ile Ser Tyr Ser Gly Ser Leu Ile Ser Tyr Ala Asp Ser Val Lys
1               5                   10                  15

Gly

<210> SEQ ID NO 105
<211> LENGTH: 8
<212> TYPE: PRT
<213> ORGANISM: Homo sapiens

<400> SEQUENCE: 105

Ile Asn Asn Asp Pro Met Asp Val
1               5

<210> SEQ ID NO 106
<211> LENGTH: 333
<212> TYPE: DNA
<213> ORGANISM: Homo sapiens

<400> SEQUENCE: 106
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggcacc acacgcatgg ggagcaccac     300
gtgttcggcg agggaccaa gttaaccgtc cta                                   333

<210> SEQ ID NO 107
<211> LENGTH: 111
<212> TYPE: PRT
<213> ORGANISM: Homo sapiens

<400> SEQUENCE: 107
```

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly His His Thr His
                85                  90                  95

Gly Glu His His Val Phe Gly Gly Gly Thr Lys Leu Thr Val Leu
            100                 105                 110
```

<210> SEQ ID NO 108
<211> LENGTH: 11
<212> TYPE: PRT
<213> ORGANISM: Homo sapiens

<400> SEQUENCE: 108

```
Ser Gly Asp Asn Leu Gly Lys Lys Tyr Val Gln
1               5                   10
```

<210> SEQ ID NO 109
<211> LENGTH: 7
<212> TYPE: PRT
<213> ORGANISM: Homo sapiens

<400> SEQUENCE: 109

```
Asp Asp Ser Asn Arg Pro Ser
1               5
```

<210> SEQ ID NO 110
<211> LENGTH: 14
<212> TYPE: PRT
<213> ORGANISM: Homo sapiens

<400> SEQUENCE: 110

```
Gln Thr Trp Asp Gly His His Thr His Gly Glu His His Val
1               5                   10
```

<210> SEQ ID NO 111
<211> LENGTH: 351
<212> TYPE: DNA
<213> ORGANISM: Homo sapiens

<400> SEQUENCE: 111

```
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctaca gcgggtcgct gatcagctac    180
gccgacagcg tgaagggcag gttcaccatc agcagggaca acagcaagaa caccctgtac    240
ctgcagatga acagcctgag ggccgaggac accgccgtgt actactgcgc ccgcatcaac    300
aacgacccta tggatgtgtg gggccagggc accctggtga cagtgagctc a             351
```

<210> SEQ ID NO 112
<211> LENGTH: 117
<212> TYPE: PRT

<213> ORGANISM: Homo sapiens

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 113
<211> LENGTH: 5
<212> TYPE: PRT
<213> ORGANISM: Homo sapiens

<400> SEQUENCE: 113

Ser Tyr Ala Met Asn
1               5

<210> SEQ ID NO 114
<211> LENGTH: 17
<212> TYPE: PRT
<213> ORGANISM: Homo sapiens

<400> SEQUENCE: 114

Thr Ile Ser Tyr Ser Gly Ser Leu Ile Ser Tyr Ala Asp Ser Val Lys
1               5                   10                  15

Gly

<210> SEQ ID NO 115
<211> LENGTH: 8
<212> TYPE: PRT
<213> ORGANISM: Homo sapiens

<400> SEQUENCE: 115

Ile Asn Asn Asp Pro Met Asp Val
1               5

<210> SEQ ID NO 116
<211> LENGTH: 333
<212> TYPE: DNA
<213> ORGANISM: Homo sapiens

<400> SEQUENCE: 116
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120 cagtccccccg tgctggtgat ctacgacgac agcaacaggc ccagcggcat ccccgagagg    180
ttcagcggca gcaacagcgg caacaccgcc accctgacca tcagcggcac ccaggcgatg    240

```
gacgaggccg actactactg ccagacctgg gaccacaacc accacacggg gcacaccaac      300
gtgttcggcg gagggaccaa gttaaccgtc cta                                   333
```

<210> SEQ ID NO 117
<211> LENGTH: 111
<212> TYPE: PRT
<213> ORGANISM: Homo sapiens

<400> SEQUENCE: 117

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp His Asn His His Thr
                85                  90                  95

Gly His Thr Asn Val Phe Gly Gly Gly Thr Lys Leu Thr Val Leu
            100                 105                 110
```

<210> SEQ ID NO 118
<211> LENGTH: 11
<212> TYPE: PRT
<213> ORGANISM: Homo sapiens

<400> SEQUENCE: 118

```
Ser Gly Asp Asn Leu Gly Lys Lys Tyr Val Gln
1               5                   10
```

<210> SEQ ID NO 119
<211> LENGTH: 7
<212> TYPE: PRT
<213> ORGANISM: Homo sapiens

<400> SEQUENCE: 119

```
Asp Asp Ser Asn Arg Pro Ser
1               5
```

<210> SEQ ID NO 120
<211> LENGTH: 14
<212> TYPE: PRT
<213> ORGANISM: Homo sapiens

<400> SEQUENCE: 120

```
Gln Thr Trp Asp His Asn His His Thr Gly His Thr Asn Val
1               5                   10
```

<210> SEQ ID NO 121
<211> LENGTH: 351
<212> TYPE: DNA
<213> ORGANISM: Homo sapiens

<400> SEQUENCE: 121

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
```

```
gccgacagcg tgaagggcag gttcaccatc agcagggaca acagcaagaa caccctgtac    240
ctgcagatga acagcctgag ggccgaggac accgccgtgt actactgcgc ccgcatcaac    300 aacgaccota tggatgtgtg gggccagggc accctggtga cagtgagctc a             351
```

<210> SEQ ID NO 122
<211> LENGTH: 117
<212> TYPE: PRT
<213> ORGANISM: Homo sapiens

<400> SEQUENCE: 122

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115
```

<210> SEQ ID NO 123
<211> LENGTH: 5
<212> TYPE: PRT
<213> ORGANISM: Homo sapiens

<400> SEQUENCE: 123

```
Ser Tyr Ala Met Asn
1               5
```

<210> SEQ ID NO 124
<211> LENGTH: 17
<212> TYPE: PRT
<213> ORGANISM: Homo sapiens

<400> SEQUENCE: 124

```
Thr Ile Ser Tyr Ser Gly Ser Leu Ile Ser Tyr Ala Asp Ser Val Lys
1               5                   10                  15

Gly
```

<210> SEQ ID NO 125
<211> LENGTH: 8
<212> TYPE: PRT
<213> ORGANISM: Homo sapiens

<400> SEQUENCE: 125

```
Ile Asn Asn Asp Pro Met Asp Val
1               5
```

<210> SEQ ID NO 126
<211> LENGTH: 333
<212> TYPE: DNA
<213> ORGANISM: Homo sapiens

<400> SEQUENCE: 126

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120 cagtccccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccacacctgg caccaccacc accacacggg ggagcacaac   300
cacttcggcg agggaccaa gttaaccgtc cta                                 333
```

<210> SEQ ID NO 127
<211> LENGTH: 111
<212> TYPE: PRT
<213> ORGANISM: Homo sapiens

<400> SEQUENCE: 127

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp His His His His Thr
                85                  90                  95

Gly Glu His Asn His Phe Gly Gly Gly Thr Lys Leu Thr Val Leu
            100                 105                 110
```

<210> SEQ ID NO 128
<211> LENGTH: 11
<212> TYPE: PRT
<213> ORGANISM: Homo sapiens

<400> SEQUENCE: 128

```
Ser Gly Asp Asn Leu Gly Lys Lys Tyr Val Gln
1               5                   10
```

<210> SEQ ID NO 129
<211> LENGTH: 7
<212> TYPE: PRT
<213> ORGANISM: Homo sapiens

<400> SEQUENCE: 129

```
Asp Asp Ser Asn Arg Pro Ser
1               5
```

<210> SEQ ID NO 130
<211> LENGTH: 14
<212> TYPE: PRT
<213> ORGANISM: Homo sapiens

<400> SEQUENCE: 130

```
His Thr Trp His His His His Thr Gly Glu His Asn His
1               5                   10
```

<210> SEQ ID NO 131

```
<211> LENGTH: 351
<212> TYPE: DNA
<213> ORGANISM: Homo sapiens

<400> SEQUENCE: 131
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca acagcaagaa cacccctgtac    240 ctgcagatga acagcctgag ggccgaggac accgccgtgt actactgcgc ccgcatcaac     300
aacgacccta tggatgtgtg gggccagggc accctggtga cagtgagctc a              351

<210> SEQ ID NO 132
<211> LENGTH: 117
<212> TYPE: PRT
<213> ORGANISM: Homo sapiens

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 133
<211> LENGTH: 5
<212> TYPE: PRT
<213> ORGANISM: Homo sapiens

<400> SEQUENCE: 133

Ser Tyr Ala Met Asn
1               5

<210> SEQ ID NO 134
<211> LENGTH: 17
<212> TYPE: PRT
<213> ORGANISM: Homo sapiens

<400> SEQUENCE: 134

Thr Ile Ser Tyr Ser Gly Ser Leu Ile Ser Tyr Ala Asp Ser Val Lys
1               5                   10                  15

Gly

<210> SEQ ID NO 135
<211> LENGTH: 8
<212> TYPE: PRT
<213> ORGANISM: Homo sapiens
```

<400> SEQUENCE: 135

Ile Asn Asn Asp Pro Met Asp Val
1               5

<210> SEQ ID NO 136
<211> LENGTH: 333
<212> TYPE: DNA
<213> ORGANISM: Homo sapiens

<400> SEQUENCE: 136

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtccccg tgctggtgat ctacgacgac agcaacaggc ccagcggcat ccccgagagg    180
ttcagcggca gcaacagcgg caacaccgcc accctgacca tcagcggcac ccaggcgatg   240
gacgaggccg actactactg ccagcactgg cacgggcacc cgcaccatgg ggagcacaac   300
gtgttcggcg gagggaccaa gttaaccgtc cta                                333
```

<210> SEQ ID NO 137
<211> LENGTH: 111
<212> TYPE: PRT
<213> ORGANISM: Homo sapiens

<400> SEQUENCE: 137

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln His Trp His Gly His Pro His His
                85                  90                  95

Gly Glu His Asn Val Phe Gly Gly Gly Thr Lys Leu Thr Val Leu
            100                 105                 110

<210> SEQ ID NO 138
<211> LENGTH: 11
<212> TYPE: PRT
<213> ORGANISM: Homo sapiens

<400> SEQUENCE: 138

Ser Gly Asp Asn Leu Gly Lys Lys Tyr Val Gln
1               5                   10

<210> SEQ ID NO 139
<211> LENGTH: 7
<212> TYPE: PRT
<213> ORGANISM: Homo sapiens

<400> SEQUENCE: 139

Asp Asp Ser Asn Arg Pro Ser
1               5

<210> SEQ ID NO 140

```
<211> LENGTH: 14
<212> TYPE: PRT
<213> ORGANISM: Homo sapiens

<400> SEQUENCE: 140

Gln His Trp His Gly His Pro His His Gly Glu His Asn Val
1               5                   10

<210> SEQ ID NO 141
<211> LENGTH: 351
<212> TYPE: DNA
<213> ORGANISM: Homo sapiens

<400> SEQUENCE: 141
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctaca gcggtcgct gatcagctac    180 gccgacagcg tgaagggcag gttcaccatc agcagggaca caagcaagaa caccctgtac   240
ctgcagatga acagcctgag ggccgaggac accgccgtgt actactgcgc ccgcatcaac   300
aacgacccta tggatgtgtg gggccagggc accctggtga cagtgagctc a            351

<210> SEQ ID NO 142
<211> LENGTH: 117
<212> TYPE: PRT
<213> ORGANISM: Homo sapiens

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 143
<211> LENGTH: 5
<212> TYPE: PRT
<213> ORGANISM: Homo sapiens

<400> SEQUENCE: 143

Ser Tyr Ala Met Asn
1               5

<210> SEQ ID NO 144
<211> LENGTH: 17
<212> TYPE: PRT
<213> ORGANISM: Homo sapiens

<400> SEQUENCE: 144
```

-continued

Thr Ile Ser Tyr Ser Gly Ser Leu Ile Ser Tyr Ala Asp Ser Val Lys
1               5                   10                  15

Gly

<210> SEQ ID NO 145
<211> LENGTH: 8
<212> TYPE: PRT
<213> ORGANISM: Homo sapiens

<400> SEQUENCE: 145

Ile Asn Asn Asp Pro Met Asp Val
1               5

<210> SEQ ID NO 146
<211> LENGTH: 333
<212> TYPE: DNA
<213> ORGANISM: Homo sapiens

<400> SEQUENCE: 146
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagcactgg gacgggaacc accaccatgg ggagaccaac     300
cacttcggcg agggaccaa gttaaccgtc cta                                   333

<210> SEQ ID NO 147
<211> LENGTH: 111
<212> TYPE: PRT
<213> ORGANISM: Homo sapiens

<400> SEQUENCE: 147

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln His Trp Asp Gly Asn His His His
                85                  90                  95

Gly Glu Thr Asn His Phe Gly Gly Gly Thr Lys Leu Thr Val Leu
            100                 105                 110

<210> SEQ ID NO 148
<211> LENGTH: 11
<212> TYPE: PRT
<213> ORGANISM: Homo sapiens

<400> SEQUENCE: 148

Ser Gly Asp Asn Leu Gly Lys Lys Tyr Val Gln
1               5                   10

<210> SEQ ID NO 149

```
<211> LENGTH: 7
<212> TYPE: PRT
<213> ORGANISM: Homo sapiens

<400> SEQUENCE: 149

Asp Asp Ser Asn Arg Pro Ser
1               5

<210> SEQ ID NO 150
<211> LENGTH: 14
<212> TYPE: PRT
<213> ORGANISM: Homo sapiens

<400> SEQUENCE: 150

Gln His Trp Asp Gly Asn His His Gly Glu Thr Asn His
1               5                   10

<210> SEQ ID NO 151
<211> LENGTH: 351
<212> TYPE: DNA
<213> ORGANISM: Homo sapiens

<400> SEQUENCE: 151
gaggtgcagc tgctggagag cggcggaggg ctggtgcagc caggcggcag cctgaggctg      60
tcctgcgccg cctccggatt cacccttcagc agctacgcca tgaactgggt gcggcaggcc    120
ccaggcaagg gcctggagtg ggtgtccacc atcagctaca gcgggtcgct gatcagctac     180
gccgacagcg tgaagggcag gttcaccatc agcagggaca acagcaagaa caccctgtac    240
ctgcagatga acagcctgag ggccgaggac accgccgtgt actactgcgc cgcatcaac     300 aacgacccta tggatgtgtg gggccagggc accctggtga cagtgagctc a             351

<210> SEQ ID NO 152
<211> LENGTH: 117
<212> TYPE: PRT
<213> ORGANISM: Homo sapiens

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Thr Ile Ser Tyr Ser Gly Ser Leu Ile Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 153
<211> LENGTH: 5
<212> TYPE: PRT
<213> ORGANISM: Homo sapiens

<400> SEQUENCE: 153
```

```
Ser Tyr Ala Met Asn
1               5
```

<210> SEQ ID NO 154
<211> LENGTH: 17
<212> TYPE: PRT
<213> ORGANISM: Homo sapiens

<400> SEQUENCE: 154

```
Thr Ile Ser Tyr Ser Gly Ser Leu Ile Ser Tyr Ala Asp Ser Val Lys
1               5                   10                  15

Gly
```

<210> SEQ ID NO 155
<211> LENGTH: 8
<212> TYPE: PRT
<213> ORGANISM: Homo sapiens

<400> SEQUENCE: 155

```
Ile Asn Asn Asp Pro Met Asp Val
1               5
```

<210> SEQ ID NO 156
<211> LENGTH: 333
<212> TYPE: DNA
<213> ORGANISM: Homo sapiens

<400> SEQUENCE: 156

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg gaccaccacc acacgacggg ggagcacaac     300
gtgttcggcg gagggaccaa gttaaccgtc cta                                  333
```

<210> SEQ ID NO 157
<211> LENGTH: 111
<212> TYPE: PRT
<213> ORGANISM: Homo sapiens

<400> SEQUENCE: 157

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp His His His Thr Thr
                85                  90                  95

Gly Glu His Asn Val Phe Gly Gly Gly Thr Lys Leu Thr Val Leu
            100                 105                 110
```

<210> SEQ ID NO 158

```
<211> LENGTH: 11
<212> TYPE: PRT
<213> ORGANISM: Homo sapiens

<400> SEQUENCE: 158

Ser Gly Asp Asn Leu Gly Lys Lys Tyr Val Gln
1               5                   10

<210> SEQ ID NO 159
<211> LENGTH: 7
<212> TYPE: PRT
<213> ORGANISM: Homo sapiens

<400> SEQUENCE: 159

Asp Asp Ser Asn Arg Pro Ser
1               5

<210> SEQ ID NO 160
<211> LENGTH: 14
<212> TYPE: PRT
<213> ORGANISM: Homo sapiens

<400> SEQUENCE: 160

His Thr Trp Asp His His Thr Thr Gly Glu His Asn Val
1               5                   10

<210> SEQ ID NO 161
<211> LENGTH: 351
<212> TYPE: DNA
<213> ORGANISM: Homo sapiens

<400> SEQUENCE: 161
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg gtgtccacc atcagctaca gcgggtcgct gatcagctac     180
gccgacagcg tgaagggcag gttcaccatc agcagggaca acagcaagaa caccctgtac     240
ctgcagatga acagcctgag ggccgaggac accgccgtgt actactgcgc ccgcatcaac     300
aacgacccta tggatgtgtg gggccagggc accctggtga cagtgagctc a              351

<210> SEQ ID NO 162
<211> LENGTH: 117
<212> TYPE: PRT
<213> ORGANISM: Homo sapiens

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110
```

<210> SEQ ID NO 163
<211> LENGTH: 5
<212> TYPE: PRT
<213> ORGANISM: Homo sapiens

<400> SEQUENCE: 163

Ser Tyr Ala Met Asn
1               5

<210> SEQ ID NO 164
<211> LENGTH: 17
<212> TYPE: PRT
<213> ORGANISM: Homo sapiens

<400> SEQUENCE: 164

Thr Ile Ser Tyr Ser Gly Ser Leu Ile Ser Tyr Ala Asp Ser Val Lys
1               5                   10                  15

Gly

<210> SEQ ID NO 165
<211> LENGTH: 8
<212> TYPE: PRT
<213> ORGANISM: Homo sapiens

<400> SEQUENCE: 165

Ile Asn Asn Asp Pro Met Asp Val
1               5

<210> SEQ ID NO 166
<211> LENGTH: 333
<212> TYPE: DNA
<213> ORGANISM: Homo sapiens

<400> SEQUENCE: 166

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccaccactgg cacgggcacc acacgacggg ggagaccaac     300
cacttcggcg agggaccaa gttaaccgtc cta                                    333
```

<210> SEQ ID NO 167
<211> LENGTH: 111
<212> TYPE: PRT
<213> ORGANISM: Homo sapiens

<400> SEQUENCE: 167

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys His His Trp His Gly His Thr Thr
                 85                  90                  95

Gly Glu Thr Asn His Phe Gly Gly Gly Thr Lys Leu Thr Val Leu
            100                 105                 110

<210> SEQ ID NO 168
<211> LENGTH: 11
<212> TYPE: PRT
<213> ORGANISM: Homo sapiens

<400> SEQUENCE: 168

Ser Gly Asp Asn Leu Gly Lys Lys Tyr Val Gln
1               5                   10

<210> SEQ ID NO 169
<211> LENGTH: 7
<212> TYPE: PRT
<213> ORGANISM: Homo sapiens

<400> SEQUENCE: 169

Asp Asp Ser Asn Arg Pro Ser
1               5

<210> SEQ ID NO 170
<211> LENGTH: 14
<212> TYPE: PRT
<213> ORGANISM: Homo sapiens

<400> SEQUENCE: 170

His His Trp His Gly His His Thr Thr Gly Glu Thr Asn His
1               5                   10

<210> SEQ ID NO 171
<211> LENGTH: 351
<212> TYPE: DNA
<213> ORGANISM: Homo sapiens

<400> SEQUENCE: 171
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa cacctgtac      240 ctgcagatga acagcctgag ggccgaggac accgccgtgt actactgcgc ccgcatcaac     300
aacgacccta tggatgtgtg ggccagggc accctggtga cagtgagctc a              351

<210> SEQ ID NO 172
<211> LENGTH: 117
<212> TYPE: PRT
<213> ORGANISM: Homo sapiens

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

```
Ser Thr Ile Ser Tyr Ser Gly Ser Leu Ile Ser Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Asn Asn Asp Pro Met Asp Val Trp Gly Gln Gly Thr Leu
            100                 105                 110

Val Thr Val Ser Ser
            115

<210> SEQ ID NO 173
<211> LENGTH: 5
<212> TYPE: PRT
<213> ORGANISM: Homo sapiens

<400> SEQUENCE: 173

Ser Tyr Ala Met Asn
 1               5

<210> SEQ ID NO 174
<211> LENGTH: 17
<212> TYPE: PRT
<213> ORGANISM: Homo sapiens

<400> SEQUENCE: 174

Thr Ile Ser Tyr Ser Gly Ser Leu Ile Ser Tyr Ala Asp Ser Val Lys
 1               5                  10                  15

Gly

<210> SEQ ID NO 175
<211> LENGTH: 8
<212> TYPE: PRT
<213> ORGANISM: Homo sapiens

<400> SEQUENCE: 175

Ile Asn Asn Asp Pro Met Asp Val
 1               5

<210> SEQ ID NO 176
<211> LENGTH: 333
<212> TYPE: DNA
<213> ORGANISM: Homo sapiens

<400> SEQUENCE: 176
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccaccactgg cacgggcacc gcacacgggg ggagcacaac     300
gtgttcggcg agggaccaa gttaaccgtc cta                                   333

<210> SEQ ID NO 177
<211> LENGTH: 111
<212> TYPE: PRT
<213> ORGANISM: Homo sapiens

<400> SEQUENCE: 177

Ser Ile Glu Leu Thr Gln Pro Pro Ser Val Ser Val Ser Pro Gly Gln
```

```
  1               5                  10                 15
Thr Ala Ser Ile Thr Cys Ser Gly Asp Asn Leu Gly Lys Lys Tyr Val
            20                  25                  30
Gln Trp Tyr Gln Gln Lys Pro Gly Gln Ser Pro Val Leu Val Ile Tyr
            35                  40                  45
Asp Asp Ser Asn Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Met
 65                  70                  75                  80
Asp Glu Ala Asp Tyr Tyr Cys His His Trp His Gly His Pro His Thr
                85                  90                  95
Gly Glu His Asn Val Phe Gly Gly Gly Thr Lys Leu Thr Val Leu
            100                 105                 110
```

<210> SEQ ID NO 178
<211> LENGTH: 11
<212> TYPE: PRT
<213> ORGANISM: Homo sapiens

<400> SEQUENCE: 178

```
Ser Gly Asp Asn Leu Gly Lys Lys Tyr Val Gln
 1               5                  10
```

<210> SEQ ID NO 179
<211> LENGTH: 7
<212> TYPE: PRT
<213> ORGANISM: Homo sapiens

<400> SEQUENCE: 179

```
Asp Asp Ser Asn Arg Pro Ser
 1               5
```

<210> SEQ ID NO 180
<211> LENGTH: 14
<212> TYPE: PRT
<213> ORGANISM: Homo sapiens

<400> SEQUENCE: 180

```
His His Trp His Gly His Pro His Thr Gly Glu His Asn Val
 1               5                  10
```

<210> SEQ ID NO 181
<211> LENGTH: 351
<212> TYPE: DNA
<213> ORGANISM: Homo sapiens

<400> SEQUENCE: 181

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac      240 ctgcagatga acagcctgag ggccgaggac accgccgtgt actactgcgc ccgcatcaac     300
aacgacccta tggatgtgtg gggccagggc accctggtga cagtgagctc a              351
```

<210> SEQ ID NO 182
<211> LENGTH: 117
<212> TYPE: PRT
<213> ORGANISM: Homo sapiens

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 183
<211> LENGTH: 5
<212> TYPE: PRT
<213> ORGANISM: Homo sapiens

<400> SEQUENCE: 183

Ser Tyr Ala Met Asn
1               5

<210> SEQ ID NO 184
<211> LENGTH: 17
<212> TYPE: PRT
<213> ORGANISM: Homo sapiens

<400> SEQUENCE: 184

Thr Ile Ser Tyr Ser Gly Ser Leu Ile Ser Tyr Ala Asp Ser Val Lys
1               5                   10                  15

Gly

<210> SEQ ID NO 185
<211> LENGTH: 8
<212> TYPE: PRT
<213> ORGANISM: Homo sapiens

<400> SEQUENCE: 185

Ile Asn Asn Asp Pro Met Asp Val
1               5

<210> SEQ ID NO 186
<211> LENGTH: 333
<212> TYPE: DNA
<213> ORGANISM: Homo sapiens

<400> SEQUENCE: 186
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120 cagtccccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccagcactgg gacgggcacc acacgacggg ggagaccaac    300
cacttcggcg agggaccaa gttaaccgtc cta 333

<210> SEQ ID NO 187
<211> LENGTH: 111
<212> TYPE: PRT
<213> ORGANISM: Homo sapiens

<400> SEQUENCE: 187

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln His Trp Asp Gly His His Thr Thr
                85                  90                  95

Gly Glu Thr Asn His Phe Gly Gly Thr Lys Leu Thr Val Leu
            100                 105                 110
```

<210> SEQ ID NO 188
<211> LENGTH: 11
<212> TYPE: PRT
<213> ORGANISM: Homo sapiens

<400> SEQUENCE: 188

```
Ser Gly Asp Asn Leu Gly Lys Lys Tyr Val Gln
1               5                   10
```

<210> SEQ ID NO 189
<211> LENGTH: 7
<212> TYPE: PRT
<213> ORGANISM: Homo sapiens

<400> SEQUENCE: 189

```
Asp Asp Ser Asn Arg Pro Ser
1               5
```

<210> SEQ ID NO 190
<211> LENGTH: 14
<212> TYPE: PRT
<213> ORGANISM: Homo sapiens

<400> SEQUENCE: 190

```
Gln His Trp Asp Gly His His Thr Thr Gly Glu Thr Asn His
1               5                   10
```

<210> SEQ ID NO 191
<211> LENGTH: 351
<212> TYPE: DNA
<213> ORGANISM: Homo sapiens

<400> SEQUENCE: 191
gaggtgcagc tgctggagag cggcggaggg ctggtgcagc caggcggcag cctgaggctg 60
tcctgcgccg cctccggatt caccttcagc agctacgcca tgaactgggt gcggcaggcc 120
ccaggcaagg gcctggagtg ggtgtccacc atcagctaca gcgggtcgct gatcagctac 180
gccgacagcg tgaagggcag gttcaccatc agcagggaca acagcaagaa caccctgtac 240

```
ctgcagatga acagcctgag ggccgaggac accgccgtgt actactgcgc ccgcatcaac    300
aacgacccta tggatgtgtg gggccagggc accctggtga cagtgagctc a             351
```

<210> SEQ ID NO 192
<211> LENGTH: 117
<212> TYPE: PRT
<213> ORGANISM: Homo sapiens

<400> SEQUENCE: 192

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115
```

<210> SEQ ID NO 193
<211> LENGTH: 5
<212> TYPE: PRT
<213> ORGANISM: Homo sapiens

<400> SEQUENCE: 193

```
Ser Tyr Ala Met Asn
1               5
```

<210> SEQ ID NO 194
<211> LENGTH: 17
<212> TYPE: PRT
<213> ORGANISM: Homo sapiens

<400> SEQUENCE: 194

```
Thr Ile Ser Tyr Ser Gly Ser Leu Ile Ser Tyr Ala Asp Ser Val Lys
1               5                   10                  15

Gly
```

<210> SEQ ID NO 195
<211> LENGTH: 8
<212> TYPE: PRT
<213> ORGANISM: Homo sapiens

<400> SEQUENCE: 195

```
Ile Asn Asn Asp Pro Met Asp Val
1               5
```

<210> SEQ ID NO 196
<211> LENGTH: 333
<212> TYPE: DNA
<213> ORGANISM: Homo sapiens

<400> SEQUENCE: 196

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggcacc accacgggg gagaccaac    300 cacttcggcg agggaccaa gttaaccgtc cta                                 333
```

<210> SEQ ID NO 197
<211> LENGTH: 111
<212> TYPE: PRT
<213> ORGANISM: Homo sapiens

<400> SEQUENCE: 197

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly His His His Thr
                85                  90                  95

Gly Glu Thr Asn His Phe Gly Gly Gly Thr Lys Leu Thr Val Leu
            100                 105                 110

<210> SEQ ID NO 198
<211> LENGTH: 11
<212> TYPE: PRT
<213> ORGANISM: Homo sapiens

<400> SEQUENCE: 198

Ser Gly Asp Asn Leu Gly Lys Lys Tyr Val Gln
1               5                   10

<210> SEQ ID NO 199
<211> LENGTH: 7
<212> TYPE: PRT
<213> ORGANISM: Homo sapiens

<400> SEQUENCE: 199

Asp Asp Ser Asn Arg Pro Ser
1               5

<210> SEQ ID NO 200
<211> LENGTH: 14
<212> TYPE: PRT
<213> ORGANISM: Homo sapiens

<400> SEQUENCE: 200

Gln Thr Trp Asp Gly His His Thr Gly Glu Thr Asn His
1               5                   10

<210> SEQ ID NO 201
<211> LENGTH: 351
<212> TYPE: DNA

<213> ORGANISM: Homo sapiens

<400> SEQUENCE: 201

```
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagccaca gcgggcacca catcagccac   180
cacgacagcc atcatggcag gttcaccatc agcagggaca cagcaagaa cacccctgtac    240
ctgcagatga acagcctgag ggccgaggac accgccgtgt actactgcgc ccgcatcaac   300
aacgacccta tggatgtgtg gggccagggc accctggtga cagtgagctc a            351
```

<210> SEQ ID NO 202
<211> LENGTH: 117
<212> TYPE: PRT
<213> ORGANISM: Homo sapiens

<400> SEQUENCE: 202

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Asn Trp Val Arg Gln Ala Pro Gly Lys Gly Leu Glu Trp Val
        35                  40                  45
Ser Thr Ile Ser His Ser Gly His His Ile Ser His Asp Ser His
    50                  55                  60
His Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Ile Asn Asn Asp Pro Met Asp Val Trp Gly Gln Gly Thr Leu
            100                 105                 110
Val Thr Val Ser Ser
        115
```

<210> SEQ ID NO 203
<211> LENGTH: 5
<212> TYPE: PRT
<213> ORGANISM: Homo sapiens

<400> SEQUENCE: 203

```
Ser Tyr Ala Met Asn
 1               5
```

<210> SEQ ID NO 204
<211> LENGTH: 17
<212> TYPE: PRT
<213> ORGANISM: Homo sapiens

<400> SEQUENCE: 204

```
Thr Ile Ser His Ser Gly His His Ile Ser His Asp Ser His His
 1               5                  10                  15
Gly
```

<210> SEQ ID NO 205
<211> LENGTH: 8
<212> TYPE: PRT
<213> ORGANISM: Homo sapiens

<400> SEQUENCE: 205

-continued

Ile Asn Asn Asp Pro Met Asp Val
1               5

<210> SEQ ID NO 206
<211> LENGTH: 333
<212> TYPE: DNA
<213> ORGANISM: Homo sapiens

<400> SEQUENCE: 206
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg gagggaccaa gttaaccgtc cta                                333

<210> SEQ ID NO 207
<211> LENGTH: 111
<212> TYPE: PRT
<213> ORGANISM: Homo sapiens

<400> SEQUENCE: 207

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 208
<211> LENGTH: 11
<212> TYPE: PRT
<213> ORGANISM: Homo sapiens

<400> SEQUENCE: 208

Ser Gly Asp Asn Leu Gly Lys Lys Tyr Val Gln
1               5                   10

<210> SEQ ID NO 209
<211> LENGTH: 7
<212> TYPE: PRT
<213> ORGANISM: Homo sapiens

<400> SEQUENCE: 209

Asp Asp Ser Asn Arg Pro Ser
1               5

<210> SEQ ID NO 210
<211> LENGTH: 14
<212> TYPE: PRT

<213> ORGANISM: Homo sapiens

<400> SEQUENCE: 210

Gln Thr Trp Asp Gly Asn Pro Thr Thr Gly Glu Thr Asn Val
1               5                   10

<210> SEQ ID NO 211
<211> LENGTH: 351
<212> TYPE: DNA
<213> ORGANISM: Homo sapiens

<400> SEQUENCE: 211

```
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagccaca gccactcgct gatcagctac   180
gcccacagcg tgcatggcag gttcaccatc agcagggaca acagcaagaa caccctgtac   240
ctgcagatga acagcctgag ggccgaggac accgccgtgt actactgcgc ccgcatcaac   300
aacgaccctc tggatgtgtg gggccagggc accctggtga cagtgagctc a            351
```

<210> SEQ ID NO 212
<211> LENGTH: 117
<212> TYPE: PRT
<213> ORGANISM: Homo sapiens

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser His Ser His Ser Leu Ile Ser Tyr Ala His Ser Val
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 213
<211> LENGTH: 5
<212> TYPE: PRT
<213> ORGANISM: Homo sapiens

<400> SEQUENCE: 213

Ser Tyr Ala Met Asn
1               5

<210> SEQ ID NO 214
<211> LENGTH: 17
<212> TYPE: PRT
<213> ORGANISM: Homo sapiens

<400> SEQUENCE: 214

Thr Ile Ser His Ser His Ser Leu Ile Ser Tyr Ala His Ser Val His

```
1               5                   10                  15
Gly

<210> SEQ ID NO 215
<211> LENGTH: 8
<212> TYPE: PRT
<213> ORGANISM: Homo sapiens

<400> SEQUENCE: 215

Ile Asn Asn Asp Pro Met Asp Val
1               5

<210> SEQ ID NO 216
<211> LENGTH: 333
<212> TYPE: DNA
<213> ORGANISM: Homo sapiens

<400> SEQUENCE: 216
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                 333

<210> SEQ ID NO 217
<211> LENGTH: 111
<212> TYPE: PRT
<213> ORGANISM: Homo sapiens

<400> SEQUENCE: 217

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 218
<211> LENGTH: 11
<212> TYPE: PRT
<213> ORGANISM: Homo sapiens

<400> SEQUENCE: 218

Ser Gly Asp Asn Leu Gly Lys Lys Tyr Val Gln
1               5                   10

<210> SEQ ID NO 219
<211> LENGTH: 7
<212> TYPE: PRT
```

<213> ORGANISM: Homo sapiens

<400> SEQUENCE: 219

Asp Asp Ser Asn Arg Pro Ser
1               5

<210> SEQ ID NO 220
<211> LENGTH: 14
<212> TYPE: PRT
<213> ORGANISM: Homo sapiens

<400> SEQUENCE: 220

Gln Thr Trp Asp Gly Asn Pro Thr Thr Gly Glu Thr Asn Val
1               5                   10

<210> SEQ ID NO 221
<211> LENGTH: 351
<212> TYPE: DNA
<213> ORGANISM: Homo sapiens

<400> SEQUENCE: 221

```
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atccaccaca gcgggcacct gcacagccac   180
gccgaccacg tgaagggcag gttcaccatc agcagggaca cagcaagaa caccctgtac   240
ctgcagatga acagcctgag ggccgaggac accgccgtgt actactgcgc ccgcatcaac   300
aacgacccta tggatgtgtg gggccagggc accctggtga cagtgagctc a            351
```

<210> SEQ ID NO 222
<211> LENGTH: 117
<212> TYPE: PRT
<213> ORGANISM: Homo sapiens

<400> SEQUENCE: 222

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile His His Ser Gly His Leu His Ser His Ala Asp His Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 223
<211> LENGTH: 5
<212> TYPE: PRT
<213> ORGANISM: Homo sapiens

<400> SEQUENCE: 223

Ser Tyr Ala Met Asn

<210> SEQ ID NO 224
<211> LENGTH: 17
<212> TYPE: PRT
<213> ORGANISM: Homo sapiens

<400> SEQUENCE: 224

Thr Ile His His Ser Gly His Leu His Ser His Ala Asp His Val Lys
1               5                   10                  15

Gly

<210> SEQ ID NO 225
<211> LENGTH: 8
<212> TYPE: PRT
<213> ORGANISM: Homo sapiens

<400> SEQUENCE: 225

Ile Asn Asn Asp Pro Met Asp Val
1               5

<210> SEQ ID NO 226
<211> LENGTH: 333
<212> TYPE: DNA
<213> ORGANISM: Homo sapiens

<400> SEQUENCE: 226
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg agggaccaa gttaaccgtc cta                                 333

<210> SEQ ID NO 227
<211> LENGTH: 111
<212> TYPE: PRT
<213> ORGANISM: Homo sapiens

<400> SEQUENCE: 227

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 228
<211> LENGTH: 11
<212> TYPE: PRT

```
<213> ORGANISM: Homo sapiens

<400> SEQUENCE: 228

Ser Gly Asp Asn Leu Gly Lys Lys Tyr Val Gln
1               5                   10

<210> SEQ ID NO 229
<211> LENGTH: 7
<212> TYPE: PRT
<213> ORGANISM: Homo sapiens

<400> SEQUENCE: 229

Asp Asp Ser Asn Arg Pro Ser
1               5

<210> SEQ ID NO 230
<211> LENGTH: 14
<212> TYPE: PRT
<213> ORGANISM: Homo sapiens

<400> SEQUENCE: 230

Gln Thr Trp Asp Gly Asn Pro Thr Thr Gly Glu Thr Asn Val
1               5                   10

<210> SEQ ID NO 231
<211> LENGTH: 351
<212> TYPE: DNA
<213> ORGANISM: Homo sapiens

<400> SEQUENCE: 231
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagccaca gcgggcacct gatccaccac    180
gccgacagcc ataagggcag gttcaccatc agcagggaca cagcaagaa caccctgtac    240 ctgcagatga acagcctgag ggccgaggac accgccgtgt actactgcgc ccgcatcaac    300
aacgacccta tggatgtgtg gggccagggc accctggtga cagtgagctc a             351

<210> SEQ ID NO 232
<211> LENGTH: 117
<212> TYPE: PRT
<213> ORGANISM: Homo sapiens

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser His Ser Gly His Leu Ile His Ala Asp Ser His
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115
```

<210> SEQ ID NO 233
<211> LENGTH: 5
<212> TYPE: PRT
<213> ORGANISM: Homo sapiens

<400> SEQUENCE: 233

Ser Tyr Ala Met Asn
1               5

<210> SEQ ID NO 234
<211> LENGTH: 17
<212> TYPE: PRT
<213> ORGANISM: Homo sapiens

<400> SEQUENCE: 234

Thr Ile Ser His Ser Gly His Leu Ile His His Ala Asp Ser His Lys
1               5                   10                  15

Gly

<210> SEQ ID NO 235
<211> LENGTH: 8
<212> TYPE: PRT
<213> ORGANISM: Homo sapiens

<400> SEQUENCE: 235

Ile Asn Asn Asp Pro Met Asp Val
1               5

<210> SEQ ID NO 236
<211> LENGTH: 333
<212> TYPE: DNA
<213> ORGANISM: Homo sapiens

<400> SEQUENCE: 236

```
agtatcgagc tgacccagcc ccccagcgtg agcgtgtccc caggccagac cgccagcatc        60
acctgcagcg gcgacaacct gggcaagaaa tacgtgcagt ggtatcagca gaagcccggc       120
cagtcccccg tgctggtgat ctacgacgac agcaacaggc ccagcggcat ccccgagagg       180
ttcagcggca gcaacagcgg caacaccgcc accctgacca tcagcggcac ccaggcgatg       240
gacgaggccg actactactg ccagacctgg gacgggaacc cgacgacggg cgagaccaac       300
gtgttcggcg agggaccaa gttaaccgtc cta                                     333
```

<210> SEQ ID NO 237
<211> LENGTH: 111
<212> TYPE: PRT
<213> ORGANISM: Homo sapiens

<400> SEQUENCE: 237

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
            85                  90                  95

Gly Glu Thr Asn Val Phe Gly Gly Gly Thr Lys Leu Thr Val Leu
            100                 105                 110

<210> SEQ ID NO 238
<211> LENGTH: 11
<212> TYPE: PRT
<213> ORGANISM: Homo sapiens

<400> SEQUENCE: 238

Ser Gly Asp Asn Leu Gly Lys Lys Tyr Val Gln
1               5                   10

<210> SEQ ID NO 239
<211> LENGTH: 7
<212> TYPE: PRT
<213> ORGANISM: Homo sapiens

<400> SEQUENCE: 239

Asp Asp Ser Asn Arg Pro Ser
1               5

<210> SEQ ID NO 240
<211> LENGTH: 14
<212> TYPE: PRT
<213> ORGANISM: Homo sapiens

<400> SEQUENCE: 240

Gln Thr Trp Asp Gly Asn Pro Thr Thr Gly Glu Thr Asn Val
1               5                   10

<210> SEQ ID NO 241
<211> LENGTH: 351
<212> TYPE: DNA
<213> ORGANISM: Homo sapiens

<400> SEQUENCE: 241
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggtcgca catcagctac     180
caccacagcc ataagggcag gttcaccatc agcagggaca cagcaagaa caccctgtac      240 ctgcagatga acagcctgag ggccgaggac accgccgtgt actactgcgc ccgcatcaac     300 aacgaccta tggatgtgtg gggccagggc accctggtga cagtgagctc a              351

<210> SEQ ID NO 242
<211> LENGTH: 117
<212> TYPE: PRT
<213> ORGANISM: Homo sapiens

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His His Ser His
    50                  55                  60

```
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ile Asn Asn Asp Pro Met Asp Val Trp Gly Gln Gly Thr Leu
            100                 105                 110
Val Thr Val Ser Ser
        115

<210> SEQ ID NO 243
<211> LENGTH: 5
<212> TYPE: PRT
<213> ORGANISM: Homo sapiens

<400> SEQUENCE: 243

Ser Tyr Ala Met Asn
1               5

<210> SEQ ID NO 244
<211> LENGTH: 17
<212> TYPE: PRT
<213> ORGANISM: Homo sapiens

<400> SEQUENCE: 244

Thr Ile Ser Tyr His Gly Ser His Ile Ser Tyr His His Ser His Lys
1               5                   10                  15
Gly

<210> SEQ ID NO 245
<211> LENGTH: 8
<212> TYPE: PRT
<213> ORGANISM: Homo sapiens

<400> SEQUENCE: 245

Ile Asn Asn Asp Pro Met Asp Val
1               5

<210> SEQ ID NO 246
<211> LENGTH: 333
<212> TYPE: DNA
<213> ORGANISM: Homo sapiens

<400> SEQUENCE: 246
agtatcgagc tgacccagcc ccccagcgtg agcgtgtccc caggccagac cgccagcatc        60
acctgcagcg gcgacaacct gggcaagaaa tacgtgcagt ggtatcagca gaagcccggc       120
cagtcccccg tgctggtgat ctacgacgac agcaacaggc ccagcggcat ccccgagagg       180
ttcagcggca gcaacagcgg caacaccgcc accctgacca tcagcggcac ccaggcgatg       240
gacgaggccg actactactg ccagacctgg gacgggaacc cgacgacggg cgagaccaac       300
gtgttcggcg agggaccaa gttaaccgtc cta                                     333

<210> SEQ ID NO 247
<211> LENGTH: 111
<212> TYPE: PRT
<213> ORGANISM: Homo sapiens

<400> SEQUENCE: 247

Ser Ile Glu Leu Thr Gln Pro Pro Ser Val Ser Val Ser Pro Gly Gln
1               5                   10                  15
```

```
Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 248
<211> LENGTH: 11
<212> TYPE: PRT
<213> ORGANISM: Homo sapiens

<400> SEQUENCE: 248

```
Ser Gly Asp Asn Leu Gly Lys Lys Tyr Val Gln
1               5                   10
```

<210> SEQ ID NO 249
<211> LENGTH: 7
<212> TYPE: PRT
<213> ORGANISM: Homo sapiens

<400> SEQUENCE: 249

```
Asp Asp Ser Asn Arg Pro Ser
1               5
```

<210> SEQ ID NO 250
<211> LENGTH: 14
<212> TYPE: PRT
<213> ORGANISM: Homo sapiens

<400> SEQUENCE: 250

```
Gln Thr Trp Asp Gly Asn Pro Thr Thr Gly Glu Thr Asn Val
1               5                   10
```

<210> SEQ ID NO 251
<211> LENGTH: 351
<212> TYPE: DNA
<213> ORGANISM: Homo sapiens

<400> SEQUENCE: 251

```
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctacc acgggtcgca catcagctac   180
gccgaccacc ataagcacag gttcaccatc agcagggaca cagcaagaa cacccctgtac   240 ctgcagatga acagcctgag gccgaggac accgccgtgt actactgcgc cgcatcaac   300 aacgacccta tggatgtgtg ggccagggc accctggtga cagtgagctc a            351
```

<210> SEQ ID NO 252
<211> LENGTH: 117
<212> TYPE: PRT
<213> ORGANISM: Homo sapiens

<400> SEQUENCE: 252

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr Ala Asp His His
    50                  55                  60

Lys His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 253
<211> LENGTH: 5
<212> TYPE: PRT
<213> ORGANISM: Homo sapiens

<400> SEQUENCE: 253

Ser Tyr Ala Met Asn
1               5

<210> SEQ ID NO 254
<211> LENGTH: 17
<212> TYPE: PRT
<213> ORGANISM: Homo sapiens

<400> SEQUENCE: 254

Thr Ile Ser Tyr His Gly Ser His Ile Ser Tyr Ala Asp His His Lys
1               5                   10                  15

His

<210> SEQ ID NO 255
<211> LENGTH: 8
<212> TYPE: PRT
<213> ORGANISM: Homo sapiens

<400> SEQUENCE: 255

Ile Asn Asn Asp Pro Met Asp Val
1               5

<210> SEQ ID NO 256
<211> LENGTH: 333
<212> TYPE: DNA
<213> ORGANISM: Homo sapiens

<400> SEQUENCE: 256
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                  333
```

<210> SEQ ID NO 257
<211> LENGTH: 111
<212> TYPE: PRT
<213> ORGANISM: Homo sapiens

<400> SEQUENCE: 257

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 258
<211> LENGTH: 11
<212> TYPE: PRT
<213> ORGANISM: Homo sapiens

<400> SEQUENCE: 258

Ser Gly Asp Asn Leu Gly Lys Lys Tyr Val Gln
1               5                   10

<210> SEQ ID NO 259
<211> LENGTH: 7
<212> TYPE: PRT
<213> ORGANISM: Homo sapiens

<400> SEQUENCE: 259

Asp Asp Ser Asn Arg Pro Ser
1               5

<210> SEQ ID NO 260
<211> LENGTH: 14
<212> TYPE: PRT
<213> ORGANISM: Homo sapiens

<400> SEQUENCE: 260

Gln Thr Trp Asp Gly Asn Pro Thr Thr Gly Glu Thr Asn Val
1               5                   10

<210> SEQ ID NO 261
<211> LENGTH: 351
<212> TYPE: DNA
<213> ORGANISM: Homo sapiens

<400> SEQUENCE: 261
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggcacct gatccactac     180
gccgaccacc atcatggcag gttcaccatc agcagggaca cagcaagaa cacccctgtac    240 ctgcagatga acagcctgag ggccgaggac accgccgtgt actactgcgc ccgcatcaac     300 aacgaccota tggatgtgtg gggccagggc accctggtga cagtgagctc a      351

<210> SEQ ID NO 262
<211> LENGTH: 117
<212> TYPE: PRT
<213> ORGANISM: Homo sapiens

<400> SEQUENCE: 262

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly His Leu Ile His Tyr Ala Asp His His
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 263
<211> LENGTH: 5
<212> TYPE: PRT
<213> ORGANISM: Homo sapiens

<400> SEQUENCE: 263

Ser Tyr Ala Met Asn
1               5

<210> SEQ ID NO 264
<211> LENGTH: 17
<212> TYPE: PRT
<213> ORGANISM: Homo sapiens

<400> SEQUENCE: 264

Thr Ile Ser Tyr Ser Gly His Leu Ile His Tyr Ala Asp His His His
1               5                   10                  15

Gly

<210> SEQ ID NO 265
<211> LENGTH: 8
<212> TYPE: PRT
<213> ORGANISM: Homo sapiens

<400> SEQUENCE: 265

Ile Asn Asn Asp Pro Met Asp Val
1               5

<210> SEQ ID NO 266
<211> LENGTH: 333
<212> TYPE: DNA
<213> ORGANISM: Homo sapiens

<400> SEQUENCE: 266
agtatcgagc tgacccagcc ccccagcgtg agcgtgtccc caggccagac cgccagcatc      60

```
acctgcagcg gcgacaacct gggcaagaaa tacgtgcagt ggtatcagca gaagcccggc      120
cagtcccccg tgctggtgat ctacgacgac agcaacaggc ccagcggcat ccccgagagg      180
ttcagcggca gcaacagcgg caacaccgcc accctgacca tcagcggcac ccaggcgatg      240
gacgaggccg actactactg ccagacctgg gacgggaacc cgacgacggg cgagaccaac      300
gtgttcggcg agggaccaa gttaaccgtc cta                                    333
```

<210> SEQ ID NO 267
<211> LENGTH: 111
<212> TYPE: PRT
<213> ORGANISM: Homo sapiens

<400> SEQUENCE: 267

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 268
<211> LENGTH: 11
<212> TYPE: PRT
<213> ORGANISM: Homo sapiens

<400> SEQUENCE: 268

Ser Gly Asp Asn Leu Gly Lys Lys Tyr Val Gln
1               5                   10

<210> SEQ ID NO 269
<211> LENGTH: 7
<212> TYPE: PRT
<213> ORGANISM: Homo sapiens

<400> SEQUENCE: 269

Asp Asp Ser Asn Arg Pro Ser
1               5

<210> SEQ ID NO 270
<211> LENGTH: 14
<212> TYPE: PRT
<213> ORGANISM: Homo sapiens

<400> SEQUENCE: 270

Gln Thr Trp Asp Gly Asn Pro Thr Thr Gly Glu Thr Asn Val
1               5                   10

<210> SEQ ID NO 271
<211> LENGTH: 351
<212> TYPE: DNA
<213> ORGANISM: Homo sapiens -continued

<400> SEQUENCE: 271

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggtcgca catcagccac     180
gccgaccacg tgcatggcag gttcaccatc agcagggaca cagcaagaa caccctgtac      240
ctgcagatga acagcctgag ggccgaggac accgccgtgt actactgcgc ccgcatcaac     300
aacgaccta tggatgtgtg gggccagggc accctggtga cagtgagctc a               351
```

<210> SEQ ID NO 272
<211> LENGTH: 117
<212> TYPE: PRT
<213> ORGANISM: Homo sapiens

<400> SEQUENCE: 272

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Asn Trp Val Arg Gln Ala Pro Gly Lys Gly Leu Glu Trp Val
        35                  40                  45
Ser Thr Ile Ser Tyr His Gly Ser His Ile Ser His Ala Asp His Val
    50                  55                  60
His Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ile Asn Asn Asp Pro Met Asp Val Trp Gly Gln Gly Thr Leu
            100                 105                 110
Val Thr Val Ser Ser
        115
```

<210> SEQ ID NO 273
<211> LENGTH: 5
<212> TYPE: PRT
<213> ORGANISM: Homo sapiens

<400> SEQUENCE: 273

```
Ser Tyr Ala Met Asn
1               5
```

<210> SEQ ID NO 274
<211> LENGTH: 17
<212> TYPE: PRT
<213> ORGANISM: Homo sapiens

<400> SEQUENCE: 274

```
Thr Ile Ser Tyr His Gly Ser His Ile Ser His Ala Asp His Val His
1               5                   10                  15
Gly
```

<210> SEQ ID NO 275
<211> LENGTH: 8
<212> TYPE: PRT
<213> ORGANISM: Homo sapiens

<400> SEQUENCE: 275

```
Ile Asn Asn Asp Pro Met Asp Val
1               5
```

```
<210> SEQ ID NO 276
<211> LENGTH: 333
<212> TYPE: DNA
<213> ORGANISM: Homo sapiens

<400> SEQUENCE: 276
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                  333

<210> SEQ ID NO 277
<211> LENGTH: 111
<212> TYPE: PRT
<213> ORGANISM: Homo sapiens

<400> SEQUENCE: 277

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 278
<211> LENGTH: 11
<212> TYPE: PRT
<213> ORGANISM: Homo sapiens

<400> SEQUENCE: 278

Ser Gly Asp Asn Leu Gly Lys Lys Tyr Val Gln
1               5                   10

<210> SEQ ID NO 279
<211> LENGTH: 7
<212> TYPE: PRT
<213> ORGANISM: Homo sapiens

<400> SEQUENCE: 279

Asp Asp Ser Asn Arg Pro Ser
1               5

<210> SEQ ID NO 280
<211> LENGTH: 14
<212> TYPE: PRT
<213> ORGANISM: Homo sapiens
```

<400> SEQUENCE: 280

Gln Thr Trp Asp Gly Asn Pro Thr Thr Gly Glu Thr Asn Val
1               5                   10

<210> SEQ ID NO 281
<211> LENGTH: 351
<212> TYPE: DNA
<213> ORGANISM: Homo sapiens

<400> SEQUENCE: 281

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggcacca catcagccac     180
gccgaccacg tgaagcacag gttcaccatc agcagggaca cagcaagaa caccctgtac      240
ctgcagatga acagcctgag ggccgaggac accgccgtgt actactgcgc ccgcatcaac     300
aacgacccta tggatgtgtg gggccagggc accctggtga cagtgagctc a              351
```

<210> SEQ ID NO 282
<211> LENGTH: 117
<212> TYPE: PRT
<213> ORGANISM: Homo sapiens

<400> SEQUENCE: 282

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser His Ala Asp His Val
    50                  55                  60

Lys His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 283
<211> LENGTH: 5
<212> TYPE: PRT
<213> ORGANISM: Homo sapiens

<400> SEQUENCE: 283

Ser Tyr Ala Met Asn
1               5

<210> SEQ ID NO 284
<211> LENGTH: 17
<212> TYPE: PRT
<213> ORGANISM: Homo sapiens

<400> SEQUENCE: 284

Thr Ile Ser Tyr His Gly His His Ile Ser His Ala Asp His Val Lys
1               5                   10                  15

His

<210> SEQ ID NO 285
<211> LENGTH: 8
<212> TYPE: PRT
<213> ORGANISM: Homo sapiens

<400> SEQUENCE: 285

Ile Asn Asn Asp Pro Met Asp Val
1               5

<210> SEQ ID NO 286
<211> LENGTH: 333
<212> TYPE: DNA
<213> ORGANISM: Homo sapiens

<400> SEQUENCE: 286

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg agggaccaa gttaaccgtc cta                                    333
```

<210> SEQ ID NO 287
<211> LENGTH: 111
<212> TYPE: PRT
<213> ORGANISM: Homo sapiens

<400> SEQUENCE: 287

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 288
<211> LENGTH: 11
<212> TYPE: PRT
<213> ORGANISM: Homo sapiens

<400> SEQUENCE: 288

Ser Gly Asp Asn Leu Gly Lys Lys Tyr Val Gln
1               5                   10

<210> SEQ ID NO 289
<211> LENGTH: 7
<212> TYPE: PRT
<213> ORGANISM: Homo sapiens

<400> SEQUENCE: 289

Asp Asp Ser Asn Arg Pro Ser
1               5

<210> SEQ ID NO 290
<211> LENGTH: 14
<212> TYPE: PRT
<213> ORGANISM: Homo sapiens

<400> SEQUENCE: 290

Gln Thr Trp Asp Gly Asn Pro Thr Thr Gly Glu Thr Asn Val
1               5                   10

<210> SEQ ID NO 291
<211> LENGTH: 351
<212> TYPE: DNA
<213> ORGANISM: Homo sapiens

<400> SEQUENCE: 291
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagccaca gcgggcacct gatccaccac    180
caccacagcg tgaagggcag gttcaccatc agcagggaca acagcaagaa caccctgtac    240
ctgcagatga acagcctgag ggccgaggac accgccgtgt actactgcgc ccgcatcaac    300 aacgaccota tggatgtgtg gggccagggc accctggtga cagtgagctc a             351

<210> SEQ ID NO 292
<211> LENGTH: 117
<212> TYPE: PRT
<213> ORGANISM: Homo sapiens

<400> SEQUENCE: 292

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser His Ser Gly His Leu Ile His His His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 293
<211> LENGTH: 5
<212> TYPE: PRT
<213> ORGANISM: Homo sapiens

<400> SEQUENCE: 293

Ser Tyr Ala Met Asn
1               5

<210> SEQ ID NO 294
<211> LENGTH: 17
<212> TYPE: PRT
<213> ORGANISM: Homo sapiens

<400> SEQUENCE: 294

Thr Ile Ser His Ser Gly His Leu Ile His His His Ser Val Lys
1               5                   10                  15

Gly

<210> SEQ ID NO 295
<211> LENGTH: 8
<212> TYPE: PRT
<213> ORGANISM: Homo sapiens

<400> SEQUENCE: 295

Ile Asn Asn Asp Pro Met Asp Val
1               5

<210> SEQ ID NO 296
<211> LENGTH: 333
<212> TYPE: DNA
<213> ORGANISM: Homo sapiens

<400> SEQUENCE: 296

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg agggaccaa gttaaccgtc cta                                  333
```

<210> SEQ ID NO 297
<211> LENGTH: 111
<212> TYPE: PRT
<213> ORGANISM: Homo sapiens

<400> SEQUENCE: 297

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 298
<211> LENGTH: 11
<212> TYPE: PRT
<213> ORGANISM: Homo sapiens

<400> SEQUENCE: 298

Ser Gly Asp Asn Leu Gly Lys Lys Tyr Val Gln
1               5                   10

<210> SEQ ID NO 299
<211> LENGTH: 7
<212> TYPE: PRT
<213> ORGANISM: Homo sapiens

<400> SEQUENCE: 299

Asp Asp Ser Asn Arg Pro Ser
1               5

<210> SEQ ID NO 300
<211> LENGTH: 14
<212> TYPE: PRT
<213> ORGANISM: Homo sapiens

<400> SEQUENCE: 300

Gln Thr Trp Asp Gly Asn Pro Thr Thr Gly Glu Thr Asn Val
1               5                   10

<210> SEQ ID NO 301
<211> LENGTH: 351
<212> TYPE: DNA
<213> ORGANISM: Homo sapiens

<400> SEQUENCE: 301

```
gaggtgcagc tgctggagag cggcggaggg ctggtgcagc caggcggcag cctgaggctg      60
tcctgcgccg cctccggatt caccttcagc agctacgcca tgaactgggt gcggcaggcc    120
ccaggcaagg gcctggagtg ggtgtccacc atcagctacc acgggtcgca catcagctac    180
cacgacagcc atcatggcag gttcaccatc agcagggaca cagcaagaa cacccctgtac    240
ctgcagatga acagcctgag ggccgaggac accgccgtgt actactgcgc ccgcatcaac    300
aacgacccta tggatgtgtg gggccagggc accctggtga cagtgagctc a             351
```

<210> SEQ ID NO 302
<211> LENGTH: 117
<212> TYPE: PRT
<213> ORGANISM: Homo sapiens

<400> SEQUENCE: 302

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser His
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

```
<210> SEQ ID NO 303
<211> LENGTH: 5
<212> TYPE: PRT
<213> ORGANISM: Homo sapiens

<400> SEQUENCE: 303

Ser Tyr Ala Met Asn
1               5

<210> SEQ ID NO 304
<211> LENGTH: 17
<212> TYPE: PRT
<213> ORGANISM: Homo sapiens

<400> SEQUENCE: 304

Thr Ile Ser Tyr His Gly Ser His Ile Ser Tyr His Asp Ser His His
1               5                   10                  15

Gly

<210> SEQ ID NO 305
<211> LENGTH: 8
<212> TYPE: PRT
<213> ORGANISM: Homo sapiens

<400> SEQUENCE: 305

Ile Asn Asn Asp Pro Met Asp Val
1               5

<210> SEQ ID NO 306
<211> LENGTH: 333
<212> TYPE: DNA
<213> ORGANISM: Homo sapiens

<400> SEQUENCE: 306
agtatcgagc tgacccagcc ccccagcgtg agcgtgtccc caggccagac cgccagcatc     60
acctgcagcg gcgacaacct gggcaagaaa tacgtgcagt ggtatcagca gaagcccggc    120
cagtcccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccagacctgg gacgggaacc cgacgacggg cgagaccaac    300
gtgttcggcg agggaccaa gttaaccgtc cta                                  333

<210> SEQ ID NO 307
<211> LENGTH: 111
<212> TYPE: PRT
<213> ORGANISM: Homo sapiens

<400> SEQUENCE: 307

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
```

85                  90                  95

Gly Glu Thr Asn Val Phe Gly Gly Gly Thr Lys Leu Thr Val Leu
            100                 105                 110

<210> SEQ ID NO 308
<211> LENGTH: 11
<212> TYPE: PRT
<213> ORGANISM: Homo sapiens

<400> SEQUENCE: 308

Ser Gly Asp Asn Leu Gly Lys Lys Tyr Val Gln
1               5                   10

<210> SEQ ID NO 309
<211> LENGTH: 7
<212> TYPE: PRT
<213> ORGANISM: Homo sapiens

<400> SEQUENCE: 309

Asp Asp Ser Asn Arg Pro Ser
1               5

<210> SEQ ID NO 310
<211> LENGTH: 14
<212> TYPE: PRT
<213> ORGANISM: Homo sapiens

<400> SEQUENCE: 310

Gln Thr Trp Asp Gly Asn Pro Thr Thr Gly Glu Thr Asn Val
1               5                   10

<210> SEQ ID NO 311
<211> LENGTH: 351
<212> TYPE: DNA
<213> ORGANISM: Homo sapiens

<400> SEQUENCE: 311
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc accaccacct gatcagccac     180
gccgacagcg tgaagggcag gttcaccatc agcagggaca cagcaagaa cacccctgtac    240 ctgcagatga acagcctgag ggccgaggac accgccgtgt actactgcgc cgcatcaac     300 aacgacccta tggatgtgtg gggccagggc accctggtga cagtgagctc a              351

<210> SEQ ID NO 312
<211> LENGTH: 117
<212> TYPE: PRT
<213> ORGANISM: Homo sapiens

<400> SEQUENCE: 312

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His His His Leu Ile Ser His Ala Asp Ser Val
    50                  55                  60

Lys Gly Arg Phe Thr Ile Ser Arg Asp Asn Ser Lys Asn Thr Leu Tyr

```
                 65                  70                  75                  80
Leu Gln Met Asn Ser Leu Arg Ala Glu Asp Thr Ala Val Tyr Tyr Cys
                     85                  90                  95

Ala Arg Ile Asn Asn Asp Pro Met Asp Val Trp Gly Gln Gly Thr Leu
            100                 105                 110

Val Thr Val Ser Ser
            115

<210> SEQ ID NO 313
<211> LENGTH: 5
<212> TYPE: PRT
<213> ORGANISM: Homo sapiens

<400> SEQUENCE: 313

Ser Tyr Ala Met Asn
1               5

<210> SEQ ID NO 314
<211> LENGTH: 17
<212> TYPE: PRT
<213> ORGANISM: Homo sapiens

<400> SEQUENCE: 314

Thr Ile Ser Tyr His His His Leu Ile Ser His Ala Asp Ser Val Lys
1               5                   10                  15

Gly

<210> SEQ ID NO 315
<211> LENGTH: 8
<212> TYPE: PRT
<213> ORGANISM: Homo sapiens

<400> SEQUENCE: 315

Ile Asn Asn Asp Pro Met Asp Val
1               5

<210> SEQ ID NO 316
<211> LENGTH: 333
<212> TYPE: DNA
<213> ORGANISM: Homo sapiens

<400> SEQUENCE: 316
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                  333

<210> SEQ ID NO 317
<211> LENGTH: 111
<212> TYPE: PRT
<213> ORGANISM: Homo sapiens

<400> SEQUENCE: 317

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30
```

```
Gln Trp Tyr Gln Gln Lys Pro Gly Gln Ser Pro Val Leu Val Ile Tyr
         35                  40                  45

Asp Asp Ser Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Thr Trp Asp Gly Asn Pro Thr Thr
                 85                  90                  95

Gly Glu Thr Asn Val Phe Gly Gly Gly Thr Lys Leu Thr Val Leu
             100                 105                 110

<210> SEQ ID NO 318
<211> LENGTH: 11
<212> TYPE: PRT
<213> ORGANISM: Homo sapiens

<400> SEQUENCE: 318

Ser Gly Asp Asn Leu Gly Lys Lys Tyr Val Gln
1               5                   10

<210> SEQ ID NO 319
<211> LENGTH: 7
<212> TYPE: PRT
<213> ORGANISM: Homo sapiens

<400> SEQUENCE: 319

Asp Asp Ser Asn Arg Pro Ser
1               5

<210> SEQ ID NO 320
<211> LENGTH: 14
<212> TYPE: PRT
<213> ORGANISM: Homo sapiens

<400> SEQUENCE: 320

Gln Thr Trp Asp Gly Asn Pro Thr Thr Gly Glu Thr Asn Val
1               5                   10

<210> SEQ ID NO 321
<211> LENGTH: 351
<212> TYPE: DNA
<213> ORGANISM: Homo sapiens

<400> SEQUENCE: 321
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctacc acgggcacca catcagccac    180
gccgaccacc ataagggcag gttcaccatc agcagggaca cagcaagaa caccctgtac    240 ctgcagatga acagcctgag ggccgaggac accgccgtgt actactgcgc ccgcatcaac    300
aacgacccta tggatgtgtg gggccagggc accctggtga cagtgagctc a             351

<210> SEQ ID NO 322
<211> LENGTH: 117
<212> TYPE: PRT
<213> ORGANISM: Homo sapiens

<400> SEQUENCE: 322

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
         20                  25                  30

Ala Met Asn Trp Val Arg Gln Ala Pro Gly Lys Gly Leu Glu Trp Val
             35                  40                  45

Ser Thr Ile Ser Tyr His Gly His His Ile Ser His Ala Asp His His
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Asn Asn Asp Pro Met Asp Val Trp Gly Gln Gly Thr Leu
            100                 105                 110

Val Thr Val Ser Ser
            115
```

<210> SEQ ID NO 323
<211> LENGTH: 5
<212> TYPE: PRT
<213> ORGANISM: Homo sapiens

<400> SEQUENCE: 323

```
Ser Tyr Ala Met Asn
1               5
```

<210> SEQ ID NO 324
<211> LENGTH: 17
<212> TYPE: PRT
<213> ORGANISM: Homo sapiens

<400> SEQUENCE: 324

```
Thr Ile Ser Tyr His Gly His His Ile Ser His Ala Asp His His Lys
1               5                   10                  15

Gly
```

<210> SEQ ID NO 325
<211> LENGTH: 8
<212> TYPE: PRT
<213> ORGANISM: Homo sapiens

<400> SEQUENCE: 325

```
Ile Asn Asn Asp Pro Met Asp Val
1               5
```

<210> SEQ ID NO 326
<211> LENGTH: 333
<212> TYPE: DNA
<213> ORGANISM: Homo sapiens

<400> SEQUENCE: 326

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc gacgacgggc gagaccaac      300 gtgttcggcg gagggaccaa gttaaccgtc cta                                  333
```

<210> SEQ ID NO 327

<211> LENGTH: 111
<212> TYPE: PRT
<213> ORGANISM: Homo sapiens

<400> SEQUENCE: 327

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 328
<211> LENGTH: 11
<212> TYPE: PRT
<213> ORGANISM: Homo sapiens

<400> SEQUENCE: 328

Ser Gly Asp Asn Leu Gly Lys Lys Tyr Val Gln
1               5                   10

<210> SEQ ID NO 329
<211> LENGTH: 7
<212> TYPE: PRT
<213> ORGANISM: Homo sapiens

<400> SEQUENCE: 329

Asp Asp Ser Asn Arg Pro Ser
1               5

<210> SEQ ID NO 330
<211> LENGTH: 14
<212> TYPE: PRT
<213> ORGANISM: Homo sapiens

<400> SEQUENCE: 330

Gln Thr Trp Asp Gly Asn Pro Thr Thr Gly Glu Thr Asn Val
1               5                   10

<210> SEQ ID NO 331
<211> LENGTH: 351
<212> TYPE: DNA
<213> ORGANISM: Homo sapiens

<400> SEQUENCE: 331
gaggtgcagc tgctggagag cggcggaggg ctggtgcagc caggcggcag cctgaggctg      60
tcctgcgccg cctccggatt caccttcagc agctacgcca tgaactgggt gcggcaggcc    120
ccaggcaagg gcctggagtg ggtgtccacc atcagctacc acgggcacca catcagctac    180
gccgacagcc atcatcacag gttcaccatc agcagggaca acagcaagaa caccctgtac    240
ctgcagatga acagcctgag ggccgaggac accgccgtgt actactgcgc ccgcatcaac    300
aacgacccta tggatgtgtg gggccagggc accctggtga cagtgagctc a             351

<210> SEQ ID NO 332
<211> LENGTH: 117
<212> TYPE: PRT
<213> ORGANISM: Homo sapiens

<400> SEQUENCE: 332

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser Tyr Ala Asp Ser His
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 333
<211> LENGTH: 5
<212> TYPE: PRT
<213> ORGANISM: Homo sapiens

<400> SEQUENCE: 333

Ser Tyr Ala Met Asn
1               5

<210> SEQ ID NO 334
<211> LENGTH: 17
<212> TYPE: PRT
<213> ORGANISM: Homo sapiens

<400> SEQUENCE: 334

Thr Ile Ser Tyr His Gly His His Ile Ser Tyr Ala Asp Ser His His
1               5                   10                  15

His

<210> SEQ ID NO 335
<211> LENGTH: 8
<212> TYPE: PRT
<213> ORGANISM: Homo sapiens

<400> SEQUENCE: 335

Ile Asn Asn Asp Pro Met Asp Val
1               5

<210> SEQ ID NO 336
<211> LENGTH: 333
<212> TYPE: DNA
<213> ORGANISM: Homo sapiens

<400> SEQUENCE: 336
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120

```
cagtcccccg tgctggtgat ctacgacgac agcaacaggc ccagcggcat ccccgagagg      180
ttcagcggca gcaacagcgg caacaccgcc accctgacca tcagcggcac ccaggcgatg      240
gacgaggccg actactactg ccagacctgg gacgggaacc cgacgacggg cgagaccaac      300
gtgttcggcg gagggaccaa gttaaccgtc cta                                  333
```

<210> SEQ ID NO 337
<211> LENGTH: 111
<212> TYPE: PRT
<213> ORGANISM: Homo sapiens

<400> SEQUENCE: 337

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 338
<211> LENGTH: 11
<212> TYPE: PRT
<213> ORGANISM: Homo sapiens

<400> SEQUENCE: 338

```
Ser Gly Asp Asn Leu Gly Lys Lys Tyr Val Gln
1               5                   10
```

<210> SEQ ID NO 339
<211> LENGTH: 7
<212> TYPE: PRT
<213> ORGANISM: Homo sapiens

<400> SEQUENCE: 339

```
Asp Asp Ser Asn Arg Pro Ser
1               5
```

<210> SEQ ID NO 340
<211> LENGTH: 14
<212> TYPE: PRT
<213> ORGANISM: Homo sapiens

<400> SEQUENCE: 340

```
Gln Thr Trp Asp Gly Asn Pro Thr Thr Gly Glu Thr Asn Val
1               5                   10
```

<210> SEQ ID NO 341
<211> LENGTH: 351
<212> TYPE: DNA
<213> ORGANISM: Homo sapiens

<400> SEQUENCE: 341

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atccaccaca gcgggcacct gcacagctac     180
caccaccacg tgaagggcag gttcaccatc agcagggaca acagcaagaa caccctgtac     240
ctgcagatga acagcctgag ggccgaggac accgccgtgt actactgcgc cgcatcaac      300 aacgacccta tggatgtgtg gggccagggc accctggtga cagtgagctc a             351
```

<210> SEQ ID NO 342
<211> LENGTH: 117
<212> TYPE: PRT
<213> ORGANISM: Homo sapiens

<400> SEQUENCE: 342

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile His His Ser Gly His Leu His Ser Tyr His His Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115
```

<210> SEQ ID NO 343
<211> LENGTH: 5
<212> TYPE: PRT
<213> ORGANISM: Homo sapiens

<400> SEQUENCE: 343

```
Ser Tyr Ala Met Asn
1               5
```

<210> SEQ ID NO 344
<211> LENGTH: 17
<212> TYPE: PRT
<213> ORGANISM: Homo sapiens

<400> SEQUENCE: 344

```
Thr Ile His His Ser Gly His Leu His Ser Tyr His His Val Lys
1               5                   10                  15

Gly
```

<210> SEQ ID NO 345
<211> LENGTH: 8
<212> TYPE: PRT
<213> ORGANISM: Homo sapiens

<400> SEQUENCE: 345

```
Ile Asn Asn Asp Pro Met Asp Val
1               5
```

<210> SEQ ID NO 346
<211> LENGTH: 333
<212> TYPE: DNA
<213> ORGANISM: Homo sapiens

<400> SEQUENCE: 346

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg gagggaccaa gttaaccgtc cta                                 333
```

<210> SEQ ID NO 347
<211> LENGTH: 111
<212> TYPE: PRT
<213> ORGANISM: Homo sapiens

<400> SEQUENCE: 347

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 348
<211> LENGTH: 11
<212> TYPE: PRT
<213> ORGANISM: Homo sapiens

<400> SEQUENCE: 348

```
Ser Gly Asp Asn Leu Gly Lys Lys Tyr Val Gln
1               5                   10
```

<210> SEQ ID NO 349
<211> LENGTH: 7
<212> TYPE: PRT
<213> ORGANISM: Homo sapiens

<400> SEQUENCE: 349

```
Asp Asp Ser Asn Arg Pro Ser
1               5
```

<210> SEQ ID NO 350
<211> LENGTH: 14
<212> TYPE: PRT
<213> ORGANISM: Homo sapiens

<400> SEQUENCE: 350

```
Gln Thr Trp Asp Gly Asn Pro Thr Thr Gly Glu Thr Asn Val
1               5                   10
```

<210> SEQ ID NO 351
<211> LENGTH: 351
<212> TYPE: DNA
<213> ORGANISM: Homo sapiens

<400> SEQUENCE: 351

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagccaca gcgggcacct gcaccactac     180
gccgacagcc ataagcacag gttcaccatc agcagggaca acagcaagaa caccctgtac     240
ctgcagatga acagcctgag ggccgaggac accgccgtgt actactgcgc ccgcatcaac     300
aacgacccta tggatgtgtg gggccagggc accctggtga cagtgagctc a              351
```

<210> SEQ ID NO 352
<211> LENGTH: 117
<212> TYPE: PRT
<213> ORGANISM: Homo sapiens

<400> SEQUENCE: 352

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser His Ser Gly His Leu His His Tyr Ala Asp Ser His
    50                  55                  60

Lys His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115
```

<210> SEQ ID NO 353
<211> LENGTH: 5
<212> TYPE: PRT
<213> ORGANISM: Homo sapiens

<400> SEQUENCE: 353

```
Ser Tyr Ala Met Asn
1               5
```

<210> SEQ ID NO 354
<211> LENGTH: 17
<212> TYPE: PRT
<213> ORGANISM: Homo sapiens

<400> SEQUENCE: 354

```
Thr Ile Ser His Ser Gly His Leu His His Tyr Ala Asp Ser His Lys
1               5                   10                  15

His
```

<210> SEQ ID NO 355
<211> LENGTH: 8
<212> TYPE: PRT
<213> ORGANISM: Homo sapiens

<400> SEQUENCE: 355

Ile Asn Asn Asp Pro Met Asp Val
1               5

<210> SEQ ID NO 356
<211> LENGTH: 333
<212> TYPE: DNA
<213> ORGANISM: Homo sapiens

<400> SEQUENCE: 356

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg gagggaccaa gttaaccgtc cta                                333
```

<210> SEQ ID NO 357
<211> LENGTH: 111
<212> TYPE: PRT
<213> ORGANISM: Homo sapiens

<400> SEQUENCE: 357

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 358
<211> LENGTH: 11
<212> TYPE: PRT
<213> ORGANISM: Homo sapiens

<400> SEQUENCE: 358

Ser Gly Asp Asn Leu Gly Lys Lys Tyr Val Gln
1               5                   10

<210> SEQ ID NO 359
<211> LENGTH: 7
<212> TYPE: PRT
<213> ORGANISM: Homo sapiens

<400> SEQUENCE: 359

```
Asp Asp Ser Asn Arg Pro Ser
1               5
```

<210> SEQ ID NO 360
<211> LENGTH: 14
<212> TYPE: PRT
<213> ORGANISM: Homo sapiens

<400> SEQUENCE: 360

```
Gln Thr Trp Asp Gly Asn Pro Thr Thr Gly Glu Thr Asn Val
1               5                   10
```

<210> SEQ ID NO 361
<211> LENGTH: 351
<212> TYPE: DNA
<213> ORGANISM: Homo sapiens

<400> SEQUENCE: 361

```
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctacc acgggtcgca catcagctac    180
cacgacagcg tgcatcacag gttcaccatc agcagggaca cagcaagaa cacccctgtac    240
ctgcagatga acagcctgag ggccgaggac accgccgtgt actactgcgc ccgcatcaac    300
aacgacccta tggatgtgtg gggccagggc accctggtga cagtgagctc a             351
```

<210> SEQ ID NO 362
<211> LENGTH: 117
<212> TYPE: PRT
<213> ORGANISM: Homo sapiens

<400> SEQUENCE: 362

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser Val
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115
```

<210> SEQ ID NO 363
<211> LENGTH: 5
<212> TYPE: PRT
<213> ORGANISM: Homo sapiens

<400> SEQUENCE: 363

```
Ser Tyr Ala Met Asn
1               5
```

<210> SEQ ID NO 364

<211> LENGTH: 17
<212> TYPE: PRT
<213> ORGANISM: Homo sapiens

<400> SEQUENCE: 364

Thr Ile Ser Tyr His Gly Ser His Ile Ser Tyr His Asp Ser Val His
1               5                   10                  15

His

<210> SEQ ID NO 365
<211> LENGTH: 8
<212> TYPE: PRT
<213> ORGANISM: Homo sapiens

<400> SEQUENCE: 365

Ile Asn Asn Asp Pro Met Asp Val
1               5

<210> SEQ ID NO 366
<211> LENGTH: 333
<212> TYPE: DNA
<213> ORGANISM: Homo sapiens

<400> SEQUENCE: 366

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg agggaccaa gttaaccgtc cta                                  333
```

<210> SEQ ID NO 367
<211> LENGTH: 111
<212> TYPE: PRT
<213> ORGANISM: Homo sapiens

<400> SEQUENCE: 367

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 368
<211> LENGTH: 11
<212> TYPE: PRT
<213> ORGANISM: Homo sapiens

<400> SEQUENCE: 368

Ser Gly Asp Asn Leu Gly Lys Lys Tyr Val Gln
1               5                  10

<210> SEQ ID NO 369
<211> LENGTH: 7
<212> TYPE: PRT
<213> ORGANISM: Homo sapiens

<400> SEQUENCE: 369

Asp Asp Ser Asn Arg Pro Ser
1               5

<210> SEQ ID NO 370
<211> LENGTH: 14
<212> TYPE: PRT
<213> ORGANISM: Homo sapiens

<400> SEQUENCE: 370

Gln Thr Trp Asp Gly Asn Pro Thr Thr Gly Glu Thr Asn Val
1               5                  10

<210> SEQ ID NO 371
<211> LENGTH: 351
<212> TYPE: DNA
<213> ORGANISM: Homo sapiens

<400> SEQUENCE: 371
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggcacca catcagccac     180
gcccaccacg tgcatggcag gttcaccatc agcagggaca cagcaagaa caccctgtac      240 ctgcagatga acagcctgag ggccgaggac accgccgtgt actactgcgc ccgcatcaac     300
aacgacccta tggatgtgtg gggccagggc accctggtga cagtgagctc a              351

<210> SEQ ID NO 372
<211> LENGTH: 117
<212> TYPE: PRT
<213> ORGANISM: Homo sapiens

<400> SEQUENCE: 372

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser His Ala His His Val
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 373

```
<211> LENGTH: 5
<212> TYPE: PRT
<213> ORGANISM: Homo sapiens

<400> SEQUENCE: 373

Ser Tyr Ala Met Asn
1               5

<210> SEQ ID NO 374
<211> LENGTH: 17
<212> TYPE: PRT
<213> ORGANISM: Homo sapiens

<400> SEQUENCE: 374

Thr Ile Ser Tyr His Gly His His Ile Ser His Ala His His Val His
1               5                   10                  15

Gly

<210> SEQ ID NO 375
<211> LENGTH: 8
<212> TYPE: PRT
<213> ORGANISM: Homo sapiens

<400> SEQUENCE: 375

Ile Asn Asn Asp Pro Met Asp Val
1               5

<210> SEQ ID NO 376
<211> LENGTH: 333
<212> TYPE: DNA
<213> ORGANISM: Homo sapiens

<400> SEQUENCE: 376
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                  333

<210> SEQ ID NO 377
<211> LENGTH: 111
<212> TYPE: PRT
<213> ORGANISM: Homo sapiens

<400> SEQUENCE: 377

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95
```

Gly Glu Thr Asn Val Phe Gly Gly Gly Thr Lys Leu Thr Val Leu
            100                 105                 110

<210> SEQ ID NO 378
<211> LENGTH: 11
<212> TYPE: PRT
<213> ORGANISM: Homo sapiens

<400> SEQUENCE: 378

Ser Gly Asp Asn Leu Gly Lys Lys Tyr Val Gln
1               5                   10

<210> SEQ ID NO 379
<211> LENGTH: 7
<212> TYPE: PRT
<213> ORGANISM: Homo sapiens

<400> SEQUENCE: 379

Asp Asp Ser Asn Arg Pro Ser
1               5

<210> SEQ ID NO 380
<211> LENGTH: 14
<212> TYPE: PRT
<213> ORGANISM: Homo sapiens

<400> SEQUENCE: 380

Gln Thr Trp Asp Gly Asn Pro Thr Thr Gly Glu Thr Asn Val
1               5                   10

<210> SEQ ID NO 381
<211> LENGTH: 351
<212> TYPE: DNA
<213> ORGANISM: Homo sapiens

<400> SEQUENCE: 381
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg gtgtccacc atcagctaca gcgggtcgct gatcagctac     180
gccgacagcg tgaagggcag gttcaccatc agcagggaca cagcaagaa caccctgtac     240 ctgcagatga acagcctgag ggccgaggac accgccgtgt actactgcgc ccgcatccac     300
caccaccctc acgatcactg gggccagggc accctggtga cagtgagctc a             351

<210> SEQ ID NO 382
<211> LENGTH: 117
<212> TYPE: PRT
<213> ORGANISM: Homo sapiens

<400> SEQUENCE: 382

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ile His His His Pro His Asp His Trp Gly Gln Gly Thr Leu
            100                 105                 110

Val Thr Val Ser Ser
            115

<210> SEQ ID NO 383
<211> LENGTH: 5
<212> TYPE: PRT
<213> ORGANISM: Homo sapiens

<400> SEQUENCE: 383

Ser Tyr Ala Met Asn
1               5

<210> SEQ ID NO 384
<211> LENGTH: 17
<212> TYPE: PRT
<213> ORGANISM: Homo sapiens

<400> SEQUENCE: 384

Thr Ile Ser Tyr Ser Gly Ser Leu Ile Ser Tyr Ala Asp Ser Val Lys
1               5                   10                  15

Gly

<210> SEQ ID NO 385
<211> LENGTH: 8
<212> TYPE: PRT
<213> ORGANISM: Homo sapiens

<400> SEQUENCE: 385

Ile His His His Pro His Asp His
1               5

<210> SEQ ID NO 386
<211> LENGTH: 333
<212> TYPE: DNA
<213> ORGANISM: Homo sapiens

<400> SEQUENCE: 386
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                  333

<210> SEQ ID NO 387
<211> LENGTH: 111
<212> TYPE: PRT
<213> ORGANISM: Homo sapiens

<400> SEQUENCE: 387

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr

```
                   35                  40                  45
Asp Asp Ser Asn Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Thr Trp Asp Gly Asn Pro Thr Thr
                 85                  90                  95

Gly Glu Thr Asn Val Phe Gly Gly Gly Thr Lys Leu Thr Val Leu
            100                 105                 110

<210> SEQ ID NO 388
<211> LENGTH: 11
<212> TYPE: PRT
<213> ORGANISM: Homo sapiens

<400> SEQUENCE: 388

Ser Gly Asp Asn Leu Gly Lys Lys Tyr Val Gln
 1               5                  10

<210> SEQ ID NO 389
<211> LENGTH: 7
<212> TYPE: PRT
<213> ORGANISM: Homo sapiens

<400> SEQUENCE: 389

Asp Asp Ser Asn Arg Pro Ser
 1               5

<210> SEQ ID NO 390
<211> LENGTH: 14
<212> TYPE: PRT
<213> ORGANISM: Homo sapiens

<400> SEQUENCE: 390

Gln Thr Trp Asp Gly Asn Pro Thr Thr Gly Glu Thr Asn Val
 1               5                  10

<210> SEQ ID NO 391
<211> LENGTH: 351
<212> TYPE: DNA
<213> ORGANISM: Homo sapiens

<400> SEQUENCE: 391
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctaca gcgggtcgct gatcagctac    180
gccgacagcg tgaagggcag gttcaccatc agcagggaca cagcaagaa cacccctgtac    240 ctgcagatga acagcctgag ggccgaggac accgccgtgt actactgcgc cgcatcaac    300 cacgacccta tggatcactg gggccagggc accctggtga cagtgagctc a             351

<210> SEQ ID NO 392
<211> LENGTH: 117
<212> TYPE: PRT
<213> ORGANISM: Homo sapiens

<400> SEQUENCE: 392

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
```

```
                    20                  25                  30
Ala Met Asn Trp Val Arg Gln Ala Pro Gly Lys Gly Leu Glu Trp Val
            35                  40                  45

Ser Thr Ile Ser Tyr Ser Gly Ser Leu Ile Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp His Trp Gly Gln Gly Thr Leu
            100                 105                 110

Val Thr Val Ser Ser
        115
```

<210> SEQ ID NO 393
<211> LENGTH: 5
<212> TYPE: PRT
<213> ORGANISM: Homo sapiens

<400> SEQUENCE: 393

```
Ser Tyr Ala Met Asn
1               5
```

<210> SEQ ID NO 394
<211> LENGTH: 17
<212> TYPE: PRT
<213> ORGANISM: Homo sapiens

<400> SEQUENCE: 394

```
Thr Ile Ser Tyr Ser Gly Ser Leu Ile Ser Tyr Ala Asp Ser Val Lys
1               5                   10                  15

Gly
```

<210> SEQ ID NO 395
<211> LENGTH: 8
<212> TYPE: PRT
<213> ORGANISM: Homo sapiens

<400> SEQUENCE: 395

```
Ile Asn His Asp Pro Met Asp His
1               5
```

<210> SEQ ID NO 396
<211> LENGTH: 333
<212> TYPE: DNA
<213> ORGANISM: Homo sapiens

<400> SEQUENCE: 396

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120 cagtccccg  tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg agggaccaa gttaaccgtc cta                                    333
```

<210> SEQ ID NO 397
<211> LENGTH: 111
<212> TYPE: PRT

-continued

<213> ORGANISM: Homo sapiens

<400> SEQUENCE: 397

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 398
<211> LENGTH: 11
<212> TYPE: PRT
<213> ORGANISM: Homo sapiens

<400> SEQUENCE: 398

```
Ser Gly Asp Asn Leu Gly Lys Lys Tyr Val Gln
1               5                   10
```

<210> SEQ ID NO 399
<211> LENGTH: 7
<212> TYPE: PRT
<213> ORGANISM: Homo sapiens

<400> SEQUENCE: 399

```
Asp Asp Ser Asn Arg Pro Ser
1               5
```

<210> SEQ ID NO 400
<211> LENGTH: 14
<212> TYPE: PRT
<213> ORGANISM: Homo sapiens

<400> SEQUENCE: 400

```
Gln Thr Trp Asp Gly Asn Pro Thr Thr Gly Glu Thr Asn Val
1               5                   10
```

<210> SEQ ID NO 401
<211> LENGTH: 351
<212> TYPE: DNA
<213> ORGANISM: Homo sapiens

<400> SEQUENCE: 401

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca acagcaagaa caccctgtac     240
ctgcagatga acagcctgag ggccgaggac accgccgtgt actactgcgc ccgcatcaac     300
aacgacccta tggatgtgtg gggccagggc accctggtga cagtgagctc a             351
```

```
<210> SEQ ID NO 402
<211> LENGTH: 117
<212> TYPE: PRT
<213> ORGANISM: Homo sapiens

<400> SEQUENCE: 402

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 403
<211> LENGTH: 5
<212> TYPE: PRT
<213> ORGANISM: Homo sapiens

<400> SEQUENCE: 403

Ser Tyr Ala Met Asn
1               5

<210> SEQ ID NO 404
<211> LENGTH: 17
<212> TYPE: PRT
<213> ORGANISM: Homo sapiens

<400> SEQUENCE: 404

Thr Ile Ser Tyr Ser Gly Ser Leu Ile Ser Tyr Ala Asp Ser Val Lys
1               5                   10                  15

Gly

<210> SEQ ID NO 405
<211> LENGTH: 8
<212> TYPE: PRT
<213> ORGANISM: Homo sapiens

<400> SEQUENCE: 405

Ile Asn Asn Asp Pro Met Asp Val
1               5

<210> SEQ ID NO 406
<211> LENGTH: 333
<212> TYPE: DNA
<213> ORGANISM: Homo sapiens

<400> SEQUENCE: 406
agtatcgagc tgacccagcc cccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
```

```
ttcagcggca gcaacagcgg caacaccgcc accctgacca tcagcggcac ccaggcgatg    240
gacgaggccg actactactg ccacacctgg gacgggcacc acacgacggg ggagaccaac    300
cacttcggcg agggaccaa gttaaccgtc cta                                  333
```

<210> SEQ ID NO 407
<211> LENGTH: 111
<212> TYPE: PRT
<213> ORGANISM: Homo sapiens

<400> SEQUENCE: 407

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp Gly His His Thr Thr
                85                  90                  95

Gly Glu Thr Asn His Phe Gly Gly Gly Thr Lys Leu Thr Val Leu
            100                 105                 110
```

<210> SEQ ID NO 408
<211> LENGTH: 11
<212> TYPE: PRT
<213> ORGANISM: Homo sapiens

<400> SEQUENCE: 408

```
Ser Gly Asp Asn Leu Gly Lys Lys Tyr Val Gln
1               5                   10
```

<210> SEQ ID NO 409
<211> LENGTH: 7
<212> TYPE: PRT
<213> ORGANISM: Homo sapiens

<400> SEQUENCE: 409

```
Asp Asp Ser Asn Arg Pro Ser
1               5
```

<210> SEQ ID NO 410
<211> LENGTH: 14
<212> TYPE: PRT
<213> ORGANISM: Homo sapiens

<400> SEQUENCE: 410

```
His Thr Trp Asp Gly His His Thr Thr Gly Glu Thr Asn His
1               5                   10
```

<210> SEQ ID NO 411
<211> LENGTH: 351
<212> TYPE: DNA
<213> ORGANISM: Homo sapiens

<400> SEQUENCE: 411

```
gaggtgcagc tgctggagag cggcggaggg ctggtgcagc caggcggcag cctgaggctg    60
```

```
tcctgcgccg cctccggatt caccttcagc agctacgcca tgaactgggt gcggcaggcc    120
ccaggcaagg gcctggagtg ggtgtccacc atcagctaca gcgggtcgct gatcagctac    180
gccgacagcg tgaagggcag gttcaccatc agcagggaca acagcaagaa caccctgtac    240
ctgcagatga acagcctgag ggccgaggac accgccgtgt actactgcgc ccgcatcaac    300
aacgacccta tggatgtgtg gggccagggc accctggtga cagtgagctc a             351
```

<210> SEQ ID NO 412
<211> LENGTH: 117
<212> TYPE: PRT
<213> ORGANISM: Homo sapiens

<400> SEQUENCE: 412

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 413
<211> LENGTH: 5
<212> TYPE: PRT
<213> ORGANISM: Homo sapiens

<400> SEQUENCE: 413

Ser Tyr Ala Met Asn
1               5

<210> SEQ ID NO 414
<211> LENGTH: 17
<212> TYPE: PRT
<213> ORGANISM: Homo sapiens

<400> SEQUENCE: 414

Thr Ile Ser Tyr Ser Gly Ser Leu Ile Ser Tyr Ala Asp Ser Val Lys
1               5                   10                  15

Gly

<210> SEQ ID NO 415
<211> LENGTH: 8
<212> TYPE: PRT
<213> ORGANISM: Homo sapiens

<400> SEQUENCE: 415

Ile Asn Asn Asp Pro Met Asp Val
1               5

<210> SEQ ID NO 416

<211> LENGTH: 333
<212> TYPE: DNA
<213> ORGANISM: Homo sapiens

<400> SEQUENCE: 416

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagcactgg gacgggcacc accacacggg ggagaccaac     300
gtgttcggcg gagggaccaa gttaaccgtc cta                                  333
```

<210> SEQ ID NO 417
<211> LENGTH: 111
<212> TYPE: PRT
<213> ORGANISM: Homo sapiens

<400> SEQUENCE: 417

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln His Trp Asp Gly His His His Thr
                85                  90                  95

Gly Glu Thr Asn Val Phe Gly Gly Gly Thr Lys Leu Thr Val Leu
            100                 105                 110

<210> SEQ ID NO 418
<211> LENGTH: 11
<212> TYPE: PRT
<213> ORGANISM: Homo sapiens

<400> SEQUENCE: 418

Ser Gly Asp Asn Leu Gly Lys Lys Tyr Val Gln
1               5                   10

<210> SEQ ID NO 419
<211> LENGTH: 7
<212> TYPE: PRT
<213> ORGANISM: Homo sapiens

<400> SEQUENCE: 419

Asp Asp Ser Asn Arg Pro Ser
1               5

<210> SEQ ID NO 420
<211> LENGTH: 14
<212> TYPE: PRT
<213> ORGANISM: Homo sapiens

<400> SEQUENCE: 420

Gln His Trp Asp Gly His His His Thr Gly Glu Thr Asn Val
1               5                   10

<210> SEQ ID NO 421
<211> LENGTH: 351
<212> TYPE: DNA
<213> ORGANISM: Homo sapiens

<400> SEQUENCE: 421
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac      240 ctgcagatga acagcctgag ggccgaggac accgccgtgt actactgcgc ccgcatcaac     300
aacgacccta tggatgtgtg gggccagggc accctggtga cagtgagctc a              351

<210> SEQ ID NO 422
<211> LENGTH: 117
<212> TYPE: PRT
<213> ORGANISM: Homo sapiens

<400> SEQUENCE: 422

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 423
<211> LENGTH: 5
<212> TYPE: PRT
<213> ORGANISM: Homo sapiens

<400> SEQUENCE: 423

Ser Tyr Ala Met Asn
1               5

<210> SEQ ID NO 424
<211> LENGTH: 17
<212> TYPE: PRT
<213> ORGANISM: Homo sapiens

<400> SEQUENCE: 424

Thr Ile Ser Tyr Ser Gly Ser Leu Ile Ser Tyr Ala Asp Ser Val Lys
1               5                   10                  15

Gly

<210> SEQ ID NO 425

```
<211> LENGTH: 8
<212> TYPE: PRT
<213> ORGANISM: Homo sapiens

<400> SEQUENCE: 425

Ile Asn Asn Asp Pro Met Asp Val
1               5

<210> SEQ ID NO 426
<211> LENGTH: 333
<212> TYPE: DNA
<213> ORGANISM: Homo sapiens

<400> SEQUENCE: 426
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagcactgg cacgggaacc cgcacacggg ggagcacaac     300
cacttcggcg agggaccaa gttaaccgtc cta                                   333

<210> SEQ ID NO 427
<211> LENGTH: 111
<212> TYPE: PRT
<213> ORGANISM: Homo sapiens

<400> SEQUENCE: 427

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln His Trp His Gly Asn Pro His Thr
                85                  90                  95

Gly Glu His Asn His Phe Gly Gly Gly Thr Lys Leu Thr Val Leu
            100                 105                 110

<210> SEQ ID NO 428
<211> LENGTH: 11
<212> TYPE: PRT
<213> ORGANISM: Homo sapiens

<400> SEQUENCE: 428

Ser Gly Asp Asn Leu Gly Lys Lys Tyr Val Gln
1               5                   10

<210> SEQ ID NO 429
<211> LENGTH: 7
<212> TYPE: PRT
<213> ORGANISM: Homo sapiens

<400> SEQUENCE: 429

Asp Asp Ser Asn Arg Pro Ser
1               5
```

```
<210> SEQ ID NO 430
<211> LENGTH: 14
<212> TYPE: PRT
<213> ORGANISM: Homo sapiens

<400> SEQUENCE: 430

Gln His Trp His Gly Asn Pro His Thr Gly Glu His Asn His
1               5                   10

<210> SEQ ID NO 431
<211> LENGTH: 351
<212> TYPE: DNA
<213> ORGANISM: Homo sapiens

<400> SEQUENCE: 431
gaggtgcagc tgctggagag cggcggaggg ctggtgcagc caggcggcag cctgaggctg      60
tcctgcgccg cctccggatt caccttcagc agctacgcca tgaactgggt gcggcaggcc    120
ccaggcaagg gcctggagtg ggtgtccacc atcagctaca gcgggtcgct gatcagctac    180
gccgacagcg tgaagggcag gttcaccatc agcagggaca acagcaagaa caccctgtac    240
ctgcagatga acagcctgag ggccgaggac accgccgtgt actactgcgc ccgcatcaac    300
aacgacccta tggatgtgtg gggccagggc accctggtga cagtgagctc a              351

<210> SEQ ID NO 432
<211> LENGTH: 117
<212> TYPE: PRT
<213> ORGANISM: Homo sapiens

<400> SEQUENCE: 432

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 433
<211> LENGTH: 5
<212> TYPE: PRT
<213> ORGANISM: Homo sapiens

<400> SEQUENCE: 433

Ser Tyr Ala Met Asn
1               5

<210> SEQ ID NO 434
<211> LENGTH: 17
<212> TYPE: PRT
```

<213> ORGANISM: Homo sapiens

<400> SEQUENCE: 434

Thr Ile Ser Tyr Ser Gly Ser Leu Ile Ser Tyr Ala Asp Ser Val Lys
1               5                   10                  15

Gly

<210> SEQ ID NO 435
<211> LENGTH: 8
<212> TYPE: PRT
<213> ORGANISM: Homo sapiens

<400> SEQUENCE: 435

Ile Asn Asn Asp Pro Met Asp Val
1               5

<210> SEQ ID NO 436
<211> LENGTH: 333
<212> TYPE: DNA
<213> ORGANISM: Homo sapiens

<400> SEQUENCE: 436
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc    120
cagtcccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccacacctgg gaccacaacc cgcaccatca tcacaccaac    300
cacttcggcg agggaccaa gttaaccgtc cta                                  333

<210> SEQ ID NO 437
<211> LENGTH: 111
<212> TYPE: PRT
<213> ORGANISM: Homo sapiens

<400> SEQUENCE: 437

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp His Asn Pro His His
                85                  90                  95

His His Thr Asn His Phe Gly Gly Gly Thr Lys Leu Thr Val Leu
            100                 105                 110

<210> SEQ ID NO 438
<211> LENGTH: 11
<212> TYPE: PRT
<213> ORGANISM: Homo sapiens

<400> SEQUENCE: 438

Ser Gly Asp Asn Leu Gly Lys Lys Tyr Val Gln
1               5                   10

<210> SEQ ID NO 439
<211> LENGTH: 7
<212> TYPE: PRT
<213> ORGANISM: Homo sapiens

<400> SEQUENCE: 439

Asp Asp Ser Asn Arg Pro Ser
1               5

<210> SEQ ID NO 440
<211> LENGTH: 14
<212> TYPE: PRT
<213> ORGANISM: Homo sapiens

<400> SEQUENCE: 440

His Thr Trp Asp His Asn Pro His His His Thr Asn His
1               5                   10

<210> SEQ ID NO 441
<211> LENGTH: 351
<212> TYPE: DNA
<213> ORGANISM: Homo sapiens

<400> SEQUENCE: 441

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac      240
ctgcagatga acagcctgag ggccgaggac accgccgtgt actactgcgc ccgcatcaac     300
aacgaccta tggatgtgtg gggccagggc accctggtga cagtgagctc a               351
```

<210> SEQ ID NO 442
<211> LENGTH: 117
<212> TYPE: PRT
<213> ORGANISM: Homo sapiens

<400> SEQUENCE: 442

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 443
<211> LENGTH: 5
<212> TYPE: PRT

```
<213> ORGANISM: Homo sapiens

<400> SEQUENCE: 443

Ser Tyr Ala Met Asn
1               5

<210> SEQ ID NO 444
<211> LENGTH: 17
<212> TYPE: PRT
<213> ORGANISM: Homo sapiens

<400> SEQUENCE: 444

Thr Ile Ser Tyr Ser Gly Ser Leu Ile Ser Tyr Ala Asp Ser Val Lys
1               5                   10                  15

Gly

<210> SEQ ID NO 445
<211> LENGTH: 8
<212> TYPE: PRT
<213> ORGANISM: Homo sapiens

<400> SEQUENCE: 445

Ile Asn Asn Asp Pro Met Asp Val
1               5

<210> SEQ ID NO 446
<211> LENGTH: 333
<212> TYPE: DNA
<213> ORGANISM: Homo sapiens

<400> SEQUENCE: 446
agtatcgagc tgacccagcc ccccagcgtg agcgtgtccc caggccagac cgccagcatc        60
acctgcagcg gcgacaacct gggcaagaaa tacgtgcagt ggtatcagca gaagcccggc       120
cagtcccccg tgctggtgat ctacgacgac agcaacaggc ccagcggcat ccccgagagg       180
ttcagcggca gcaacagcgg caacaccgcc accctgacca tcagcggcac ccaggcgatg       240
gacgaggccg actactactg ccaccactgg caccacaacc cgacgcatca tgagaccaac       300
gtgttcggcg gagggaccaa gttaaccgtc cta                                   333

<210> SEQ ID NO 447
<211> LENGTH: 111
<212> TYPE: PRT
<213> ORGANISM: Homo sapiens

<400> SEQUENCE: 447

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His His Trp His His Asn Pro Thr His
                85                  90                  95

His Glu Thr Asn Val Phe Gly Gly Gly Thr Lys Leu Thr Val Leu
            100                 105                 110
```

<210> SEQ ID NO 448
<211> LENGTH: 11
<212> TYPE: PRT
<213> ORGANISM: Homo sapiens

<400> SEQUENCE: 448

Ser Gly Asp Asn Leu Gly Lys Lys Tyr Val Gln
1               5                   10

<210> SEQ ID NO 449
<211> LENGTH: 7
<212> TYPE: PRT
<213> ORGANISM: Homo sapiens

<400> SEQUENCE: 449

Asp Asp Ser Asn Arg Pro Ser
1               5

<210> SEQ ID NO 450
<211> LENGTH: 14
<212> TYPE: PRT
<213> ORGANISM: Homo sapiens

<400> SEQUENCE: 450

His His Trp His His Asn Pro Thr His His Glu Thr Asn Val
1               5                   10

<210> SEQ ID NO 451
<211> LENGTH: 351
<212> TYPE: DNA
<213> ORGANISM: Homo sapiens

<400> SEQUENCE: 451
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac      240 ctgcagatga acagcctgag ggccgaggac accgccgtgt actactgcgc ccgcatcaac     300
aacgacccta tggatgtgtg gggccagggc accctggtga cagtgagctc a              351

<210> SEQ ID NO 452
<211> LENGTH: 117
<212> TYPE: PRT
<213> ORGANISM: Homo sapiens

<400> SEQUENCE: 452

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 453
<211> LENGTH: 5
<212> TYPE: PRT
<213> ORGANISM: Homo sapiens

<400> SEQUENCE: 453

Ser Tyr Ala Met Asn
1               5

<210> SEQ ID NO 454
<211> LENGTH: 17
<212> TYPE: PRT
<213> ORGANISM: Homo sapiens

<400> SEQUENCE: 454

Thr Ile Ser Tyr Ser Gly Ser Leu Ile Ser Tyr Ala Asp Ser Val Lys
1               5                   10                  15

Gly

<210> SEQ ID NO 455
<211> LENGTH: 8
<212> TYPE: PRT
<213> ORGANISM: Homo sapiens

<400> SEQUENCE: 455

Ile Asn Asn Asp Pro Met Asp Val
1               5

<210> SEQ ID NO 456
<211> LENGTH: 333
<212> TYPE: DNA
<213> ORGANISM: Homo sapiens

<400> SEQUENCE: 456
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagcactgg cacgggcacc accacacggg ggagaccaac     300
gtgttcggcg agggaccaa gttaaccgtc cta                                    333

<210> SEQ ID NO 457
<211> LENGTH: 111
<212> TYPE: PRT
<213> ORGANISM: Homo sapiens

<400> SEQUENCE: 457

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

```
Asp Asp Ser Asn Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln His Trp His Gly His His His Thr
                85                  90                  95
Gly Glu Thr Asn Val Phe Gly Gly Gly Thr Lys Leu Thr Val Leu
            100                 105                 110
```

<210> SEQ ID NO 458
<211> LENGTH: 11
<212> TYPE: PRT
<213> ORGANISM: Homo sapiens

<400> SEQUENCE: 458

```
Ser Gly Asp Asn Leu Gly Lys Lys Tyr Val Gln
1               5                   10
```

<210> SEQ ID NO 459
<211> LENGTH: 7
<212> TYPE: PRT
<213> ORGANISM: Homo sapiens

<400> SEQUENCE: 459

```
Asp Asp Ser Asn Arg Pro Ser
1               5
```

<210> SEQ ID NO 460
<211> LENGTH: 14
<212> TYPE: PRT
<213> ORGANISM: Homo sapiens

<400> SEQUENCE: 460

```
Gln His Trp His Gly His His His Thr Gly Glu Thr Asn Val
1               5                   10
```

<210> SEQ ID NO 461
<211> LENGTH: 351
<212> TYPE: DNA
<213> ORGANISM: Homo sapiens

<400> SEQUENCE: 461

```
gaggtgcagc tgctcgagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctaca gcgggtcgct gatccactac    180
gccgacagcg tgaagggcag gttcaccatc agcagggaca acagcaagaa caccctgtac    240
ctgcagatga acagcctgag ggccgaggac accgccgtgt actactgcgc ccgcatcaac    300
cacgacccta tggatgtgtg gggccagggc accctggtga cagtgagctc a            351
```

<210> SEQ ID NO 462
<211> LENGTH: 117
<212> TYPE: PRT
<213> ORGANISM: Homo sapiens

<400> SEQUENCE: 462

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
```

```
Ala Met Asn Trp Val Arg Gln Ala Pro Gly Lys Gly Leu Glu Trp Val
            35                  40                  45
Ser Thr Ile Ser Tyr Ser Gly Ser Leu Ile His Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ile Asn His Asp Pro Met Asp Val Trp Gly Gln Gly Thr Leu
            100                 105                 110
Val Thr Val Ser Ser
        115
```

<210> SEQ ID NO 463
<211> LENGTH: 5
<212> TYPE: PRT
<213> ORGANISM: Homo sapiens

<400> SEQUENCE: 463

```
Ser Tyr Ala Met Asn
 1               5
```

<210> SEQ ID NO 464
<211> LENGTH: 17
<212> TYPE: PRT
<213> ORGANISM: Homo sapiens

<400> SEQUENCE: 464

```
Thr Ile Ser Tyr Ser Gly Ser Leu Ile His Tyr Ala Asp Ser Val Lys
 1               5                  10                  15
Gly
```

<210> SEQ ID NO 465
<211> LENGTH: 8
<212> TYPE: PRT
<213> ORGANISM: Homo sapiens

<400> SEQUENCE: 465

```
Ile Asn His Asp Pro Met Asp Val
 1               5
```

<210> SEQ ID NO 466
<211> LENGTH: 333
<212> TYPE: DNA
<213> ORGANISM: Homo sapiens

<400> SEQUENCE: 466

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggccatg   240
gacgaggccg actactactg ccagacctgg gacgggaacc cgacgacggg cgagaccaac   300
gtgttcggcg gagggaccaa gttaaccgtc cta                                 333
```

<210> SEQ ID NO 467
<211> LENGTH: 111
<212> TYPE: PRT
<213> ORGANISM: Homo sapiens -continued

<400> SEQUENCE: 467

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 468
<211> LENGTH: 11
<212> TYPE: PRT
<213> ORGANISM: Homo sapiens

<400> SEQUENCE: 468

Ser Gly Asp Asn Leu Gly Lys Lys Tyr Val Gln
1               5                   10

<210> SEQ ID NO 469
<211> LENGTH: 7
<212> TYPE: PRT
<213> ORGANISM: Homo sapiens

<400> SEQUENCE: 469

Asp Asp Ser Asn Arg Pro Ser
1               5

<210> SEQ ID NO 470
<211> LENGTH: 14
<212> TYPE: PRT
<213> ORGANISM: Homo sapiens

<400> SEQUENCE: 470

Gln Thr Trp Asp Gly Asn Pro Thr Thr Gly Glu Thr Asn Val
1               5                   10

<210> SEQ ID NO 471
<211> LENGTH: 351
<212> TYPE: DNA
<213> ORGANISM: Homo sapiens

<400> SEQUENCE: 471
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagccaca gcgggcacca catcagccac    180
cacgacagcc atcatggcag gttcaccatc agcagggaca cagcaagaa cacccctgtac    240
ctgcagatga acagcctgag ggccgaggac accgccgtgt actactgcgc ccgcatcaac    300
cacgacccta tggatgtgtg gggccagggc accctggtga cagtgagctc a             351

<210> SEQ ID NO 472
<211> LENGTH: 117

```
<212> TYPE: PRT
<213> ORGANISM: Homo sapiens

<400> SEQUENCE: 472

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser His Ser Gly His His Ile Ser His His Asp Ser His
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 473
<211> LENGTH: 5
<212> TYPE: PRT
<213> ORGANISM: Homo sapiens

<400> SEQUENCE: 473

Ser Tyr Ala Met Asn
1               5

<210> SEQ ID NO 474
<211> LENGTH: 17
<212> TYPE: PRT
<213> ORGANISM: Homo sapiens

<400> SEQUENCE: 474

Thr Ile Ser His Ser Gly His His Ile Ser His His Asp Ser His His
1               5                   10                  15

Gly

<210> SEQ ID NO 475
<211> LENGTH: 8
<212> TYPE: PRT
<213> ORGANISM: Homo sapiens

<400> SEQUENCE: 475

Ile Asn His Asp Pro Met Asp Val
1               5

<210> SEQ ID NO 476
<211> LENGTH: 333
<212> TYPE: DNA
<213> ORGANISM: Homo sapiens

<400> SEQUENCE: 476
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
```

```
gacgaggccg actactactg ccagacctgg gacgggaacc cgacgacggg cgagaccaac    300
gtgttcggcg gagggaccaa gttaaccgtc cta                                 333
```

<210> SEQ ID NO 477
<211> LENGTH: 111
<212> TYPE: PRT
<213> ORGANISM: Homo sapiens

<400> SEQUENCE: 477

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 478
<211> LENGTH: 11
<212> TYPE: PRT
<213> ORGANISM: Homo sapiens

<400> SEQUENCE: 478

```
Ser Gly Asp Asn Leu Gly Lys Lys Tyr Val Gln
1               5                   10
```

<210> SEQ ID NO 479
<211> LENGTH: 7
<212> TYPE: PRT
<213> ORGANISM: Homo sapiens

<400> SEQUENCE: 479

```
Asp Asp Ser Asn Arg Pro Ser
1               5
```

<210> SEQ ID NO 480
<211> LENGTH: 14
<212> TYPE: PRT
<213> ORGANISM: Homo sapiens

<400> SEQUENCE: 480

```
Gln Thr Trp Asp Gly Asn Pro Thr Thr Gly Glu Thr Asn Val
1               5                   10
```

<210> SEQ ID NO 481
<211> LENGTH: 351
<212> TYPE: DNA
<213> ORGANISM: Homo sapiens

<400> SEQUENCE: 481

```
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
```

```
ccaggcaagg gcctggagtg ggtgtccacc atcagccaca gcgggcacct gatccaccac    180
gccgacagcc ataagggcag gttcaccatc agcagggaca cagcaagaa caccctgtac     240 ctgcagatga acagcctgag ggccgaggac accgccgtgt actactgcgc ccgcatcaac    300
cacgacccta tggatgtgtg gggccagggc accctggtga cagtgagctc a             351
```

<210> SEQ ID NO 482
<211> LENGTH: 117
<212> TYPE: PRT
<213> ORGANISM: Homo sapiens

<400> SEQUENCE: 482

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser His Ser Gly His Leu Ile His His Ala Asp Ser His
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115
```

<210> SEQ ID NO 483
<211> LENGTH: 5
<212> TYPE: PRT
<213> ORGANISM: Homo sapiens

<400> SEQUENCE: 483

```
Ser Tyr Ala Met Asn
1               5
```

<210> SEQ ID NO 484
<211> LENGTH: 17
<212> TYPE: PRT
<213> ORGANISM: Homo sapiens

<400> SEQUENCE: 484

```
Thr Ile Ser His Ser Gly His Leu Ile His His Ala Asp Ser His Lys
1               5                   10                  15

Gly
```

<210> SEQ ID NO 485
<211> LENGTH: 8
<212> TYPE: PRT
<213> ORGANISM: Homo sapiens

<400> SEQUENCE: 485

```
Ile Asn His Asp Pro Met Asp Val
1               5
```

<210> SEQ ID NO 486
<211> LENGTH: 333
<212> TYPE: DNA

-continued

<213> ORGANISM: Homo sapiens

<400> SEQUENCE: 486

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg gagggaccaa gttaaccgtc cta                                333
```

<210> SEQ ID NO 487
<211> LENGTH: 111
<212> TYPE: PRT
<213> ORGANISM: Homo sapiens

<400> SEQUENCE: 487

```
Ser Ile Glu Leu Thr Gln Pro Pro Ser Val Ser Val Ser Pro Gly Gln
1               5                   10                  15
Thr Ala Ser Ile Thr Cys Ser Gly Asp Asn Leu Gly Lys Lys Tyr Val
            20                  25                  30
Gln Trp Tyr Gln Gln Lys Pro Gly Gln Ser Pro Val Leu Val Ile Tyr
        35                  40                  45
Asp Asp Ser Asn Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ala Met
65                  70                  75                  80
Asp Glu Ala Asp Tyr Tyr Cys Gln Thr Trp Asp Gly Asn Pro Thr Thr
                85                  90                  95
Gly Glu Thr Asn Val Phe Gly Gly Gly Thr Lys Leu Thr Val Leu
            100                 105                 110
```

<210> SEQ ID NO 488
<211> LENGTH: 11
<212> TYPE: PRT
<213> ORGANISM: Homo sapiens

<400> SEQUENCE: 488

```
Ser Gly Asp Asn Leu Gly Lys Lys Tyr Val Gln
1               5                   10
```

<210> SEQ ID NO 489
<211> LENGTH: 7
<212> TYPE: PRT
<213> ORGANISM: Homo sapiens

<400> SEQUENCE: 489

```
Asp Asp Ser Asn Arg Pro Ser
1               5
```

<210> SEQ ID NO 490
<211> LENGTH: 14
<212> TYPE: PRT
<213> ORGANISM: Homo sapiens

<400> SEQUENCE: 490

```
Gln Thr Trp Asp Gly Asn Pro Thr Thr Gly Glu Thr Asn Val
1               5                   10
```

<210> SEQ ID NO 491
<211> LENGTH: 351
<212> TYPE: DNA
<213> ORGANISM: Homo sapiens

<400> SEQUENCE: 491

```
gaggtgcagc tgctggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctaca gcgggcacct gatccactac   180
gccgaccacc atcatggcag gttcaccatc agcagggaca acagcaagaa caccctgtac   240
ctgcagatga acagcctgag ggccgaggac accgccgtgt actactgcgc ccgcatcaac   300
cacgacccta tggatgtgtg gggccagggc accctggtga cagtgagctc a            351
```

<210> SEQ ID NO 492
<211> LENGTH: 117
<212> TYPE: PRT
<213> ORGANISM: Homo sapiens

<400> SEQUENCE: 492

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly His Leu Ile His Tyr Ala Asp His His
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 493
<211> LENGTH: 5
<212> TYPE: PRT
<213> ORGANISM: Homo sapiens

<400> SEQUENCE: 493

Ser Tyr Ala Met Asn
1               5

<210> SEQ ID NO 494
<211> LENGTH: 17
<212> TYPE: PRT
<213> ORGANISM: Homo sapiens

<400> SEQUENCE: 494

Thr Ile Ser Tyr Ser Gly His Leu Ile His Tyr Ala Asp His His
1               5                   10                  15

Gly

<210> SEQ ID NO 495
<211> LENGTH: 8
<212> TYPE: PRT

<213> ORGANISM: Homo sapiens

<400> SEQUENCE: 495

Ile Asn His Asp Pro Met Asp Val
1               5

<210> SEQ ID NO 496
<211> LENGTH: 333
<212> TYPE: DNA
<213> ORGANISM: Homo sapiens

<400> SEQUENCE: 496

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg gagggaccaa gttaaccgtc cta                                333
```

<210> SEQ ID NO 497
<211> LENGTH: 111
<212> TYPE: PRT
<213> ORGANISM: Homo sapiens

<400> SEQUENCE: 497

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 498
<211> LENGTH: 11
<212> TYPE: PRT
<213> ORGANISM: Homo sapiens

<400> SEQUENCE: 498

Ser Gly Asp Asn Leu Gly Lys Lys Tyr Val Gln
1               5                   10

<210> SEQ ID NO 499
<211> LENGTH: 7
<212> TYPE: PRT
<213> ORGANISM: Homo sapiens

<400> SEQUENCE: 499

Asp Asp Ser Asn Arg Pro Ser
1               5

<210> SEQ ID NO 500
<211> LENGTH: 14
<212> TYPE: PRT
<213> ORGANISM: Homo sapiens

<400> SEQUENCE: 500

Gln Thr Trp Asp Gly Asn Pro Thr Thr Gly Glu Thr Asn Val
1               5                   10

<210> SEQ ID NO 501
<211> LENGTH: 351
<212> TYPE: DNA
<213> ORGANISM: Homo sapiens

<400> SEQUENCE: 501
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggtcgca catcagccac     180
gccgaccacg tgcatggcag gttcaccatc agcagggaca acagcaagaa cacccctgtac    240 ctgcagatga acagcctgag ggccgaggac accgccgtgt actactgcgc ccgcatcaac     300
cacgacccta tggatgtgtg gggccagggc accctggtga cagtgagctc a              351

<210> SEQ ID NO 502
<211> LENGTH: 117
<212> TYPE: PRT
<213> ORGANISM: Homo sapiens

<400> SEQUENCE: 502

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser His Ala Asp His Val
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 503
<211> LENGTH: 5
<212> TYPE: PRT
<213> ORGANISM: Homo sapiens

<400> SEQUENCE: 503

Ser Tyr Ala Met Asn
1               5

<210> SEQ ID NO 504
<211> LENGTH: 17
<212> TYPE: PRT
<213> ORGANISM: Homo sapiens

```
<400> SEQUENCE: 504

Thr Ile Ser Tyr His Gly Ser His Ile Ser His Ala Asp His Val His
1               5                   10                  15

Gly

<210> SEQ ID NO 505
<211> LENGTH: 8
<212> TYPE: PRT
<213> ORGANISM: Homo sapiens

<400> SEQUENCE: 505

Ile Asn His Asp Pro Met Asp Val
1               5

<210> SEQ ID NO 506
<211> LENGTH: 333
<212> TYPE: DNA
<213> ORGANISM: Homo sapiens

<400> SEQUENCE: 506
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120 cagtccccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg agggaccaa gttaaccgtc cta                                 333

<210> SEQ ID NO 507
<211> LENGTH: 111
<212> TYPE: PRT
<213> ORGANISM: Homo sapiens

<400> SEQUENCE: 507

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 508
<211> LENGTH: 11
<212> TYPE: PRT
<213> ORGANISM: Homo sapiens

<400> SEQUENCE: 508

Ser Gly Asp Asn Leu Gly Lys Lys Tyr Val Gln
1               5                   10
```

```
<210> SEQ ID NO 509
<211> LENGTH: 7
<212> TYPE: PRT
<213> ORGANISM: Homo sapiens

<400> SEQUENCE: 509

Asp Asp Ser Asn Arg Pro Ser
1               5

<210> SEQ ID NO 510
<211> LENGTH: 14
<212> TYPE: PRT
<213> ORGANISM: Homo sapiens

<400> SEQUENCE: 510

Gln Thr Trp Asp Gly Asn Pro Thr Thr Gly Glu Thr Asn Val
1               5                   10

<210> SEQ ID NO 511
<211> LENGTH: 351
<212> TYPE: DNA
<213> ORGANISM: Homo sapiens

<400> SEQUENCE: 511
gaggtgcagc tgctggagag cggcggaggg ctggtgcagc aggcggcag cctgaggctg      60 tcctgcgccg cctccggatt caccttcagc agctacgcca tgaactgggt gcggcaggcc    120
ccaggcaagg gcctggagtg ggtgtccacc atcagctacc acgggtcgca catcagctac    180
cacgacagcc atcatggcag gttcaccatc agcagggaca cagcaagaa cacccctgtac   240 ctgcagatga acagcctgag ggccgaggac accgccgtgt actactgcgc ccgcatcaac    300
cacgacccta tggatgtgtg gggccagggc accctggtga cagtgagctc a             351

<210> SEQ ID NO 512
<211> LENGTH: 117
<212> TYPE: PRT
<213> ORGANISM: Homo sapiens

<400> SEQUENCE: 512

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser His
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 513
<211> LENGTH: 5
<212> TYPE: PRT
<213> ORGANISM: Homo sapiens
```

<400> SEQUENCE: 513

Ser Tyr Ala Met Asn
1               5

<210> SEQ ID NO 514
<211> LENGTH: 17
<212> TYPE: PRT
<213> ORGANISM: Homo sapiens

<400> SEQUENCE: 514

Thr Ile Ser Tyr His Gly Ser His Ile Ser Tyr His Asp Ser His His
1               5                   10                  15

Gly

<210> SEQ ID NO 515
<211> LENGTH: 8
<212> TYPE: PRT
<213> ORGANISM: Homo sapiens

<400> SEQUENCE: 515

Ile Asn His Asp Pro Met Asp Val
1               5

<210> SEQ ID NO 516
<211> LENGTH: 333
<212> TYPE: DNA
<213> ORGANISM: Homo sapiens

<400> SEQUENCE: 516

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggaacc cgacgacggg cgagaccaac     300
gtgttcggcg gagggaccaa gttaaccgtc cta                                 333
```

<210> SEQ ID NO 517
<211> LENGTH: 111
<212> TYPE: PRT
<213> ORGANISM: Homo sapiens

<400> SEQUENCE: 517

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

-continued

```
<210> SEQ ID NO 518
<211> LENGTH: 11
<212> TYPE: PRT
<213> ORGANISM: Homo sapiens

<400> SEQUENCE: 518

Ser Gly Asp Asn Leu Gly Lys Lys Tyr Val Gln
1               5                   10

<210> SEQ ID NO 519
<211> LENGTH: 7
<212> TYPE: PRT
<213> ORGANISM: Homo sapiens

<400> SEQUENCE: 519

Asp Asp Ser Asn Arg Pro Ser
1               5

<210> SEQ ID NO 520
<211> LENGTH: 14
<212> TYPE: PRT
<213> ORGANISM: Homo sapiens

<400> SEQUENCE: 520

Gln Thr Trp Asp Gly Asn Pro Thr Thr Gly Glu Thr Asn Val
1               5                   10

<210> SEQ ID NO 521
<211> LENGTH: 351
<212> TYPE: DNA
<213> ORGANISM: Homo sapiens

<400> SEQUENCE: 521
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggcacca catcagctac     180
gccgacagcc atcatcacag gttcaccatc agcagggaca acagcaagaa caccctgtac     240
ctgcagatga acagcctgag ggccgaggac accgccgtgt actactgcgc ccgcatcaac     300
cacgacccta tggatgtgtg gggccagggc accctggtga cagtgagctc a              351

<210> SEQ ID NO 522
<211> LENGTH: 117
<212> TYPE: PRT
<213> ORGANISM: Homo sapiens

<400> SEQUENCE: 522

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His Ile Ser Tyr Ala Asp Ser His
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
```

```
                      100                 105                 110
Val Thr Val Ser Ser
            115

<210> SEQ ID NO 523
<211> LENGTH: 5
<212> TYPE: PRT
<213> ORGANISM: Homo sapiens

<400> SEQUENCE: 523

Ser Tyr Ala Met Asn
1               5

<210> SEQ ID NO 524
<211> LENGTH: 17
<212> TYPE: PRT
<213> ORGANISM: Homo sapiens

<400> SEQUENCE: 524

Thr Ile Ser Tyr His Gly His His Ile Ser Tyr Ala Asp Ser His His
1               5                   10                  15
His

<210> SEQ ID NO 525
<211> LENGTH: 8
<212> TYPE: PRT
<213> ORGANISM: Homo sapiens

<400> SEQUENCE: 525

Ile Asn His Asp Pro Met Asp Val
1               5

<210> SEQ ID NO 526
<211> LENGTH: 333
<212> TYPE: DNA
<213> ORGANISM: Homo sapiens

<400> SEQUENCE: 526
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg gagggaccaa gttaaccgtc cta                                333

<210> SEQ ID NO 527
<211> LENGTH: 111
<212> TYPE: PRT
<213> ORGANISM: Homo sapiens

<400> SEQUENCE: 527

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60
```

```
Asn Ser Gly Asn Thr Ala Thr Leu Thr Ile Ser Gly Thr Gln Ala Met
 65                  70                  75                  80

Asp Glu Ala Asp Tyr Tyr Cys Gln Thr Trp Asp Gly Asn Pro Thr Thr
                 85                  90                  95

Gly Glu Thr Asn Val Phe Gly Gly Gly Thr Lys Leu Thr Val Leu
            100                 105                 110
```

<210> SEQ ID NO 528
<211> LENGTH: 11
<212> TYPE: PRT
<213> ORGANISM: Homo sapiens

<400> SEQUENCE: 528

```
Ser Gly Asp Asn Leu Gly Lys Lys Tyr Val Gln
1               5                   10
```

<210> SEQ ID NO 529
<211> LENGTH: 7
<212> TYPE: PRT
<213> ORGANISM: Homo sapiens

<400> SEQUENCE: 529

```
Asp Asp Ser Asn Arg Pro Ser
1               5
```

<210> SEQ ID NO 530
<211> LENGTH: 14
<212> TYPE: PRT
<213> ORGANISM: Homo sapiens

<400> SEQUENCE: 530

```
Gln Thr Trp Asp Gly Asn Pro Thr Thr Gly Glu Thr Asn Val
1               5                   10
```

<210> SEQ ID NO 531
<211> LENGTH: 351
<212> TYPE: DNA
<213> ORGANISM: Homo sapiens

<400> SEQUENCE: 531

```
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctacc acgggtcgca catcagctac    180
cacgacagcg tgcatcacag gttcaccatc agcagggaca cagcaagaa cacccctgtac    240
ctgcagatga acagcctgag ggccgaggac accgccgtgt actactgcgc ccgcatcaac    300
cacgacccta tggatgtgtg gggccagggc accctggtga cagtgagctc a            351
```

<210> SEQ ID NO 532
<211> LENGTH: 117
<212> TYPE: PRT
<213> ORGANISM: Homo sapiens

<400> SEQUENCE: 532

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45
```

```
Ser Thr Ile Ser Tyr His Gly Ser His Ile Ser Tyr His Asp Ser Val
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
            115

<210> SEQ ID NO 533
<211> LENGTH: 5
<212> TYPE: PRT
<213> ORGANISM: Homo sapiens

<400> SEQUENCE: 533

Ser Tyr Ala Met Asn
1               5

<210> SEQ ID NO 534
<211> LENGTH: 17
<212> TYPE: PRT
<213> ORGANISM: Homo sapiens

<400> SEQUENCE: 534

Thr Ile Ser Tyr His Gly Ser His Ile Ser Tyr His Asp Ser Val His
1               5                   10                  15

His

<210> SEQ ID NO 535
<211> LENGTH: 8
<212> TYPE: PRT
<213> ORGANISM: Homo sapiens

<400> SEQUENCE: 535

Ile Asn His Asp Pro Met Asp Val
1               5

<210> SEQ ID NO 536
<211> LENGTH: 333
<212> TYPE: DNA
<213> ORGANISM: Homo sapiens

<400> SEQUENCE: 536
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc    120
cagtcccccg tgctggtgat ctacgacgac agcaacaggc cagcggcat ccccgagagg     180 ttcagcggca gcaacagcgg caacaccgcc accctgacca tcagcggcac ccaggcgatg    240
gacgaggccg actactactg ccagacctgg gacgggaacc cgacgacggg cgagaccaac    300
gtgttcggcg gagggaccaa gttaaccgtc cta                                 333

<210> SEQ ID NO 537
<211> LENGTH: 111
<212> TYPE: PRT
<213> ORGANISM: Homo sapiens

<400> SEQUENCE: 537
```

-continued

```
Ser Ile Glu Leu Thr Gln Pro Pro Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 538
<211> LENGTH: 11
<212> TYPE: PRT
<213> ORGANISM: Homo sapiens

<400> SEQUENCE: 538

```
Ser Gly Asp Asn Leu Gly Lys Lys Tyr Val Gln
1               5                   10
```

<210> SEQ ID NO 539
<211> LENGTH: 7
<212> TYPE: PRT
<213> ORGANISM: Homo sapiens

<400> SEQUENCE: 539

```
Asp Asp Ser Asn Arg Pro Ser
1               5
```

<210> SEQ ID NO 540
<211> LENGTH: 14
<212> TYPE: PRT
<213> ORGANISM: Homo sapiens

<400> SEQUENCE: 540

```
Gln Thr Trp Asp Gly Asn Pro Thr Thr Gly Glu Thr Asn Val
1               5                   10
```

<210> SEQ ID NO 541
<211> LENGTH: 351
<212> TYPE: DNA
<213> ORGANISM: Homo sapiens

<400> SEQUENCE: 541

```
gaggtgcagc tgctcgagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctaca cgggtcgct gatccactac     180 gccgacagcg tgaagggcag gttcaccatc agcagggaca cagcaagaa caccctgtac    240 ctgcagatga acagcctgag ggccgaggac accgccgtgt actactgcgc ccgcatccac    300
cacgacccta tggatgtgtg gggccagggc accctggtga cagtgagctc a            351
```

<210> SEQ ID NO 542
<211> LENGTH: 117
<212> TYPE: PRT
<213> ORGANISM: Homo sapiens

<400> SEQUENCE: 542

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
            115

<210> SEQ ID NO 543
<211> LENGTH: 5
<212> TYPE: PRT
<213> ORGANISM: Homo sapiens

<400> SEQUENCE: 543

Ser Tyr Ala Met Asn
1               5

<210> SEQ ID NO 544
<211> LENGTH: 17
<212> TYPE: PRT
<213> ORGANISM: Homo sapiens

<400> SEQUENCE: 544

Thr Ile Ser Tyr Ser Gly Ser Leu Ile His Tyr Ala Asp Ser Val Lys
1               5                   10                  15

Gly

<210> SEQ ID NO 545
<211> LENGTH: 8
<212> TYPE: PRT
<213> ORGANISM: Homo sapiens

<400> SEQUENCE: 545

Ile His His Asp Pro Met Asp Val
1               5

<210> SEQ ID NO 546
<211> LENGTH: 333
<212> TYPE: DNA
<213> ORGANISM: Homo sapiens

<400> SEQUENCE: 546
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggccatg     240
gacgaggccg actactactg ccagacctgg gacgggaacc cgacgacggg cgagaccaac     300
gtgttcggcg agggaccaa gttaaccgtc cta          333

<210> SEQ ID NO 547
<211> LENGTH: 111
<212> TYPE: PRT
<213> ORGANISM: Homo sapiens

<400> SEQUENCE: 547

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 548
<211> LENGTH: 11
<212> TYPE: PRT
<213> ORGANISM: Homo sapiens

<400> SEQUENCE: 548

Ser Gly Asp Asn Leu Gly Lys Lys Tyr Val Gln
1               5                   10

<210> SEQ ID NO 549
<211> LENGTH: 7
<212> TYPE: PRT
<213> ORGANISM: Homo sapiens

<400> SEQUENCE: 549

Asp Asp Ser Asn Arg Pro Ser
1               5

<210> SEQ ID NO 550
<211> LENGTH: 14
<212> TYPE: PRT
<213> ORGANISM: Homo sapiens

<400> SEQUENCE: 550

Gln Thr Trp Asp Gly Asn Pro Thr Thr Gly Glu Thr Asn Val
1               5                   10

<210> SEQ ID NO 551
<211> LENGTH: 351
<212> TYPE: DNA
<213> ORGANISM: Homo sapiens

<400> SEQUENCE: 551
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagccaca gcgggcacca catcagccac    180

-continued

```
cacgacagcc atcatggcag gttcaccatc agcagggaca acagcaagaa caccctgtac    240
ctgcagatga acagcctgag ggccgaggac accgccgtgt actactgcgc ccgcatccac    300 cacgaccota tggatgtgtg gggccagggc accctggtga cagtgagctc a             351
```

<210> SEQ ID NO 552
<211> LENGTH: 117
<212> TYPE: PRT
<213> ORGANISM: Homo sapiens

<400> SEQUENCE: 552

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Thr Ile Ser His Ser Gly His His Ile Ser His His Asp Ser His
     50                  55                  60

His Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile His His Asp Pro Met Asp Val Trp Gly Gln Gly Thr Leu
            100                 105                 110

Val Thr Val Ser Ser
        115
```

<210> SEQ ID NO 553
<211> LENGTH: 5
<212> TYPE: PRT
<213> ORGANISM: Homo sapiens

<400> SEQUENCE: 553

```
Ser Tyr Ala Met Asn
 1               5
```

<210> SEQ ID NO 554
<211> LENGTH: 17
<212> TYPE: PRT
<213> ORGANISM: Homo sapiens

<400> SEQUENCE: 554

```
Thr Ile Ser His Ser Gly His His Ile Ser His Asp Ser His His
 1               5                  10                  15

Gly
```

<210> SEQ ID NO 555
<211> LENGTH: 8
<212> TYPE: PRT
<213> ORGANISM: Homo sapiens

<400> SEQUENCE: 555

```
Ile His His Asp Pro Met Asp Val
 1               5
```

<210> SEQ ID NO 556
<211> LENGTH: 333
<212> TYPE: DNA
<213> ORGANISM: Homo sapiens

<400> SEQUENCE: 556

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg gagggaccaa gttaaccgtc cta                                333
```

<210> SEQ ID NO 557
<211> LENGTH: 111
<212> TYPE: PRT
<213> ORGANISM: Homo sapiens

<400> SEQUENCE: 557

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 558
<211> LENGTH: 11
<212> TYPE: PRT
<213> ORGANISM: Homo sapiens

<400> SEQUENCE: 558

Ser Gly Asp Asn Leu Gly Lys Lys Tyr Val Gln
1               5                   10

<210> SEQ ID NO 559
<211> LENGTH: 7
<212> TYPE: PRT
<213> ORGANISM: Homo sapiens

<400> SEQUENCE: 559

Asp Asp Ser Asn Arg Pro Ser
1               5

<210> SEQ ID NO 560
<211> LENGTH: 14
<212> TYPE: PRT
<213> ORGANISM: Homo sapiens

<400> SEQUENCE: 560

Gln Thr Trp Asp Gly Asn Pro Thr Thr Gly Glu Thr Asn Val
1               5                   10

<210> SEQ ID NO 561
<211> LENGTH: 351

<212> TYPE: DNA
<213> ORGANISM: Homo sapiens

<400> SEQUENCE: 561

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggcacct gatccactac     180
gccgaccacc atcatggcag gttcaccatc agcagggaca cagcaagaa cacccctgtac     240
ctgcagatga acagcctgag ggccgaggac accgccgtgt actactgcgc ccgcatccac     300
cacgacccta tggatgtgtg gggccagggc accctggtga cagtgagctc a              351
```

<210> SEQ ID NO 562
<211> LENGTH: 117
<212> TYPE: PRT
<213> ORGANISM: Homo sapiens

<400> SEQUENCE: 562

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
            20                  25                  30
Ala Met Asn Trp Val Arg Gln Ala Pro Gly Lys Gly Leu Glu Trp Val
        35                  40                  45
Ser Thr Ile Ser Tyr Ser Gly His Leu Ile His Tyr Ala Asp His His
    50                  55                  60
His Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ile His His Asp Pro Met Asp Val Trp Gly Gln Gly Thr Leu
            100                 105                 110
Val Thr Val Ser Ser
        115
```

<210> SEQ ID NO 563
<211> LENGTH: 5
<212> TYPE: PRT
<213> ORGANISM: Homo sapiens

<400> SEQUENCE: 563

```
Ser Tyr Ala Met Asn
 1               5
```

<210> SEQ ID NO 564
<211> LENGTH: 17
<212> TYPE: PRT
<213> ORGANISM: Homo sapiens

<400> SEQUENCE: 564

```
Thr Ile Ser Tyr Ser Gly His Leu Ile His Tyr Ala Asp His His
 1               5                  10                  15
Gly
```

<210> SEQ ID NO 565
<211> LENGTH: 8
<212> TYPE: PRT
<213> ORGANISM: Homo sapiens

<400> SEQUENCE: 565

Ile His His Asp Pro Met Asp Val
1               5

<210> SEQ ID NO 566
<211> LENGTH: 333
<212> TYPE: DNA
<213> ORGANISM: Homo sapiens

<400> SEQUENCE: 566
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggcgatg   240
gacgaggccg actactactg ccagacctgg gacgggaacc cgacgacggg cgagaccaac   300
gtgttcggcg agggaccaa gttaaccgtc cta                                  333

<210> SEQ ID NO 567
<211> LENGTH: 111
<212> TYPE: PRT
<213> ORGANISM: Homo sapiens

<400> SEQUENCE: 567

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 568
<211> LENGTH: 11
<212> TYPE: PRT
<213> ORGANISM: Homo sapiens

<400> SEQUENCE: 568

Ser Gly Asp Asn Leu Gly Lys Lys Tyr Val Gln
1               5                   10

<210> SEQ ID NO 569
<211> LENGTH: 7
<212> TYPE: PRT
<213> ORGANISM: Homo sapiens

<400> SEQUENCE: 569

Asp Asp Ser Asn Arg Pro Ser
1               5

<210> SEQ ID NO 570
<211> LENGTH: 14

```
<212> TYPE: PRT
<213> ORGANISM: Homo sapiens

<400> SEQUENCE: 570

Gln Thr Trp Asp Gly Asn Pro Thr Thr Gly Glu Thr Asn Val
1               5                   10

<210> SEQ ID NO 571
<211> LENGTH: 351
<212> TYPE: DNA
<213> ORGANISM: Homo sapiens

<400> SEQUENCE: 571
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggtcgca catcagccac     180
gccgaccacg tgcatggcag gttcaccatc agcagggaca acagcaagaa cacccctgtac    240 ctgcagatga acagcctgag ggccgaggac accgccgtgt actactgcgc ccgcatccac     300
cacgacccta tggatgtgtg gggccagggc accctggtga cagtgagctc a              351

<210> SEQ ID NO 572
<211> LENGTH: 117
<212> TYPE: PRT
<213> ORGANISM: Homo sapiens

<400> SEQUENCE: 572

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser His Ala Asp His Val
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115

<210> SEQ ID NO 573
<211> LENGTH: 5
<212> TYPE: PRT
<213> ORGANISM: Homo sapiens

<400> SEQUENCE: 573

Ser Tyr Ala Met Asn
1               5

<210> SEQ ID NO 574
<211> LENGTH: 17
<212> TYPE: PRT
<213> ORGANISM: Homo sapiens

<400> SEQUENCE: 574
```

```
Thr Ile Ser Tyr His Gly Ser His Ile Ser His Ala Asp His Val His
1               5                   10                  15

Gly

<210> SEQ ID NO 575
<211> LENGTH: 8
<212> TYPE: PRT
<213> ORGANISM: Homo sapiens

<400> SEQUENCE: 575

Ile His His Asp Pro Met Asp Val
1               5

<210> SEQ ID NO 576
<211> LENGTH: 333
<212> TYPE: DNA
<213> ORGANISM: Homo sapiens

<400> SEQUENCE: 576
agtatcgagc tgacccagcc ccccagcgtg agcgtgtccc caggccagac cgccagcatc        60
acctgcagcg gcgacaacct gggcaagaaa tacgtgcagt ggtatcagca gaagcccggc       120
cagtcccccg tgctggtgat ctacgacgac agcaacaggc ccagcggcat ccccgagagg       180
ttcagcggca gcaacagcgg caacaccgcc accctgacca tcagcggcac ccaggcgatg       240
gacgaggccg actactactg ccagacctgg gacgggaacc cgacgacggg cgagaccaac       300
gtgttcggcg agggaccaa gttaaccgtc cta                                     333

<210> SEQ ID NO 577
<211> LENGTH: 111
<212> TYPE: PRT
<213> ORGANISM: Homo sapiens

<400> SEQUENCE: 577

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 578
<211> LENGTH: 11
<212> TYPE: PRT
<213> ORGANISM: Homo sapiens

<400> SEQUENCE: 578

Ser Gly Asp Asn Leu Gly Lys Lys Tyr Val Gln
1               5                   10

<210> SEQ ID NO 579
<211> LENGTH: 7
```

```
<212> TYPE: PRT
<213> ORGANISM: Homo sapiens

<400> SEQUENCE: 579

Asp Asp Ser Asn Arg Pro Ser
1               5

<210> SEQ ID NO 580
<211> LENGTH: 14
<212> TYPE: PRT
<213> ORGANISM: Homo sapiens

<400> SEQUENCE: 580

Gln Thr Trp Asp Gly Asn Pro Thr Thr Gly Glu Thr Asn Val
1               5                   10

<210> SEQ ID NO 581
<211> LENGTH: 351
<212> TYPE: DNA
<213> ORGANISM: Homo sapiens

<400> SEQUENCE: 581
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctacc acgggtcgca catcagctac    180
cacgacagcc atcatggcag gttcaccatc agcagggaca acagcaagaa caccctgtac    240
ctgcagatga acagcctgag ggccgaggac accgccgtgt actactgcgc ccgcatccac    300
cacgacccta tggatgtgtg gggccagggc accctggtga cagtgagctc a             351

<210> SEQ ID NO 582
<211> LENGTH: 117
<212> TYPE: PRT
<213> ORGANISM: Homo sapiens

<400> SEQUENCE: 582

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser His
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115

<210> SEQ ID NO 583
<211> LENGTH: 5
<212> TYPE: PRT
<213> ORGANISM: Homo sapiens

<400> SEQUENCE: 583
```

```
Ser Tyr Ala Met Asn
1               5
```

<210> SEQ ID NO 584
<211> LENGTH: 17
<212> TYPE: PRT
<213> ORGANISM: Homo sapiens

<400> SEQUENCE: 584

```
Thr Ile Ser Tyr His Gly Ser His Ile Ser Tyr His Asp Ser His
1               5                   10                  15

Gly
```

<210> SEQ ID NO 585
<211> LENGTH: 8
<212> TYPE: PRT
<213> ORGANISM: Homo sapiens

<400> SEQUENCE: 585

```
Ile His His Asp Pro Met Asp Val
1               5
```

<210> SEQ ID NO 586
<211> LENGTH: 333
<212> TYPE: DNA
<213> ORGANISM: Homo sapiens

<400> SEQUENCE: 586

```
agtatcgagc tgacccagcc ccccagcgtg agcgtgtccc caggccagac cgccagcatc     60
acctgcagcg gcgacaacct gggcaagaaa tacgtgcagt ggtatcagca gaagcccggc    120
cagtcccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccagacctgg gacgggaacc cgacgacggg cgagaccaac    300
gtgttcggcg gagggaccaa gttaaccgtc cta                                 333
```

<210> SEQ ID NO 587
<211> LENGTH: 111
<212> TYPE: PRT
<213> ORGANISM: Homo sapiens

<400> SEQUENCE: 587

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 588
<211> LENGTH: 11

<212> TYPE: PRT
<213> ORGANISM: Homo sapiens

<400> SEQUENCE: 588

Ser Gly Asp Asn Leu Gly Lys Lys Tyr Val Gln
1               5                   10

<210> SEQ ID NO 589
<211> LENGTH: 7
<212> TYPE: PRT
<213> ORGANISM: Homo sapiens

<400> SEQUENCE: 589

Asp Asp Ser Asn Arg Pro Ser
1               5

<210> SEQ ID NO 590
<211> LENGTH: 14
<212> TYPE: PRT
<213> ORGANISM: Homo sapiens

<400> SEQUENCE: 590

Gln Thr Trp Asp Gly Asn Pro Thr Thr Gly Glu Thr Asn Val
1               5                   10

<210> SEQ ID NO 591
<211> LENGTH: 351
<212> TYPE: DNA
<213> ORGANISM: Homo sapiens

<400> SEQUENCE: 591
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctacc acgggcacca catcagctac    180
gccgacagcc atcatcacag gttcaccatc agcagggaca cagcaagaa caccctgtac    240
ctgcagatga acagcctgag ggccgaggac accgccgtgt actactgcgc ccgcatccac    300
cacgacccta tggatgtgtg gggccagggc accctggtga cagtgagctc a              351

<210> SEQ ID NO 592
<211> LENGTH: 117
<212> TYPE: PRT
<213> ORGANISM: Homo sapiens

<400> SEQUENCE: 592

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser Tyr Ala Asp Ser His
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

-continued

Val Thr Val Ser Ser
        115

<210> SEQ ID NO 593
<211> LENGTH: 5
<212> TYPE: PRT
<213> ORGANISM: Homo sapiens

<400> SEQUENCE: 593

Ser Tyr Ala Met Asn
1               5

<210> SEQ ID NO 594
<211> LENGTH: 17
<212> TYPE: PRT
<213> ORGANISM: Homo sapiens

<400> SEQUENCE: 594

Thr Ile Ser Tyr His Gly His His Ile Ser Tyr Ala Asp Ser His His
1               5                   10                  15

His

<210> SEQ ID NO 595
<211> LENGTH: 8
<212> TYPE: PRT
<213> ORGANISM: Homo sapiens

<400> SEQUENCE: 595

Ile His His Asp Pro Met Asp Val
1               5

<210> SEQ ID NO 596
<211> LENGTH: 333
<212> TYPE: DNA
<213> ORGANISM: Homo sapiens

<400> SEQUENCE: 596
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120 cagtccccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccagacctgg gacgggaacc cgacgacggg cgagaccaac    300
gtgttcggcg agggaccaa gttaaccgtc cta                                  333

<210> SEQ ID NO 597
<211> LENGTH: 111
<212> TYPE: PRT
<213> ORGANISM: Homo sapiens

<400> SEQUENCE: 597

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met

```
            65                  70                  75                  80
Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110
```

<210> SEQ ID NO 598
<211> LENGTH: 11
<212> TYPE: PRT
<213> ORGANISM: Homo sapiens

<400> SEQUENCE: 598

```
Ser Gly Asp Asn Leu Gly Lys Lys Tyr Val Gln
1               5                   10
```

<210> SEQ ID NO 599
<211> LENGTH: 7
<212> TYPE: PRT
<213> ORGANISM: Homo sapiens

<400> SEQUENCE: 599

```
Asp Asp Ser Asn Arg Pro Ser
1               5
```

<210> SEQ ID NO 600
<211> LENGTH: 14
<212> TYPE: PRT
<213> ORGANISM: Homo sapiens

<400> SEQUENCE: 600

```
Gln Thr Trp Asp Gly Asn Pro Thr Thr Gly Glu Thr Asn Val
1               5                   10
```

<210> SEQ ID NO 601
<211> LENGTH: 351
<212> TYPE: DNA
<213> ORGANISM: Homo sapiens

<400> SEQUENCE: 601

```
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggcacca catcagctac     180
gccgacagcc atcatcacag gttcaccatc agcagggaca cagcaagaa cacccttgtac    240 ctgcagatga acagcctgag ggccgaggac accgccgtgt actactgcgc ccgcatccac     300
cacgacccta tggatcactg gggccagggc accctggtga cagtgagctc a              351
```

<210> SEQ ID NO 602
<211> LENGTH: 117
<212> TYPE: PRT
<213> ORGANISM: Homo sapiens

<400> SEQUENCE: 602

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser Tyr Ala Asp Ser His
```

```
                50              55                  60
His His Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile His His Asp Pro Met Asp His Trp Gly Gln Gly Thr Leu
            100                 105                 110

Val Thr Val Ser Ser
        115
```

<210> SEQ ID NO 603
<211> LENGTH: 5
<212> TYPE: PRT
<213> ORGANISM: Homo sapiens

<400> SEQUENCE: 603

```
Ser Tyr Ala Met Asn
1               5
```

<210> SEQ ID NO 604
<211> LENGTH: 17
<212> TYPE: PRT
<213> ORGANISM: Homo sapiens

<400> SEQUENCE: 604

```
Thr Ile Ser Tyr His Gly His His Ile Ser Tyr Ala Asp Ser His His
1               5                   10                  15

His
```

<210> SEQ ID NO 605
<211> LENGTH: 8
<212> TYPE: PRT
<213> ORGANISM: Homo sapiens

<400> SEQUENCE: 605

```
Ile His His Asp Pro Met Asp His
1               5
```

<210> SEQ ID NO 606
<211> LENGTH: 333
<212> TYPE: DNA
<213> ORGANISM: Homo sapiens

<400> SEQUENCE: 606

```
agtatcgagc tgacccagcc ccccagcgtg agcgtgtccc caggccagac cgccagcatc     60
acctgcagcg gcgacaacct gggcaagaaa tacgtgcagt ggtatcagca gaagcccggc    120
cagtcccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccagacctgg gacgggaacc cgacgacggg cgagaccaac    300
gtgttcggcg gagggaccaa gttaaccgtc cta                                 333
```

<210> SEQ ID NO 607
<211> LENGTH: 111
<212> TYPE: PRT
<213> ORGANISM: Homo sapiens

<400> SEQUENCE: 607

```
Ser Ile Glu Leu Thr Gln Pro Pro Ser Val Ser Val Ser Pro Gly Gln
1               5                   10                  15
```

```
Thr Ala Ser Ile Thr Cys Ser Gly Asp Asn Leu Gly Lys Lys Tyr Val
             20                  25                  30

Gln Trp Tyr Gln Gln Lys Pro Gly Gln Ser Pro Val Leu Val Ile Tyr
         35                  40                  45

Asp Asp Ser Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ser Trp Asp Gly Asn Pro Thr Thr
                 85                  90                  95

Gly Glu Thr Asn Val Phe Gly Gly Gly Thr Lys Leu Thr Val Leu
            100                 105                 110
```

<210> SEQ ID NO 608
<211> LENGTH: 11
<212> TYPE: PRT
<213> ORGANISM: Homo sapiens

<400> SEQUENCE: 608

```
Ser Gly Asp Asn Leu Gly Lys Lys Tyr Val Gln
1               5                   10
```

<210> SEQ ID NO 609
<211> LENGTH: 7
<212> TYPE: PRT
<213> ORGANISM: Homo sapiens

<400> SEQUENCE: 609

```
Asp Asp Ser Asn Arg Pro Ser
1               5
```

<210> SEQ ID NO 610
<211> LENGTH: 14
<212> TYPE: PRT
<213> ORGANISM: Homo sapiens

<400> SEQUENCE: 610

```
Gln Thr Trp Asp Gly Asn Pro Thr Thr Gly Glu Thr Asn Val
1               5                   10
```

<210> SEQ ID NO 611
<211> LENGTH: 351
<212> TYPE: DNA
<213> ORGANISM: Homo sapiens

<400> SEQUENCE: 611

| | | |
|---|---|---|
| gaggtgcagc tgctggagag cggcggaggg ctggtgcagc caggcggcag cctgaggctg | 60 |
| tcctgcgccg cctccggatt caccttcagc agctacgcca tgaactgggt gcggcaggcc | 120 |
| ccaggcaagg gcctggagtg ggtgtccacc atcagctacc acgggtcgca catcagctac | 180 |
| cacgacagcg tgcatcacag gttcaccatc agcagggaca cagcaagaa cacccctgtac | 240 |
| ctgcagatga acagcctgag ggccgaggac accgccgtgt actactgcgc ccgcatccac | 300 |
| cacgacccta tggatcactg gggccagggc accctggtga cagtgagctc a | 351 |

<210> SEQ ID NO 612
<211> LENGTH: 117
<212> TYPE: PRT
<213> ORGANISM: Homo sapiens

<400> SEQUENCE: 612

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser Val
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp His Trp Gly Gln Gly Thr Leu
            100                 105                 110

Val Thr Val Ser Ser
            115

<210> SEQ ID NO 613
<211> LENGTH: 5
<212> TYPE: PRT
<213> ORGANISM: Homo sapiens

<400> SEQUENCE: 613

Ser Tyr Ala Met Asn
1               5

<210> SEQ ID NO 614
<211> LENGTH: 17
<212> TYPE: PRT
<213> ORGANISM: Homo sapiens

<400> SEQUENCE: 614

Thr Ile Ser Tyr His Gly Ser His Ile Ser Tyr His Asp Ser Val His
1               5                   10                  15

His

<210> SEQ ID NO 615
<211> LENGTH: 8
<212> TYPE: PRT
<213> ORGANISM: Homo sapiens

<400> SEQUENCE: 615

Ile His His Asp Pro Met Asp His
1               5

<210> SEQ ID NO 616
<211> LENGTH: 333
<212> TYPE: DNA
<213> ORGANISM: Homo sapiens

<400> SEQUENCE: 616
agtatcgagc tgacccagcc ccccagcgtg agcgtgtccc caggccagac cgccagcatc     60
acctgcagcg gcgacaacct gggcaagaaa tacgtgcagt ggtatcagca gaagcccggc    120
cagtcccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccagacctgg gacgggaacc cgacgacggg cgagaccaac    300
gtgttcggcg gagggaccaa gttaaccgtc cta                                 333
```

<210> SEQ ID NO 617
<211> LENGTH: 111
<212> TYPE: PRT
<213> ORGANISM: Homo sapiens

<400> SEQUENCE: 617

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr Thr
                85                  90                  95

Gly Glu Thr Asn Val Phe Gly Gly Gly Thr Lys Leu Thr Val Leu
            100                 105                 110

<210> SEQ ID NO 618
<211> LENGTH: 11
<212> TYPE: PRT
<213> ORGANISM: Homo sapiens

<400> SEQUENCE: 618

Ser Gly Asp Asn Leu Gly Lys Lys Tyr Val Gln
1               5                   10

<210> SEQ ID NO 619
<211> LENGTH: 7
<212> TYPE: PRT
<213> ORGANISM: Homo sapiens

<400> SEQUENCE: 619

Asp Asp Ser Asn Arg Pro Ser
1               5

<210> SEQ ID NO 620
<211> LENGTH: 14
<212> TYPE: PRT
<213> ORGANISM: Homo sapiens

<400> SEQUENCE: 620

Gln Thr Trp Asp Gly Asn Pro Thr Thr Gly Glu Thr Asn Val
1               5                   10

<210> SEQ ID NO 621
<211> LENGTH: 351
<212> TYPE: DNA
<213> ORGANISM: Homo sapiens

<400> SEQUENCE: 621
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac     240

```
ctgcagatga acagcctgag ggccgaggac accgccgtgt actactgcgc ccgcatcaac    300
cacgacccta tggatgtgtg gggccagggc accctggtca ccgtctcctc a             351
```

<210> SEQ ID NO 622
<211> LENGTH: 117
<212> TYPE: PRT
<213> ORGANISM: Homo sapiens

<400> SEQUENCE: 622

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115
```

<210> SEQ ID NO 623
<211> LENGTH: 5
<212> TYPE: PRT
<213> ORGANISM: Homo sapiens

<400> SEQUENCE: 623

```
Ser Tyr Ala Met Asn
1               5
```

<210> SEQ ID NO 624
<211> LENGTH: 17
<212> TYPE: PRT
<213> ORGANISM: Homo sapiens

<400> SEQUENCE: 624

```
Thr Ile Ser Tyr Ser Gly Ser Leu Ile Ser Tyr Ala Asp Ser Val Lys
1               5                   10                  15

Gly
```

<210> SEQ ID NO 625
<211> LENGTH: 8
<212> TYPE: PRT
<213> ORGANISM: Homo sapiens

<400> SEQUENCE: 625

```
Ile Asn His Asp Pro Met Asp Val
1               5
```

<210> SEQ ID NO 626
<211> LENGTH: 333
<212> TYPE: DNA
<213> ORGANISM: Homo sapiens

<400> SEQUENCE: 626

```
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggccatg   240
gacgaggccg actactactg ccagacctgg gacgggaacc cgacgcacgg cgagaccaac   300
gtgttcggcg agggaccaa gctgaccgtc cta                                  333
```

<210> SEQ ID NO 627
<211> LENGTH: 111
<212> TYPE: PRT
<213> ORGANISM: Homo sapiens

<400> SEQUENCE: 627

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr His
                85                  90                  95

Gly Glu Thr Asn Val Phe Gly Gly Gly Thr Lys Leu Thr Val Leu
            100                 105                 110

<210> SEQ ID NO 628
<211> LENGTH: 11
<212> TYPE: PRT
<213> ORGANISM: Homo sapiens

<400> SEQUENCE: 628

Ser Gly Asp Asn Leu Gly Lys Lys Tyr Val Gln
1               5                   10

<210> SEQ ID NO 629
<211> LENGTH: 7
<212> TYPE: PRT
<213> ORGANISM: Homo sapiens

<400> SEQUENCE: 629

Asp Asp Ser Asn Arg Pro Ser
1               5

<210> SEQ ID NO 630
<211> LENGTH: 14
<212> TYPE: PRT
<213> ORGANISM: Homo sapiens

<400> SEQUENCE: 630

Gln Thr Trp Asp Gly Asn Pro Thr His Gly Glu Thr Asn Val
1               5                   10

<210> SEQ ID NO 631
<211> LENGTH: 351
<212> TYPE: DNA
<213> ORGANISM: Homo sapiens

<400> SEQUENCE: 631

```
gaggtgcagc tgttggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctaca gcgggtcgct gatcagctac   180
gccgacagcg tgaagggcag gttcaccatc agcagggaca acagcaagaa caccctgtac   240
ctgcagatga acagcctgag ggccgaggac accgccgtgt actactgcgc ccgcatccac   300
cacgacccta tggatgtgtg gggccagggc accctggtca ccgtctcctc a            351
```

<210> SEQ ID NO 632
<211> LENGTH: 117
<212> TYPE: PRT
<213> ORGANISM: Homo sapiens

<400> SEQUENCE: 632

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Asn Trp Val Arg Gln Ala Pro Gly Lys Gly Leu Glu Trp Val
        35                  40                  45
Ser Thr Ile Ser Tyr Ser Gly Ser Leu Ile Ser Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ile His His Asp Pro Met Asp Val Trp Gly Gln Gly Thr Leu
            100                 105                 110
Val Thr Val Ser Ser
        115
```

<210> SEQ ID NO 633
<211> LENGTH: 5
<212> TYPE: PRT
<213> ORGANISM: Homo sapiens

<400> SEQUENCE: 633

```
Ser Tyr Ala Met Asn
1               5
```

<210> SEQ ID NO 634
<211> LENGTH: 17
<212> TYPE: PRT
<213> ORGANISM: Homo sapiens

<400> SEQUENCE: 634

```
Thr Ile Ser Tyr Ser Gly Ser Leu Ile Ser Tyr Ala Asp Ser Val Lys
1               5                   10                  15
Gly
```

<210> SEQ ID NO 635
<211> LENGTH: 8
<212> TYPE: PRT
<213> ORGANISM: Homo sapiens

<400> SEQUENCE: 635

Ile His His Asp Pro Met Asp Val
1               5

<210> SEQ ID NO 636
<211> LENGTH: 333
<212> TYPE: DNA
<213> ORGANISM: Homo sapiens

<400> SEQUENCE: 636
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggccatg   240
gacgaggccg actactactg ccagacctgg gacgggaacc cgacgcacgg cgagaccaac   300
gtgttcggcg gagggaccaa gctgaccgtc cta                                333

<210> SEQ ID NO 637
<211> LENGTH: 111
<212> TYPE: PRT
<213> ORGANISM: Homo sapiens

<400> SEQUENCE: 637

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr His
                85                  90                  95

Gly Glu Thr Asn Val Phe Gly Gly Gly Thr Lys Leu Thr Val Leu
            100                 105                 110

<210> SEQ ID NO 638
<211> LENGTH: 11
<212> TYPE: PRT
<213> ORGANISM: Homo sapiens

<400> SEQUENCE: 638

Ser Gly Asp Asn Leu Gly Lys Lys Tyr Val Gln
1               5                   10

<210> SEQ ID NO 639
<211> LENGTH: 7
<212> TYPE: PRT
<213> ORGANISM: Homo sapiens

<400> SEQUENCE: 639

Asp Asp Ser Asn Arg Pro Ser
1               5

<210> SEQ ID NO 640
<211> LENGTH: 14
<212> TYPE: PRT
<213> ORGANISM: Homo sapiens

<400> SEQUENCE: 640

Gln Thr Trp Asp Gly Asn Pro Thr His Gly Glu Thr Asn Val
1               5                   10

<210> SEQ ID NO 641
<211> LENGTH: 351
<212> TYPE: DNA
<213> ORGANISM: Homo sapiens

<400> SEQUENCE: 641
gaggtgcagc tgttggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctacc acgggcacca catcagctac   180
gccgacagcc atcatcacag gttcaccatc agcagggaca acagcaagaa caccctgtac   240
ctgcagatga acagcctgag ggccgaggac accgccgtgt actactgcgc ccgcatcaac   300
aacgaccctca tggatgtgtg gggccagggc accctggtca ccgtctcctc a           351

<210> SEQ ID NO 642
<211> LENGTH: 117
<212> TYPE: PRT
<213> ORGANISM: Homo sapiens

<400> SEQUENCE: 642

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser Tyr Ala Asp Ser His
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 643
<211> LENGTH: 5
<212> TYPE: PRT
<213> ORGANISM: Homo sapiens

<400> SEQUENCE: 643

Ser Tyr Ala Met Asn
1               5

<210> SEQ ID NO 644
<211> LENGTH: 17
<212> TYPE: PRT
<213> ORGANISM: Homo sapiens

<400> SEQUENCE: 644

Thr Ile Ser Tyr His Gly His His Ile Ser Tyr Ala Asp Ser His His
1               5                   10                  15

His

<210> SEQ ID NO 645
<211> LENGTH: 8
<212> TYPE: PRT
<213> ORGANISM: Homo sapiens

<400> SEQUENCE: 645

Ile Asn Asn Asp Pro Met Asp Val
1               5

<210> SEQ ID NO 646
<211> LENGTH: 333
<212> TYPE: DNA
<213> ORGANISM: Homo sapiens

<400> SEQUENCE: 646
agtatcgagc tgacccagcc ccccagcgtg agcgtgtccc caggccagac cgccagcatc    60
acctgcagcg gcgacaacct gggcaagaaa tacgtgcagt ggtatcagca gaagcccggc   120
cagtcccccg tgctggtgat ctacgacgac agcaacaggc ccagcggcat ccccgagagg   180
ttcagcggca gcaacagcgg caacaccgcc accctgacca tcagcggcac ccaggccatg   240
gacgaggccg actactactg ccagacctgg gacgggaacc cgacgcacgg cgagaccaac   300
gtgttcggcg agggaccaa gctgaccgtc cta                                 333

<210> SEQ ID NO 647
<211> LENGTH: 111
<212> TYPE: PRT
<213> ORGANISM: Homo sapiens

<400> SEQUENCE: 647

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr His
                85                  90                  95

Gly Glu Thr Asn Val Phe Gly Gly Gly Thr Lys Leu Thr Val Leu
            100                 105                 110

<210> SEQ ID NO 648
<211> LENGTH: 11
<212> TYPE: PRT
<213> ORGANISM: Homo sapiens

<400> SEQUENCE: 648

Ser Gly Asp Asn Leu Gly Lys Lys Tyr Val Gln
1               5                   10

<210> SEQ ID NO 649
<211> LENGTH: 7
<212> TYPE: PRT
<213> ORGANISM: Homo sapiens

<400> SEQUENCE: 649

Asp Asp Ser Asn Arg Pro Ser
1               5

<210> SEQ ID NO 650
<211> LENGTH: 14
<212> TYPE: PRT
<213> ORGANISM: Homo sapiens

<400> SEQUENCE: 650

Gln Thr Trp Asp Gly Asn Pro Thr His Gly Glu Thr Asn Val
1               5                   10

<210> SEQ ID NO 651
<211> LENGTH: 351
<212> TYPE: DNA
<213> ORGANISM: Homo sapiens

<400> SEQUENCE: 651
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggcacca catcagctac     180
gccgacagcc atcatcacag gttcaccatc agcagggaca cagcaagaa caccctgtac      240 ctgcagatga acagcctgag ggccgaggac accgccgtgt actactgcgc ccgcatcaac     300
cacgacccta tggatgtgtg gggccagggc accctggtca ccgtctcctc a              351

<210> SEQ ID NO 652
<211> LENGTH: 117
<212> TYPE: PRT
<213> ORGANISM: Homo sapiens

<400> SEQUENCE: 652

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Thr Ile Ser Tyr His Gly His His Ile Ser Tyr Ala Asp Ser His
        50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 653
<211> LENGTH: 5
<212> TYPE: PRT
<213> ORGANISM: Homo sapiens

<400> SEQUENCE: 653

Ser Tyr Ala Met Asn
1               5

<210> SEQ ID NO 654
<211> LENGTH: 17
<212> TYPE: PRT
<213> ORGANISM: Homo sapiens

<400> SEQUENCE: 654

Thr Ile Ser Tyr His Gly His His Ile Ser Tyr Ala Asp Ser His His
1               5                   10                  15

His

<210> SEQ ID NO 655
<211> LENGTH: 8
<212> TYPE: PRT
<213> ORGANISM: Homo sapiens

<400> SEQUENCE: 655

Ile Asn His Asp Pro Met Asp Val
1               5

<210> SEQ ID NO 656
<211> LENGTH: 333
<212> TYPE: DNA
<213> ORGANISM: Homo sapiens

<400> SEQUENCE: 656
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggccatg     240
gacgaggccg actactactg ccagacctgg gacgggaacc cgacgcacgg cgagaccaac     300
gtgttcggcg gagggaccaa gctgaccgtc cta                                  333

<210> SEQ ID NO 657
<211> LENGTH: 111
<212> TYPE: PRT
<213> ORGANISM: Homo sapiens

<400> SEQUENCE: 657

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly Asn Pro Thr His
                85                  90                  95

Gly Glu Thr Asn Val Phe Gly Gly Gly Thr Lys Leu Thr Val Leu
            100                 105                 110

<210> SEQ ID NO 658
<211> LENGTH: 11
<212> TYPE: PRT
<213> ORGANISM: Homo sapiens

<400> SEQUENCE: 658

Ser Gly Asp Asn Leu Gly Lys Lys Tyr Val Gln
1               5                   10

<210> SEQ ID NO 659
<211> LENGTH: 7
<212> TYPE: PRT
<213> ORGANISM: Homo sapiens

<400> SEQUENCE: 659

Asp Asp Ser Asn Arg Pro Ser
1               5

<210> SEQ ID NO 660
<211> LENGTH: 14
<212> TYPE: PRT
<213> ORGANISM: Homo sapiens

<400> SEQUENCE: 660

Gln Thr Trp Asp Gly Asn Pro Thr His Gly Glu Thr Asn Val
1               5                   10

<210> SEQ ID NO 661
<211> LENGTH: 351
<212> TYPE: DNA
<213> ORGANISM: Homo sapiens

<400> SEQUENCE: 661

```
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca acagcaagaa caccctgtac     240
ctgcagatga acagcctgag ggccgaggac accgccgtgt actactgcgc ccgcatcaac     300
cacgacccta tggatgtgtg gggccagggc accctggtca ccgtctcctc a             351
```

<210> SEQ ID NO 662
<211> LENGTH: 117
<212> TYPE: PRT
<213> ORGANISM: Homo sapiens

<400> SEQUENCE: 662

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 663
<211> LENGTH: 5
<212> TYPE: PRT
<213> ORGANISM: Homo sapiens

<400> SEQUENCE: 663

Ser Tyr Ala Met Asn
1               5

<210> SEQ ID NO 664
<211> LENGTH: 17
<212> TYPE: PRT
<213> ORGANISM: Homo sapiens

<400> SEQUENCE: 664

Thr Ile Ser Tyr Ser Gly Ser Leu Ile Ser Tyr Ala Asp Ser Val Lys
1               5                   10                  15

Gly

<210> SEQ ID NO 665
<211> LENGTH: 8
<212> TYPE: PRT
<213> ORGANISM: Homo sapiens

<400> SEQUENCE: 665

Ile Asn His Asp Pro Met Asp Val
1               5

<210> SEQ ID NO 666
<211> LENGTH: 333
<212> TYPE: DNA
<213> ORGANISM: Homo sapiens

<400> SEQUENCE: 666
agtatcgagc tgacccagcc ccccagcgtg agcgtgtccc caggccagac cgccagcatc       60
acctgcagcg gcgacaacct gggcaagaaa tacgtgcagt ggtatcagca gaagcccggc      120
cagtcccccg tgctggtgat ctacgacgac agcaacaggc ccagcggcat ccccgagagg      180
ttcagcggca gcaacagcgg caacaccgcc accctgacca tcagcggcac ccaggcgatg      240
gacgaggccg actactactg ccacacctgg caccaccacc cgacgcatgg ggagcacaac      300
gtgttcggcg agggaccaa gctgaccgtc cta                                   333

<210> SEQ ID NO 667
<211> LENGTH: 111
<212> TYPE: PRT
<213> ORGANISM: Homo sapiens

<400> SEQUENCE: 667

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

```
Asp Glu Ala Asp Tyr Tyr Cys His Thr Trp His His Pro Thr His
                85                  90                  95

Gly Glu His Asn Val Phe Gly Gly Gly Thr Lys Leu Thr Val Leu
            100                 105                 110

<210> SEQ ID NO 668
<211> LENGTH: 11
<212> TYPE: PRT
<213> ORGANISM: Homo sapiens

<400> SEQUENCE: 668

Ser Gly Asp Asn Leu Gly Lys Lys Tyr Val Gln
1               5                   10

<210> SEQ ID NO 669
<211> LENGTH: 7
<212> TYPE: PRT
<213> ORGANISM: Homo sapiens

<400> SEQUENCE: 669

Asp Asp Ser Asn Arg Pro Ser
1               5

<210> SEQ ID NO 670
<211> LENGTH: 14
<212> TYPE: PRT
<213> ORGANISM: Homo sapiens

<400> SEQUENCE: 670

His Thr Trp His His His Pro Thr His Gly Glu His Asn Val
1               5                   10

<210> SEQ ID NO 671
<211> LENGTH: 351
<212> TYPE: DNA
<213> ORGANISM: Homo sapiens

<400> SEQUENCE: 671
gaggtgcagc tgttggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg gtgtccacc atcagctacc acgggcacca catcagctac     180
gccgacagcc atcatcacag gttcaccatc agcaggaca cagcaagaa cacccctgtac     240 ctgcagatga cagcctgag ggccgaggac accgccgtgt actactgcgc ccgcatcaac     300 aacgaccta tggatgtgtg gggccagggc accctggtca ccgtctcctc a              351

<210> SEQ ID NO 672
<211> LENGTH: 117
<212> TYPE: PRT
<213> ORGANISM: Homo sapiens

<400> SEQUENCE: 672

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His Ile Ser Tyr Ala Asp Ser His
    50                  55                  60
```

```
His His Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Asn Asn Asp Pro Met Asp Val Trp Gly Gln Gly Thr Leu
            100                 105                 110

Val Thr Val Ser Ser
            115

<210> SEQ ID NO 673
<211> LENGTH: 5
<212> TYPE: PRT
<213> ORGANISM: Homo sapiens

<400> SEQUENCE: 673

Ser Tyr Ala Met Asn
1               5

<210> SEQ ID NO 674
<211> LENGTH: 17
<212> TYPE: PRT
<213> ORGANISM: Homo sapiens

<400> SEQUENCE: 674

Thr Ile Ser Tyr His Gly His His Ile Ser Tyr Ala Asp Ser His His
1               5                   10                  15

His

<210> SEQ ID NO 675
<211> LENGTH: 8
<212> TYPE: PRT
<213> ORGANISM: Homo sapiens

<400> SEQUENCE: 675

Ile Asn Asn Asp Pro Met Asp Val
1               5

<210> SEQ ID NO 676
<211> LENGTH: 333
<212> TYPE: DNA
<213> ORGANISM: Homo sapiens

<400> SEQUENCE: 676
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg caccaccacc cgacgcatgg ggagcacaac     300
gtgttcggcg agggaccaa gctgaccgtc cta                                   333

<210> SEQ ID NO 677
<211> LENGTH: 111
<212> TYPE: PRT
<213> ORGANISM: Homo sapiens

<400> SEQUENCE: 677

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
```

```
            20                  25                  30
Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp His His Pro Thr His
                85                  90                  95

Gly Glu His Asn Val Phe Gly Gly Gly Thr Lys Leu Thr Val Leu
            100                 105                 110

<210> SEQ ID NO 678
<211> LENGTH: 11
<212> TYPE: PRT
<213> ORGANISM: Homo sapiens

<400> SEQUENCE: 678

Ser Gly Asp Asn Leu Gly Lys Lys Tyr Val Gln
1               5                   10

<210> SEQ ID NO 679
<211> LENGTH: 7
<212> TYPE: PRT
<213> ORGANISM: Homo sapiens

<400> SEQUENCE: 679

Asp Asp Ser Asn Arg Pro Ser
1               5

<210> SEQ ID NO 680
<211> LENGTH: 14
<212> TYPE: PRT
<213> ORGANISM: Homo sapiens

<400> SEQUENCE: 680

His Thr Trp His His Pro Thr His Gly Glu His Asn Val
1               5                   10

<210> SEQ ID NO 681
<211> LENGTH: 351
<212> TYPE: DNA
<213> ORGANISM: Homo sapiens

<400> SEQUENCE: 681
gaggtgcagc tgctggagag cggcggaggg ctggtgcagc caggcggcag cctgaggctg     60
tcctgcgccg cctccggatt caccttcagc agctacgcca tgaactgggt gcggcaggcc    120
ccaggcaagg gcctggagtg ggtgtccacc atcagctacc acgggcacca catcagctac    180
gccgacagcc atcatcacag gttcaccatc agcagggaca cagcaagaa cccctgtac     240 ctgcagatga acagcctgag ggccgaggac accgccgtgt actactgcgc ccgcatcaac    300
cacgacccta tggatgtgtg gggccagggc accctggtca ccgtctcctc a             351

<210> SEQ ID NO 682
<211> LENGTH: 117
<212> TYPE: PRT
<213> ORGANISM: Homo sapiens

<400> SEQUENCE: 682

Glu Val Gln Leu Leu Glu Ser Gly Gly Gly Leu Val Gln Pro Gly Gly
```

-continued

```
                1               5                   10                  15
Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Thr Ile Ser Tyr His Gly His His Ile Ser Tyr Ala Asp Ser His
        50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
                100                 105                 110

Val Thr Val Ser Ser
            115
```

<210> SEQ ID NO 683
<211> LENGTH: 5
<212> TYPE: PRT
<213> ORGANISM: Homo sapiens

<400> SEQUENCE: 683

```
Ser Tyr Ala Met Asn
1               5
```

<210> SEQ ID NO 684
<211> LENGTH: 17
<212> TYPE: PRT
<213> ORGANISM: Homo sapiens

<400> SEQUENCE: 684

```
Thr Ile Ser Tyr His Gly His His Ile Ser Tyr Ala Asp Ser His His
1               5                   10                  15

His
```

<210> SEQ ID NO 685
<211> LENGTH: 8
<212> TYPE: PRT
<213> ORGANISM: Homo sapiens

<400> SEQUENCE: 685

```
Ile Asn His Asp Pro Met Asp Val
1               5
```

<210> SEQ ID NO 686
<211> LENGTH: 333
<212> TYPE: DNA
<213> ORGANISM: Homo sapiens

<400> SEQUENCE: 686

```
agtatcgagc tgacccagcc ccccagcgtg agcgtgtccc caggccagac cgccagcatc       60
acctgcagcg gcgacaacct gggcaagaaa tacgtgcagt ggtatcagca gaagcccggc      120
cagtcccccg tgctggtgat ctacgacgac agcaacaggc ccagcggcat ccccgagagg      180
ttcagcggca gcaacagcgg caacaccgcc accctgacca tcagcggcac ccaggcgatg      240
gacgaggccg actactactg ccacacctgg caccaccacc cgacgcatgg ggagcacaac      300
gtgttcggcg gagggaccaa gctgaccgtc cta                                   333
```

```
-continued

<210> SEQ ID NO 687
<211> LENGTH: 111
<212> TYPE: PRT
<213> ORGANISM: Homo sapiens

<400> SEQUENCE: 687

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp His His Pro Thr His
                85                  90                  95

Gly Glu His Asn Val Phe Gly Gly Gly Thr Lys Leu Thr Val Leu
            100                 105                 110

<210> SEQ ID NO 688
<211> LENGTH: 11
<212> TYPE: PRT
<213> ORGANISM: Homo sapiens

<400> SEQUENCE: 688

Ser Gly Asp Asn Leu Gly Lys Lys Tyr Val Gln
1               5                   10

<210> SEQ ID NO 689
<211> LENGTH: 7
<212> TYPE: PRT
<213> ORGANISM: Homo sapiens

<400> SEQUENCE: 689

Asp Asp Ser Asn Arg Pro Ser
1               5

<210> SEQ ID NO 690
<211> LENGTH: 14
<212> TYPE: PRT
<213> ORGANISM: Homo sapiens

<400> SEQUENCE: 690

His Thr Trp His His His Pro Thr His Gly Glu His Asn Val
1               5                   10

<210> SEQ ID NO 691
<211> LENGTH: 351
<212> TYPE: DNA
<213> ORGANISM: Homo sapiens

<400> SEQUENCE: 691
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca cagcaagaa caccctgtac      240 ctgcagatga acagcctgag ggccgaggac accgccgtgt actactgcgc ccgcatcaac     300
``` cacgaccta tggatgtgtg gggccagggc accctggtca ccgtctcctc a    351

<210> SEQ ID NO 692
<211> LENGTH: 117
<212> TYPE: PRT
<213> ORGANISM: Homo sapiens

<400> SEQUENCE: 692

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 693
<211> LENGTH: 5
<212> TYPE: PRT
<213> ORGANISM: Homo sapiens

<400> SEQUENCE: 693

Ser Tyr Ala Met Asn
1               5

<210> SEQ ID NO 694
<211> LENGTH: 17
<212> TYPE: PRT
<213> ORGANISM: Homo sapiens

<400> SEQUENCE: 694

Thr Ile Ser Tyr Ser Gly Ser Leu Ile Ser Tyr Ala Asp Ser Val Lys
1               5                   10                  15

Gly

<210> SEQ ID NO 695
<211> LENGTH: 8
<212> TYPE: PRT
<213> ORGANISM: Homo sapiens

<400> SEQUENCE: 695

Ile Asn His Asp Pro Met Asp Val
1               5

<210> SEQ ID NO 696
<211> LENGTH: 333
<212> TYPE: DNA
<213> ORGANISM: Homo sapiens

<400> SEQUENCE: 696
agtatcgagc tgacccagcc ccccagcgtg agcgtgtccc caggccagac cgccagcatc    60

-continued

```
acctgcagcg gcgacaacct gggcaagaaa tacgtgcagt ggtatcagca gaagcccggc      120
cagtcccccg tgctggtgat ctacgacgac agcaacaggc ccagcggcat ccccgagagg      180
ttcagcggca gcaacagcgg caacaccgcc accctgacca tcagcggcac ccaggcgatg      240
gacgaggccg actactactg ccacacctgg gaccaccacc acacgacggg ggagcacaac      300
gtgttcggcg gagggaccaa gctgaccgtc cta                                   333
```

<210> SEQ ID NO 697
<211> LENGTH: 111
<212> TYPE: PRT
<213> ORGANISM: Homo sapiens

<400> SEQUENCE: 697

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp His His His Thr Thr
                85                  90                  95

Gly Glu His Asn Val Phe Gly Gly Gly Thr Lys Leu Thr Val Leu
            100                 105                 110

<210> SEQ ID NO 698
<211> LENGTH: 11
<212> TYPE: PRT
<213> ORGANISM: Homo sapiens

<400> SEQUENCE: 698

Ser Gly Asp Asn Leu Gly Lys Lys Tyr Val Gln
1               5                   10

<210> SEQ ID NO 699
<211> LENGTH: 7
<212> TYPE: PRT
<213> ORGANISM: Homo sapiens

<400> SEQUENCE: 699

Asp Asp Ser Asn Arg Pro Ser
1               5

<210> SEQ ID NO 700
<211> LENGTH: 14
<212> TYPE: PRT
<213> ORGANISM: Homo sapiens

<400> SEQUENCE: 700

His Thr Trp Asp His His His Thr Thr Gly Glu His Asn Val
1               5                   10

<210> SEQ ID NO 701
<211> LENGTH: 351
<212> TYPE: DNA
<213> ORGANISM: Homo sapiens

<400> SEQUENCE: 701

```
gaggtgcagc tgttggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctaca gcgggtcgct gatcagctac   180
gccgacagcg tgaagggcag gttcaccatc agcagggaca cagcaagaa cacccctgtac   240 ctgcagatga acagcctgag ggccgaggac accgccgtgt actactgcgc ccgcatccac   300
cacgacccta tggatgtgtg gggccagggc accctggtca ccgtctcctc a            351
```

<210> SEQ ID NO 702
<211> LENGTH: 117
<212> TYPE: PRT
<213> ORGANISM: Homo sapiens

<400> SEQUENCE: 702

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115
```

<210> SEQ ID NO 703
<211> LENGTH: 5
<212> TYPE: PRT
<213> ORGANISM: Homo sapiens

<400> SEQUENCE: 703

```
Ser Tyr Ala Met Asn
1               5
```

<210> SEQ ID NO 704
<211> LENGTH: 17
<212> TYPE: PRT
<213> ORGANISM: Homo sapiens

<400> SEQUENCE: 704

```
Thr Ile Ser Tyr Ser Gly Ser Leu Ile Ser Tyr Ala Asp Ser Val Lys
1               5                   10                  15

Gly
```

<210> SEQ ID NO 705
<211> LENGTH: 8
<212> TYPE: PRT
<213> ORGANISM: Homo sapiens

<400> SEQUENCE: 705

```
Ile His His Asp Pro Met Asp Val
1               5
```

<210> SEQ ID NO 706
<211> LENGTH: 333
<212> TYPE: DNA
<213> ORGANISM: Homo sapiens

<400> SEQUENCE: 706

```
agtatcgagc tgacccagcc ccccagcgtg agcgtgtccc caggccagac cgccagcatc     60
acctgcagcg gcgacaacct gggcaagaaa tacgtgcagt ggtatcagca gaagcccggc    120
cagtcccccg tgctggtgat ctacgacgac agcaacaggc ccagcggcat ccccgagagg    180
ttcagcggca gcaacagcgg caacaccgcc accctgacca tcagcggcac ccaggcgatg    240
gacgaggccg actactactg ccacacctgg gaccaccacc acacgacggg ggagcacaac    300
gtgttcggcg agggaccaa gctgaccgtc cta                                  333
```

<210> SEQ ID NO 707
<211> LENGTH: 111
<212> TYPE: PRT
<213> ORGANISM: Homo sapiens

<400> SEQUENCE: 707

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp His His His Thr Thr
                85                  90                  95

Gly Glu His Asn Val Phe Gly Gly Gly Thr Lys Leu Thr Val Leu
            100                 105                 110

<210> SEQ ID NO 708
<211> LENGTH: 11
<212> TYPE: PRT
<213> ORGANISM: Homo sapiens

<400> SEQUENCE: 708

Ser Gly Asp Asn Leu Gly Lys Lys Tyr Val Gln
1               5                   10

<210> SEQ ID NO 709
<211> LENGTH: 7
<212> TYPE: PRT
<213> ORGANISM: Homo sapiens

<400> SEQUENCE: 709

Asp Asp Ser Asn Arg Pro Ser
1               5

<210> SEQ ID NO 710
<211> LENGTH: 14
<212> TYPE: PRT
<213> ORGANISM: Homo sapiens

<400> SEQUENCE: 710

His Thr Trp Asp His His His Thr Thr Gly Glu His Asn Val
1               5                   10

<210> SEQ ID NO 711
<211> LENGTH: 351
<212> TYPE: DNA
<213> ORGANISM: Homo sapiens

<400> SEQUENCE: 711
gaggtgcagc tgttggagag cggcggaggg ctggtgcagc caggcggcag cctgaggctg    60
tcctgcgccg cctccggatt caccttcagc agctacgcca tgaactgggt gcggcaggcc   120
ccaggcaagg gcctggagtg ggtgtccacc atcagctacc acgggcacca catcagctac   180
gccgacagcc atcatcacag gttcaccatc agcagggaca acagcaagaa caccctgtac   240
ctgcagatga acagcctgag ggccgaggac accgccgtgt actactgcgc ccgcatcaac   300
aacgacccta tggatgtgtg gggccagggc accctggtca ccgtctcctc a            351

<210> SEQ ID NO 712
<211> LENGTH: 117
<212> TYPE: PRT
<213> ORGANISM: Homo sapiens

<400> SEQUENCE: 712

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser Tyr Ala Asp Ser His
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 713
<211> LENGTH: 5
<212> TYPE: PRT
<213> ORGANISM: Homo sapiens

<400> SEQUENCE: 713

Ser Tyr Ala Met Asn
1               5

<210> SEQ ID NO 714
<211> LENGTH: 17
<212> TYPE: PRT
<213> ORGANISM: Homo sapiens

<400> SEQUENCE: 714

Thr Ile Ser Tyr His Gly His His Ile Ser Tyr Ala Asp Ser His His
1               5                   10                  15

His

<210> SEQ ID NO 715
<211> LENGTH: 8
<212> TYPE: PRT
<213> ORGANISM: Homo sapiens

<400> SEQUENCE: 715

Ile Asn Asn Asp Pro Met Asp Val
1               5

<210> SEQ ID NO 716
<211> LENGTH: 333
<212> TYPE: DNA
<213> ORGANISM: Homo sapiens

<400> SEQUENCE: 716
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg gaccaccacc acacgacggg ggagcacaac     300
gtgttcggcg gagggaccaa gctgaccgtc cta                                  333

<210> SEQ ID NO 717
<211> LENGTH: 111
<212> TYPE: PRT
<213> ORGANISM: Homo sapiens

<400> SEQUENCE: 717

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp His His Thr Thr
                85                  90                  95

Gly Glu His Asn Val Phe Gly Gly Gly Thr Lys Leu Thr Val Leu
            100                 105                 110

<210> SEQ ID NO 718
<211> LENGTH: 11
<212> TYPE: PRT
<213> ORGANISM: Homo sapiens

<400> SEQUENCE: 718

Ser Gly Asp Asn Leu Gly Lys Lys Tyr Val Gln
1               5                   10

<210> SEQ ID NO 719
<211> LENGTH: 7
<212> TYPE: PRT
<213> ORGANISM: Homo sapiens

<400> SEQUENCE: 719

Asp Asp Ser Asn Arg Pro Ser
1               5

<210> SEQ ID NO 720
<211> LENGTH: 14
<212> TYPE: PRT
<213> ORGANISM: Homo sapiens

<400> SEQUENCE: 720

His Thr Trp Asp His His His Thr Thr Gly Glu His Asn Val
1               5                   10

<210> SEQ ID NO 721
<211> LENGTH: 351
<212> TYPE: DNA
<213> ORGANISM: Homo sapiens

<400> SEQUENCE: 721
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca acagcaagaa caccctgtac     240
ctgcagatga acagcctgag ggccgaggac accgccgtgt actactgcgc ccgcatcaac     300
cacgacccta tggatgtgtg gggccagggc accctggtca ccgtctcctc a              351

<210> SEQ ID NO 722
<211> LENGTH: 117
<212> TYPE: PRT
<213> ORGANISM: Homo sapiens

<400> SEQUENCE: 722

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 723
<211> LENGTH: 5
<212> TYPE: PRT
<213> ORGANISM: Homo sapiens

<400> SEQUENCE: 723

Ser Tyr Ala Met Asn
1               5

<210> SEQ ID NO 724
<211> LENGTH: 17
<212> TYPE: PRT
<213> ORGANISM: Homo sapiens

<400> SEQUENCE: 724

Thr Ile Ser Tyr Ser Gly Ser Leu Ile Ser Tyr Ala Asp Ser Val Lys
1               5                   10                  15

Gly

<210> SEQ ID NO 725
<211> LENGTH: 8
<212> TYPE: PRT
<213> ORGANISM: Homo sapiens

<400> SEQUENCE: 725

Ile Asn His Asp Pro Met Asp Val
1               5

<210> SEQ ID NO 726
<211> LENGTH: 333
<212> TYPE: DNA
<213> ORGANISM: Homo sapiens

<400> SEQUENCE: 726
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggcacc accacgggg gagaccaac      300 cacttcggcg gagggaccaa gctgaccgtc cta                                  333

<210> SEQ ID NO 727
<211> LENGTH: 111
<212> TYPE: PRT
<213> ORGANISM: Homo sapiens

<400> SEQUENCE: 727

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly His His His Thr
                85                  90                  95

Gly Glu Thr Asn His Phe Gly Gly Gly Thr Lys Leu Thr Val Leu
            100                 105                 110

<210> SEQ ID NO 728
<211> LENGTH: 11
<212> TYPE: PRT
<213> ORGANISM: Homo sapiens

<400> SEQUENCE: 728

```
Ser Gly Asp Asn Leu Gly Lys Lys Tyr Val Gln
1               5                   10
```

<210> SEQ ID NO 729
<211> LENGTH: 7
<212> TYPE: PRT
<213> ORGANISM: Homo sapiens

<400> SEQUENCE: 729

```
Asp Asp Ser Asn Arg Pro Ser
1               5
```

<210> SEQ ID NO 730
<211> LENGTH: 14
<212> TYPE: PRT
<213> ORGANISM: Homo sapiens

<400> SEQUENCE: 730

```
Gln Thr Trp Asp Gly His His His Thr Gly Glu Thr Asn His
1               5                   10
```

<210> SEQ ID NO 731
<211> LENGTH: 351
<212> TYPE: DNA
<213> ORGANISM: Homo sapiens

<400> SEQUENCE: 731

| | |
|---|---|
| gaggtgcagc tgttggagag cggcggaggg ctggtgcagc caggcggcag cctgaggctg | 60 |
| tcctgcgccg cctccggatt caccttcagc agctacgcca tgaactgggt gcggcaggcc | 120 |
| ccaggcaagg gcctggagtg ggtgtccacc atcagctaca gcgggtcgct gatcagctac | 180 |
| gccgacagcg tgaagggcag gttcaccatc agcagggaca cagcaagaa caccctgtac | 240 |
| ctgcagatga acagcctgag ggccgaggac accgccgtgt actactgcgc ccgcatccac | 300 |
| cacgacccta tggatgtgtg gggccagggc accctggtca ccgtctcctc a | 351 |

<210> SEQ ID NO 732
<211> LENGTH: 117
<212> TYPE: PRT
<213> ORGANISM: Homo sapiens

<400> SEQUENCE: 732

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115
```

<210> SEQ ID NO 733
<211> LENGTH: 5
<212> TYPE: PRT
<213> ORGANISM: Homo sapiens

<400> SEQUENCE: 733

Ser Tyr Ala Met Asn
1               5

<210> SEQ ID NO 734
<211> LENGTH: 17
<212> TYPE: PRT
<213> ORGANISM: Homo sapiens

<400> SEQUENCE: 734

Thr Ile Ser Tyr Ser Gly Ser Leu Ile Ser Tyr Ala Asp Ser Val Lys
1               5                   10                  15

Gly

<210> SEQ ID NO 735
<211> LENGTH: 8
<212> TYPE: PRT
<213> ORGANISM: Homo sapiens

<400> SEQUENCE: 735

Ile His His Asp Pro Met Asp Val
1               5

<210> SEQ ID NO 736
<211> LENGTH: 333
<212> TYPE: DNA
<213> ORGANISM: Homo sapiens

<400> SEQUENCE: 736
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggcacc accacacggg ggagaccaac     300
cacttcggcg agggaccaa gctgaccgtc cta                                   333

<210> SEQ ID NO 737
<211> LENGTH: 111
<212> TYPE: PRT
<213> ORGANISM: Homo sapiens

<400> SEQUENCE: 737

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
                20                  25                  30

Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly His His His Thr
                85                  90                  95

Gly Glu Thr Asn His Phe Gly Gly Gly Thr Lys Leu Thr Val Leu
            100                 105                 110

<210> SEQ ID NO 738
<211> LENGTH: 11
<212> TYPE: PRT
<213> ORGANISM: Homo sapiens

<400> SEQUENCE: 738

Ser Gly Asp Asn Leu Gly Lys Lys Tyr Val Gln
1               5                   10

<210> SEQ ID NO 739
<211> LENGTH: 7
<212> TYPE: PRT
<213> ORGANISM: Homo sapiens

<400> SEQUENCE: 739

Asp Asp Ser Asn Arg Pro Ser
1               5

<210> SEQ ID NO 740
<211> LENGTH: 14
<212> TYPE: PRT
<213> ORGANISM: Homo sapiens

<400> SEQUENCE: 740

Gln Thr Trp Asp Gly His His Thr Gly Glu Thr Asn His
1               5                   10

<210> SEQ ID NO 741
<211> LENGTH: 351
<212> TYPE: DNA
<213> ORGANISM: Homo sapiens

<400> SEQUENCE: 741
gaggtgcagc tgttggagag cggcggaggg ctggtgcagc aggcggcag cctgaggctg      60 tcctgcgccg cctccggatt caccttcagc agctacgcca tgaactgggt gcggcaggcc    120
ccaggcaagg gcctggagtg ggtgtccacc atcagctacc acgggcacca catcagctac    180
gccgacagcc atcatcacag gttcaccatc agcagggaca acagcaagaa caccctgtac    240
ctgcagatga acagcctgag ggccgaggac accgccgtgt actactgcgc ccgcatcaac    300
aacgaccgta tggatgtgtg gggccagggc accctggtca ccgtctcctc a             351

<210> SEQ ID NO 742
<211> LENGTH: 117
<212> TYPE: PRT
<213> ORGANISM: Homo sapiens

<400> SEQUENCE: 742

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser Tyr Ala Asp Ser His
    50                  55                  60

His His Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                 85                  90                  95

Ala Arg Ile Asn Asn Asp Pro Met Asp Val Trp Gly Gln Gly Thr Leu
            100                 105                 110

Val Thr Val Ser Ser
        115

<210> SEQ ID NO 743
<211> LENGTH: 5
<212> TYPE: PRT
<213> ORGANISM: Homo sapiens

<400> SEQUENCE: 743

Ser Tyr Ala Met Asn
1               5

<210> SEQ ID NO 744
<211> LENGTH: 17
<212> TYPE: PRT
<213> ORGANISM: Homo sapiens

<400> SEQUENCE: 744

Thr Ile Ser Tyr His Gly His His Ile Ser Tyr Ala Asp Ser His His
1               5                   10                  15

His

<210> SEQ ID NO 745
<211> LENGTH: 8
<212> TYPE: PRT
<213> ORGANISM: Homo sapiens

<400> SEQUENCE: 745

Ile Asn Asn Asp Pro Met Asp Val
1               5

<210> SEQ ID NO 746
<211> LENGTH: 333
<212> TYPE: DNA
<213> ORGANISM: Homo sapiens

<400> SEQUENCE: 746
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggcacc accacacggg ggagaccaac     300
cacttcggcg gagggaccaa gctgaccgtc cta                                  333

<210> SEQ ID NO 747
<211> LENGTH: 111
<212> TYPE: PRT
<213> ORGANISM: Homo sapiens

<400> SEQUENCE: 747

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30
```

```
Gln Trp Tyr Gln Gln Lys Pro Gly Gln Ser Pro Val Leu Val Ile Tyr
            35                  40                  45

Asp Asp Ser Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Thr Trp Asp Gly His His His Thr
                 85                  90                  95

Gly Glu Thr Asn His Phe Gly Gly Gly Thr Lys Leu Thr Val Leu
            100                 105                 110
```

```
<210> SEQ ID NO 748
<211> LENGTH: 11
<212> TYPE: PRT
<213> ORGANISM: Homo sapiens

<400> SEQUENCE: 748

Ser Gly Asp Asn Leu Gly Lys Lys Tyr Val Gln
1               5                   10

<210> SEQ ID NO 749
<211> LENGTH: 7
<212> TYPE: PRT
<213> ORGANISM: Homo sapiens

<400> SEQUENCE: 749

Asp Asp Ser Asn Arg Pro Ser
1               5

<210> SEQ ID NO 750
<211> LENGTH: 14
<212> TYPE: PRT
<213> ORGANISM: Homo sapiens

<400> SEQUENCE: 750

Gln Thr Trp Asp Gly His His Thr Gly Glu Thr Asn His
1               5                   10

<210> SEQ ID NO 751
<211> LENGTH: 351
<212> TYPE: DNA
<213> ORGANISM: Homo sapiens

<400> SEQUENCE: 751
gaggtgcagc tgctggagag cggcggaggg ctggtgcagc caggcggcag cctgaggctg       60
tcctgcgccg cctccggatt caccttcagc agctacgcca tgaactgggt gcggcaggcc      120
ccaggcaagg gcctggagtg ggtgtccacc atcagctacc acgggcacca catcagctac      180
gccgacagcc atcatcacag gttcaccatc agcagggaca acagcaagaa caccctgtac      240
ctgcagatga acagcctgag ggccgaggac accgccgtgt actactgcgc ccgcatcaac      300
cacgacccta tggatgtgtg gggccagggc accctggtca ccgtctcctc a               351

<210> SEQ ID NO 752
<211> LENGTH: 117
<212> TYPE: PRT
<213> ORGANISM: Homo sapiens

<400> SEQUENCE: 752

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Ser Tyr His Gly His His Ile Ser Tyr Ala Asp Ser His
        50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 753
<211> LENGTH: 5
<212> TYPE: PRT
<213> ORGANISM: Homo sapiens

<400> SEQUENCE: 753

Ser Tyr Ala Met Asn
1               5

<210> SEQ ID NO 754
<211> LENGTH: 17
<212> TYPE: PRT
<213> ORGANISM: Homo sapiens

<400> SEQUENCE: 754

Thr Ile Ser Tyr His Gly His His Ile Ser Tyr Ala Asp Ser His His
1               5                   10                  15

His

<210> SEQ ID NO 755
<211> LENGTH: 8
<212> TYPE: PRT
<213> ORGANISM: Homo sapiens

<400> SEQUENCE: 755

Ile Asn His Asp Pro Met Asp Val
1               5

<210> SEQ ID NO 756
<211> LENGTH: 333
<212> TYPE: DNA
<213> ORGANISM: Homo sapiens

<400> SEQUENCE: 756
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccagacctgg gacgggcacc accacgggg gagaccaac      300 cacttcggcg agggaccaa gctgaccgtc cta                                   333

<210> SEQ ID NO 757
<211> LENGTH: 111

<212> TYPE: PRT
<213> ORGANISM: Homo sapiens

<400> SEQUENCE: 757

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Thr Trp Asp Gly His His His Thr
                85                  90                  95

Gly Glu Thr Asn His Phe Gly Gly Gly Thr Lys Leu Thr Val Leu
            100                 105                 110
```

<210> SEQ ID NO 758
<211> LENGTH: 11
<212> TYPE: PRT
<213> ORGANISM: Homo sapiens

<400> SEQUENCE: 758

```
Ser Gly Asp Asn Leu Gly Lys Lys Tyr Val Gln
1               5                   10
```

<210> SEQ ID NO 759
<211> LENGTH: 7
<212> TYPE: PRT
<213> ORGANISM: Homo sapiens

<400> SEQUENCE: 759

```
Asp Asp Ser Asn Arg Pro Ser
1               5
```

<210> SEQ ID NO 760
<211> LENGTH: 14
<212> TYPE: PRT
<213> ORGANISM: Homo sapiens

<400> SEQUENCE: 760

```
Gln Thr Trp Asp Gly His His His Thr Gly Glu Thr Asn His
1               5                   10
```

<210> SEQ ID NO 761
<211> LENGTH: 351
<212> TYPE: DNA
<213> ORGANISM: Homo sapiens

<400> SEQUENCE: 761

```
gaggtgcagc tgctcgagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctaca gcgggtcgct gatcagctac     180
gccgacagcg tgaagggcag gttcaccatc agcagggaca acagcaagaa caccctgtac     240
ctgcagatga acagcctgag ggccgaggac accgccgtgt actactgcgc ccgcatcaac     300
cacgacccta tggatgtgtg gggccagggc accctggtca ccgtctcctc a              351
```

<210> SEQ ID NO 762
<211> LENGTH: 117
<212> TYPE: PRT
<213> ORGANISM: Homo sapiens

<400> SEQUENCE: 762

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 763
<211> LENGTH: 5
<212> TYPE: PRT
<213> ORGANISM: Homo sapiens

<400> SEQUENCE: 763

Ser Tyr Ala Met Asn
1               5

<210> SEQ ID NO 764
<211> LENGTH: 17
<212> TYPE: PRT
<213> ORGANISM: Homo sapiens

<400> SEQUENCE: 764

Thr Ile Ser Tyr Ser Gly Ser Leu Ile Ser Tyr Ala Asp Ser Val Lys
1               5                   10                  15

Gly

<210> SEQ ID NO 765
<211> LENGTH: 8
<212> TYPE: PRT
<213> ORGANISM: Homo sapiens

<400> SEQUENCE: 765

Ile Asn His Asp Pro Met Asp Val
1               5

<210> SEQ ID NO 766
<211> LENGTH: 333
<212> TYPE: DNA
<213> ORGANISM: Homo sapiens

<400> SEQUENCE: 766
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120

| | |
|---|---:|
| cagtcccccg tgctggtgat ctacgacgac agcaacaggc ccagcggcat ccccgagagg | 180 |
| ttcagcggca gcaacagcgg caacaccgcc accctgacca tcagcggcac ccaggcgatg | 240 |
| gacgaggccg actactactg ccacacctgg gacgggcacc acacgacggg ggagaccaac | 300 |
| cacttcggcg agggaccaa gctgaccgtc cta | 333 |

<210> SEQ ID NO 767
<211> LENGTH: 111
<212> TYPE: PRT
<213> ORGANISM: Homo sapiens

<400> SEQUENCE: 767

```
Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp Gly His His Thr Thr
                85                  90                  95

Gly Glu Thr Asn His Phe Gly Gly Gly Thr Lys Leu Thr Val Leu
            100                 105                 110
```

<210> SEQ ID NO 768
<211> LENGTH: 11
<212> TYPE: PRT
<213> ORGANISM: Homo sapiens

<400> SEQUENCE: 768

```
Ser Gly Asp Asn Leu Gly Lys Lys Tyr Val Gln
1               5                   10
```

<210> SEQ ID NO 769
<211> LENGTH: 7
<212> TYPE: PRT
<213> ORGANISM: Homo sapiens

<400> SEQUENCE: 769

```
Asp Asp Ser Asn Arg Pro Ser
1               5
```

<210> SEQ ID NO 770
<211> LENGTH: 14
<212> TYPE: PRT
<213> ORGANISM: Homo sapiens

<400> SEQUENCE: 770

```
His Thr Trp Asp Gly His His Thr Thr Gly Glu Thr Asn His
1               5                   10
```

<210> SEQ ID NO 771
<211> LENGTH: 351
<212> TYPE: DNA
<213> ORGANISM: Homo sapiens

<400> SEQUENCE: 771

| | |
|---|---:|
| gaggtgcagc tgttggagag cggcggaggg ctggtgcagc caggcggcag cctgaggctg | 60 |

```
tcctgcgccg cctccggatt caccttcagc agctacgcca tgaactgggt gcggcaggcc    120
ccaggcaagg gcctggagtg ggtgtccacc atcagctaca gcgggtcgct gatcagctac    180
gccgacagcg tgaagggcag gttcaccatc agcagggaca acagcaagaa caccctgtac    240
ctgcagatga acagcctgag ggccgaggac accgccgtgt actactgcgc ccgcatccac    300
cacgacccta tggatgtgtg gggccagggc accctggtca ccgtctcctc a             351
```

<210> SEQ ID NO 772
<211> LENGTH: 117
<212> TYPE: PRT
<213> ORGANISM: Homo sapiens

<400> SEQUENCE: 772

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115
```

<210> SEQ ID NO 773
<211> LENGTH: 5
<212> TYPE: PRT
<213> ORGANISM: Homo sapiens

<400> SEQUENCE: 773

```
Ser Tyr Ala Met Asn
1               5
```

<210> SEQ ID NO 774
<211> LENGTH: 17
<212> TYPE: PRT
<213> ORGANISM: Homo sapiens

<400> SEQUENCE: 774

```
Thr Ile Ser Tyr Ser Gly Ser Leu Ile Ser Tyr Ala Asp Ser Val Lys
1               5                   10                  15

Gly
```

<210> SEQ ID NO 775
<211> LENGTH: 8
<212> TYPE: PRT
<213> ORGANISM: Homo sapiens

<400> SEQUENCE: 775

```
Ile His His Asp Pro Met Asp Val
1               5
```

-continued

<210> SEQ ID NO 776
<211> LENGTH: 333
<212> TYPE: DNA
<213> ORGANISM: Homo sapiens

<400> SEQUENCE: 776

```
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg gacgggcacc acacgacggg ggagaccaac     300
cacttcggcg gagggaccaa gctgaccgtc cta                                  333
```

<210> SEQ ID NO 777
<211> LENGTH: 111
<212> TYPE: PRT
<213> ORGANISM: Homo sapiens

<400> SEQUENCE: 777

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp Gly His His Thr Thr
                85                  90                  95

Gly Glu Thr Asn His Phe Gly Gly Gly Thr Lys Leu Thr Val Leu
            100                 105                 110

<210> SEQ ID NO 778
<211> LENGTH: 11
<212> TYPE: PRT
<213> ORGANISM: Homo sapiens

<400> SEQUENCE: 778

Ser Gly Asp Asn Leu Gly Lys Lys Tyr Val Gln
1               5                   10

<210> SEQ ID NO 779
<211> LENGTH: 7
<212> TYPE: PRT
<213> ORGANISM: Homo sapiens

<400> SEQUENCE: 779

Asp Asp Ser Asn Arg Pro Ser
1               5

<210> SEQ ID NO 780
<211> LENGTH: 14
<212> TYPE: PRT
<213> ORGANISM: Homo sapiens

<400> SEQUENCE: 780

His Thr Trp Asp Gly His His Thr Thr Gly Glu Thr Asn His

<210> SEQ ID NO 781
<211> LENGTH: 351
<212> TYPE: DNA
<213> ORGANISM: Homo sapiens

<400> SEQUENCE: 781

```
gaggtgcagc tgttggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggcacca catcagctac     180
gccgacagcc atcatcacag gttcaccatc agcagggaca cagcaagaa caccctgtac      240
ctgcagatga acagcctgag ggccgaggac accgccgtgt actactgcgc ccgcatcaac     300
aacgacccta tggatgtgtg gggccagggc accctggtca ccgtctcctc a              351
```

<210> SEQ ID NO 782
<211> LENGTH: 117
<212> TYPE: PRT
<213> ORGANISM: Homo sapiens

<400> SEQUENCE: 782

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Asn Trp Val Arg Gln Ala Pro Gly Lys Gly Leu Glu Trp Val
        35                  40                  45
Ser Thr Ile Ser Tyr His Gly His His Ile Ser Tyr Ala Asp Ser His
    50                  55                  60
His His Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ile Asn Asn Asp Pro Met Asp Val Trp Gly Gln Gly Thr Leu
            100                 105                 110
Val Thr Val Ser Ser
        115
```

<210> SEQ ID NO 783
<211> LENGTH: 5
<212> TYPE: PRT
<213> ORGANISM: Homo sapiens

<400> SEQUENCE: 783

```
Ser Tyr Ala Met Asn
1               5
```

<210> SEQ ID NO 784
<211> LENGTH: 17
<212> TYPE: PRT
<213> ORGANISM: Homo sapiens

<400> SEQUENCE: 784

```
Thr Ile Ser Tyr His Gly His His Ile Ser Tyr Ala Asp Ser His His
1               5                   10                  15
His
```

```
<210> SEQ ID NO 785
<211> LENGTH: 8
<212> TYPE: PRT
<213> ORGANISM: Homo sapiens

<400> SEQUENCE: 785

Ile Asn Asn Asp Pro Met Asp Val
1               5

<210> SEQ ID NO 786
<211> LENGTH: 333
<212> TYPE: DNA
<213> ORGANISM: Homo sapiens

<400> SEQUENCE: 786
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg gacgggcacc acacgacggg ggagaccaac     300
cacttcggcg agggaccaa gctgaccgtc cta                                   333

<210> SEQ ID NO 787
<211> LENGTH: 111
<212> TYPE: PRT
<213> ORGANISM: Homo sapiens

<400> SEQUENCE: 787

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp Gly His His Thr Thr
                85                  90                  95

Gly Glu Thr Asn His Phe Gly Gly Gly Thr Lys Leu Thr Val Leu
            100                 105                 110

<210> SEQ ID NO 788
<211> LENGTH: 11
<212> TYPE: PRT
<213> ORGANISM: Homo sapiens

<400> SEQUENCE: 788

Ser Gly Asp Asn Leu Gly Lys Lys Tyr Val Gln
1               5                   10

<210> SEQ ID NO 789
<211> LENGTH: 7
<212> TYPE: PRT
<213> ORGANISM: Homo sapiens

<400> SEQUENCE: 789

Asp Asp Ser Asn Arg Pro Ser
1               5
```

<210> SEQ ID NO 790
<211> LENGTH: 14
<212> TYPE: PRT
<213> ORGANISM: Homo sapiens

<400> SEQUENCE: 790

His Thr Trp Asp Gly His His Thr Thr Gly Glu Thr Asn His
1               5                   10

<210> SEQ ID NO 791
<211> LENGTH: 351
<212> TYPE: DNA
<213> ORGANISM: Homo sapiens

<400> SEQUENCE: 791
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggcacca catcagctac     180
gccgacagcc atcatcacag gttcaccatc agcagggaca cagcaagaa cacccctgtac     240 ctgcagatga acagcctgag ggccgaggac accgccgtgt actactgcgc ccgcatcaac     300
cacgacccta tggatgtgtg gggccagggc accctggtca ccgtctcctc a              351

<210> SEQ ID NO 792
<211> LENGTH: 117
<212> TYPE: PRT
<213> ORGANISM: Homo sapiens

<400> SEQUENCE: 792

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly His His Ile Ser Tyr Ala Asp Ser His
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 793
<211> LENGTH: 5
<212> TYPE: PRT
<213> ORGANISM: Homo sapiens

<400> SEQUENCE: 793

Ser Tyr Ala Met Asn
1               5

<210> SEQ ID NO 794
<211> LENGTH: 17

```
<212> TYPE: PRT
<213> ORGANISM: Homo sapiens

<400> SEQUENCE: 794

Thr Ile Ser Tyr His Gly His His Ile Ser Tyr Ala Asp Ser His His
1               5                   10                  15

His

<210> SEQ ID NO 795
<211> LENGTH: 8
<212> TYPE: PRT
<213> ORGANISM: Homo sapiens

<400> SEQUENCE: 795

Ile Asn His Asp Pro Met Asp Val
1               5

<210> SEQ ID NO 796
<211> LENGTH: 333
<212> TYPE: DNA
<213> ORGANISM: Homo sapiens

<400> SEQUENCE: 796
agtatcgagc tgacccagcc ccccagcgtg agcgtgtccc caggccagac cgccagcatc      60
acctgcagcg gcgacaacct gggcaagaaa tacgtgcagt ggtatcagca gaagcccggc     120
cagtcccccg tgctggtgat ctacgacgac agcaacaggc ccagcggcat ccccgagagg     180
ttcagcggca gcaacagcgg caacaccgcc accctgacca tcagcggcac ccaggcgatg     240
gacgaggccg actactactg ccacacctgg gacgggcacc acacgacggg ggagaccaac     300
cacttcggcg agggaccaa gctgaccgtc cta                                   333

<210> SEQ ID NO 797
<211> LENGTH: 111
<212> TYPE: PRT
<213> ORGANISM: Homo sapiens

<400> SEQUENCE: 797

Ser Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Lys Lys Tyr Val
            20                  25                  30

Gln Trp Tyr Gln Gln Lys Pro Gly Gln Ser Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys His Thr Trp Asp Gly His His Thr Thr
                85                  90                  95

Gly Glu Thr Asn His Phe Gly Gly Gly Thr Lys Leu Thr Val Leu
            100                 105                 110

<210> SEQ ID NO 798
<211> LENGTH: 11
<212> TYPE: PRT
<213> ORGANISM: Homo sapiens

<400> SEQUENCE: 798

Ser Gly Asp Asn Leu Gly Lys Lys Tyr Val Gln
1               5                   10
```

<210> SEQ ID NO 799
<211> LENGTH: 7
<212> TYPE: PRT
<213> ORGANISM: Homo sapiens

<400> SEQUENCE: 799

Asp Asp Ser Asn Arg Pro Ser
1               5

<210> SEQ ID NO 800
<211> LENGTH: 14
<212> TYPE: PRT
<213> ORGANISM: Homo sapiens

<400> SEQUENCE: 800

His Thr Trp Asp Gly His His Thr Thr Gly Glu Thr Asn His
1               5                   10

<210> SEQ ID NO 801
<211> LENGTH: 397
<212> TYPE: PRT
<213> ORGANISM: Homo sapiens

<400> SEQUENCE: 801

Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe Ser Val Asp Glu Phe
    50                  55                  60

Ser Ala Ser Val Leu Thr Gly Lys Leu Thr Thr Val Phe Leu Pro Ile
65                  70                  75                  80

Val Tyr Thr Ile Val Phe Val Val Gly Leu Pro Ser Asn Gly Met Ala
                85                  90                  95

Leu Trp Val Phe Leu Phe Arg Thr Lys Lys Lys His Pro Ala Val Ile
            100                 105                 110

Tyr Met Ala Asn Leu Ala Leu Ala Asp Leu Leu Ser Val Ile Trp Phe
        115                 120                 125

Pro Leu Lys Ile Ala Tyr His Ile His Gly Asn Asn Trp Ile Tyr Gly
    130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
            180                 185                 190

Gly Ile Ser Leu Ala Ile Trp Leu Leu Ile Leu Leu Val Thr Ile Pro
        195                 200                 205

Leu Tyr Val Val Lys Gln Thr Ile Phe Ile Pro Ala Leu Asn Ile Thr
    210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

```
Leu Thr Ala Ser Ala Tyr Val Leu Met Ile Arg Met Leu Arg Ser Ser
            260                 265                 270

Ala Met Asp Glu Asn Ser Glu Lys Arg Lys Arg Ala Ile Lys Leu
        275                 280                 285

Ile Val Thr Val Leu Ala Met Tyr Leu Ile Cys Phe Thr Pro Ser Asn
            290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
            325                 330                 335

Ser Cys Ile Asp Pro Phe Val Tyr Tyr Phe Val Ser His Asp Phe Arg
            340                 345                 350

Asp His Ala Lys Asn Ala Leu Leu Cys Arg Ser Val Arg Thr Val Lys
            355                 360                 365

Gln Met Gln Val Ser Leu Thr Ser Lys Lys His Ser Arg Lys Ser Ser
            370                 375                 380

Ser Tyr Ser Ser Ser Ser Thr Thr Val Lys Thr Ser Tyr
385                 390                 395

<210> SEQ ID NO 802
<211> LENGTH: 39
<212> TYPE: PRT
<213> ORGANISM: Homo sapiens

<400> SEQUENCE: 802

Ser Leu Ile Gly Lys Val Asp Gly Thr Ser His Val Thr Gly Lys Gly
1               5                   10                  15

Val Thr Val Glu Thr Val Phe Ser Val Asp Glu Phe Ser Ala Ser Val
            20                  25                  30

Leu Thr Gly Lys Leu Thr Thr
            35

<210> SEQ ID NO 803
<211> LENGTH: 30
<212> TYPE: PRT
<213> ORGANISM: Homo sapiens

<400> SEQUENCE: 803

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 804
<211> LENGTH: 14
<212> TYPE: PRT
<213> ORGANISM: Homo sapiens

<400> SEQUENCE: 804

Trp Val Arg Gln Ala Pro Gly Lys Gly Leu Glu Trp Val Ser
1               5                   10

<210> SEQ ID NO 805
<211> LENGTH: 32
<212> TYPE: PRT
<213> ORGANISM: Homo sapiens

<400> SEQUENCE: 805

Arg Phe Thr Ile Ser Arg Asp Asn Ser Lys Asn Thr Leu Tyr Leu Gln
```

```
                1               5                  10                 15
Met Asn Ser Leu Arg Ala Glu Asp Thr Ala Val Tyr Tyr Cys Ala Arg
                20                 25                 30
```

<210> SEQ ID NO 806
<211> LENGTH: 11
<212> TYPE: PRT
<213> ORGANISM: Homo sapiens

<400> SEQUENCE: 806

```
Trp Gly Gln Gly Thr Leu Val Thr Val Ser Ser
1               5                  10
```

<210> SEQ ID NO 807
<211> LENGTH: 22
<212> TYPE: PRT
<213> ORGANISM: Homo sapiens

<400> SEQUENCE: 807

```
Ser Ile Glu Leu Thr Gln Pro Pro Ser Val Ser Val Ser Pro Gly Gln
1               5                  10                 15
Thr Ala Ser Ile Thr Cys
                20
```

<210> SEQ ID NO 808
<211> LENGTH: 15
<212> TYPE: PRT
<213> ORGANISM: Homo sapiens

<400> SEQUENCE: 808

```
Trp Tyr Gln Gln Lys Pro Gly Gln Ser Pro Val Leu Val Ile Tyr
1               5                  10                 15
```

<210> SEQ ID NO 809
<211> LENGTH: 32
<212> TYPE: PRT
<213> ORGANISM: Homo sapiens

<400> SEQUENCE: 809

```
Gly Ile Pro Glu Arg Phe Ser Gly Ser Asn Ser Gly Asn Thr Ala Thr
1               5                  10                 15
Leu Thr Ile Ser Gly Thr Gln Ala Met Asp Glu Ala Asp Tyr Tyr Cys
                20                 25                 30
```

<210> SEQ ID NO 810
<211> LENGTH: 10
<212> TYPE: PRT
<213> ORGANISM: Homo sapiens

<400> SEQUENCE: 810

```
Phe Gly Gly Gly Thr Lys Leu Thr Val Leu
1               5                  10
```

<210> SEQ ID NO 811
<211> LENGTH: 17
<212> TYPE: PRT
<213> ORGANISM: Homo sapiens

<400> SEQUENCE: 811

```
Thr Ile Ser Tyr Ser Gly Ser His Ile Ser Tyr His Asp Ser Val His
1               5                  10                 15
His
```

<210> SEQ ID NO 812
<211> LENGTH: 17
<212> TYPE: PRT
<213> ORGANISM: Homo sapiens

<400> SEQUENCE: 812

Thr Ile Ser Tyr His Gly Ser Leu Ile Ser Tyr His Asp Ser Val His
1               5                   10                  15

His

<210> SEQ ID NO 813
<211> LENGTH: 17
<212> TYPE: PRT
<213> ORGANISM: Homo sapiens

<400> SEQUENCE: 813

Thr Ile Ser Tyr His Gly Ser His Ile Ser Tyr Ala Asp Ser Val His
1               5                   10                  15

His

<210> SEQ ID NO 814
<211> LENGTH: 17
<212> TYPE: PRT
<213> ORGANISM: Homo sapiens

<400> SEQUENCE: 814

Thr Ile Ser Tyr His Gly Ser His Ile Ser Tyr His Asp Ser Val Lys
1               5                   10                  15

His

<210> SEQ ID NO 815
<211> LENGTH: 17
<212> TYPE: PRT
<213> ORGANISM: Homo sapiens

<400> SEQUENCE: 815

Thr Ile Ser Tyr His Gly Ser His Ile Ser Tyr His Asp Ser Val His
1               5                   10                  15

Gly

<210> SEQ ID NO 816
<211> LENGTH: 17
<212> TYPE: PRT
<213> ORGANISM: Homo sapiens

<400> SEQUENCE: 816

Thr Ile Ser Tyr His Gly Ser Leu Ile Ser Tyr Ala Asp Ser Val Lys
1               5                   10                  15

Gly

<210> SEQ ID NO 817
<211> LENGTH: 17
<212> TYPE: PRT
<213> ORGANISM: Homo sapiens

<400> SEQUENCE: 817

Thr Ile Ser Tyr Ser Gly Ser His Ile Ser Tyr Ala Asp Ser Val Lys
1               5                   10                  15

Gly

```
<210> SEQ ID NO 818
<211> LENGTH: 17
<212> TYPE: PRT
<213> ORGANISM: Homo sapiens

<400> SEQUENCE: 818

Thr Ile Ser Tyr His Gly Ser His Ile Ser Tyr Ala Asp Ser Val Lys
1               5                   10                  15

Gly

<210> SEQ ID NO 819
<211> LENGTH: 8
<212> TYPE: PRT
<213> ORGANISM: Homo sapiens

<400> SEQUENCE: 819

Ile His Asn Asp Pro Met Asp Val
1               5

<210> SEQ ID NO 820
<211> LENGTH: 8
<212> TYPE: PRT
<213> ORGANISM: Homo sapiens

<400> SEQUENCE: 820

Ile Asn His Asp Pro Met Asp Val
1               5

<210> SEQ ID NO 821
<211> LENGTH: 117
<212> TYPE: PRT
<213> ORGANISM: Homo sapiens

<400> SEQUENCE: 821

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser Val
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115

<210> SEQ ID NO 822
<211> LENGTH: 117
<212> TYPE: PRT
<213> ORGANISM: Homo sapiens

<400> SEQUENCE: 822

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Asn Trp Val Arg Gln Ala Pro Gly Lys Gly Leu Glu Trp Val
            35                  40                  45

Ser Thr Ile Ser Tyr Ser Gly Ser His Ile Ser Tyr His Asp Ser Val
        50                  55                  60

His His Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
            115

<210> SEQ ID NO 823
<211> LENGTH: 117
<212> TYPE: PRT
<213> ORGANISM: Homo sapiens

<400> SEQUENCE: 823

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Ser Tyr His Gly Ser Leu Ile Ser Tyr His Asp Ser Val
        50                  55                  60

His His Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
            115

<210> SEQ ID NO 824
<211> LENGTH: 117
<212> TYPE: PRT
<213> ORGANISM: Homo sapiens

<400> SEQUENCE: 824

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Ser Tyr His Gly Ser His Ile Ser Tyr Ala Asp Ser Val
        50                  55                  60

His His Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110
```

Val Thr Val Ser Ser
        115

<210> SEQ ID NO 825
<211> LENGTH: 117
<212> TYPE: PRT
<213> ORGANISM: Homo sapiens

<400> SEQUENCE: 825

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser Val
    50                  55                  60

Lys His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115

<210> SEQ ID NO 826
<211> LENGTH: 117
<212> TYPE: PRT
<213> ORGANISM: Homo sapiens

<400> SEQUENCE: 826

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr His Asp Ser Val
    50                  55                  60

His Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115

<210> SEQ ID NO 827
<211> LENGTH: 117
<212> TYPE: PRT
<213> ORGANISM: Homo sapiens

<400> SEQUENCE: 827

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Ser Tyr His Gly Ser His Ile Ser Tyr His Asp Ser Val
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Asn His Asp Pro Met Asp Val Trp Gly Gln Gly Thr Leu
            100                 105                 110

Val Thr Val Ser Ser
        115

<210> SEQ ID NO 828
<211> LENGTH: 117
<212> TYPE: PRT
<213> ORGANISM: Homo sapiens

<400> SEQUENCE: 828

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Ser Tyr His Gly Ser His Ile Ser Tyr His Asp Ser Val
    50                  55                  60

His His Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His Asn Asp Pro Met Asp Val Trp Gly Gln Gly Thr Leu
            100                 105                 110

Val Thr Val Ser Ser
        115

<210> SEQ ID NO 829
<211> LENGTH: 117
<212> TYPE: PRT
<213> ORGANISM: Homo sapiens

<400> SEQUENCE: 829

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Thr Ile Ser Tyr His Gly Ser Leu Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ile His His Asp Pro Met Asp Val Trp Gly Gln Gly Thr Leu
            100                 105                 110

Val Thr Val Ser Ser
        115

<210> SEQ ID NO 830
<211> LENGTH: 117
<212> TYPE: PRT
<213> ORGANISM: Homo sapiens

<400> SEQUENCE: 830

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr Ser Gly Ser His Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115

<210> SEQ ID NO 831
<211> LENGTH: 117
<212> TYPE: PRT
<213> ORGANISM: Homo sapiens

<400> SEQUENCE: 831

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Tyr His Gly Ser His Ile Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile His His Asp Pro Met Asp Val Trp Gly Gln Gly Thr Leu
            100                 105                 110

Val Thr Val Ser Ser
        115

<210> SEQ ID NO 832
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (6)..(6)
<223> OTHER INFORMATION: Ornithine

<400> SEQUENCE: 832

Leu Ile Gly Arg Leu Xaa
1               5

<210> SEQ ID NO 833
<211> LENGTH: 351
<212> TYPE: DNA
<213> ORGANISM: Homo sapiens

<400> SEQUENCE: 833
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctact ccgggtcgca catcagctac     180
cacgacagcg tgcatcacag gttcaccatc agcaggaca acagcaagaa caccctgtac      240
ctgcagatga acagcctgag gccgaggac accgccgtgt actactgcgc ccgcatccac      300
cacgacccta tggatgtgtg gggccagggc accctggtga cagtgagctc a              351

<210> SEQ ID NO 834
<211> LENGTH: 351
<212> TYPE: DNA
<213> ORGANISM: Homo sapiens

<400> SEQUENCE: 834
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggtcgct catcagctac     180
cacgacagcg tgcatcacag gttcaccatc agcaggaca acagcaagaa caccctgtac      240
ctgcagatga acagcctgag gccgaggac accgccgtgt actactgcgc ccgcatccac      300
cacgacccta tggatgtgtg gggccagggc accctggtga cagtgagctc a              351

<210> SEQ ID NO 835
<211> LENGTH: 351
<212> TYPE: DNA
<213> ORGANISM: Homo sapiens

<400> SEQUENCE: 835
gaggtgcagc tgctggagag cggcggaggg ctggtgcagc caggcggcag cctgaggctg      60
tcctgcgccg cctccggatt caccttcagc agctacgcca tgaactgggt gcggcaggcc     120
ccaggcaagg gcctggagtg ggtgtccacc atcagctacc acgggtcgca catcagctac     180
gccgacagcg tgcatcacag gttcaccatc agcaggaca acagcaagaa caccctgtac      240
ctgcagatga acagcctgag gccgaggac accgccgtgt actactgcgc ccgcatccac      300
cacgacccta tggatgtgtg gggccagggc accctggtga cagtgagctc a              351

<210> SEQ ID NO 836
<211> LENGTH: 351
<212> TYPE: DNA
<213> ORGANISM: Homo sapiens

<400> SEQUENCE: 836
gaggtgcagc tgctggagag cggcggaggg ctggtgcagc caggcggcag cctgaggctg      60
```

| | |
|---|---|
| tcctgcgccg cctccggatt caccttcagc agctacgcca tgaactgggt gcggcaggcc | 120 |
| ccaggcaagg gcctggagtg ggtgtccacc atcagctacc acgggtcgca catcagctac | 180 |
| cacgacagcg tgaagcacag gttcaccatc agcaggaca acagcaagaa caccctgtac | 240 |
| ctgcagatga acagcctgag ggccgaggac accgccgtgt actactgcgc ccgcatccac | 300 |
| cacgacccta tggatgtgtg gggccagggc accctggtga cagtgagctc a | 351 |

<210> SEQ ID NO 837
<211> LENGTH: 351
<212> TYPE: DNA
<213> ORGANISM: Homo sapiens

<400> SEQUENCE: 837

| | |
|---|---|
| gaggtgcagc tgctggagag cggcggaggg ctggtgcagc caggcggcag cctgaggctg | 60 |
| tcctgcgccg cctccggatt caccttcagc agctacgcca tgaactgggt gcggcaggcc | 120 |
| ccaggcaagg gcctggagtg ggtgtccacc atcagctacc acgggtcgca catcagctac | 180 |
| cacgacagcg tgcatggcag gttcaccatc agcaggaca acagcaagaa caccctgtac | 240 |
| ctgcagatga acagcctgag ggccgaggac accgccgtgt actactgcgc ccgcatccac | 300 |
| cacgacccta tggatgtgtg gggccagggc accctggtga cagtgagctc a | 351 |

<210> SEQ ID NO 838
<211> LENGTH: 351
<212> TYPE: DNA
<213> ORGANISM: Homo sapiens

<400> SEQUENCE: 838

| | |
|---|---|
| gaggtgcagc tgctggagag cggcggaggg ctggtgcagc caggcggcag cctgaggctg | 60 |
| tcctgcgccg cctccggatt caccttcagc agctacgcca tgaactgggt gcggcaggcc | 120 |
| ccaggcaagg gcctggagtg ggtgtccacc atcagctacc acgggtcgca catcagctac | 180 |
| cacgacagcg tgcatcacag gttcaccatc agcaggaca acagcaagaa caccctgtac | 240 |
| ctgcagatga acagcctgag ggccgaggac accgccgtgt actactgcgc ccgcatccac | 300 |
| aacgacccta tggatgtgtg gggccagggc accctggtga cagtgagctc a | 351 |

<210> SEQ ID NO 839
<211> LENGTH: 351
<212> TYPE: DNA
<213> ORGANISM: Homo sapiens

<400> SEQUENCE: 839

| | |
|---|---|
| gaggtgcagc tgctggagag cggcggaggg ctggtgcagc caggcggcag cctgaggctg | 60 |
| tcctgcgccg cctccggatt caccttcagc agctacgcca tgaactgggt gcggcaggcc | 120 |
| ccaggcaagg gcctggagtg ggtgtccacc atcagctacc acgggtcgct catcagctac | 180 |
| gccgacagcg tgaagggcag gttcaccatc agcaggaca acagcaagaa caccctgtac | 240 |
| ctgcagatga acagcctgag ggccgaggac accgccgtgt actactgcgc ccgcatccac | 300 |
| cacgacccta tggatgtgtg gggccagggc accctggtga cagtgagctc a | 351 |

<210> SEQ ID NO 840
<211> LENGTH: 351
<212> TYPE: DNA
<213> ORGANISM: Homo sapiens

<400> SEQUENCE: 840

| | |
|---|---|
| gaggtgcagc tgctggagag cggcggaggg ctggtgcagc caggcggcag cctgaggctg | 60 |

```
tcctgcgccg cctccggatt caccttcagc agctacgcca tgaactgggt gcggcaggcc      120
ccaggcaagg gcctggagtg ggtgtccacc atcagctact ccgggtcgca catcagctac      180
gccgacagcg tgaagggcag gttcaccatc agcagggaca acagcaagaa caccctgtac      240
ctgcagatga acagcctgag ggccgaggac accgccgtgt actactgcgc ccgcatccac      300
cacgacccta tggatgtgtg gggccagggc accctggtga cagtgagctc a              351

<210> SEQ ID NO 841
<211> LENGTH: 351
<212> TYPE: DNA
<213> ORGANISM: Homo sapiens

<400> SEQUENCE: 841
gaggtgcagc tgctggagag cggcggaggg ctggtgcagc caggcggcag cctgaggctg       60
tcctgcgccg cctccggatt caccttcagc agctacgcca tgaactgggt gcggcaggcc      120
ccaggcaagg gcctggagtg ggtgtccacc atcagctacc acgggtcgca catcagctac      180
gccgacagcg tgaagggcag gttcaccatc agcagggaca acagcaagaa caccctgtac      240
ctgcagatga acagcctgag ggccgaggac accgccgtgt actactgcgc ccgcatccac      300
cacgacccta tggatgtgtg gggccagggc accctggtga cagtgagctc a              351
```